US010010597B2

(12) United States Patent
Brosch et al.

(10) Patent No.: US 10,010,597 B2
(45) Date of Patent: Jul. 3, 2018

(54) **RECOMBINANT *MYCOBACTERIUM BOVIS* BCG EXPRESSING ANTIGENS OF THE *MYCOBACTERIUM MARINUM* ESX-1 SECRETION SYSTEM**

(71) Applicant: INSTITUT PASTEUR, Paris (FR)

(72) Inventors: Roland Brosch, Paris (FR); Laleh Majlessi, Montigny-le-Bretonneux (FR); Nadine Honore, Colombes (FR); Matthias Groschel, Nuremberg (DE); Fadel Sayes, Malakoff (FR); Roxane Simeone, Paris (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 15/315,783

(22) PCT Filed: Jun. 3, 2015

(86) PCT No.: PCT/EP2015/062457
§ 371 (c)(1),
(2) Date: Dec. 2, 2016

(87) PCT Pub. No.: WO2015/185669
PCT Pub. Date: Dec. 10, 2015

(65) Prior Publication Data

US 2017/0106073 A1 Apr. 20, 2017

Related U.S. Application Data

(60) Provisional application No. 62/007,161, filed on Jun. 3, 2014.

(51) Int. Cl.
*A61K 39/04* (2006.01)
*C07K 14/35* (2006.01)
*C12N 1/20* (2006.01)
*A61K 39/00* (2006.01)

(52) U.S. Cl.
CPC .............. *A61K 39/04* (2013.01); *C07K 14/35* (2013.01); *C12N 1/20* (2013.01); *A61K 2039/523* (2013.01); *A61K 2039/57* (2013.01); *A61K 2039/58* (2013.01)

(58) Field of Classification Search
None
See application file for complete search history.

(56) References Cited

FOREIGN PATENT DOCUMENTS

| | | |
|---|---|---|
| WO | 03/085098 A2 | 10/2003 |
| WO | 07/010413 A2 | 1/2007 |

OTHER PUBLICATIONS

Raviglione M, Marais B, Floyd K, Lönnroth K, Getahun H, Migliori GB, et al. Scaling up interventions to achieve global tuberculosis control: progress and new developments. Lancet. May 19, 2002;379(9829):1902-13.

WHO. Global Tuberculosis Report 2013. World Health Organization. Geneva.

Taylor GM, Young DB, Mays SA. Genotypic analysis of the earliest known prehistoric case of tuberculosis in Britain. Journal of Clinical Microbiology. May 2005;43(5):2236-40.

Jakubowiak WM, Bogorodskaya EM, Borisov SE, Borisov ES, Danilova ID, Danilova DI, et al. Risk factors associated with default among new pulmonary TB patients and social support in six Russian regions. Int J Tuberc Lung Dis. Jan. 2007;11(1):46-53.

Faustini A. Risk factors for multidrug resistant tuberculosis in Europe: a systematic review. Thorax. Jan. 16, 2006;61(2):158-63.

Van Der Werf MJ, Langendam MW, Huitric E, Manissero D. Multidrug resistance after inappropriate tuberculosis treatment: a meta-analysis. Eur Respir J. Jun. 2012;39(6):1511-9.

Migliori GB, Centis R, D'Ambrosio L, Spanevello A, Borroni E, Cirillo DM, et al. Totally Drug-Resistant and Extremely Drug-Resistant Tuberculosis: The Same Disease? Clin Infect Dis. Apr. 9, 2012;54(9):1379-80.

Raghavan S, Alagarasu K, Selvaraj P. Immunogenetics of HIV and HIV associated tuberculosis. Tuberculosis (Edinb) Elsevier Ltd; Jan. 1, 2012;92(1):18-30.

Prabowo SA, Gröschel MI, Schmidt EDL, Skrahina A, Mihaescu T, Hastürk S, et al. Targeting multidrug-resistant tuberculosis (MDR-TB) by therapeutic vaccines. Med Microbiol Immunol. Nov. 10, 2012;202(2):95-104.

(Continued)

*Primary Examiner* — Oluwatosin A Ogunbiyi
(74) *Attorney, Agent, or Firm* — Arrigo, Lee, Guttmann & Mouta-Bellum LLP

(57) ABSTRACT

Recombinant strains of *Mycobacterium bovis* bacille Calmette-Guerin (*M. bovis* BCG) comprising a heterologous nucleic acid sequence of *Mycobacterium marinum* (*M. marinum*) are provided. In some embodiments the heterologous nucleic acid sequence of *M. marinum* comprises a plurality of open reading frames, wherein the plurality of open reading frames comprise open reading frames that encode proteins each at least 95% homologous to the *Mycobacterium marinum* (*M. marinum*) proteins MMAR5445, MMAR5446, MMAR5447, MMAR5448, MMAR5449, MMAR5450, MMAR5451, MMAR5452, MMAR5453, and MMAR5455. In some embodiments the plurality of open reading frames further comprise an open reading frame that encodes a protein at least 95% homologous to the *M. marinum* proteins MMAR5443, MMAR5444, and MMAR5457. In some embodiments the plurality of open reading frames further comprise open reading frames that encode proteins at least 95% homologous to the *M. marinum* proteins MMAR5429, MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5454, MMAR5456, MMAR5458, MMAR5459, MMAR5460, and MMAR5461. Pharmaceutical compositions, kits, methods of inducing an immune response against *M. tuberculosis* in a subject, and methods of treating an *M. tuberculosis* infection in a subject are also provided, among other things.

16 Claims, 28 Drawing Sheets

(56) References Cited

OTHER PUBLICATIONS

Hett EC, Rubin EJ. Bacterial growth and cell division: a mycobacterial perspective. Microbiol Mol Biol Rev. Mar. 2008;72(1):126-56.
Bayan N, Houssin C, Chami M, Leblon G. Mycomembrane and S-layer: two important structures of Corynebacterium glutamicum cell envelope with promising biotechnology applications. J Biotechnol. Sep. 4, 2003;104 (1-3):55-67.
Faller M, Niederweis M, Schulz GE. The structure of a mycobacterial outer-membrane channel. Science. Feb. 20, 2004;303(5661):1189-92.
Houben ENG, Korotkov KV, Bitter W. Take five—Type VII secretion systems of Mycobacteria. Biochim Biophys Acta. Nov. 18, 2013.
Sørensen AL, Nagai S, Houen G, Andersen P, Andersen AB. Purification and characterization of a low-molecular-mass T-cell antigen secreted by *Mycobacterium tuberculosis*. Infect Immun. May 1995;63(5):1710-7.
Fletcher ME, Sullivan JT, Braunstein M. Protein export systems of *Mycobacterium tuberculosis*: novel targets for drug development? Future Microbial. Oct. 2010;5(10):1581-97.
Simeone R, Bottai D, Brosch R. ESX/type VII secretion systems and their role in host-pathogen interaction. Curr Opin Microbiol. Feb. 2009;12(1):4-10.
Cole ST, Brosch R, Parkhill J, Garnier T, Churcher C, Harris D, et al. Deciphering the biology of *Mycobacterium tuberculosis* from the complete genome sequence. Nat Med. Jun. 11, 1998;393(6685):537-44.
Stoop EJM, Bitter W, Van Der Sar AM. Tubercle bacilli rely on a type VII army for pathogenicity. Trends Microbiol. Oct. 2012;20(10):477-84.
Stanley SA, Cox JS. Host-Pathogen Interactions During *Mycobacterium tuberculosis* infections. Curr Top Microbiol Immunol. 2013;374:211-41.
Johnson TL, Abendroth J, Hol WGJ, Sandkvist M. Type II secretion: from structure to function. FEMS Microbiol Lett. Feb. 2006;255(2):175-86.
Palmer T, Berks BC. The twin-arginine translocation (Tat) protein export pathway. Nat Rev Microbiol. Jul. 2012:10(7):483-96.
Bingle LE, Bailey CM, Pallen MJ. Type VI secretion: a beginner's guide. Curr Opin Microbiol. Feb. 2008;11(1):3-8.
Abdallah AM, Gey Van Pittius NC, Champion PAD, Cox J, Luirink J, Vandenbroucke-Grauls CMJE, et al. Type VII secretion—mycobacteria show the way. Nat Rev Microbiol. Nov. 2007;5(11):883-91.
Brodin P, Rosenkrands I, Andersen P, Cole ST, Brosch R. ESAT-6 proteins: protective antigens and virulence factors?Trends Microbiol. Nov. 2004;12(11):500-8.
Gey Van Pittius NC, Gamieldien J, Hide W, Brown GD, Siezen RJ, Beyers AD. The ESAT-6 gene cluster of *Mycobacterium tuberculosis* and other high G+C Gram-positive bacteria. Genome Biol. 2001;2(10):RESEARCH0044.
Brown GD, Dave JA, Gey Van Pittius NC, Stevens L, Ehlers MR, Beyers AD. The mycosins of *Mycobacterium tuberculosis* H37Rv: a family of subtilisin-like serine proteases. Gene. Aug. 22, 2000;254(1-2):147-55.
Bitter W, Houben ENG, Bottai D, Brodin P, Brown EJ, Cox JS, et al. Systematic genetic nomenclature for type VII secretion systems. PLoS Pathog. Oct. 2009;5(10):e1000507.
Tekaia F, Gordon SV, Garnier T, Brosch R, Barrell BG, Cole ST. Analysis of the proteome of *Mycobacterium tuberculosis* in silico. Tuber Lung Dis. 1999;79(6):329-42.
Målen H, Berven FS, Fladmark KE, Wiker HG. Comprehensive analysis of exported proteins from *Mycobacterium tuberculosis* H37Rv. Proteomics. May 2007;7(10):1702-18.
Bassetti CM, Boyd DH, Rubin EJ. Genes required for mycobacterial growth defined by high density mutagenesis. Mol Microbiol. Apr. 2003;48(1):77-84.
Lightbody KL, Ilghari D, Waters LC, Carey G, Bailey MA, Williamson RA, et al. Molecular features governing the stability and specificity of functional complex formation by *Mycobacterium tuberculosis* CFP-10/ESAT-6 family proteins. J Biol Chem. Jun. 20, 2008;283(25):17681-90.
Sayes F, Sun L, Di Luca M, Simeone R, Degaiffier N, Fiette L, et al. Strong immunogenicity and cross-reactivity of *Mycobacterium tuberculosis* ESX-5 type VII secretion: encoded PE-PPE proteins predicts vaccine potential. Cell Host & Microbe. Apr. 19, 2012;11(4):352-63.
Weerdenburg EM, Abdallah AM, Mitra S, De Punder K, Van Der Wel NN, Bird S, et al. ESX-5-deficient *Mycobacterium marinum* is hypervirulent in adult zebrafish. Cell Microbiol. May 2012;14(5):728-39.
Abdallah AM, Bestebroer J, Savage NDL, De Punder K, Van Zon M, Wilson L, et al Mycobacterial secretion systems ESX-1 and ESX-5 play distinct roles in host cell death and inflammasome activation. J Immunol. Nov. 1, 2011;187(9):4744-53.
Daleke MH, Cascioferro A, De Punder K, Ummels R, Abdallah AM, Van Der Wel N, et al. Conserved Pro-Glu (PE) and Pro-Pro-Glu (PPE) protein domains target LipY lipases of pathogenic mycobacteria to the cell surface via the ESX-5 pathway. J Biol Chem. May 27, 2011;286(21):19024-34.
Abdallah AM, Savage NDL, Van Zon M, Wilson L, Vandenbroucke-Grauls CMJE, Van Der Wel NN, et al. The ESX-5 secretion system of *Mycobacterium marinum* modulates the macrophage response. J Immunol. Nov. 15, 2008;181(10):7166-75.
Gey Van Pittius NC, Sampson SL, Lee H, Kim Y, Van Helden PD, Warren RM. Evolution and expansion of the *Mycobacterium tuberculosis* PE and PPE multigene families and their association with the duplication of the ESAT-6 (esx) gene cluster regions. BMC Evol Biol. 2006;6:95.
Bottai D, Di Luca M, Majlessi L, Frigui W, Simeone R, Sayes F, et al. Disruption of the ESX-5 system of *Mycobacterium tuberculosis* causes loss of PPE protein secretion, reduction of cell wall integrity and strong attenuation. Mol Microbiol. Mar. 2012;83(6):1195-209.
Di Luca M, Bottai D, Batoni G, Orgeur M, Aulicino A, Counoupas C, et al. The ESX-5 associated eccB-EccC locus is essential for *Mycobacterium tuberculosis* viability. PLoS One. 2012;7(12):e52059.
Burts ML, Williams WA, Debord K, Missiakas DM. EsxA and EsxB are secreted by an ESAT-6-like system that is required for the pathogenesis of *Staphylococcus aureus* infections. Proc Natl Acad Sci USA. Jan. 25, 2005;102(4)1169-74.
São-José C, Baptista C, Santos MA. Bacillus subtilis operon encoding a membrane receptor for bacteriophage SPP1. Journal of Bacteriology. Dec. 2004;186(24):8337-46.
Geluk A, Van Meijgaarden KE, Franken KLMC, Subronto YW, Wieles B, Arend SM, et al. Identification and characterization of the ESAT-6 homologue of *Mycobacterium leprae* and T-cell cross-reactivity with *Mycobacterium tuberculosis*. Infect Immun. May 2002;70(5):2544-8.
Cole ST, Eiglmeier K, Parkhill J, James KD, Thomson NR, Wheeler PR, et al. Massive gene decay in be leprosy bacillus. Nat Med. Feb. 22, 2001;409(6823)1007-11.
Pallen MJ. The ESAT-6/WXG100 superfamily—and a new Gram-positive secretion system? Trends Microbial. 2002 May;10(5):209-12.
Pym AS, Brodin P, Brosch R, Huerre M, Cole St. Loss of RD1 contributed to the attenuation of the live tuberculosis vaccines *Mycobacterium bovis* BCG and *Mycobacterium microti*. Mol Microbiol. Nov. 2002;46(3):709-17.
Teutschbein J, Schumann G, Möllmann U, Grabley S, Cole ST, Munder T. A protein linkage map of the ESAT-6 secretion system 1 (ESX-1) of *Mycobacterium tuberculosis*. Microbiol Res. 2009;164(3)153-9.
Renshaw PS, Panagiotidou P, Whelan A, Gordon SV, Hewinson RG, Williamson RA, et al. Conclusive evidence that the major T-cell antigens of the *Mycobacterium tuberculosis* complex ESAT-6 and CFP-10 form a tight, 1:1 complex and characterization of the structural properties of ESAT-6, CFP-10, and the ESAT-6*CFP-10 complex. Implications for pathogenesis and virulence. J Biol Chem. Jun. 14, 2002;277(24)21598-603.

(56) References Cited

OTHER PUBLICATIONS

Stanley SA, Raghavan S, Hwang WW, Cox JS. Acute infection and macrophage subversion by *Mycobacterium tuberculosis* require a specialized secretion system. Proc Natl Acad Sci USA. Oct. 28, 2003;100(22):13001-6.
Renshaw PS, Lightbody KL, Veverka V, Muskett FW, Kelly G, Frenkiel TA, et al. Structure and function of the complex formed by the tuberculosis virulence factors CFP-10 and ESAT-6. EMBO J. Jul. 20, 2005;24(14)2491-8.
Brodin P, De Jonge MI, Majlessi L, Leclerc C, Nilges M, Cole ST, et al. Functional analysis of early secreted antigenic target-6, the dominant T-cell antigen of *Mycobacterium tuberculosis*, reveals key residues involved in secretion, complex formation, virulence, and immunogenicity. J Biol Chem. Oct. 7, 2005;280(40):33953-9.
Champion PAD, Stanley SA, Champion MM, Brown EJ, Cox JS. C-terminal signal sequence promotes virulence factor secretion in *Mycobacterium tuberculosis*. Science. Sep. 15, 2006;313(5793):1632-6.
Daleke MH, Ummels R, Bawono P, Heringa J, Vandenbroucke-Grauls CMJE, Luirink J, et al. General secretion signal for the mycobacterial type VII secretion pathway. Proc Natl Acad Sci USA. Jul. 10, 2012;109(28):11342-7.
Christie PJ, Atmakuri K, Krishnamoorthy V, Jakubowski S, Cascales E. Biogenesis, architecture, and function of bacterial type IV secretion systems. Annu Rev Microbial. 2005;59:451-85.
Houben ENG, Bestebroer J, Ummels R, Wilson L, Piersma SR, Jiménez CR, et al. Composition of the type VII secretion system membrane complex. Mol Microbial. Oct. 2012;86(2):472-84.
Mahairas GG, Sabo PJ, Hickey MJ, Singh DC, Stover CK. Molecular analysis of genetic differences between *Mycobacterium bovis* BCG and virulent M. bovis. Journal of Bacteriology. Mar. 1996;178(5):1274-82.
Weltman AC, Rose DN. The safety of Bacille Calmette-Guérin vaccination in HIV infection and AIDS. AIDS. Feb. 1993;7(2):149-57.
McShane H. Tuberculosis vaccines: beyond bacille Calmette-Guerin. Philos Trans R Soc Land B Biol Sci. Oct. 12, 2011;366(1579):2782-9.
Kaufmann SH, Hussey G, Lambert P-H. New vaccines for tuberculosis. The Lancet. Elsevier Ltd; Jun. 12, 2010;375(9731):2110-9.
Lewis KN, Liao R, Guinn KM, Hickey MJ, Smith S, Behr MA, et al. Deletion of RD1 from *Mycobacterium tuberculosis* mimics bacille Calmette-Guérin attenuation. J Infect Dis. Jan. 1, 2003;187(1):117-23.
Brosch R, Gordon SV, Garnier T, Eiglmeier K, Frigui W, Valenti P, et al. Genome plasticity of BCG and impact on vaccine efficacy. Proc Natl Acad Sci USA. Mar. 27, 2007;104(13):5596-601.
Pym AS, Brodin P, Majlessi L, Brosch R, Demangel C, Williams A, et al. Recombinant BCG exporting ESAT-6 confers enhanced protection against tuberculosis. Nat Med. May 2003;9(5):533-9.
Hsu T, Hingley-Wilson SM, Chen B, Chen M, Dai AZ, Morin PM, et al. The primary mechanism of attenuation of bacillus Calmette-Guerin is a loss of secreted lytic function required for invasion of lung interstitial tissue. Proc Natl Acad Sci USA. Oct. 14, 2003;100(21):12420-5.
Brosch R, Pym AS, Gordon SV, Cole ST. The evolution of mycobacterial pathogenicity: clues from comparative genomics. Trends Microbiol. Sep. 2001;9(9):452-8.
Brosch R, Gordon SV, Marmiesse M, Brodin P, Buchrieser C, Eiglmeier K, et al. A new evolutionary scenario for the *Mycobacterium tuberculosis* complex. Proc Natl Acad Sci USA. Mar. 19, 2002;99(6):3684-9.
Travis WD, Travis LB, Roberts GD, Su DW, Weiland LW. The histopathologic spectrum in *Mycobacterium marinum* infection. Arch Pathol Lab Med. Dec. 1985;109(12):1109-13.
Gao L-Y, Guo S, McLaughlin B, Morisaki H, Engel JN, Brown EJ. A mycobacterial virulence gene cluster extending RD1 is required for cytolysis, bacterial spreading and ESAT-6 secretion. Mol Microbial. Sep. 2004;53(6):1677-93.
Zumla A, Atun R, Maeurer M, Kim PS, Jean-Philippe P, Hafner R, et al. Eliminating Tuberculosis and Tuberculosis-HIV Co-Disease in the 21st Century: Key Perspectives, Controversies, Unresolved Issues, and Needs. J Infect Dis. Apr. 23, 2012;205(suppl 2):5141-6.
Beresford B, Sadoff JC. Update on Research and Development Pipeline: Tuberculosis Vaccines. Clin Infect Dis [Internet]. May 15, 2010;50(s3):S178-83.
Tameris MD, Hatherill M, Landry BS, Scriba TJ, Snowden MA, Lockhart S, et al. Safety and efficacy of MVA85A, a new tuberculosis vaccine, in infants previously vaccinated with BCG: a randomised, placebo-controlled phase 2b trial. Lancet. Mar. 23, 2013;381(9871):1021-8.
Hoft DF, Blazevic A, Abate G, Hanekom WA, Kaplan G, Soler JH, et al. A new recombinant bacille Calmette-Guérin vaccine safely induces significantly enhanced tuberculosis-specific immunity in human volunteers. J Infect Dis. Nov. 15, 2008;198(10):1491-501.
Ottenhoff THM, Kaufmann SHE. Vaccines against Tuberculosis: Where Are We and Where Do We Need to Go? Chitnis CE, editor. PLoS Pathog. May 10, 2012;8(5):e1002607-12.
Kamath AB, Woodworth J, Xiong X, Taylor C, Weng Y, Behar SM. Cytolytic CD8+ T cells recognizing CFP10 are recruited to the lung after *Mycobacterium tuberculosis* infection. J Exp Med. Dec. 6, 2004;200(11):1479-89.
Bange FC, Collins FM, Jacobs WR. Survival of mice infected with *Mycobacterium smegmatis* containing large DNA fragments from *Mycobacterium tuberculosis*. Tuber Lung Dis. 1999;79(3):171-80.
Gradmann C. Robert Koch and the pressures of scientific research: tuberculosis and tuberculin. Medical history. 2001 45:1-32.
Grange JM, Brunet LR, Rieder HL. Immune protection against tuberculosis—When is immunotherapy preferable to vaccination? Tuberculosis (Edinb). Elsevier Ltd; Mar. 1, 2011;91(2):179-85.
Van Der Wel N, Hava D, Houben D, Fluitsma D, Van Zon M, Pierson J, et al. *M. tuberculosis* and *M. eprae* translocate from the phagolysosome to the cytosol in myeloid cells. Cell. Jun. 29, 2007;129(7):1287-98.
Houben D, Demangel C, Van Ingen J, Perez J, Baldeón L, Abdallah AM, et al. ESX-1-mediated translocation to the cytosol controls virulence of mycobacteria. Cell Microbial. Aug. 2012;14(8):1287-98.
Simeone R, Bobard A, Lippmann J, Bitter W, Majlessi L, Brosch R, et al. Phagosomal rupture by *Mycobacterium tuberculosis* results in toxicity and host cell death. PLoS Pathog. Feb. 2012;8(2):e1002507.
Nothelfer K, Dias Rodrigues C, Bobard A, Phalipon A, Enninga J. Monitoring Shigella flexneri vacuolar escape by flow cytometry. Virulence. Jan. 2011;2(1):54-7.
Voladri RK, Lakey DL, Hennigan SH, Menzies BE, Edwards KM, Kernodle DS. Recombinant expression and characterization of the major beta-lactamase of *Mycobacterium tuberculosis*. Antimicrob Agents Chemother. Jun. 1998;42(6):1375-81.
Fortune SM, Jaeger A, Sarracino DA, Chase MR, Sassetti CM, Sherman DR, et al. Mutually dependent secretion of proteins required for mycobacterial virulence. Proc Natl Acad Sci USA. Jul. 26, 2005;102(30):10676-81.
Abdallah AM, Verboom T, Weerdenburg EM, Gey Van Pittius NC, Mahasha PW, Jiménez C, et al. PPE and PE_PGRS proteins of *Mycobacterium marinum* are transported via the type VII secretion system ESX-5. Mol Vlicrobiol. Aug. 2009;73(3):329-40.
MacGurn JA, Cox JS. A genetic screen for *Mycobacterium tuberculosis* mutants defective for phagosome maturation arrest identifies components of the ESX-1 secretion system. Infect Immun. Jun. 2007;75(6):2668-78.
Way SS, Wilson CB. The *Mycobacterium tuberculosis* ESAT-6 homologue in Listeria monocytogenes is dispensable for growth in vitro and in vivo. Infect Immun. Sep. 2005;73(9):6151-3.
Majlessi L, Brodin P, Brosch R, Rojas M-J, Khun H, Huerre M, et al. Influence of ESAT-6 secretion system 1 (RD1) of *Mycobacterium tuberculosis* on the interaction between mycobacteria and the host immune system. J Immunol. Mar. 15, 2005;174(6):3570-9.
Rohde KH, Veiga DFT, Caldwell S, Balazsi G, Russell DG. Linking the transcriptional profiles and the physiological states of *Mycobacterium tuberculosis* during an extended intracellular infection. PLoS Pathog. 2012;8(6):e1002769.

(56) References Cited

OTHER PUBLICATIONS

De Jonge MI, Pehau-Arnaudet G, Fretz MM, Romain F, Bottai D, Brodin P, et al. ESAT-6 from *Mycobacterium tuberculosis* dissociates from its putative chaperone CFP-10 under acidic conditions and exhibits membrane-lysing activity. Journal of Bacteriology. Aug. 2007;189(16):6028-34.

Stamm LM, Morisaki JH, Gao L-Y, Jeng RL, Mcdonald KL, Roth R, et al. *Mycobacterium marinum* escapes from phagosomes and is propelled by actin-based motility. J Exp Med. Nov. 3, 2003;198(9):1361-8.

Smith J, Manoranjan J, Pan M, Bohsali A, Xu J, Liu J, et al. Evidence for pore formation in host cell membranes by ESX-1-secreted ESAT- 6 and its role in *Mycobacterium marinum* escape from the vacuole. Infect Immun. Dec. 2008;76(12):5478-87.

Hesseling AC, Marais BJ, Gie RP, Schaaf HS, Fine PEM, Godfrey-Faussett P, et al. The risk of disseminated Bacille Calmette-Guerin (BCG) disease in HIV-infected children. Vaccine. Jan. 2007;25(1):14-8.

Wells, A. Q. 1937. Tuberculosis in wild voles. Lancet i:1221.

Van Soolingen, D., A. G. M. Van Der Zanden, P. E. W. De Haas, G. T. Noordhoek, A. Kiers, N. A. Foudraine, F. Portaels, A. H. J. Kolk, K. Kremer, and J. D. A. Van Embden. 1998. Diagnosis of *Mycobacterium microti* infections among humans by using novel genetic markers. J. Clin. Microbiol. 36:1840-1845.

Brodin P, Eiglmeier K, Marmiesse M, Billault A, Garnier T, Niemann S, Cole ST, Brosch R. 2002. Bacterial artificial chromosome-based comparative genomic analysis identifies *Mycobacterium microti* as a natural ESAT-6 deletion mutant. Infect Immun. 70(10):5568-78.

A

B

A

B

A

B

A

B

SEQUENCE LISTING

```
<160> NUMBER OF SEQ ID NOS: 68

<210> SEQ ID NO 1
<211> LENGTH: 38701
<212> TYPE: DNA
<213> ORGANISM: Mycobacterium Marinum
<220> FEATURE:
<221> NAME/KEY: misc_feature
<223> OTHER INFORMATION: fragment from M. Marinum

<400> SEQUENCE: 1

actagtagcg attgtgtcgg tcttgcttgt ggtttgcatt ggtttggaac tgcaggggcc      60

cgagggccaa cttgtgtcct tctattccgc actacccata tgcggtaccg cgttgtttgt     120

cgccgctgtc gccctgacct tcttggcggt cacgacgtcg cggaatgcca gcgccgtgca     180

ggcggcgacg cagcgattga ccgccatggt ggcggccctg accaccggcc ccgacgcagt     240

tcccggttcg cccgaaatgc ctactccccc aaaatattgc ctctcggagt tcgatctcgc     300

cgaggacacc gggcccaccc caccgcagct gcccgatctg ggctcggctt tcaccgactt     360

acccggcgcc cccgaatttc acctggccac cggaaccggc gcgggcctcc ccgacttcgg     420

cgcaccgcag ttacccatcc ccgcgctgac cggcctgcca accctgcccg gacccacaaa     480
```

-continued

```
cctgaccgac ctaaccagcg tcctagccgg cctgcccacg atcgctcaac tcagcaccac    540
cctgagccaa ctcaccaacc tcgccggacc caccagcacc accacccaac cggcccaaca    600
gcacaccacc ccggccgacc accccaccca ggacgacgcc accgacacac ccgacaccgc    660
cgccgcagcc accaccacca gcggcgagcg cgcacccctg ggcagcacaa cccgccccac    720
ccaacaaaac caagacctcg tcgtgtgagg ccacacagat cacaccaccg atcaaccttc    780
aacagccggc tcaacgtgaa accgaaggaa agtccaacgc atgaacctca acggaacaat    840
gaggaatctg attcgacgac taatcgcaga agacccagag gggaacgaag aaaatcccca    900
atggctgcgc cgaggcagcg ttgtttgcct ggtgaccgac tgcatccttg gcggcgaact    960
ggcatggctt ggacatgcgt cccccgacca aggtggttgc ctggtcaaag gcgcggcgat   1020
gttcgacgac ctcggcgccc agatcgccgc tcttgttccc gatagcggtt ggcagggcag   1080
cgcggcccgc tcctatgggg cccacaccct cgcccagtcc cgacactcca cgctgatggc   1140
tgatctggac cggctcgccg ccgagctggt gtcatcccaa gccgacgacg tgaagcaagc   1200
gcgcaccgca ctgtgggcag caatcggctt tgtctcggtc tacctattga tttgcctcgg   1260
catagaactt caggggcccg agggccagct actctccttc aacttcgccg tagtcgtatg   1320
cggtgccgtg ctaggtatct ctgctctcgt tctgcacgac ttggcgaaga agacgtcgcg   1380
cagggccagc agtctgcaga cgactacgca gcgactgtcc gacatggtgg cgggcctggc   1440
tacacggtcg gacatgattc ccggctcacc cgaaatgagc ctgcccccag cgcattccct   1500
gtcagagttc catctcaccg atagcagcgc cgcctccccg ccgcacctcc ccgatctgga   1560
ctcggctttc gccgacctac ccggcgcccc cgaatttcac ctgcccaccg cggccggcgc   1620
cggcttgccc gacttcggcg caccgcagct gcccatcccc gcgctgagcg gcctaccaac   1680
cctgcccgat ccgacagacc cgaccgacct atccagcatg ctggccggcc tgcccacgat   1740
cacccagctg cccgccatcc tcagtcaact caacaacctc gccgggccaa ccagcgccgt   1800
gagccaactg gccaacaccg ccacccaaca cgcacaaatg atctccaccc tggcccaaca   1860
gggcgcccat ccgcacacca ccctgaccga tcaccacacc acagacgaaa cccccgacac   1920
cgacgccgcc accgcagcca ccagcagcgg cgaacgcgca cccctggaca ccacaaccca   1980
ccccacccaa caccgcctag accacatcgt gtgagcccaa caggccacac caataactgg   2040
gggcggccgg cacaacgtgg gcccgaaagg aacgttcatc tcatgtatct cagtcaactt   2100
cagcgtttgg ttcagcaaat ctcgcgatgg gtacgcggag atggaaatct gcagaacttc   2160
caagacatcc aagagggagg cggaaatccg ccgccggcgc aggaggggc gcccgacaat   2220
tccccttggg cgcgtcgagg aagcgttgtt tgcggggtga ccgagggcat cctcggcctt   2280
ctactggcat tgcttggaga ggccgtccca tcccggggcg aatccctgga ccgcagtgga   2340
tcgatgttcg acggtgtcag cacccagatc gcgacccttg atcccgacgg cggttggcgg   2400
ggcaacgcag cgcgggccta cggggccaag aacctcgccc aatcccaaca caccacgctg   2460
atcgctgatc tggaccggct caccggcgag ctggtgtcat cccaggccga cgccgtgaag   2520
cgggcacgcg acctgctatc ggccgaaatt tggattgtct tggtcttgct tgtggtttgc   2580
attggcttgg agttgcacgg gcccgagggc caaatcctgt ccttccatat cgcaataccc   2640
atatgcacta tggcggtgtt tacggccgct accgccctgg gcgtgttggc ggccacgacg   2700
tcgcagaatg ccagcgccgt gcaagcggcg acgcagcgat tgaccgccat ggcggcggcc   2760
ctgaccaccg gggcggacac agttcccagt tcgcccaaaa tgacctttcc accaatacat   2820
```

```
tccctgtcgg agttcgatct caccgaggcc accggcccca ccccaccgca gcttcccgat   2880
ctgcagtcga cgttggccga gttacccggt gcccccgagt ttcacctggc caccagggcc   2940
ggcgcgggct tccccgactt cggcgcaccg cagctgccca tcaccgaatt gaccggcctg   3000
ccaaccctgc ccgatcccac aaacctgacc gacccaacca gcatgctggc cgacctgccc   3060
acgatcgcgc aactcagcac caccctgagc caactcacca acctcgccgg acccaccagc   3120
gccaccaccc aaccggcgca acagcacacc accccggccg atcaccgcac ccaagacgac   3180
gccaccaaca cccccgacac cgccaccgcc actgcagcca ccagcagcag tgaacgcgca   3240
ccgctggaca cccaaaccca cccccaccgg cagcgcctac tgacttgacc ggctttgcca   3300
accatgccca tcatggtccc cgattcgcta gacctggctg acttgtagcg ggacaaaacg   3360
aattggctgc gttgcccgat ctccgcgacg gtatagcctg gcctcttcgg tcgggccgcc   3420
gcaactttgc ccgtccaagc cgccgtggtc ttggttcacg ggcggcgatc gggactagcc   3480
agttgttgca gtgaagtcgt tcttgtatcg ggtggcgaac acctcttctt ctgccgcggc   3540
cgcctgctcg ggcgtcggca agttcattgt cttctcgacg atttcgcgca gcacggcgcg   3600
ttgctcttcg tcgtccactt catccatgcc ttggagcatg aaggcgtgct gcgcggcccg   3660
cgccttctgc cgggccaggt ccgcaagaac aaatatctcc tcggcaagcc tcggttcgga   3720
catgttgtcg accttgtccg acagctcgac ccggtggatg tccccgccca tgacggccga   3780
caccgaaacg ctcccttgag gattggttac cgtgaacagt tcgcactcat cggttttgtc   3840
ctcctcggtc gccccaagga ttgctgacat gtcggatccg gtgtcctcgg gttgggccgg   3900
tgcgtagctg agcaacgcgt cgatggcgga gtcggtctct ccggttgcgg ggccggagaa   3960
acccagtccc gctagatagt tatgggcgtc gtacccgggc tggtcggtca tgacatgcct   4020
ttctgagatg ggttgcgggc gtggcgagaa gctagcccga ggtttgggcc tcggcgtggt   4080
ctggccacgc gccgagcggg aacatcagtt gtcaatctgc tcgtcgagga tctcggcgcc   4140
acgttggtcc gtatcggtgt aggcggcgag ggcccgggtc agattcgtgg aaagcccatc   4200
agcgaccccc tccagggctc gccccgcgct agcgcggact gcctcgtagg cgcttagtgc   4260
attgttgaag gtcgacgtga atgggccgtg ggtctcggcg actgtcgcac cgatcccggc   4320
gggcgccgcc gtcgctgccc gcagacttgt tgcggtggcg tcgtgcccac tggcaagccg   4380
gttcacgacg tcgggctgca acgtcaacat gtcattcatc ggctgaactt cacttttcgt   4440
cggtggggct tcgttttcgg tttggtgtgg ttaggggtgg gtttggttga tggcggcaga   4500
gagggtggcc agggtggtgg ccagggcgtg gttggcggcg ttgtcgtagg cgtggacggc   4560
ttgtttggcg ttgtggaggg cttggttgac gcggtgggcg acgccttggg agccgagttg   4620
tttgaggagg ccgtcttgga tgcggatgcc ggtgagccag ttgtatccgt tgagggtgac   4680
ctgcacggtg tgggtgttgt ctgaggcttt gaagttgccg gcgttcattt ggtggaagcg   4740
gttttgcagg gcggtgtgga attgggtgag ccctgcgagc aggtgtgcgg cggtggggtc   4800
gaggttcatg gttggtgctc cgtgttggtg ctgttggggg tggtgaggtg gggtcgggcg   4860
gggccgatga gcgcttcggt ccagggtcgt tgttcggtgt agagggctcg gtcgtcttgc   4920
tgggtgcgtt tggttttggc gttttgggct tgcccgtttg cccccatggg catgcccccc   4980
atggggcccg cgcccagggg gcggccggtg ggcgcggtgc cggggcccag ggcgcctggc   5040
gcactcgggg gtgtggggcc cgcgcccagg ggggcggtca aggggatggc ggcgccggcg   5100
cccccgccga gtgcggcggg tttgacggtg gggccggtgg cgagtgtggc cgcggcgcgg   5160
gcggcttcag tggtgtcggg ggttgcggcg gggggtgggg tgaacggcat cgtcggcatc   5220
```

-continued

```
ggtggtgtgc cggtgaaggg cagtgtgggg tccccgccgg gcggtagcgg tggtagcggc   5280

ggtgggggtt tggggtcgtt gtgggtgggg gctgccggtg gtcggggtgg ttgcacgggc   5340

tcggtgattg tcctggtggc gtatccggtc agcacttcct cggatttctt ctgacattgc   5400

gcgtagacct tcattaacgg ttttttatcg ggcactctgg ggtcacgaag gagttcttct   5460

agcgtggtga tatccgccaa tgtcgggtgt tgaccaatgg cccagtggtg ggcttgttcg   5520

aggcctgagg cttgtttggc catcgtggta ctcaaccgcg ccatcaggcg cagccagtcc   5580

cggtgttgat cgaatgcggc ctgcaccgcg gcggccgctt caccttccca atcctcgaag   5640

tcacggaacc ggcccagggc ctgctgaatt gtcaggttgt aggcattcca gtcatgggcg   5700

aacttcttca gcgatacacc ctggtcgggc ttgttgaggt tgatcgcggc cagtttgaca   5760

ccggtatatg gaaacggagg cgctgctggc gcggtagggg tatcgctcag cgcgaccgga   5820

gccaggtccg tacccgcggg taccggcggt gctccgatgc cgtggccgtt ggtgcccaaa   5880

gccgttgccg cgccttcgtc gatctgttcg taggccttgg ccgcgtcccg catgaacttc   5940

gcaagccgtt gccgcgcttg ggcgcccgac tgcagataag cgcgcatgct ctcggccgac   6000

aacgccagtt gtgtggcccc cgcaaccgcc gggtccaggg cgcacgcggc caacaccgca   6060

ccgccgggcg gatcagcgat cggggcttcc acctcggtgg ccctggccac gatctcgctg   6120

ggatccaccg ccagcatcca cggctgcgac atgccgaaac tccttcatcg tgctatagct   6180

attatcgtcg ctgaattcga tggttcgcgc accaaattcc agcactttta tttcagaact   6240

accttctgaa ataaatcaga attagattcc gaaacataaa cccgaattgg cttctgaaat   6300

gggtcaccag gtgctctgca ccctccccgc gcgctaaatc attgcacact ttttcggggg   6360

catccggcag gaacgttccg gaccagagat atatggcgaa tcgtcaactt gtaattgcac   6420

gcacgcagga cttgatggcg caatccggca ggtccggcgc cgggcccgga tccaactagg   6480

ccaatcggcc accccagggc acaagccccc gaaccgggca acacagcggt tcacgggggt   6540

gtcgggccaa accggccggc cggcgagagt gccagtcgat gcttggatac tggtcggtgt   6600

ttggcattgg cagtctgatg cgaccgagga gcccatgaac gaacgcgagg agtttctgcg   6660

agaccgggtc cggccggacc agcccagcgt tcccgacgcg agtcggtctc atcagcgttc   6720

cggtatgcac cggacggcga cggacgcgtc aggccctccg gtagcgccca ctcaccaacc   6780

tcggcccgcc ccgccccgtc cgccgactcc gcagccttca cccgttccac cgcgggggc    6840

caacccgcat cccccgccgc caccggcgcc accttcggtc ccggcgccgc cgccccccacc  6900

ggtggcgcat ccacccaacg ggcacaactc gccgccacaa gctgccccac acgaaccgat   6960

gccggaggtt ccaccgccaa gcctttgggc cgagcccaca ccggcgcgca cccccggcga   7020

gcctccatcc accgaccacg gctggcgcca catcattcgg gtcgcgtcgt tcgggctgat   7080

caacccacgc ccatcggcgg cgcagcgcga tgccgccgaa ttcgaagcgg ccattcgagc   7140

cccgttgcgc ggcacccaca aggttggtgt gctgggcaag ggcggcgtcg gcaagacgtc   7200

agtcgccgcc agcatcgggt cactcctggc cgaattgcga cagcaggacc gcatcgtggc   7260

agtcgacgcc gataccgctt ttggccggtt gagcagcagg atcgatccca cggcgcgtgg   7320

ctcgttctgg gacctgaccg ccgataggaa tctggcgtcg ttcgccgatg tggttgcccg   7380

cttgggccga aacgctgcgg gcctgcacgt tttgcccggc gaggcggccg tcggtggtcg   7440

ccggttactt gaccccgcga tttatcgcga agcggcgcta cgactcgacc gccatttcac   7500

catctcgatc attgactgcg gctccacgat ggacgcgccc ctaactcagg aagtgttgcg   7560
```

-continued

```
cgacctagac gcgcttatcg tggtgtcctc cccctgggcg gacggtgcct cggcggccgc   7620
caagacaatg gaatggctcg cggaccgcaa actcagcggc ttgctgcggc gcagcgtcgt   7680
ggtgctcaac gattcggacg ggcattccga caagcgcacg cgttcagtgc ttgcgcgcga   7740
gttcgtcgac catggacagc aggttgtcga ggtgcctttt gatccgcatc tgcgccccgg   7800
cggtgttatc gatgtgagcc atgagttgga gccgggaacg cggctgaagt ttctgcaaat   7860
cgccgcaacg attaccggac acttcgccgc gcggtccgct gccgacgacg acccccgtcc   7920
caccgaaaac gtagcgtctg agacctaggg cttctggtcc gctggatgct cgaatgcaaa   7980
acagcgcgag aaatcgttgg atttctcgcg ctgtttgcct acgtggcaat tcaccccggc   8040
gtcgccgcag acccctcgca gcagcggcgg acgcggccgg gcatcatgcc gattgggcgg   8100
tgatccgctc gcgcgccggg aaaccgttgc gctctgccag cgaccgaagt tggcccaacg   8160
cgaacgcccg cgcccggcct gcttccggaa tcacaacacc cgcccaaagt ccttccgcac   8220
ccggcgactc aaccgcgtcc cgcgcacacg cccaccgacg cgggcacgcg cgacacagcg   8280
tcttggcctc ctcgtcgggc gttgtcgtcc aacggtcggg gtcctgcgtg caaacgccca   8340
gcggaatctc gtacagagca gttgcagtca tatctaagcg ttcctccata aagcaaaagc   8400
gttgcaggtt cgtaacctct gcccgaggat cgtatagcac taaccgtcgc agtgcaacag   8460
ttcccgatgc agggccgcac accctcctgc tacaacttcg ctgcgcgatg ggccatgata   8520
agcatctaac ctggcataac cagcggtaat tagctgtcaa tcggctgggt gacacggcgc   8580
tccgccaacc ccgacgcaca cccttccgga cagaaactgt tccactgcgc aatgcttcgg   8640
ggtaggatca aacgtagcgg tggcccggtt taaccagaca acggtcgctt cggaaccccg   8700
ctggatgtcg ttcaagaaac gtagcgaagg cataccaatg gaagggtgca acggttagga   8760
tgttggtcag cggaacgcgc gccttgccac ccgcctcagt agccgcgagc gaggaatcga   8820
cgtacatgcc cgacgccgaa tcgactgctc ggccggccct gcgagtcgcc cgtggcggcg   8880
actcaccggg cctggtaacg cccggtcacc gacccgtcgg ccgcggcgcg ctgaccaacg   8940
cacgactgga tgatcccgtg ttatcgcaga cacatgtgcg agcggtttcc gatggtgggc   9000
agcggcggat cgtcaccaac agcccaaacg gtatgttcgt cgacggaaca cggaaaagtt   9060
ctgtggctgt cagcgacaag accattgtcc ggttcggcga tcccactgga ggcaaggcgt   9120
tgacgttcga agtcgtcagg ccctcgaatt cgcctgaaga agacagccgt gaacagcgac   9180
cggccgagca atcggactct cagaccaacg aagccgatcc tggtgtggtt cgcgccgggg   9240
ccgccgccgc ggcacgacgc cgagagctcg acatcagtca gcgcagcctg gcagccgacg   9300
ggatcatcaa cgccggcgca ctgatcgcgt tcgagaaggg ccgcagctgg ccacgcgaac   9360
gcacccgcgc caagctggaa gaagtcctgc agtggcccgc gggaaccatc gcgcggatac   9420
gccagggcga gtccgttgcg ccagagcccg ctcccgaagc cagcgtggag gcgccgacct   9480
ccgacggccc agcgtcgctg atcgcgcagg cggttgccgc cgcggtcgat acctgcagcc   9540
tcgcgatcgc cgcattgccc gcacccgagg aacctgactt caccgagcgg gccgcaccga   9600
tccttgccga tttgcgccag ctcgagggca tcgccgtcca ggcgacccgc atcagccgca   9660
tcacaccgga actgatcaag gcgcttggtg ctgttcggcg ctatcacgac aaattgatga   9720
cgctcagcgc aaccgcacca ggagccacac tggcgcagcg tttgtatgcc gcccggcggc   9780
gggcgaatct gtccacttcg gaaaccgcgc aagccgccgg agtgaccgaa gaattgatcg   9840
tccgcgcgga agccgaggaa gctttgcatg ccgaagccgc cgaggctatt gaagcgctca   9900
tccgtcaaat caattgaggt tggtgcccag tggcaactca ccttgaatcg ctcgagtccg   9960
```

```
aacgaccggg gaacttcgcg ttaccccggt tttcgagcat gcggaccttg gtgctgtgcg  10020
cgcgaaagtg cccgcactac caagaaattc gtgcgtcgac cacggtcgga gcactgctaa  10080
gctcaatgta cagaccaaag gtgcacacaa aaagacagtg cacgaaacag cgagtgtaag  10140
gaattccgcg aatggtgcca aagggaagcg gtctttgcaa gacaacaagt aatttcattt  10200
ggggtcagtt gcttttgctt ggagaaggca tccccgaccc gggcgatatc ttcaacaccg  10260
gttcgacgct cttcaaagga atcgccgaca agatgggtct ggcgattccg ggcaccaact  10320
ggctcggcca ggcggcggac gcctatttga accagaacat cgctcaagaa cttcgcgcga  10380
aggtgatggg tgacgtcgac tatctgaccg gcaacctgat ttcgaatcag gccgaatatg  10440
tgtcgaacac ccgcgacgtg ctgcgcgcga tgaagaagat gatcgacggc gtctacaagg  10500
tctgcaaagg cctcgaaaag gtgccgatac tcggctggtt gtggtcgtgg gagctcgccc  10560
tgccgatgtc gggcattgcg atggccaccg tcggcggcgc gctgctttac ctgaccatca  10620
tgacgttgat gaacctgacc aacctgaagg gcctgctcgg caggttggtc gaaatgttgg  10680
ccagcctgcc atcgctgatc ggcggcctac tcccgaacat tccgggcatc atcgacgacc  10740
tgtggccgcc caagttgccc gaccttccca tcccgggtct gccgaacatc ccgggcctgc  10800
ccgatttcac ctggccaccc aagatcgaca ttccggattg gaacttgccg atcccggggc  10860
tccccggttt cgaattcccg ccgacctcgg gaatccccgg catcgacttc ccgttcccca  10920
acatcccggg cttgcccagc ttccccagcc ttcctgggtt gccgagcatc ccggacctgt  10980
tccccggctt gcccggcctg ggtgacctgt tctccgggat cgggaaatgg ggcacgttgc  11040
ccacctggac cgacttggcg gccctacccg acttcttggg tggcttcgcc gggctaccca  11100
gcctgagctt ctccaacctg ctcggcttcg cccaattgcc caacgtcggt tcgctgaccg  11160
cgacgatggg ccagctgcaa cacctggtct cggccgctgg cggacctggc caactgggca  11220
gtatggcggg ccagcaggcc agcatgatct cgtcgcaggc ttcccaaggc ggtcaacagg  11280
ccaccctggt gagcgacaag aaggaagacg acgaagacgg tgcggccgcg ggcagcgccg  11340
gtgcggaacg cgctcccatc gatgcgggaa gcaacacagg gcaaggcaac gaggggaccc  11400
tcctctagtc cgggcaaccg gcggcggctc actggcctac caaagccata gcgagccaaa  11460
cccatagcga gtagaaagtt agacgtagag gaaaggtcta cccccatgac aggactactg  11520
aacgtcgtgc cttcattctt gaaggtgctg gcgggcatgc acaacgagat agtcggcgaa  11580
ctcaaatcgg cgaccaacgt cgtgagcgga atcggctcgc gggtccagct gacccacggc  11640
tcattcacct cgaatttcaa cgacacgctc gtcgagttcg aaaccacccg caacagcgcc  11700
gggacaggcc tgcagggcgt cacgggcaag ttggccaaca atctgatctc ggccgctggc  11760
gcctatctga actccgacga agggctcgct ggcatcatcg acaagatttt tggctgatat  11820
gaccggtccg ctcgctaccg gtcgcgcggg caccggtgac gatgtcgtcg gagtcgaggt  11880
aaccatcgac ggcatgctgg tgatcgcgga ccggttacac ctggtcgatt tccctgtcac  11940
gcttgggatc cggccgaaca tcccgcaaga ggatctgcga gagatcgtct gggaccaggt  12000
ggcgcgcgac cttactgcgc agggcgtgtt ggaccacaat ggccagccgc atccggcggt  12060
tgcggcgatg gtcgacacgc tcagcagggc ggaccgcacc ttggaaggtc gctggtggcg  12120
ccgcgacgtt ggcggcgtga tggtgcggtt cgtggtatgc cgcaagggcg aaagacatgt  12180
catcgcagtt cgcgatggcg acatgctggt actgcagctg gtggctccgc gggtcggcct  12240
ggcaggcatg gtgacggccg tgctgggcac cgcggaaccc gccaatgtcg aaccgctgac  12300
```

-continued

```
cggcattgcc agcgaactgg gtgagtgcac caacgccgca cagctgaccc gatatgggct  12360
cacgccgacc accgcccgcc tgtacaccga aatcgtcacc aatccgaaga gctgggtgga  12420
aatcgtcgcc agcgaacgcc atccgggcgg tacgaccacc cacaccaagg ctgccgcggg  12480
ggtcttggat tcagcacatg gcaggcttgt ctcgcttccc cgccaagttg gcggggaact  12540
gtacggcagc ttcctccccg gtaccgagca gaatctccag cgggcgctgg acagtctgct  12600
cgaactactt ccgtcaggct cgtggttgga tcgcgccgac gccaccgccc gaggttgact  12660
taatcctctc cgttacgagt tcagaaaggg acgccacagt ggacctgccc gggaacgacg  12720
actacaacca agatctcggc gccctagatt tctccggcgg cggtacgtct gaggactctg  12780
gactcggtgc actcgacgag tacgcgcccc ccgagcccca ggaaaccgag caagccggag  12840
ccgacctgga tgcacttcac gggctgaccg agaaggaaga cgagcccgac attgcgatgt  12900
tcaccgtgac caacccgcaa gggagcgtgt cggtcaccac catgatgggt ggcatcgtcc  12960
agcaagttac ggtgaccgac aaggctgcga acatgtcgga atccgctctg gccgaagaga  13020
tctttgtcat cgctgatctg gcccgccaaa aggcgcgcgc cgcacaacac acgttcatgg  13080
tggaagccat ggccagcgaa ctgagcgacg agaccgaaga agaaggtgcg ctgttgcgcg  13140
agttcgtcgg tatgacgctc aacttgccga cgccggagga agcagaagcg gccgaagccg  13200
aggtattcgc cacccgctac gaggtcgact acacctctcg ttacaacgaa cggtgataca  13260
tgactgatcg cctggccggt ttgttcgaaa gtgccgtcag catgcttccg ctgtcggagt  13320
caaggtccat ggacctattc accgagatca caaactatga cgaatcagcg tgcgatgctt  13380
gggtcggccg gatccgatgt ggcgatgtcg accgggtgac tttgttccgt gcctggtact  13440
cgcgccgcaa cttcggtcag ctggcaggca cggcgcagat ctcgatgagc accctcaacg  13500
ccagggtccc cataggtggt ttgtacggag acatcaccta ccccgttacc tccccccctgg  13560
ccatcaccat gggcttcgcc gcatccgaag ccgcgcaggg caactacgcg gacgcgatgg  13620
aggccatcga cgctggcgcg gtcaccggtt cggagcatct ggtgtcgtgg ctcaaggcgg  13680
tcatcttcgg cgctgccgag cgctggaccg acgttatcga tgaagtcaag ggtgccggga  13740
agtggccgga caagttcctg gccggagccg ccagcgtcgc ccatggggtt gcggcggcca  13800
gccttggcct gttcaccgaa gccgaacgca gactgaccga agccaatgac tcaccggccg  13860
gcgaagcctg cgcgcaggcc atcgcgtggt atctggccat ggcccggcgg ggccaaggca  13920
acgaggaagc cgcggtggca ctgctggaat ggttgcagac cacgcatccg gctccgaaag  13980
tctctgctgc gttgaaggat ccgtcctacc ggctcaagac gaccaacgcc gaacagattg  14040
cgtcccgttc ggatccatgg gatccgacca gcgtggtgac cgacaattcc ggtcgcgaaa  14100
agttgttggc cgaagcccaa gaagaactcg accgccaaat cggattatcc cgggtaaaaa  14160
gccagctcga gcggtaccgc gcggcgacca tgatggctcg tatccgcgag gccaaaggca  14220
tgaaagtcgc acagcccagc aagcacatga tctttaccgg gccccctggc accgggaaga  14280
ccacgatcgc gcgggtggtc gccaacatgc tcgccggact aggcgtcatc gccgaaccca  14340
agctggtcga gacgtcacgt aaagacttcg ttgccgagta cgagggccag tcagcagcca  14400
agaccgccaa gacgatcgat caggctctag gggcgtgct gttcatcgac gaggcttacg  14460
ccctcgtgca ggagcgcgac ggacgcaccg acccgttcgg ccaggaagcg atggataccc  14520
tgctggcccg gatggagaac gaccgcgatc gcttggtggt catcatcgcc ggctacagct  14580
ccgacatcga tcggctgctg gaaaccaacg agggtctacg ctcgcgattt gccacccgta  14640
tcgaattcga cacctacagc ccggaagagc tcctcgagat cgcgaaagtc attgcggctg  14700
```

ggaatgactc gacgctgagc acggcggccg cggatgaact cctgcaggca gccaaaacgc 14760
tgcacgaacg tacgttgcgg ggccgtccgg ctctcgacat cgccggcaac ggccgatatg 14820
cgcgacaatt ggttgaggcc tctgagcagt accgtgacat gcggctagca cagggcctcg 14880
acatcgaggc cctcgatgtg gacagactgc aagagatcaa cggcgcggac atggccgagg 14940
caatcgccac ggtgcatgca cacctcaata tgagagagtg aaacatgggg cttcgcctga 15000
ccaccaaggt tcaggtaagc ggctggcgct tcctgcttcg ccgagtcgag catgccatcg 15060
tgcggcgcga cacccgcatg ttcgatgatc cgctgcagtt ctacagccgc tcgatagcgc 15120
tgggcatcgt tgtcgccgta ttgatcttgg ccggtgccgg cctgctggcc tacttcaaac 15180
cagctggaaa acttggtggc agcaacctgc tgaccgaccg cgcgactaac cagctctatg 15240
tactgctgtc cgggcagttg caccctgtct acaacctcac ctcggcgcgc ctcgtgttgg 15300
gcacccctgc cgcccccgtc accgtcaagt cctccgaatt gagccagttg cccttgggcc 15360
aaaccatcgg aatccccggc gcccccctacg ccaccccggt ttccggggac accacttcaa 15420
cctggaccct ttgcgacacc gtcagccggg cgggtaccgc ctccgcctcg gtcgagacat 15480
cgctgctggt gatgccgctg cggatcgatg ccgcgatcga tccgatcgag cccaacgagg 15540
cgatgctggc ggactatcac ggccagacct ggatcgtcac atcaaaggga cgccactcga 15600
tcgacctcaa cgatcgtgcg ctcacatcgg ccgtgggcat ccccatcacc gcccagacgg 15660
tccccatttc cgagggaatg ttcaatgcgc ttccggccag gggcccctgg caattgccac 15720
ccatccccgc cgccggagag ccaaacaccc tcgggcttcc ggaagatttg gtaatcggat 15780
cggtgtttca aatccacacc gacaaggggc cgcaatatta cgtagtgctg accgacggca 15840
tcgccgcggt aaatggcacc actgccgcgg cactgcgcgc cactcagtcc catgggctgg 15900
tggcgccgcc cgcggtggtg ccgagcctgg tcgtcaggat ccccgaacgg gtttactcat 15960
caccgctgcc cgacgagacc ctcaacctca tgtcccggcc ggacgacccg gtcttgtgtt 16020
gggaatggga gcgtagcgct ggggaccagg cccccaatac gacggttctc accggacggc 16080
acttgcccat cccgccctcg gccatgaaga ccggcctcaa gcagattcag ggcaggtcaa 16140
ccgtctatat cgacggcggg aaatttgttc agttgcagtc acccgatccc cgatacggcg 16200
aatcgatgta ctacatcgac ccggaagggg tgcgctacgg ggtgcccgac gccgactcgg 16260
ccaaggcgct gggcctgggc atgccgaaga cggcgccgtg ggagatcgtt cgcctcctgg 16320
tggacggtcc agtgttatcc aaagacgccg ctctgctcga acacgaaacg ttgccctccg 16380
accccaatcc tcgaaaagtt ccagctggga cacccggagc acctcaatga cgacaaagaa 16440
attcacccca acgatcaccc gtggccccccg gctcaccccg ggcgagatca gcctcacgcc 16500
accggatgat ctcggtatcg acatcccgcc gtcgggcgtg cagaagatcc tgccctacgt 16560
catgggcggc gcgatgctgg gcatgatcgt gatcatggtt gccggcggca ccagacagct 16620
atcgccatac atgctgatga tgcccctgat gatgatcgtg atgatggtgg gcacactcgc 16680
cgggggcagc ggcggcggca gcaagaaggt gcccgagatc aatgcggacc gcaaggagta 16740
cttgcggtat ctcgccggcc tgcgcggccg cgtaacgacg tcggccacct cccaggtctc 16800
gttcttcggc taccacgcgc cccatcccga cgatcttctg tccatcgtcg gcacccagcg 16860
gcagtggtcg aggccggcca acagcgactt ctatgcggca gcccgcatcg ggatcggcga 16920
ccagccggcg gtggaccggc tactgaagcc ggcggtcggc ggcgagctgg cggccagcag 16980
cgcggccccc cagccctatc tcgagccggt aagccacatg tgggtggtca agttcctgcg 17040
tacccacggg ttgatccacg actgcccgaa actcgtgcag ctgcgcagtt ttccaacgat 17100
cgcgatcggc ggtgatcgac cgggagccga tcgactgttg accgcgatga tctgccacct 17160
ggcggtcttc catccgcccg acctgttgca gatccgcgtc ctcaccgagg accccgagga 17220
tcccgactgg tcctggttga aatggctgcc acacgtccag caccagaccg aaaccgacgg 17280
ggccgggccg gtccggatga tctccacgcg cccggacggc ctcgccgacc tggccgcccg 17340
gggaccccac gcgcccgaca ctctccccac cggtccctac gtcgtggtcc tcgacctgac 17400
cggcggcaag gcgggcttcc cgccagacgg cagggccggg gtgacggtaa tcacgctggg 17460
caaccatcgc gggtccgcct atcgcatcag agtggccgag aacggcaccg ccgacgaccg 17520
gctgcctggg cagcagttcc ggctggtgac cgcggccgcc gacagcatga cgccgcagga 17580
ggccacccgc ctcgcccgca agttggccgg atggtcgatc accggaacca tcctcgacaa 17640
gacccaacgt atccagaaga aggtcgcgac cgagttccat cagttggtca acgccaagag 17700
cgtcgaggac atcaccccgg gccgttggcg catgtacacc gacaccgatc gagaccggct 17760
caagatcccg ttcggtcacg aactcaagac cggcaatgtc atgtacttgg acatcaagga 17820
aggtgcggag ttcggcggcg ggccgcacgg catgctcatc ggcaccaccg gttccggcaa 17880
atccgagttc ctgcgcacca tgatcctgtc gttggtggcg atgacccacc ccgatcaggt 17940
gaacctgctg cttaccgact tcaagggcgg ctcgacattt ctggggatgg agaagctccc 18000
gcacaccgcg gctgtgatca ccaacatggc cgaggaagcc gagctggtaa gccggatggg 18060
cgaggtgctg accggcgaac tggaccgccg ccagtcgatc ctgcgtcagg cggggatgaa 18120
ggtcggcgcg gccggcgcgc tgtccggcgt ggccgagtac gagaagtacc gcgaacgcgg 18180
cgctgacctc ccgccgctgc cgacactttt cgttgtggtg gacgagtttg ccgaacttct 18240
gcagagtcac ccggatttca tcggcctgtt cgaccgaatt tgccgagtcg ggcgatcatt 18300
gcgggtgcac ctgctactgg ccacccagtc actacaaacc ggcggtgtcc gcatcgacaa 18360
gctcgaaccc aacctgacgt atcgcatcgc gttgcgtacc accagctctc atgaatccaa 18420
agcggtgatc ggaaccccgg aggcccagta catcaccaac aaggaaagcg gtgtcggctt 18480
tctccgggtc ggcatggagg accccatcaa gttcagcacg ctctatatca gtgggccata 18540
cgttccgccg gcgaccgctg aaaccaacgg cgatggcagc ggacccagta cccagttcgc 18600
caagcgagcc ttgcagatcc gcgagttcac cgcggctccg gttctcgagg aagcgctgac 18660
accatgatcc acgccggcaa tgctgcagca cgaagcaacg aaagggagcg gcgctcatga 18720
ctgccgaacc tgaagtacgg acgttgcgtg aggtcatcct cgaccagctc agcaccgtcg 18780
agtcacgcgc ctacaagatg tggttgccgc cgctggttga tccgaccccg ctcgacgagc 18840
tggtcgcccg cgatcggcga caaccacttc gcttcgcgct gggaatcatg gacgagccgc 18900
gccgccacct gcaggacgtt tggggcgtcg acgtgtcggg cgctggcgga aacatcggta 18960
tcggcggtgc cccccagacc ggcaagtcga cactgctgca gacgttggtc atgtcggccg 19020
ctgccacgca ctcgccgcgc aaggtccagt tctattgcat cgacctcggt ggtggcggcc 19080
tgatctatct ggagaacctg ccccatgtgg gcggggtcgc gggccggtcc gaacccgaca 19140
aagtccaccg ggtggtcgcg gagatgcaag ccgtgatgcg acaacgagag gccaccttca 19200
aggaacaccg ggtcggctcg atcgcgatgt atcgccagct gcgtgacgac cccaaccagg 19260
ccgtcgcctc agacccctac ggcgatgtat tcctgatcat cgatggatgg cccgccttcg 19320
tcagtgagtt tcccgacctc gaaggccagg tccaggacct ggccgcacag gggctgtcct 19380
ttggtgtgca cacgattctg tccacgccgc ggtggacgga attgaaatca cgtgtccgcg 19440

-continued actacctggg caccaagatc gaattccggc tcggcgacgt caacgaaacc cagatcgacc 19500
gcatcacccg ggagatcccg gcgaaccgcc cgggtcgggc ggtgtccatg gaaaagcacc 19560
acctgatgat cggggtgccc aggctcgacg gtgtgcacag cgccgacaac ctggtggagg 19620
cgataacggc gggcgtagct caaatcgcag cccagcacac ggacaaggca cctccggtac 19680
gaaccctgcc ggaacgcatc cacctccacg agctggatcc caaccctccc gggcccgaat 19740
ccgactaccg cacccgctgg gagatcccga tcggattgcg cgaatccgac atggaagtgg 19800
cttacagcca catgcacacc aacccgcacc tgctcatctt cggtgccgcc aagtcgggca 19860
agacgaccat tgcccacgcg atcgcacgcg ccatctgcgc tcgaaacagc cccgaccagg 19920
tgcggttcat gctcgccgac tatcgctccg gactcctcga tgcggtgccc gacacacacc 19980
tgctctcggc cggagccatc aaccgcaaca gcgcgacgtt ggacgaggcc gtcaaagccc 20040
tggccgccaa cttgaagaat cggctgcccc cagccgacct cacgacggct caactgcgct 20100
cgcgttcgtg gtggagcgga ttcgacgttg tgctgctcgt cgacgactgg cacatgattg 20160
tcggcgctgc cggcggcatg cccccgatgg cgccacttgc gcccttattg ccggcggcga 20220
ccgatatcgg cttgcacatc attgtgacct gtcagatgag ccaggcctac aaggcgacca 20280
tggacaagtt cgtcggtgcc gcattcggtt cgggcgctcc aacaatgttc ctttccggtg 20340
acaagcagga attcccctcc agcgagttca aggtcaagcg gcgccccccc ggccaggcgt 20400
ttctggtctc gcccgacggc aaagaggtca tccaggcccc ttacatcgag ccgccagaag 20460
aagtgttcgc agcaccccca agccccggtt aggattattt cattgccagc gacgcatcac 20520
ccgagctgac ggaaatcaag cccgggaggc gatcaccggc aggccgtttc ggcgacaacc 20580
aaatgaggat ttgtccgaag cgcaaataaa ggagaagaag caggcaaatg gaacaaaagt 20640
cacacggcgc ggcgatcgcc gacatcggca cactattgag cggcaacgct cgcattggtg 20700
tgacctccga tgcggcagcg ttggcgtcgg tgaccggggt ggttccagct ggagcagacg 20760
aggtgtcgac gcaagcggcc acagccttcg ccgccgaggg cgcccagttg ctggcttcga 20820
gctcggcggc tcagcgggag atccaccgag ccggcgaatc gccccaccgt atcgccccta 20880
accctgcaga agtcagcgac ggcgcagcca gcgtcatcgt gtagaaaatc agtcaccaga 20940
cacggcgcga caagaaggag tgatcaccat gctgtggcac gcaatgccac cggagctgaa 21000
taccgctcgc ctgatggccg gcgcgggccc ggccccgatg ctggccgcgg ccgccggatg 21060
ggaggctctg gcagccgcct tggacgctca ggccgtcgaa ttgaccgcgc gcttgaactc 21120
gctcggcgaa gcgtggaccg gaggcggcag cgagaaagcc ctggcggccg ccctgccgat 21180
ggtgacctgg ttgcagaccg cctcgaccca ggccaagacg cgtggcctcc aagccggcgc 21240
ccaggccgct gcatacatgc aggccatggc cacaacgcct tcgctacccg agatctttgc 21300
caaccacatc accaacgtga tcctcaacgc gaccaacttc ttcggcatca acacggttcc 21360
catcgccttc aacgagatgg attacttcgt ccgcatgtgg aatcaggcgg cgctggcgat 21420
ggatgtctac caggccgaga cgacggccaa cacgctgttc gaacagctcg agccgatgac 21480
gtcgatcctc gatcccgcca ctgcacagag catgccgact tcgtcgactc cgctgctgga 21540
catggcgtca caggtcaccg gcataccgag cagtgagctt cagcagaccg ccacgcaggt 21600
cgccgaggcg agtggcccca tgcagcagct ggcacaaccg gcgcagcaga tgacgtcggc 21660
gttcagcaac accggcagct cgggcaacgg cgcggacgaa gaaggcttcc ggatgggcct 21720
gctcggcgcc ggcgcgctgt ccaatcaccc gctggcgggt gggtcaggcc cgaccaccgg 21780

-continued

```
cgcgggcctg ctgcgcggtg aatcgctgcc cggcgccggc gggaccctga cccgcacgcc  21840
actgatcagc gaactcgtcg aaaagccgat gggtccgtca gtgcagccgg ctgcggctgc  21900
cggatcgtcg gcaagcagtg gcgccgcccc ggtgggcgcc ggcggaatgg gggcaggagc  21960
tggcgccggt gctggcggtt cgtcgcggcc aggcatggcc gccccggcga cgctgaccca  22020
ggagcgggac gaggccgacg aagacgactg ggatgacgag gacgactggt gagcgtcgtc  22080
aacacgaaca gacttcccgg ccacccgggc cggaagactt gccaacaatt tggcgaggaa  22140
agaaagagag aaagtagtcc agcatggcag agatgaagac cgatgccgct accctcgcgc  22200
aggaggcagg taatttcgag cggatctccg gtgacctgaa gacccagatc gaccaggttg  22260
agtcgaccgc cggttcgctg caggcccagt ggcgcggtgc ggctggtacc gccgctcagg  22320
ctgcggtggt ccgtttccag gaagccgcca acaagcagaa ggccgaactc gacgagattt  22380
cgacgaacat ccgtcaggcc ggtgtccagt actcccgggc cgacgacgag cagcagcagg  22440
cgctgtcctc gcaaatgggc ttctgattcc cctaaaacga taaagaaacg gagcaatacg  22500
acatgacaga acagcagtgg aatttcgccg gcattgaggc agcatccagc gcaattcagg  22560
gaaatgtcac cagcattcat tcccttctgg atgagggcaa gcagtcgctg cacaagctgg  22620
ccgcagcctg gggtggtagc ggttcggagg cctaccgggg tgtgcagcag aattgggact  22680
ccaccgcgca ggagctcaac aactcgctgc agaacctggc tcgcaccatc agcgaggccg  22740
gtcaggcaat gtcctccacc gagggcaacg tcacggggat gtttgcttaa tccccccctct  22800
cgttcgcgta gaataccgaa gcacgagatc ggggcgagtt tcaacctttc ggaatctcgc  22860
cccttctcgt gcttcgtttt attggcgaac ttctgagagg ttcctatgcc ggcggactac  22920
gacgagctat ttcagcccgc cgagggttcc ggacctccag atgacgaaac tgggcaaacc  22980
ttctttgatc ctggtaccgc gtatccgccg cccgtgaaac ccaacggcga cgggcactcg  23040
gcgcctaagg actggtcgcg cgcatttcca ccggcggaag atgagtcgcc gtcagactcc  23100
gcagaaccgg cagctggccc cgccaagtcg ccgttgcccc ccatgcccat cggcgggcct  23160
gcgccgacac ccccagaacc accaccggcc cccccggagc taccaccggc acccccggaa  23220
cctccaccgg ctcgtccgga ggcacctccg caagcgccga cagccgaggc tgaacctccg  23280
gacgaggcaa tacccgttag cgggcccccg cctggcggca agtcgccgct gcctccgatg  23340
cctatcggtg ggccgccacc ggcatctccg gagccacctg cggctccacc ggaaccgacg  23400
gcgccagcag aaccaccgca gccgccggag gctgctgcac aaccgccgca ggccgtcgag  23460
gaacaggccc acgcaaccgc cgaaccccca gcggcaccaa acccgccgcg tccccccatg  23520
cccatcggcg ggcccccacc cacacccccg gccgcaccgg aaccacaaca ggacatagca  23580
gaagaaccgg cgccggcggc cgccgaagcc ccagcggcac caccgaagtc accgctaccg  23640
cccatgccgg tcagcggacc gccaccggaa ccgcccgaac tgccaccggc tccaccggaa  23700
ccgacggcct cagcagagcc accgcagccg ccgcagtccg tcgaggaaca ggcccacgca  23760
accgccgaac ccccagcggc accaaaaccg acgcgtcccc ccatgcccat cggcgggccc  23820
ccacccacac cggaaccaca acagggcgcg ccgcaaccac accaggacat agcagaagaa  23880
ccgaacccgg cggccgccga agccccagcg gcaccaccga aatcaccgcg gccccccatg  23940
ccggtcaacg ggccggcacc cacccggccc gagccaccgc taccaccggg ccccccgcgt  24000
cgccgcgctc aaccgccaac ggcgccaccg aaccagcccg ggcaaccgaa gcccatcagc  24060
ggacacccgc cgcccccacc gaggccagcg gcgttcgcgc ccccagcacg cggcgccacg  24120
ccaaaccggc atgaatcggc cgaacctccg ccaccgcgcc gggtccggat cggtggcccg  24180
```

```
cctcagcctc cagggccacc ggaggctgaa tccgaggctc ctcggcactc gcggcatgcc  24240
cgacggacgc atcgttatcg gcccgagccc gaaaccgatg acctcgaggc cacggcggta  24300
cggccgcttc cgacgcgcga gccgatgagg cgaaacggac ccgcggcgga cgaaagctca  24360
accgcgtcct tcgcgtggct gcagcagagc cagccgaccc tcgatcggcc ttctggaccc  24420
atgcccgccg cccctggggc ccccgtcgag tccgcgccgg gtcgcgctga tggtcgtagg  24480
gccaggcggc gcgccgaatc ccggacttcg gccgcttcga cgccatctcc gctggtgcca  24540
accagggctc aaccgccggg ccccaccagg gctcagccgc cgcgcaccgc cgccccggct  24600
caacccgcta ctgagcccct gccggacgcc ggcgccccgg ccgagcagtc gaagaagccg  24660
aataagccgg tgccacaacg gggttggcgg cgttgggttt acgcggtcac gcggataaac  24720
ttcggtcttt ctcccgatga gaagtatgaa ttggacctgc gcacgcggat cggtcgaaag  24780
ccccgcggct cgtatcagat cgcgatcttg ggcctcaagg gcggcgccgg gaagacgacc  24840
acgacggtca ctcttggcac cacactgacg cacgtgcgcg gggatcggat cctggtgctt  24900
gacgccgatc cgggcgccgg aaatctcgcc gaacgttcgg gacgttcgtc gccatcatcg  24960
attgccgatc tgctggcgga tccgcggctg tcgcactaca acgatgtccg cgcacacacc  25020
agcgtcaatg ccgccaatct cgaaattctc cccaccgcgg aatacacctc cgcgcagcgc  25080
gggctcagcg gcgaagactt gcgatcggcc gtcgataccg tgtcgaagtt ctacaacctg  25140
gtcctggccg attgcggggc agggctattc gatccggtga cactgggtgt gctcgatacc  25200
gcctcagcga tcgtgatctt gactaacgtt tccatcgaca gtgcgcgcca agccgcaatc  25260
gcactggact ggttgcgcaa acacggttac caggatttgg cgagccgcgc atgcgtagcg  25320
ataaaccatg tcgccgttgg cgaaaccaac gtgtcggaac agcagttggt ccgggacttt  25380
gaacagcagc tccaacccgg gcgcgtggtg gtcttgccat gggaccggca catcgcggcc  25440
ggcaccgaaa ttcatctcga ccagcttggc cccgtctacc gacgacgggt tctcgagctg  25500
gccgcggctc tgtccgacga ttttgaaagg gctggacgtc gttgagcgca cctgcagttg  25560
ccgccccctc cgccgccacg ggaaccaccc cacccaagcc ggcaaccacc cgggtcaccg  25620
tccttaccgg cagacggatg acagatctag tgctgcccgc ggcggcaccc atggagagct  25680
atgtcgacga gaccgtcgcg atcttggccg atctgctcga agacactccc gcggaggtgc  25740
tggccggctt cgacttcgaa gctcagggcg tttggacgtt cgcgcggccc ggattcccgc  25800
cgctgaagct cgaccagtcc ctcgatgagg ccggcgttgt cgacggatcg ctgctgacct  25860
tggtcttggc cagtcgcacc gagcggtatc ggcccctcgt cgaggacgtc atcgacgcga  25920
tcgcggtgct cgacgagtcg cccgagttca accgcaccgc tctggaacgc ttcctcgccg  25980
tggcaatccc cctcttcgcc ctgcccatca cggccgttgc catgcgggcc tggtggcaaa  26040
ctgggcgcag cgtgttctgg ccgctggcga tcggcctaat tgggctcgcc gccttggccg  26100
gttccttcgt cgcaaaacgg ttctaccaaa actcgcggct cgccgagagc ctgctggtga  26160
cgtcgtacgg cgtcatcgcc gcggcggcag ctatcgccgt tccgctgccg cgcgggttcc  26220
attcgctggg ggcgccccag ctcgccgccg ccgccacagc ggtgttgttc atcaccttga  26280
tgatgcgcgg cgggccgtac aaacgccacg acatcgcggc gtttgtggtg attacatcga  26340
tcgcggtcat ttcggcggcg gtcgccttcg gatacggata tcagcaatgg gtgccggccg  26400
gggcgattgc gttcgggttg ttcatcgtga cgaacgcggc caaactgact gtcgccgtcg  26460
cgcggatcgc gctgccgccc atccccgttc ccggagagac cgtggacaac gaggaactgc  26520
```

-continued

```
tcgatcccat caccgcccaa gacgcgacca acgaagagac accgacctgg caagccatca  26580
tcgcctccgc cccggcgtcg gcagcccggc tcactgagcg cagcaaattg gctaagcagc  26640
tgctcgtcgg ctacgtcacc gcgggaacgc tgattcttgc ggtcggttcg atagccgtgg  26700
tggtacacgg ccacttcttc atacacagca tgattgtggc gggtctgatc acggtgatct  26760
gttcgttccg atcgcggctg tacgcggatc cgtggtgcgc atgggcgctg ctggcggcga  26820
ccgtcgccat cccgaccggg cttgccgtga agctgagcct ttggtacccc cactatgcct  26880
ggctgttgtt gacgatctac ctcgcggcgg ccctcgttac gctcatctcg gtcggcgcga  26940
tgaaccaggt acgtcgcgtt tcgccagtca tgaaacgggc cctggaattg ttcgatggcg  27000
cgatggtcgc gtcaatcgtc ccgctgctgc tgtggattac cggcgtctat gacctggttc  27060
gaaacatccg attctgagtc accggcgggc tacgtccggg cggtcgtggt accggatcgg  27120
cccgcaccga aattggcgca atcgggcttg ttccaggtcg ggtaaaattt gctcaaccca  27180
ttacgtacag gagggattct gcgatggctg agcctctggc cgtcgatccc gcccgtctga  27240
ttgctgcggg aagcaagctc gccgagctgg tttttccggc gccaccagcg ccgatagcag  27300
caactggagg ggatccggtt tcggctgcaa tcaacgacac aatgcctggc atcgagtcct  27360
tggtatccga cgggatgccc ggtgtaaccg ccgccttgaa acgaaccgct tccagcatgt  27420
cgactgccgc agacatctac gcgaaagccg accaagccct tggcgatgca ttgacgcagt  27480
accaattcgg cggcgacggc caagcgctag gcgcaagcgg tgcaaacgct gtggcacaga  27540
gccaggccgg acagaccgtg caatcattgg ccgcgcccgc cgcggggcta ttgggcgcgc  27600
ccgtggcgca agcattggcc gcgcccgcga ccgggctgct gggtgtaccc gcggcggccg  27660
cgacacagat cggcgaggcg gtcagcgctc aggcggaagc cctgtcgccc cgagtggccg  27720
ccacaattcc ccagctggtg caactggccc cgcaagccgg tcagatggcg cagcaggcct  27780
caccgatcgc gcagaccatc agtcagtcgg cccaacaggg gtcctcgcag ggcggcgcag  27840
cgccggcaca gctcgtctcg gacaccaaac ccgacgaaga cgcggagctg gctgacgaga  27900
ccaaagaggg cgaggaagac gccatggcag cggccggtgc agaaggcgcc gcggccggcc  27960
acgccacact ggtgagcgct cccgtcgaaa gcaccggcgg tggcgagacg tcgacgggtt  28020
cggtctcagc tccgatctga taattcggcg aaagccgcac cccgatcggg cgtacggcgg  28080
ctacgcgcgg tgttaccggc gacatccaac cgcggccggg cgccggacgg gggcgtgccc  28140
acatcgggcg ccgtcatacc ggccggcccg gggatcgcgt ccaagcgtgc cgaccgtgcc  28200
gccaacattt cggtcgctcg ctgtgtcgcc gcccgcaggc tgctggcgtt cgaggaggtc  28260
ttgttcgcca acccgatcag ggtggcggcg gcggcaacct gcacaacacc gcatgcggcg  28320
accgcaatgt ggaaggacgg gagctggccc tcgggccccc ctagttccag gccagcacaa  28380
accatcagca cacccaggac taccgcgatc agtaccgaca gccgctcgcg ggcttgcttg  28440
acggcatcgg cttgggagga caccagcccg gcggtgagcc ggtccagctc agccatcagc  28500
gtggcgtgcc gcgactgtgc gaggttctga acccaatagg cctgcgccgc attgccccgc  28560
caaccgccgt ccggatcaag ggcggcgacc tgggcgccga cgtcgtcgaa caatgaccca  28620
ctgctcgcca agcgatcacc ctgctcgggt ggcgaatctc caagccatcc ccacatgaca  28680
ccaaggatgg tcagggtcga cgcgcaaaca acggttcctc ggcatagctc gtggggatta  28740
tcggccgccc ccgcttccgc ttctcgctca atctcccctg cgtccgattc gaatccgtca  28800
aattgggtct cccatgcgtc cgattcgaat ccgtcaggtt caaacggtcc tgcgtccggc  28860
gcgaagcggt tgagtaaatc gtcaagcatt cggtcatatg tggccgcttc atccgggtgc  28920
```

atgagacgaa gattcctttc gagctatcgt tgtgccgacc cagcacggct gtcccgcatc 28980
gtcatgtcga aaacggtgct aggccggctg cacgcctgtc cgcacgccga cgcactcgag 29040
agcgaacatc gggtgttcgc atctgctctg ccgcgccgaa ccacccgta aggcaccagc 29100
aattatcgcc accgaattcg ccgggtctca cacgaaattc aggcctggat atttcagaat 29160
caacttctga tataaatcag aactaacttc tgaaattgat cgcagaagaa tcgtgtatga 29220
attgcggaat caactataac ttactttcga aaaacgcact ggcagcggcc ttgttcaggc 29280
acgcgcgcag cagtgtcgtc tccgctccgc cccggcgtgg gatcggatca ctccgaattc 29340
aggacgcgtc cgccaaagcg ttggcaagca gcccggcgac ataacgccag tacagccagt 29400
cggcgaccgc gggccgctgg gcttcagcgt ctgccgcgct gtatgcctgg tgcagcgcga 29460
tctcctggca atgttcggca taggcgcgga atgcccgcag gtgcgcgacc tcgcgtccgg 29520
tggcgttact cgtcatcggc ttcatcaggt cgaaccagaa catgtgccgc tcgtcgtctg 29580
gcggattggc gtcggccggc gccggcggca gcaactccag cagccgcaga tcttcggtct 29640
ctgccagctg ggccgccgcc gaggggtcta ccacctcgag ccgcggacgt ccggtcatct 29700
tgccgctctc cggaatgtcg tcggcttcca ggatgatctt ggccgcgccc gcgtccgagt 29760
tggccaattg ttcggccgtc ccgatcaccg cgcgcagctt caagtcgtga aacgccgccc 29820
aaccctgcac ggccaacacc gggtaggtgg cgaaccgggc ctgctcatcg gccgggatcg 29880
catggtcagc gctggccatg tagaccttgt gcggtagctc gacattctcg ggtatgtagg 29940
ccagcccata actgttggcc accacgatgt cgccgtcggt ggtcaccgcg gtgatccaga 30000
agaacccgta gtcgcccttg ttgtaggtgt cgggcgcgtt caacgcggcc gcgatgcgtc 30060
gcgccaaccg caaggggtcc ttcttttgac tgcgacgaga cgccgaagcg atggcatcgc 30120
gcgcggcccg cgccgccgag accggaacca tcggcgatgg cgtaacggca tcgggcgctt 30180
cggacttctc tttttcgtcc ggcttgggtc gctccggagc cggacgggtc ggcgatgcgg 30240
tgcgagccgc cgccgggcgc ggcgcggccg tattggggcc ccggccgccc gactccaccg 30300
gtgcgcgccc cgaggcggca cgcgagccgg cacccgaggc cgctgactgg cttgtgctcg 30360
aactcgctcc ggccgaggac aggcccgagc ttgatcctgc ggacactcct cgaccgccgc 30420
ccggcatcgc gctggcggca ggtgcggccg cgccccctcc cgacgagtcg tcgccgtgcg 30480
cagggcccga aggtcccgac ggctgggttg acggtgccgt ggacgtctcc gttgccgctg 30540
ccggcttcac gtgagccggg tcggttgacg gctgccccgg cgtggacggc gaccccggct 30600
gcgatggcgc gggctgcgga ctcgcgcccg ggtcggcggg ccccggctgc ggaccgggcc 30660
ccggagctgg cgcgggctgc ggtgccggcg ctggggcagg tgccggggcg ggcgcagggg 30720
ccggcgctgg ggccggcgct ggggccggcg ctggtgcagg ggttggctcg accggcaaga 30780
ccggggtgtc gggcttccct ggcttcggct tgcccggggt gaccggcgtc accggcttgc 30840
ccggggtgat cggagtacct ggggtgatcg gagtacccgg gatacccggg atacccgggg 30900
tccccggggt acccgggata cccggggtaa ccgggtgcgt tggcccgccg ggtgtcggaa 30960
ccaccggagc acccggcttc gggttcaccg gcgtgcccgg tccgcccggg gtaaccggct 31020
tgtgcgggtt gaccggcgtg ggttcgaacg gcttcggtcc cggtggcctc ggggctggct 31080
gacctggcgt cggcacggtc accgacggaa tgcccggggc cggaggcgtc acctggtgca 31140
gcagatcctt gagcgcattg tgcggcggct tccagtttct ggatgccaga acctgctcag 31200
cggcttcggc caccagaccc gagttggcct cgtgagctga gcggatcagg gatgcgatcg 31260

```
ccgccttgcg ctcctcgggg tcaaggtcgg cgttgccctc cagaacccgt atttcgcgat  31320
gagcaccgtc cacgttgttg tcaatgtttg ccttcgcctc ggcgatcaac ccagccacat  31380
gctggtgcca ggtaataacc gtggcgagat agtcctgcag cgtgctcatt tgctcgagat  31440
tgccgcccag cgcaccgttg gccgcactgg cggcaccacc ggaccagaca ccaccgtcga  31500
agacctcgac ctgctggtgc cgacaggcgt ccatcacatc ggtaaacagg tgcaggaccc  31560
ggttgtactc gcgagcccgg tcgtagtgga tgtcctcgtc agcgtcgggc cacccacccg  31620
cctcgagcat ccgcccggcg tactcccccg tcggcctcgg aatacccatt gcctactctc  31680
ctccccgcag catccaggcc gcagcgacca gacctgtcag gtaggtaccc gcagtggatc  31740
gttggaccgg cgcgcacacc gcaccgccgt tgcgctggct tgcgggccgc gtcagctggt  31800
cagtggtacc ggacgtcatg gttaacaagc ctaaccgagg ttaagaccag ctagatgcgc  31860
caatttgggg atcgggacgg gccgacgaaa atgacaccac agcacggcag accgccgtat  31920
cggagagatt tcgcgcaggg ttgagccgcg cgcagaacga cgcagacgcc gcgacacgca  31980
ggcaccacgg cggtggcgtc aatggtccgc tagcgcgaac caacagccgc tgacaggcgc  32040
gccgaggggga ctgcttccac cccggcgcag ggacggatca gaccatcccg ttgttcattg  32100
tttgagacat tgaggacaac accgcggtca gcttttctcc cgccgcgtcg ttgtatttgg  32160
atgcggcggc ctgggcgttc ttcaacgcct ggttgacccg cgcactaacg acctccggac  32220
caacttcctt cagcaggccg tcgtcgatgc gcacagcggt gagccactgg tgcccattga  32280
tcgtcacctc gaccgtctcg gtgtcgtctt tgccacggaa attgccggta ttcatttggt  32340
tcagcgttcc gtccaaggcc gactggaacc gtgccgccaa cgccaacacc tgcgcgactt  32400
gggggtccat ctccatgctg gtcaccttga ctccttactg tcctgacgac tgtcctgacg  32460
gctacttgtt gtcctgacgg cggcggttac cgattacggc ctcggtccac tcgcggtcct  32520
cggtgtagag cgcttcctcg tcttgttgag cgcccttgga cttggcgccg ccctggccct  32580
ggccagcgcc gcccatcggc attcccatgc cgcctccggc cattccgcga cctgcggcac  32640
caccaccctg gccggcaccg gcgatgtccc ctgccgcggc cggtcgcacg gactcgccgc  32700
cggccagggc cgcatcaccc atcggcatcc cgccgagacc accaccgccg ccgcccaaag  32760
acatcggttt gacgccgagg cccttggaca ggttggacgc cgcctcgcga cccgccgagg  32820
tgagctcggc ggtgttgacg tcgggtgtgc cgcccgctcc accggtgggc ggaatcatcg  32880
ggggcgtcat tcccgaggcc agcccggtgg aaccgtcgcc gggcggcatc aagaagcccg  32940
ggatcaggcc ctgcggttgc gcgggtggcg gcgggtcgat cttgatcgcc gccggaggct  33000
tcggcggatt caccggctcc agatcagcct tggtgttgta ttcgctcaac accttctccg  33060
aggtctcttg atactcggcg tagagcttga tggcttgctc ttgatagtcc gggtctttcg  33120
ccagtctctc gagttcgacg atgtcggcca gggtggggtg cccccgcctg gcccacagct  33180
gcagttgcgc catgaaattg gcctgcttgg ccagcgatgc actcagcttg gccatgtgga  33240
gtatccactc cttctgctgg tccatcgagg cctcgcaggc ggtagcggcg tcaccctccc  33300
agttctcgaa gatccggaac cgcttgatgt cgcgttgcag cgacaggttg aagttgttcc  33360
acccgtcagc gaagttgacc atcgacgtgc cctggtcacc ggattcgagc tttgtcgccg  33420
cggtcttgag gtcggtgaag tctgattcac ccgcggccgc caccttgggg gtttcctcca  33480
gagactcggt ctggccggcg ccggcaccgc ccgctgattg ggcgtcgacc tcaccgttgc  33540
cgtcgttatc gagcgcggtt gccgactcgt cctcgacctc gccataagcc gcggcagcgt  33600
tgcgcagcga cgtcgccaga cgttgccgct cccgctcgcc tgcctgcagg tataggcgga  33660
```

```
cgttgtcggc ggagacggcc agttgttcgg ccgcgttgtt ggctgccgtg aggccggacg  33720
gtgcctgggg cacatcagtg ggcggagtcg ccatcggcgc ctccacctcg tctgccctgt  33780
tcaagatttc ctgctgatcc accgtgacgg tctgcggctg gctcatgtcg gatcgtcctc  33840
cttagtgctc catgccatta tcgtcgctga aacgaccgct tgctgcacca aaaaatttcg  33900
ccgcctcttc cagcccactt ggacctactt gggcagggcc atctggaagc gactttcctc  33960
cggtggagag acccgccgga tcggcaactt gcggtgtcgc ggggtgccga ccaagttgtg  34020
acgcaggatc acccggtcga taccagggtg cgcgcccaga taggtcgtcg cgttcggcca  34080
caccaccttg gcctccgcgc cgacatgggc accgatgagc ccggcgaact gttcgaagtg  34140
tggtcccacg gtgaccacgc cgccggcagc cgccgaacgc acggcgaact gggtgaacgt  34200
ctgggcgtcc cccaggttga cggtcgcgtc cacatcatcg aacggcatgt acaccgggcg  34260
gcggttcacg gtctcgccga ttaacacgcc cgctgatccg attggcagtt ggcagtggtg  34320
attggcaacc agggtctgcc cttccaacgc cggccgctgg ctgccgaaca ggcgcgagaa  34380
gccccgggga gtcttgggct ttcccactgt ggtcaacaac actgtggacc gcggcggcat  34440
cccgggcgca atccggaccc tggtaatggt gtgatctgct cgtgcggacc accacaaatc  34500
cgggccgccg ggcgcggtgt aggcggcggt gtagctgtca gcgcccttga tcatcgacca  34560
tttttcccgc acataaccga tgtcggtggc gcggtcgtag tcgtcgaagc tgcggccgca  34620
tactgcgtcg acgccgttgc tggccaggcc atcggcgatg cgagtcgccg acgccaccag  34680
atagcgagcc aaaccggcga ggccggcctc gcgacgctgc gcagacttgc gggtttgttc  34740
cgggtcggct cgcagcatga tccaggtccg ccggtttgcc ggagccggat cggcgccgat  34800
cacccgctgg taaaggctca ccacctcttc ggaggcggtg ttgccaacgc ggtagcccgc  34860
cgagaccaca tctgcttcca ggtccgggca atgcaccgac agcaggtcct cgagtaggcg  34920
ggtgtccagc acgtcgtcgg tgtgagcctt gccgtcgacg atgaccgtcg gggtaaacgg  34980
gcggggcttg agctcgatca ccgcaatcag gtggtcgcgt cgccaacgca ccgcaacgtg  35040
atcacccggc ttcacggtgg caccgaccac cggttcggac ggcacatccg gcggtcggcg  35100
acgccgacgc agccaggcga acacggtggc cacccacccg gtgacccgac gaccggagaa  35160
agtcaccgtc gccacgatga cgcccagcgc taccagcgcg atgcccaccc accagtagcg  35220
catgtgcagg aacatcatga tgcagggcgg cgccagcacc gcgacgacaa gtgtgtgacc  35280
ggtgctgacc cggaaccgta ttgaactgaa ggggttcctc atcggcgcct cagcgcccgg  35340
gcggccaacg tgcccaatcc gagcaccagc gtcagcccca gtaccgacac cgccaccatt  35400
gtgatcgggc ggtgatccgg gccgggttcg atgcgtgggg gcggtagtcg tctgacgctg  35460
gggggcaccg acgccgggcc cggcgggata tcccacgtca gcgccgcgac agcattgacc  35520
accccggcgc cgacgagatt gtcgataccg cctccgggat gtcgcgcggt agcggtgatc  35580
cggttcatca cctgcaccgg cgtcagctcc ggaaaccgtt gccggaccag cgcggccaga  35640
cccgagacat aggccgccgc aaacgaggtg ccggcgatcg ggacgggtcc ttctcgacct  35700
tgcagggcgt tgaccggttc gccgtgatca ccgagcgcga tgatgttctc cgcgggtgcc  35760
gctacccccca cccacggtcc gtgcatggaa aacgaactcg gcaccccatt ctggccgatg  35820
cccccgacag tcagcaccaa gggcgcatac caagccggtg tgaccaccgt ctgcaccttg  35880
ttccagcccc ggggatcatt gggtgtcgac gcgtcgggca tcggattctg cgagcagtcg  35940
ccgccggtgt tacccgcggc gacgaccacc acggcgttct tggcgttgac cgcatagtcg  36000
```

-continued

```
atggccgcgc ccagacttat ttcgtcgatc ggcctgctca ccttgtaaca cgccgcctcg  36060
ctgatgttga tcactcccgc cccgaggttg gccgcatgca ccaccgcacg ggcaagactg  36120
cggatggacc cggccgccgg cgtcgcgttg ggatcattgg ggttgggttg cgagccaacc  36180
ggttcgaagg cctccgatgt ctggcgcaac gaaagcagtc gcacgtcggg ggcaacgcca  36240
acgaaaccat ccgtcggtgc ggggcgcccg ccgataatcg aggccgtgag cgtgccgtgc  36300
gcatcacagt ccgacagtcc gtcgccggcc tgatcgacga agtccccgcc cggctcggcc  36360
gggacccgtg gtgaggcgtc cacgccggta tcgatcaccg ccaccgtgac gccggccccg  36420
gtcgcaaact tgtgggcctc tccgacaccc atataggcgt tactccacgg cggatcgtga  36480
aagctggaat cgggcagcgt cgtggggctg gtacagagca ctctctgctc ggtgggttgg  36540
tcgggaccgg ttacatccgg cggtaccgcg ccgggatcaa tcgagggagg atcgattgcc  36600
aaagccggcg gtgcggtcag caacgccagc gcgaccatcg tcagcaaggt ccggtgcacc  36660
ccggaatcac tccgttctct agccgcagtg aagctctggc acgctcgtgt cagtcctgcc  36720
tgcattttag acgtaacggg cgcgtaaacg acgctattca acccggtgcc agcctgtcca  36780
tcctgaactg tgaccaagcg gcgtcggcaa ctggctccgc acgccgtgcc gcgccggccc  36840
gggcgtcgct caaagctgca cgaacacatg ccattccacg cgcccgggct taccctcgcc  36900
aaccggcgcg acccgtcacc aaacgatggc ggccatgtca cggttgtccg cgcacacgct  36960
gcgcaccgcg gcttcgacat caccagcggc gatcatctga agatcctcga cggacaccgc  37020
tcgccccgct cgcttctggg cgaccactcg agtgtcccga tatccctcgg cgcgctcgat  37080
gacgttgcgc gcgaaccgcc cgttctgcat ggcatcgatc ccgtgttgcc cacccggggt  37140
ggtgtagttg cggatggtgg tggccgcatc caaaaaggtc tcgcgcgccg cctcatcgag  37200
caggctggcg cgcggcgcgg catagcgctg cccgatctcg acgatttccg tcggcgaata  37260
ggactcaaag cgcagcttgc gattgaatcg gccggccaaa cccggattca cgctgaggaa  37320
ttcgtcgacc tgatcctcat agcccgcacc gatgaaacag aaatcgaatc ggtgggtctc  37380
caacttgacc aggagctggt tgaccgcctc catgccaatc atgtccggtg ttccgtcctg  37440
gtgacgttcc accagtgagt aaaactcgtg tttcatccgc accgagaagc gggtggtcgc  37500
cgcacgcagc ctgcggttgt agaagaggtg cccggagttt tggtcccggt tggacaagct  37560
caatggcatt gctcagtacc cccttgggga acgacgtgga tcggcttgct ggatccgatc  37620
tgccaggttc gatgcatcag cggcaacccc gtagcggccc tgcgcgtagt tgatgaacgc  37680
gcatgcctgg gccaccaggt tggtgatgtt ggtcgaggtg cccagctggt ggtaggccgc  37740
gaaggtcggt gcgatgaact gccacgctcc cctactcggc gtgccctgag acgcgttagc  37800
gtcccagtcg ttcaccgcgc tggcgttgta gcccgactct cggcgggcca ccagatccat  37860
cccgcgtgtc cagcgtgctc gtgctgcggg gtcgtgaata ccctcgatat cgagggcttt  37920
acggatcgcc gccaacacag cgggccgacc tgtgggtgga acgtgatgat gctgtcgcct  37980
ggcggctgcc tgtcggtacc gcagccggcg cagccgcaac accagttgtc gcgcccgtac  38040
gcgcgaccgc acgatgtggc ggcgctgggc tcgcagtctt gccgccatgc ggaccatggc  38100
ttcgcgccgg ccaagcggcg tatcggccgc gagcccgcta tcggcgtggg ctgcctgcag  38160
gatggcgcgc gtggcccttc tcgcgtgcgc gtgatcggtc tgggctatcg acatgatctg  38220
tgcgagttcc cggtcggtgt cgatggaccg tcgtacggcc tggacgacgg cgtgcgatcg  38280
cgctgcggcc cgatcgggaa gccggtcccc tcttgtctgc gatacggagt cggccagtgc  38340
ctgaagctgc ggctcgtggc ggcttctttc gtcgactaag cgaccggcga acagcccgtg  38400
```

```
cccgcgggac aaggtcgcca gcgtctgaag gatcagcgga tcagtcaaga attcctccgc  38460

cgccgtgccg aaaccggccc acgtctgtca gcagaccact ccgcctggaa acaaacaccc  38520

aagccactac tcccgtacct ccgggtcagc gaaacgcggc gcaccatggg cgcggacacc  38580

gtcgcccgcc catcgcaggg tagctgcagc gcatttgcgc gcgcatttcg attgaccggg  38640

ccaccatcgg taatggcgac acccgtgacg agattacttc ggctcggagg agccgactag  38700

t                                                                  38701
```

<210> SEQ ID NO 2
<211> LENGTH: 8562
<212> TYPE: DNA
<213> ORGANISM: artificial
<220> FEATURE:
<223> OTHER INFORMATION: integrating cosmid vector
<220> FEATURE:
<221> NAME/KEY: misc_feature
<222> LOCATION: (3119)..(3119)
<223> OTHER INFORMATION: n is a, c, g, or t
<220> FEATURE:
<221> NAME/KEY: misc_feature
<222> LOCATION: (4201)..(4201)
<223> OTHER INFORMATION: n is a, c, g, or t

<400> SEQUENCE: 2

```
ttgaagacga aagggcctcg tgatacgcct atttttatag gttaatgtca tgataataat     60

ggtttcttag acgtcaggtg gcacttttcg gggaaatgtg cgcggaaccc ctatttgttt    120

atttttctaa atacattcaa atatgtatcc gctcatgaga caataaccct gataaatgct    180

tcaataatat tgaaaaagga agagtatgag tattcaacat ttccgtgtcg cccttattcc    240

cttttttgcg gcattttgcc ttcctgtttt tgctcaccca gaaacgctgg tgaaagtaaa    300

agatgctgaa gatcagttgg gtgcacgagt gggttacatc gaactggatc tcaacagcgg    360

taagatcctt gagagttttc gccccgaaga acgttttcca atgatgagca cttttaaagt    420

tctgctatgt ggcgcggtat tatcccgtgt tgacgccggg caagagcaac tcggtcgccg    480

catacactat tctcagaatg acttggttga gtactcacca gtcacagaaa agcatcttac    540

ggatggcatg acagtaagag aattatgcag tgctgccata accatgagtg ataacactgc    600

ggccaactta cttctgacaa cgatcggagg accgaaggag ctaaccgctt ttttgcacaa    660

catgggggat catgtaactc gccttgatcg ttgggaaccg gagctgaatg aagccatacc    720

aaacgacgag cgtgacacca cgatgcctgc agcaatggca acaacgttgc gcaaactatt    780

aactggcgaa ctacttactc tagcttcccg gcaacaatta atagactgga tggaggcgga    840

taaagttgca ggaccacttc tgcgctcggc ccttccggct ggctggttta ttgctgataa    900

atctggagcc ggtgagcgtg ggtctcgcgg tatcattgca gcactggggc cagatggtaa    960

gccctcccgt atcgtagtta tctacacgac ggggagtcag gcaactatgg atgaacgaaa   1020

tagacagatc gctgagatag gtgcctcact gattaagcat tggtaactgt cagaccaagt   1080

ttactcatat atactttaga ttgatttaaa acttcatttt taatttaaaa ggatctaggt   1140

gaagatcctt tttgataatc tcatgaccaa aatcccttaa cgtgagtttt cgttcgactg   1200

agcgtcagac cccgtagaaa atatcaaagg atcttcttga gatccttttt ttctgcgcgt   1260

aatctgctgc ttgcaaacaa aaaaaccacc gctaccagcg gtggtttgtt tgccggatca   1320

agagctacca actctttttc cgaaggtaac tggcttcagc agagcgcaga taccaaatac   1380

tgtccttcta gtgtagccgt agttaggcca ccacttcaag aactctgtag caccgcctac   1440
```

-continued

```
atacctcgct ctgctaatcc tgttaccagt ggctgctgcc agtggcgata agtcgtgtct   1500
taccgggttg gactcaagac gatagttacc ggataaggcg cagcggtcgg gctgaacggg   1560
gggttcgtgc acacagccca gcttggagcg aacgacctac accgaactga gatacctaca   1620
gcgtgagcta tgagaaagcg ccacgcttcc cgaagggaga aaggcggaca ggtatccggt   1680
aagcggcagg gtcggaacag gagagcgcac gagggagctt ccagggggaa acgcctggta   1740
tctttatagt cctgtcgggt ttcgccacct ctgacttgag cgtcgatttt tgtgatgctc   1800
gtcagggggg cggagcctat ggaaaaacgc cagcaacgcg gcctttttac ggttcctggc   1860
cttttgctgg ccttttgctg gccttttgct cacatgttct ttcctgcgtt atcccctgat   1920
tctgtggata accgtattac cgcctttgag tgagctgata ccgctcgccg cagccgaacg   1980
accgagcgca gcgagtcagt gagcgaggaa gcggaagagc gctgacttcc gcgtttccag   2040
actttacgaa acacggaaac cgaagaccat tcatgttgtt gctcaggtcg cagacgtttt   2100
gcagcagcag tcgcttcacg ttcgctcgcg tatcggtgat tcattctgct aaccagtaag   2160
gcaaccccgc cagcctagcc gggtcctcaa cgacaggagc acgatcatgc gcacccgtca   2220
gatccagaca tgataagata cattgatgag tttggacaaa ccacaactag aatgcagtga   2280
aaaaaatgct ttatttgtga aatttgtgat gctattgctt tatttgtaac cattataagc   2340
tgcaataaac aagttcgaac gccagcaaga cgtagcccag cgcgtcggcc gccatgccgg   2400
cgataatggc ctgcttctcg ccgaaacgtt tggtggcggg accagtgacg aaggcttgag   2460
cgagggcgtg gaagattccg aataccgcaa gcgacaggcc gatcatcgtc gcgctccagc   2520
gaaaggggtc ctcgccgaaa atgacccaga gcgctgccgg cacctgtcct acgagttgca   2580
tgataaagaa gacagtcata agtgcggcga cgatagtcat gccccgcgcc caccggaagg   2640
agctgactgg gttgaaggct ctcaagggca tcggtcgagg aactttcggc ggctttgctg   2700
tgcgacaggc tcacgtctaa aaggaaataa atcatgggtc ataaaaatta tcacgttgtc   2760
ggcgcggcga cggatgttct gtatgcgctg ttttccgttg gccgttgctg tctggtgatc   2820
tgccttctaa atctgcacag ccgaattgcg cgagcttggt tttgctgaaa ccgacacaca   2880
gcaactgaat accagaaaga aaatcacttt gcctttctga catcagaagg gcagaaattt   2940
gccgttgaac acctggtcaa tacgcgtttt ggtgagcagc aatattgcgc ttcgatgagc   3000
cttggcgttg agattgatac ctctgctgca caaaaggcaa tcgaccgagc tggaccagcg   3060
cattcgtgac accgtctcct tcgaacttat tcgcaatgga gtgtcattca tcaaggacng   3120
cctgatcgca aatggtgcta tccacgcagc ggcaatcgaa aaccctcagc cggtgaccaa   3180
tatctacaac atcagccttg gtatcctgcg tgatgagcca gcgcagaaca aggtaaccgt   3240
cagtgccgat aagttcaaag ttaaacctgg tgttgatacc aacattgaaa cgttgatcga   3300
aaacgcgctg aaaaacgctg ctgaatgtgc ggcgctggat gtcacaaagc aaatggcagc   3360
agacaagaaa gcgatggatg aactggcttc ctatgtccgc acggccatca tgatggaatg   3420
tttccccggt ggtgttatct ggcagcagtg ccgtcgatag tatgcaattg ataattatta   3480
tcatttgcgg gtcctttccg gcgatccgcc ttgttacggg gcggcgacct cgcgggtttt   3540
cgctatttat gaaaattttc cggtttaagg cgtttccgtt cttcttcgtc ataacttaat   3600
gtttttattt aaaataccct ctgaaaagaa aggaaacgac aggtgctgaa agcgagcttt   3660
ttggcctctg tcgtttcctt tctctgtttt tgtccgtgga atgaacaatg gaagtcaaca   3720
aaaagcagac gtatctagac acgtctgaag ctagcttcga ggaactttcg gcggctttgc   3780
tgtgcgacag gctcacgtct aaaaggaaat aaatcatggg tcataaaaat tatcacgttg   3840
```

tcggcgcggc gacggatgtt ctgtatgcgc tgttttccgt tggccgttgc tgtctggtga 3900
tctgccttct aaatctgcac agccgaattg cgcgagcttg gttttgctga aaccgacaca 3960
cagcaactga ataccagaaa gaaaatcact ttgcctttct gacatcagaa gggcagaaat 4020
ttgccgttga acacctggtc aatacgcgtt ttggtgagca gcaatattgc gcttcgatga 4080
gccttggcgt tgagattgat acctctgctg cacaaaaggc aatcgaccga gctggaccag 4140
cgcattcgtg acaccgtctc cttcgaactt attcgcaatg gagtgtcatt catcaaggac 4200
ngcctgatag caaatggtgc tatccacgca gcggcaatcg aaaaccctca gccggtgacc 4260
aatatctaca acatcagcct tggtatcctg cgtgatgagc cagcgcagaa caaggtaacc 4320
gtcagtgccg ataagttcaa agttaaacct ggtgttgata ccaacattga aacgttgatc 4380
gaaaacgcgc tgaaaaacgc tgctgaatgt gcggcgctgg atgtcacaaa gcaaatggca 4440
gcagacaaga aagcgatgga tggactggct tcctatgtcc gcacggccat catgatggaa 4500
tgtttccccg gtggtgttat ctggcagcag tgccgtcgat agtatgcaat tgataattat 4560
tatcatttgc gggtcctttc cggcgatccg ccttgttacg gggcggcgac ctcgcgggtt 4620
ttcgctattt atgaaaattt tccggtttaa ggcgtttccg ttcttcttcg tcataactta 4680
atgtttttat ttaaaatacc ctctgaaaag aaaggaaacg acaggtgctg aaagcgagct 4740
ttttggcctc tgtcgtttcc tttctctgtt tttgtccgtg gaatgaacaa tggaagtcaa 4800
caaaaagcag agcttatcgc gatactagag tcgaccacca agggcaccat ctctgcttgg 4860
gccaccccgt tggccgcagc cagctcgctg agagccgtga acgacagggc gaacgccagc 4920
ccgccgacgg cgagggttcc gaccgctgca actcccggtg caaccttgtc ccggtctatt 4980
ctcttcactg caccagctcc aatctggtgt gaatgcccct cgtctgttcg cgcaggcggg 5040
gggctctatt cgtttgtcag catcgaaagt agccagatca gggatgcgtt gcaaccgcgt 5100
atgcccaggt cagaagagtc gcacaagagt tgcagacccc tggaaagaaa aatggccaga 5160
gggcgaaaac accctctgac cagcggagcg ggcgacggga atcgaacccg cgtagctagt 5220
ttggaagaat gggtgtctgc cgaccacata tgggccggtc aagataggtt tttaccccct 5280
ctcggctgca tcctctaagt ggaaagaaat tgcaggtcgt agaagcgcgt tgaagcctga 5340
gagttgcaca ggagttgcaa cccggtagcc ttgttcacga cgagaggaga cctagttggc 5400
acgtcgcgga tggggatcgc tgaagactca gcgcagcggg aggatccaag cctcatacgt 5460
caacccgcag gacggtgtga ggtactacgc gctgcagacc tacgacaaca agatggacgc 5520
cgaagcctgg ctcgcgggcg agaagcggct catcgagatg gagacctgga cccctccaca 5580
ggaccgggcg aagaaggcag ccgccagcgc catcacgctg gaggagtaca cccggaagtg 5640
gctcgtggag cgcgacctcg cagacggcac cagggatctg tacagcgggc acgcggagcg 5700
ccgcatctac ccggtgctag gtgaagtggc ggtcacagag atgacgccag ctctggtgcg 5760
tgcgtggtgg gccgggatgg gtaggaagca cccgactgcc cgccggcatg cctacaacgt 5820
cctccgggcg gtgatgaaca cagcggtcga ggacaagctg atcgcagaga acccgtgccg 5880
gatcgagcag aaggcagccg atgagcgcga cgtagaggcg ctgacgcctg aggagctgga 5940
catcgtcgcc gctgagatct tcgagcacta ccggatcgcg gcatacatcc tggcgtggac 6000
gagcctccgg ttcggagagc tgatcgagct tcgccgcaag gacatcgtgg acgacggcat 6060
gacgatgaag ctccgggtgc gccgtggcgc ttcccgcgtg gggaacaaga tcgtcgttgg 6120
caacgccaag accgtccggt cgaagcgtcc tgtgacggtt ccgcctcacg tcgcggagat 6180

-continued

```
gatccgagcg cacatgaagg accgtacgaa gatgaacaag ggccccgagg cattcctggt   6240
gaccacgacg cagggcaacc ggctgtcgaa gtccgcgttc accaagtcgc tgaagcgtgg   6300
ctacgccaag atcggtcggc cggaactccg catccacgac ctccgcgctg tcggcgctac   6360
gttcgccgct caggcaggtg cgacgaccaa ggagctgatg gcccgtctcg gtcacacgac   6420
tcctaggatg gcgatgaagt accagatggc gtctgaggcc cgcgacgagg ctatcgctga   6480
ggcgatgtcc aagctggcca agacctcctg aaacgcaaaa agcccccctc ccaaggacac   6540
tgagtcctaa agaggggggt ttcttgtcag tacgcgaaga accacgcctg gccgcgagcg   6600
ccagcaccgc cgctctgtgc ggagacctgg gcaccagccc cgccgccgcc aggagcattg   6660
ccgttcccgc cagaaatcta gtgatccttg ccgagctggg atggaagctc ggccgaccac   6720
cctggaggag atgatcgagg atgccagggc ctttcacgcc cgccgctgct gagcgtccgc   6780
cgccgggccc gcaccgccgt cggccggccc gctccgggct cgcagcagcg ggcttcggcg   6840
cgggcccggg gctcccgagc gcgggcgggg ctccgggcgg ccgccggggg ccgggggcgg   6900
cgccgggcgg cccggggcgt caggcgccgg gggcggtgtc cggcggcccc cagaggaact   6960
gcgccagttc ctccggatcg gtgaagccgg agagatccag cggggtctcc tcgaacacct   7020
cgaagtcgtg caggaaggtg aaggcgagca gttcgcgggc gaagtcctcg gtccgcttcc   7080
actgcgcccc gtcgagcagc gcggccagga tctcgcggtc gccccggaag gcgttgagat   7140
gcagttgcac caggctgtag cgggagtctc ccgcatagac gtcggtgaag tcgacgatcc   7200
cggtgacctc ggtcgcggcc aggtccacga agatgttggt cccgtgcagg tcgccgtgga   7260
cgaaccgggg ttcgcggccg gccagcagcg tgtccacgtc cggcagccag tcctccaggc   7320
ggtccagcag ccggggcgag aggtagcccc acccgcggtg gtcctcgacg gtcgccgcgc   7380
ggcgttcccg cagcagttcc gggaagacct cggaatgggg ggtgagcacg gtgttcccgg   7440
tcagcggcac cctgtgcagc cggccgagca cccggccgag ttcgcgggcc agggcgagca   7500
gcgcgttccg gtcggtcgtg ccgtccatcg cggaccgcca ggtggtgccg gtcatccggc   7560
tcatcaccag gtagggccac ggccaggctc cggtgccggg ccgcagctcg ccgcggccga   7620
ggaggcgggg caccggcacc ggggcgtccg ccaggaccgc gtacgcctcc gactccgacg   7680
cgaggctctc cggaccgcac cagtgctcgc cgaacagctt gatgaccggg tcgggctcgc   7740
cgaccagtac ggggttggtg ctctcgccgg gcacccgcag caccggcggc accggcagcc   7800
cgagctcctc cagggctcgg cgggccagcg gctcccagaa ttcctggtcg ttccgcaggc   7860
tcgcgtagga atcatccgaa tcaatacggt cgagaagtaa cagggattct tgtgtcacag   7920
cggacctcta ttcacagggt acgggccggc ttaattccgc acggccggtc gcgacacggc   7980
ctgtccgcac cgcggtcagg cgttgacgat gacgggctgg tcggccacgt cggggacgtt   8040
ctcggtggtg ctgcggtcgg gatcgccaat ctctacgggc cgaccgaggc gacggtgtac   8100
gccaccgcct ggttctgcga cggcgaggcg ccgccaggcc ccgccgatcc ccgtccccgg   8160
cgtcgtcgag cgcggtgccg acgacaccgc cgcgtggctc gtcacggagg ccgtccccgg   8220
cgtcgcggcg gccgaggagt ggcccgagca ccagcggttc gccgtggtcg aggcgatggc   8280
ggagctggcc cgcgccctcc acgagctgcc cgtggaggac tgcccctccg accggcgcct   8340
cgacgcggcg gtcgccgagg cccggcggaa cgtcgccgag ggcttggtgg acctcgacga   8400
cctgcaggca tgcaagctca ggatatcatc gcgatgataa gcggtcaaac atgagaattc   8460
gcggccgcat aatacgactc actataggga tcttaattaa ggcgcctgat caggatcctt   8520
aattaagatc ctttagtgag ggttaattgc ggccgcgaat tc                      8562
```

<210> SEQ ID NO 3
<211> LENGTH: 397
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5430

<400> SEQUENCE: 3

```
Met Asn Leu Asn Gly Thr Met Arg Asn Leu Ile Arg Arg Leu Ile Ala
1               5                   10                  15

Glu Asp Pro Glu Gly Asn Glu Glu Asn Pro Gln Trp Leu Arg Arg Gly
            20                  25                  30

Ser Val Val Cys Leu Val Thr Asp Cys Ile Leu Gly Gly Glu Leu Ala
        35                  40                  45

Trp Leu Gly His Ala Ser Pro Asp Gln Gly Gly Cys Leu Val Lys Gly
    50                  55                  60

Ala Ala Met Phe Asp Asp Leu Gly Ala Gln Ile Ala Ala Leu Val Pro
65                  70                  75                  80

Asp Ser Gly Trp Gln Gly Ser Ala Ala Arg Ser Tyr Gly Ala His Thr
                85                  90                  95

Leu Ala Gln Ser Arg His Ser Thr Leu Met Ala Asp Leu Asp Arg Leu
            100                 105                 110

Ala Ala Glu Leu Val Ser Ser Gln Ala Asp Asp Val Lys Gln Ala Arg
        115                 120                 125

Thr Ala Leu Trp Ala Ala Ile Gly Phe Val Ser Val Tyr Leu Leu Ile
    130                 135                 140

Cys Leu Gly Ile Glu Leu Gln Gly Pro Glu Gly Gln Leu Leu Ser Phe
145                 150                 155                 160

Asn Phe Ala Val Val Val Cys Gly Ala Val Leu Gly Ile Ser Ala Leu
                165                 170                 175

Val Leu His Asp Leu Ala Lys Lys Thr Ser Arg Arg Ala Ser Ser Leu
            180                 185                 190

Gln Thr Thr Thr Gln Arg Leu Ser Asp Met Val Ala Gly Leu Ala Thr
        195                 200                 205

Arg Ser Asp Met Ile Pro Gly Ser Pro Glu Met Ser Leu Pro Pro Ala
    210                 215                 220

His Ser Leu Ser Glu Phe His Leu Thr Asp Ser Ser Ala Ala Ser Pro
225                 230                 235                 240

Pro His Leu Pro Asp Leu Asp Ser Ala Phe Ala Asp Leu Pro Gly Ala
                245                 250                 255

Pro Glu Phe His Leu Pro Thr Ala Ala Gly Ala Gly Leu Pro Asp Phe
            260                 265                 270

Gly Ala Pro Gln Leu Pro Ile Pro Ala Leu Ser Gly Leu Pro Thr Leu
        275                 280                 285

Pro Asp Pro Thr Asp Pro Thr Asp Leu Ser Ser Met Leu Ala Gly Leu
    290                 295                 300

Pro Thr Ile Thr Gln Leu Pro Ala Ile Leu Ser Gln Leu Asn Asn Leu
305                 310                 315                 320

Ala Gly Pro Thr Ser Ala Val Ser Gln Leu Ala Asn Thr Ala Thr Gln
                325                 330                 335

His Ala Gln Met Ile Ser Thr Leu Ala Gln Gln Gly Ala His Pro His
            340                 345                 350

Thr Thr Leu Thr Asp His His Thr Thr Asp Glu Thr Pro Asp Thr Asp
```

```
        355                 360                 365

Ala Ala Thr Ala Ala Thr Ser Ser Gly Glu Arg Ala Pro Leu Asp Thr
    370                 375                 380

Thr Thr His Pro Thr Gln His Arg Leu Asp His Ile Val
385                 390                 395


<210> SEQ ID NO 4
<211> LENGTH: 401
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5431

<400> SEQUENCE: 4

Met Tyr Leu Ser Gln Leu Gln Arg Leu Val Gln Gln Ile Ser Arg Trp
1               5                   10                  15

Val Arg Gly Asp Gly Asn Leu Gln Asn Phe Gln Asp Ile Gln Glu Gly
            20                  25                  30

Gly Gly Asn Pro Pro Pro Ala Gln Glu Gly Ala Pro Asp Asn Ser Pro
        35                  40                  45

Trp Ala Arg Arg Gly Ser Val Val Cys Gly Val Thr Glu Gly Ile Leu
    50                  55                  60

Gly Leu Leu Leu Ala Leu Leu Gly Glu Ala Val Pro Ser Arg Gly Glu
65                  70                  75                  80

Ser Leu Asp Arg Ser Gly Ser Met Phe Asp Gly Val Ser Thr Gln Ile
                85                  90                  95

Ala Thr Leu Asp Pro Asp Gly Gly Trp Arg Gly Asn Ala Ala Arg Ala
            100                 105                 110

Tyr Gly Ala Lys Asn Leu Ala Gln Ser Gln His Thr Thr Leu Ile Ala
        115                 120                 125

Asp Leu Asp Arg Leu Thr Gly Glu Leu Val Ser Ser Gln Ala Asp Ala
    130                 135                 140

Val Lys Arg Ala Arg Asp Leu Leu Ser Ala Glu Ile Trp Ile Val Leu
145                 150                 155                 160

Val Leu Leu Val Val Cys Ile Gly Leu Glu Leu His Gly Pro Glu Gly
                165                 170                 175

Gln Ile Leu Ser Phe His Ile Ala Ile Pro Ile Cys Thr Met Ala Val
            180                 185                 190

Phe Thr Ala Ala Thr Ala Leu Gly Val Leu Ala Ala Thr Thr Ser Gln
        195                 200                 205

Asn Ala Ser Ala Val Gln Ala Ala Thr Gln Arg Leu Thr Ala Met Ala
    210                 215                 220

Ala Ala Leu Thr Thr Gly Ala Asp Thr Val Pro Ser Ser Pro Lys Met
225                 230                 235                 240

Thr Phe Pro Pro Ile His Ser Leu Ser Glu Phe Asp Leu Thr Glu Ala
                245                 250                 255

Thr Gly Pro Thr Pro Pro Gln Leu Pro Asp Leu Gln Ser Thr Leu Ala
            260                 265                 270

Glu Leu Pro Gly Ala Pro Glu Phe His Leu Ala Thr Arg Ala Gly Ala
        275                 280                 285

Gly Phe Pro Asp Phe Gly Ala Pro Gln Leu Pro Ile Thr Glu Leu Thr
    290                 295                 300

Gly Leu Pro Thr Leu Pro Asp Pro Thr Asn Leu Thr Asp Pro Thr Ser
305                 310                 315                 320
```

-continued

```
Met Leu Ala Asp Leu Pro Thr Ile Ala Gln Leu Ser Thr Thr Leu Ser
                325                 330                 335

Gln Leu Thr Asn Leu Ala Gly Pro Thr Ser Ala Thr Thr Gln Pro Ala
            340                 345                 350

Gln Gln His Thr Thr Pro Ala Asp His Arg Thr Gln Asp Asp Ala Thr
        355                 360                 365

Asn Thr Pro Asp Thr Ala Thr Ala Thr Ala Ala Thr Ser Ser Ser Glu
    370                 375                 380

Arg Ala Pro Leu Asp Thr Gln Thr His Pro His Arg Gln Arg Leu Leu
385                 390                 395                 400

Thr


<210> SEQ ID NO 5
<211> LENGTH: 178
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5432

<400> SEQUENCE: 5

Met Thr Asp Gln Pro Gly Tyr Asp Ala His Asn Tyr Leu Ala Gly Leu
1               5                   10                  15

Gly Phe Ser Gly Pro Ala Thr Gly Glu Thr Asp Ser Ala Ile Asp Ala
            20                  25                  30

Leu Leu Ser Tyr Ala Pro Ala Gln Pro Glu Asp Thr Gly Ser Asp Met
        35                  40                  45

Ser Ala Ile Leu Gly Ala Thr Glu Glu Asp Lys Thr Asp Glu Cys Glu
    50                  55                  60

Leu Phe Thr Val Thr Asn Pro Gln Gly Ser Val Ser Val Ser Ala Val
65                  70                  75                  80

Met Gly Gly Asp Ile His Arg Val Glu Leu Ser Asp Lys Val Asp Asn
                85                  90                  95

Met Ser Glu Pro Arg Leu Ala Glu Glu Ile Phe Val Leu Ala Asp Leu
            100                 105                 110

Ala Arg Gln Lys Ala Arg Ala Ala Gln His Ala Phe Met Leu Gln Gly
        115                 120                 125

Met Asp Glu Val Asp Asp Glu Glu Gln Arg Ala Val Leu Arg Glu Ile
    130                 135                 140

Val Glu Lys Thr Met Asn Leu Pro Thr Pro Glu Gln Ala Ala Ala Ala
145                 150                 155                 160

Glu Glu Glu Val Phe Ala Thr Arg Tyr Lys Asn Asp Phe Thr Ala Thr
                165                 170                 175

Thr Gly


<210> SEQ ID NO 6
<211> LENGTH: 104
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5433

<400> SEQUENCE: 6

Met Asn Asp Met Leu Thr Leu Gln Pro Asp Val Val Asn Arg Leu Ala
1               5                   10                  15

Ser Gly His Asp Ala Thr Ala Thr Ser Leu Arg Ala Ala Thr Ala Ala
            20                  25                  30
```

Pro Ala Gly Ile Gly Ala Thr Val Ala Glu Thr His Gly Pro Phe Thr
35 40 45

Ser Thr Phe Asn Asn Ala Leu Ser Ala Tyr Glu Ala Val Arg Ala Ser
50 55 60

Ala Gly Arg Ala Leu Glu Gly Val Ala Asp Gly Leu Ser Thr Asn Leu
65 70 75 80

Thr Arg Ala Leu Ala Ala Tyr Thr Asp Thr Asp Gln Arg Gly Ala Glu
85 90 95

Ile Leu Asp Glu Gln Ile Asp Asn
100

<210> SEQ ID NO 7
<211> LENGTH: 112
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5434

<400> SEQUENCE: 7

Met Asn Leu Asp Pro Thr Ala Ala His Leu Leu Ala Gly Leu Thr Gln
1 5 10 15

Phe His Thr Ala Leu Gln Asn Arg Phe His Gln Met Asn Ala Gly Asn
20 25 30

Phe Lys Ala Ser Asp Asn Thr His Thr Val Gln Val Thr Leu Asn Gly
35 40 45

Tyr Asn Trp Leu Thr Gly Ile Arg Ile Gln Asp Gly Leu Leu Lys Gln
50 55 60

Leu Gly Ser Gln Gly Val Ala His Arg Val Asn Gln Ala Leu His Asn
65 70 75 80

Ala Lys Gln Ala Val His Ala Tyr Asp Asn Ala Ala Asn His Ala Leu
85 90 95

Ala Thr Thr Leu Ala Thr Leu Ser Ala Ala Ile Asn Gln Thr His Pro
100 105 110

<210> SEQ ID NO 8
<211> LENGTH: 448
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5435

<400> SEQUENCE: 8

Met Ser Gln Pro Trp Met Leu Ala Val Asp Pro Ser Glu Ile Val Ala
1 5 10 15

Arg Ala Thr Glu Val Glu Ala Pro Ile Ala Asp Pro Pro Gly Gly Ala
20 25 30

Val Leu Ala Ala Cys Ala Leu Asp Pro Ala Val Ala Gly Ala Thr Gln
35 40 45

Leu Ala Leu Ser Ala Glu Ser Met Arg Ala Tyr Leu Gln Ser Gly Ala
50 55 60

Gln Ala Arg Gln Arg Leu Ala Lys Phe Met Arg Asp Ala Ala Lys Ala
65 70 75 80

Tyr Glu Gln Ile Asp Glu Gly Ala Ala Thr Ala Leu Gly Thr Asn Gly
85 90 95

His Gly Ile Gly Ala Pro Pro Val Pro Ala Gly Thr Asp Leu Ala Pro
100 105 110

-continued

Val Ala Leu Ser Asp Thr Pro Thr Ala Pro Ala Ala Pro Pro Phe Pro
115 120 125

Tyr Thr Gly Val Lys Leu Ala Ala Ile Asn Leu Asn Lys Pro Asp Gln
130 135 140

Gly Val Ser Leu Lys Lys Phe Ala His Asp Trp Asn Ala Tyr Asn Leu
145 150 155 160

Thr Ile Gln Gln Ala Leu Gly Arg Phe Arg Asp Phe Glu Asp Trp Glu
165 170 175

Gly Glu Ala Ala Ala Ala Val Gln Ala Ala Phe Asp Gln His Arg Asp
180 185 190

Trp Leu Arg Leu Met Ala Arg Leu Ser Thr Thr Met Ala Lys Gln Ala
195 200 205

Ser Gly Leu Glu Gln Ala His His Trp Ala Ile Gly Gln His Pro Thr
210 215 220

Leu Ala Asp Ile Thr Thr Leu Glu Glu Leu Leu Arg Asp Pro Arg Val
225 230 235 240

Pro Asp Lys Lys Pro Leu Met Lys Val Tyr Ala Gln Cys Gln Lys Lys
245 250 255

Ser Glu Glu Val Leu Thr Gly Tyr Ala Thr Arg Thr Ile Thr Glu Pro
260 265 270

Val Gln Pro Pro Arg Pro Pro Ala Ala Pro Thr His Asn Asp Pro Lys
275 280 285

Pro Pro Pro Pro Leu Pro Pro Leu Pro Pro Gly Gly Asp Pro Thr Leu
290 295 300

Pro Phe Thr Gly Thr Pro Pro Met Pro Thr Met Pro Phe Thr Pro Pro
305 310 315 320

Pro Ala Ala Thr Pro Asp Thr Thr Glu Ala Ala Arg Ala Ala Ala Thr
325 330 335

Leu Ala Thr Gly Pro Thr Val Lys Pro Ala Ala Leu Gly Gly Gly Ala
340 345 350

Gly Ala Ala Ile Pro Leu Thr Ala Pro Leu Gly Ala Gly Pro Thr Pro
355 360 365

Pro Ser Ala Pro Gly Ala Leu Gly Pro Gly Thr Ala Pro Thr Gly Arg
370 375 380

Pro Leu Gly Ala Gly Pro Met Gly Gly Met Pro Met Gly Ala Asn Gly
385 390 395 400

Gln Ala Gln Asn Ala Lys Thr Lys Arg Thr Gln Gln Asp Asp Arg Ala
405 410 415

Leu Tyr Thr Glu Gln Arg Pro Trp Thr Glu Ala Leu Ile Gly Pro Ala
420 425 430

Arg Pro His Leu Thr Thr Pro Asn Ser Thr Asn Thr Glu His Gln Pro
435 440 445

<210> SEQ ID NO 9
<211> LENGTH: 437
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5436

<400> SEQUENCE: 9

Met Asn Glu Arg Glu Glu Phe Leu Arg Asp Arg Val Arg Pro Asp Gln
1 5 10 15

Pro Ser Val Pro Asp Ala Ser Arg Ser His Gln Arg Ser Gly Met His

-continued

```
                20                  25                  30

Arg Thr Ala Thr Asp Ala Ser Gly Pro Pro Val Ala Pro Thr His Gln
        35                  40                  45

Pro Arg Pro Ala Pro Pro Arg Pro Pro Thr Pro Gln Pro Ser Pro Val
    50                  55                  60

Pro Pro Arg Gly Ala Asn Pro His Pro Pro Pro Pro Pro Ala Pro Pro
65                  70                  75                  80

Ser Val Pro Ala Pro Pro Pro Pro Pro Val Ala His Pro Pro Asn Gly
                85                  90                  95

His Asn Ser Pro Pro Gln Ala Ala Pro His Glu Pro Met Pro Glu Val
            100                 105                 110

Pro Pro Pro Ser Leu Trp Ala Glu Pro Thr Pro Ala Arg Thr Pro Gly
        115                 120                 125

Glu Pro Pro Ser Thr Asp His Gly Trp Arg His Ile Ile Arg Val Ala
    130                 135                 140

Ser Phe Gly Leu Ile Asn Pro Arg Pro Ser Ala Ala Gln Arg Asp Ala
145                 150                 155                 160

Ala Glu Phe Glu Ala Ala Ile Arg Ala Pro Leu Arg Gly Thr His Lys
                165                 170                 175

Val Gly Val Leu Gly Lys Gly Gly Val Gly Lys Thr Ser Val Ala Ala
            180                 185                 190

Ser Ile Gly Ser Leu Leu Ala Glu Leu Arg Gln Gln Asp Arg Ile Val
        195                 200                 205

Ala Val Asp Ala Asp Thr Ala Phe Gly Arg Leu Ser Ser Arg Ile Asp
    210                 215                 220

Pro Thr Ala Arg Gly Ser Phe Trp Asp Leu Thr Ala Asp Arg Asn Leu
225                 230                 235                 240

Ala Ser Phe Ala Asp Val Val Ala Arg Leu Gly Arg Asn Ala Ala Gly
                245                 250                 255

Leu His Val Leu Pro Gly Glu Ala Ala Val Gly Gly Arg Arg Leu Leu
            260                 265                 270

Asp Pro Ala Ile Tyr Arg Glu Ala Ala Leu Arg Leu Asp Arg His Phe
        275                 280                 285

Thr Ile Ser Ile Ile Asp Cys Gly Ser Thr Met Asp Ala Pro Leu Thr
    290                 295                 300

Gln Glu Val Leu Arg Asp Leu Asp Ala Leu Ile Val Val Ser Ser Pro
305                 310                 315                 320

Trp Ala Asp Gly Ala Ser Ala Ala Ala Lys Thr Met Glu Trp Leu Ala
                325                 330                 335

Asp Arg Lys Leu Ser Gly Leu Leu Arg Arg Ser Val Val Val Leu Asn
            340                 345                 350

Asp Ser Asp Gly His Ser Asp Lys Arg Thr Arg Ser Val Leu Ala Arg
        355                 360                 365

Glu Phe Val Asp His Gly Gln Gln Val Val Glu Val Pro Phe Asp Pro
    370                 375                 380

His Leu Arg Pro Gly Gly Val Ile Asp Val Ser His Glu Leu Glu Pro
385                 390                 395                 400

Gly Thr Arg Leu Lys Phe Leu Gln Ile Ala Ala Thr Ile Thr Gly His
                405                 410                 415

Phe Ala Ala Arg Ser Ala Ala Asp Asp Asp Pro Arg Pro Thr Glu Asn
            420                 425                 430

Val Ala Ser Glu Thr
        435
```

<210> SEQ ID NO 10
<211> LENGTH: 95
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5437

<400> SEQUENCE: 10

```
Met Thr Ala Thr Ala Leu Tyr Glu Ile Pro Leu Gly Val Cys Thr Gln
1               5                   10                  15

Asp Pro Asp Arg Trp Thr Thr Thr Pro Asp Glu Glu Ala Lys Thr Leu
            20                  25                  30

Cys Arg Ala Cys Pro Arg Arg Trp Ala Cys Ala Arg Asp Ala Val Glu
        35                  40                  45

Ser Pro Gly Ala Glu Gly Leu Trp Ala Gly Val Val Ile Pro Glu Ala
    50                  55                  60

Gly Arg Ala Arg Ala Phe Ala Leu Gly Gln Leu Arg Ser Leu Ala Glu
65                  70                  75                  80

Arg Asn Gly Phe Pro Ala Arg Glu Arg Ile Thr Ala Gln Ser Ala
                85                  90                  95
```

<210> SEQ ID NO 11
<211> LENGTH: 385
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5438

<400> SEQUENCE: 11

```
Met Leu Val Ser Gly Thr Arg Ala Leu Pro Pro Ala Ser Val Ala Ala
1               5                   10                  15

Ser Glu Glu Ser Thr Tyr Met Pro Asp Ala Glu Ser Thr Ala Arg Pro
            20                  25                  30

Ala Leu Arg Val Ala Arg Gly Gly Asp Ser Pro Gly Leu Val Thr Pro
        35                  40                  45

Gly His Arg Pro Val Gly Arg Gly Ala Leu Thr Asn Ala Arg Leu Asp
    50                  55                  60

Asp Pro Val Leu Ser Gln Thr His Val Arg Ala Val Ser Asp Gly Gly
65                  70                  75                  80

Gln Arg Arg Ile Val Thr Asn Ser Pro Asn Gly Met Phe Val Asp Gly
                85                  90                  95

Thr Arg Lys Ser Ser Val Ala Val Ser Asp Lys Thr Ile Val Arg Phe
            100                 105                 110

Gly Asp Pro Thr Gly Gly Lys Ala Leu Thr Phe Glu Val Val Arg Pro
        115                 120                 125

Ser Asn Ser Pro Glu Glu Asp Ser Arg Glu Gln Arg Pro Ala Glu Gln
    130                 135                 140

Ser Asp Ser Gln Thr Asn Glu Ala Asp Pro Gly Val Val Arg Ala Gly
145                 150                 155                 160

Ala Ala Ala Ala Ala Arg Arg Arg Glu Leu Asp Ile Ser Gln Arg Ser
                165                 170                 175

Leu Ala Ala Asp Gly Ile Ile Asn Ala Gly Ala Leu Ile Ala Phe Glu
            180                 185                 190

Lys Gly Arg Ser Trp Pro Arg Glu Arg Thr Arg Ala Lys Leu Glu Glu
        195                 200                 205
```

Val Leu Gln Trp Pro Ala Gly Thr Ile Ala Arg Ile Arg Gln Gly Glu
    210                 215                 220

Ser Val Ala Pro Glu Pro Ala Pro Glu Ala Ser Val Glu Ala Pro Thr
225                 230                 235                 240

Ser Asp Gly Pro Ala Ser Leu Ile Ala Gln Ala Val Ala Ala Ala Val
                245                 250                 255

Asp Thr Cys Ser Leu Ala Ile Ala Ala Leu Pro Ala Pro Glu Glu Pro
            260                 265                 270

Asp Phe Thr Glu Arg Ala Ala Pro Ile Leu Ala Asp Leu Arg Gln Leu
        275                 280                 285

Glu Gly Ile Ala Val Gln Ala Thr Arg Ile Ser Arg Ile Thr Pro Glu
    290                 295                 300

Leu Ile Lys Ala Leu Gly Ala Val Arg Arg Tyr His Asp Lys Leu Met
305                 310                 315                 320

Thr Leu Ser Ala Thr Ala Pro Gly Ala Thr Leu Ala Gln Arg Leu Tyr
                325                 330                 335

Ala Ala Arg Arg Arg Ala Asn Leu Ser Thr Ser Glu Thr Ala Gln Ala
            340                 345                 350

Ala Gly Val Thr Glu Glu Leu Ile Val Arg Ala Glu Ala Glu Glu Ala
        355                 360                 365

Leu His Ala Glu Ala Ala Glu Ala Ile Glu Ala Leu Ile Arg Gln Ile
    370                 375                 380

Asn
385

<210> SEQ ID NO 12
<211> LENGTH: 418
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5439

<400> SEQUENCE: 12

Met Val Pro Lys Gly Ser Gly Leu Cys Lys Thr Thr Ser Asn Phe Ile
1               5                   10                  15

Trp Gly Gln Leu Leu Leu Leu Gly Glu Gly Ile Pro Asp Pro Gly Asp
            20                  25                  30

Ile Phe Asn Thr Gly Ser Thr Leu Phe Lys Gly Ile Ala Asp Lys Met
        35                  40                  45

Gly Leu Ala Ile Pro Gly Thr Asn Trp Leu Gly Gln Ala Ala Asp Ala
    50                  55                  60

Tyr Leu Asn Gln Asn Ile Ala Gln Glu Leu Arg Ala Lys Val Met Gly
65                  70                  75                  80

Asp Val Asp Tyr Leu Thr Gly Asn Leu Ile Ser Asn Gln Ala Glu Tyr
                85                  90                  95

Val Ser Asn Thr Arg Asp Val Leu Arg Ala Met Lys Lys Met Ile Asp
            100                 105                 110

Gly Val Tyr Lys Val Cys Lys Gly Leu Glu Lys Val Pro Ile Leu Gly
        115                 120                 125

Trp Leu Trp Ser Trp Glu Leu Ala Leu Pro Met Ser Gly Ile Ala Met
    130                 135                 140

Ala Thr Val Gly Gly Ala Leu Leu Tyr Leu Thr Ile Met Thr Leu Met
145                 150                 155                 160

Asn Leu Thr Asn Leu Lys Gly Leu Leu Gly Arg Leu Val Glu Met Leu

```
                165                 170                 175

Ala Ser Leu Pro Ser Leu Ile Gly Gly Leu Leu Pro Asn Ile Pro Gly
            180                 185                 190

Ile Ile Asp Asp Leu Trp Pro Pro Lys Leu Pro Asp Leu Pro Ile Pro
        195                 200                 205

Gly Leu Pro Asn Ile Pro Gly Leu Pro Asp Phe Thr Trp Pro Pro Lys
    210                 215                 220

Ile Asp Ile Pro Asp Trp Asn Leu Pro Ile Pro Gly Leu Pro Gly Phe
225                 230                 235                 240

Glu Phe Pro Pro Thr Ser Gly Ile Pro Gly Ile Asp Phe Pro Phe Pro
                245                 250                 255

Asn Ile Pro Gly Leu Pro Ser Phe Pro Ser Leu Pro Gly Leu Pro Ser
            260                 265                 270

Ile Pro Asp Leu Phe Pro Gly Leu Pro Gly Leu Gly Asp Leu Phe Ser
        275                 280                 285

Gly Ile Gly Lys Trp Gly Thr Leu Pro Thr Trp Thr Asp Leu Ala Ala
    290                 295                 300

Leu Pro Asp Phe Leu Gly Gly Phe Ala Gly Leu Pro Ser Leu Ser Phe
305                 310                 315                 320

Ser Asn Leu Leu Gly Phe Ala Gln Leu Pro Asn Val Gly Ser Leu Thr
                325                 330                 335

Ala Thr Met Gly Gln Leu Gln His Leu Val Ser Ala Ala Gly Gly Pro
            340                 345                 350

Gly Gln Leu Gly Ser Met Ala Gly Gln Gln Ala Ser Met Ile Ser Ser
        355                 360                 365

Gln Ala Ser Gln Gly Gly Gln Gln Ala Thr Leu Val Ser Asp Lys Lys
    370                 375                 380

Glu Asp Asp Glu Asp Gly Ala Ala Ala Gly Ser Ala Gly Ala Glu Arg
385                 390                 395                 400

Ala Pro Ile Asp Ala Gly Ser Asn Thr Gly Gln Gly Asn Glu Gly Thr
                405                 410                 415

Leu Leu


<210> SEQ ID NO 13
<211> LENGTH: 103
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5440

<400> SEQUENCE: 13

Met Thr Gly Leu Leu Asn Val Val Pro Ser Phe Leu Lys Val Leu Ala
1               5                   10                  15

Gly Met His Asn Glu Ile Val Gly Glu Leu Lys Ser Ala Thr Asn Val
            20                  25                  30

Val Ser Gly Ile Gly Ser Arg Val Gln Leu Thr His Gly Ser Phe Thr
        35                  40                  45

Ser Asn Phe Asn Asp Thr Leu Val Glu Phe Glu Thr Thr Arg Asn Ser
    50                  55                  60

Ala Gly Thr Gly Leu Gln Gly Val Thr Gly Lys Leu Ala Asn Asn Leu
65                  70                  75                  80

Ile Ser Ala Ala Gly Ala Tyr Leu Asn Ser Asp Glu Gly Leu Ala Gly
                85                  90                  95

Ile Ile Asp Lys Ile Phe Gly
```

100

<210> SEQ ID NO 14
<211> LENGTH: 279
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5441

<400> SEQUENCE: 14

```
Met Thr Gly Pro Leu Ala Thr Gly Arg Ala Gly Thr Gly Asp Asp Val
1               5                   10                  15

Val Gly Val Glu Val Thr Ile Asp Gly Met Leu Val Ile Ala Asp Arg
            20                  25                  30

Leu His Leu Val Asp Phe Pro Val Thr Leu Gly Ile Arg Pro Asn Ile
        35                  40                  45

Pro Gln Glu Asp Leu Arg Glu Ile Val Trp Asp Gln Val Ala Arg Asp
    50                  55                  60

Leu Thr Ala Gln Gly Val Leu Asp His Asn Gly Gln Pro His Pro Ala
65                  70                  75                  80

Val Ala Ala Met Val Asp Thr Leu Ser Arg Ala Asp Arg Thr Leu Glu
                85                  90                  95

Gly Arg Trp Trp Arg Arg Asp Val Gly Gly Val Met Val Arg Phe Val
            100                 105                 110

Val Cys Arg Lys Gly Glu Arg His Val Ile Ala Val Arg Asp Gly Asp
        115                 120                 125

Met Leu Val Leu Gln Leu Val Ala Pro Arg Val Gly Leu Ala Gly Met
    130                 135                 140

Val Thr Ala Val Leu Gly Thr Ala Glu Pro Ala Asn Val Glu Pro Leu
145                 150                 155                 160

Thr Gly Ile Ala Ser Glu Leu Gly Glu Cys Thr Asn Ala Ala Gln Leu
                165                 170                 175

Thr Arg Tyr Gly Leu Thr Pro Thr Thr Ala Arg Leu Tyr Thr Glu Ile
            180                 185                 190

Val Thr Asn Pro Lys Ser Trp Val Glu Ile Val Ala Ser Glu Arg His
        195                 200                 205

Pro Gly Gly Thr Thr Thr His Thr Lys Ala Ala Ala Gly Val Leu Asp
    210                 215                 220

Ser Ala His Gly Arg Leu Val Ser Leu Pro Arg Gln Val Gly Gly Glu
225                 230                 235                 240

Leu Tyr Gly Ser Phe Leu Pro Gly Thr Glu Gln Asn Leu Gln Arg Ala
                245                 250                 255

Leu Asp Ser Leu Leu Glu Leu Leu Pro Ser Gly Ser Trp Leu Asp Arg
            260                 265                 270

Ala Asp Ala Thr Ala Arg Gly
        275
```

<210> SEQ ID NO 15
<211> LENGTH: 185
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5442

<400> SEQUENCE: 15

```
Met Asp Leu Pro Gly Asn Asp Asp Tyr Asn Gln Asp Leu Gly Ala Leu
```

1 5 10 15

Asp Phe Ser Gly Gly Gly Thr Ser Glu Asp Ser Gly Leu Gly Ala Leu
20 25 30

Asp Glu Tyr Ala Pro Pro Glu Pro Gln Glu Thr Glu Gln Ala Gly Ala
35 40 45

Asp Leu Asp Ala Leu His Gly Leu Thr Glu Lys Glu Asp Glu Pro Asp
50 55 60

Ile Ala Met Phe Thr Val Thr Asn Pro Gln Gly Ser Val Ser Val Thr
65 70 75 80

Thr Met Met Gly Gly Ile Val Gln Gln Val Thr Val Thr Asp Lys Ala
85 90 95

Ala Asn Met Ser Glu Ser Ala Leu Ala Glu Glu Ile Phe Val Ile Ala
100 105 110

Asp Leu Ala Arg Gln Lys Ala Arg Ala Ala Gln His Thr Phe Met Val
115 120 125

Glu Ala Met Ala Ser Glu Leu Ser Asp Glu Thr Glu Glu Glu Gly Ala
130 135 140

Leu Leu Arg Glu Phe Val Gly Met Thr Leu Asn Leu Pro Thr Pro Glu
145 150 155 160

Glu Ala Glu Ala Ala Glu Ala Glu Val Phe Ala Thr Arg Tyr Glu Val
165 170 175

Asp Tyr Thr Ser Arg Tyr Asn Glu Arg
180 185

<210> SEQ ID NO 16
<211> LENGTH: 573
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5443

<400> SEQUENCE: 16

Met Thr Asp Arg Leu Ala Gly Leu Phe Glu Ser Ala Val Ser Met Leu
1 5 10 15

Pro Leu Ser Glu Ser Arg Ser Met Asp Leu Phe Thr Glu Ile Thr Asn
20 25 30

Tyr Asp Glu Ser Ala Cys Asp Ala Trp Val Gly Arg Ile Arg Cys Gly
35 40 45

Asp Val Asp Arg Val Thr Leu Phe Arg Ala Trp Tyr Ser Arg Arg Asn
50 55 60

Phe Gly Gln Leu Ala Gly Thr Ala Gln Ile Ser Met Ser Thr Leu Asn
65 70 75 80

Ala Arg Val Pro Ile Gly Gly Leu Tyr Gly Asp Ile Thr Tyr Pro Val
85 90 95

Thr Ser Pro Leu Ala Ile Thr Met Gly Phe Ala Ala Ser Glu Ala Ala
100 105 110

Gln Gly Asn Tyr Ala Asp Ala Met Glu Ala Ile Asp Ala Gly Ala Val
115 120 125

Thr Gly Ser Glu His Leu Val Ser Trp Leu Lys Ala Val Ile Phe Gly
130 135 140

Ala Ala Glu Arg Trp Thr Asp Val Ile Asp Glu Val Lys Gly Ala Gly
145 150 155 160

Lys Trp Pro Asp Lys Phe Leu Ala Gly Ala Ala Ser Val Ala His Gly
165 170 175

```
Val Ala Ala Ala Ser Leu Gly Leu Phe Thr Glu Ala Glu Arg Arg Leu
            180                 185                 190

Thr Glu Ala Asn Asp Ser Pro Ala Gly Glu Ala Cys Ala Gln Ala Ile
        195                 200                 205

Ala Trp Tyr Leu Ala Met Ala Arg Arg Gly Gln Gly Asn Glu Glu Ala
    210                 215                 220

Ala Val Ala Leu Leu Glu Trp Leu Gln Thr Thr His Pro Ala Pro Lys
225                 230                 235                 240

Val Ser Ala Ala Leu Lys Asp Pro Ser Tyr Arg Leu Lys Thr Thr Asn
                245                 250                 255

Ala Glu Gln Ile Ala Ser Arg Ser Asp Pro Trp Asp Pro Thr Ser Val
            260                 265                 270

Val Thr Asp Asn Ser Gly Arg Glu Lys Leu Leu Ala Glu Ala Gln Glu
        275                 280                 285

Glu Leu Asp Arg Gln Ile Gly Leu Ser Arg Val Lys Ser Gln Leu Glu
    290                 295                 300

Arg Tyr Arg Ala Ala Thr Met Met Ala Arg Ile Arg Glu Ala Lys Gly
305                 310                 315                 320

Met Lys Val Ala Gln Pro Ser Lys His Met Ile Phe Thr Gly Pro Pro
                325                 330                 335

Gly Thr Gly Lys Thr Thr Ile Ala Arg Val Val Ala Asn Met Leu Ala
            340                 345                 350

Gly Leu Gly Val Ile Ala Glu Pro Lys Leu Val Glu Thr Ser Arg Lys
        355                 360                 365

Asp Phe Val Ala Glu Tyr Glu Gly Gln Ser Ala Ala Lys Thr Ala Lys
    370                 375                 380

Thr Ile Asp Gln Ala Leu Gly Gly Val Leu Phe Ile Asp Glu Ala Tyr
385                 390                 395                 400

Ala Leu Val Gln Glu Arg Asp Gly Arg Thr Asp Pro Phe Gly Gln Glu
                405                 410                 415

Ala Met Asp Thr Leu Leu Ala Arg Met Glu Asn Asp Arg Asp Arg Leu
            420                 425                 430

Val Val Ile Ile Ala Gly Tyr Ser Ser Asp Ile Asp Arg Leu Leu Glu
        435                 440                 445

Thr Asn Glu Gly Leu Arg Ser Arg Phe Ala Thr Arg Ile Glu Phe Asp
    450                 455                 460

Thr Tyr Ser Pro Glu Glu Leu Leu Glu Ile Ala Lys Val Ile Ala Ala
465                 470                 475                 480

Gly Asn Asp Ser Thr Leu Ser Thr Ala Ala Ala Asp Glu Leu Leu Gln
                485                 490                 495

Ala Ala Lys Thr Leu His Glu Arg Thr Leu Arg Gly Arg Pro Ala Leu
            500                 505                 510

Asp Ile Ala Gly Asn Gly Arg Tyr Ala Arg Gln Leu Val Glu Ala Ser
        515                 520                 525

Glu Gln Tyr Arg Asp Met Arg Leu Ala Gln Gly Leu Asp Ile Glu Ala
    530                 535                 540

Leu Asp Val Asp Arg Leu Gln Glu Ile Asn Gly Ala Asp Met Ala Glu
545                 550                 555                 560

Ala Ile Ala Thr Val His Ala His Leu Asn Met Arg Glu
                565                 570
```

<210> SEQ ID NO 17
<211> LENGTH: 481
<212> TYPE: PRT

<213> ORGANISM: Mycobacterium marinum
<220> FEATURE:
<221> NAME/KEY: MISC_FEATURE
<223> OTHER INFORMATION: M. marinum MMAR_5444

<400> SEQUENCE: 17

```
Met Gly Leu Arg Leu Thr Thr Lys Val Gln Val Ser Gly Trp Arg Phe
1               5                   10                  15

Leu Leu Arg Arg Val Glu His Ala Ile Val Arg Arg Asp Thr Arg Met
            20                  25                  30

Phe Asp Asp Pro Leu Gln Phe Tyr Ser Arg Ser Ile Ala Leu Gly Ile
        35                  40                  45

Val Val Ala Val Leu Ile Leu Ala Gly Ala Gly Leu Leu Ala Tyr Phe
    50                  55                  60

Lys Pro Ala Gly Lys Leu Gly Gly Ser Asn Leu Leu Thr Asp Arg Ala
65                  70                  75                  80

Thr Asn Gln Leu Tyr Val Leu Leu Ser Gly Gln Leu His Pro Val Tyr
                85                  90                  95

Asn Leu Thr Ser Ala Arg Leu Val Leu Gly Thr Pro Ala Ala Pro Val
            100                 105                 110

Thr Val Lys Ser Ser Glu Leu Ser Gln Leu Pro Leu Gly Gln Thr Ile
        115                 120                 125

Gly Ile Pro Gly Ala Pro Tyr Ala Thr Pro Val Ser Gly Asp Thr Thr
    130                 135                 140

Ser Thr Trp Thr Leu Cys Asp Thr Val Ser Arg Ala Gly Thr Ala Ser
145                 150                 155                 160

Ala Ser Val Glu Thr Ser Leu Leu Val Met Pro Leu Arg Ile Asp Ala
                165                 170                 175

Ala Ile Asp Pro Ile Glu Pro Asn Glu Ala Met Leu Ala Asp Tyr His
            180                 185                 190

Gly Gln Thr Trp Ile Val Thr Ser Lys Gly Arg His Ser Ile Asp Leu
        195                 200                 205

Asn Asp Arg Ala Leu Thr Ser Ala Val Gly Ile Pro Ile Thr Ala Gln
    210                 215                 220

Thr Val Pro Ile Ser Glu Gly Met Phe Asn Ala Leu Pro Ala Arg Gly
225                 230                 235                 240

Pro Trp Gln Leu Pro Pro Ile Pro Ala Ala Gly Glu Pro Asn Thr Leu
                245                 250                 255

Gly Leu Pro Glu Asp Leu Val Ile Gly Ser Val Phe Gln Ile His Thr
            260                 265                 270

Asp Lys Gly Pro Gln Tyr Tyr Val Val Leu Thr Asp Gly Ile Ala Ala
        275                 280                 285

Val Asn Gly Thr Thr Ala Ala Ala Leu Arg Ala Thr Gln Ser His Gly
    290                 295                 300

Leu Val Ala Pro Pro Ala Val Val Pro Ser Leu Val Val Arg Ile Pro
305                 310                 315                 320

Glu Arg Val Tyr Ser Ser Pro Leu Pro Asp Glu Thr Leu Asn Leu Met
                325                 330                 335

Ser Arg Pro Asp Asp Pro Val Leu Cys Trp Glu Trp Glu Arg Ser Ala
            340                 345                 350

Gly Asp Gln Ala Pro Asn Thr Thr Val Leu Thr Gly Arg His Leu Pro
        355                 360                 365

Ile Pro Pro Ser Ala Met Lys Thr Gly Leu Lys Gln Ile Gln Gly Arg
    370                 375                 380
```

```
Ser Thr Val Tyr Ile Asp Gly Gly Lys Phe Val Gln Leu Gln Ser Pro
385                 390                 395                 400

Asp Pro Arg Tyr Gly Glu Ser Met Tyr Tyr Ile Asp Pro Glu Gly Val
                405                 410                 415

Arg Tyr Gly Val Pro Asp Ala Asp Ser Ala Lys Ala Leu Gly Leu Gly
            420                 425                 430

Met Pro Lys Thr Ala Pro Trp Glu Ile Val Arg Leu Leu Val Asp Gly
        435                 440                 445

Pro Val Leu Ser Lys Asp Ala Ala Leu Leu Glu His Glu Thr Leu Pro
    450                 455                 460

Ser Asp Pro Asn Pro Arg Lys Val Pro Ala Gly Thr Pro Gly Ala Pro
465                 470                 475                 480

Gln


<210> SEQ ID NO 18
<211> LENGTH: 746
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5445

<400> SEQUENCE: 18

Met Thr Thr Lys Lys Phe Thr Pro Thr Ile Thr Arg Gly Pro Arg Leu
1               5                   10                  15

Thr Pro Gly Glu Ile Ser Leu Thr Pro Pro Asp Asp Leu Gly Ile Asp
            20                  25                  30

Ile Pro Pro Ser Gly Val Gln Lys Ile Leu Pro Tyr Val Met Gly Gly
        35                  40                  45

Ala Met Leu Gly Met Ile Val Ile Met Val Ala Gly Gly Thr Arg Gln
    50                  55                  60

Leu Ser Pro Tyr Met Leu Met Met Pro Leu Met Met Ile Val Met Met
65                  70                  75                  80

Val Gly Thr Leu Ala Gly Gly Ser Gly Gly Gly Ser Lys Lys Val Pro
                85                  90                  95

Glu Ile Asn Ala Asp Arg Lys Glu Tyr Leu Arg Tyr Leu Ala Gly Leu
            100                 105                 110

Arg Gly Arg Val Thr Thr Ser Ala Thr Ser Gln Val Ser Phe Phe Gly
        115                 120                 125

Tyr His Ala Pro His Pro Asp Asp Leu Leu Ser Ile Val Gly Thr Gln
    130                 135                 140

Arg Gln Trp Ser Arg Pro Ala Asn Ser Asp Phe Tyr Ala Ala Ala Arg
145                 150                 155                 160

Ile Gly Ile Gly Asp Gln Pro Ala Val Asp Arg Leu Leu Lys Pro Ala
                165                 170                 175

Val Gly Gly Glu Leu Ala Ala Ser Ser Ala Ala Pro Gln Pro Tyr Leu
            180                 185                 190

Glu Pro Val Ser His Met Trp Val Val Lys Phe Leu Arg Thr His Gly
        195                 200                 205

Leu Ile His Asp Cys Pro Lys Leu Val Gln Leu Arg Ser Phe Pro Thr
    210                 215                 220

Ile Ala Ile Gly Gly Asp Arg Pro Gly Ala Asp Arg Leu Leu Thr Ala
225                 230                 235                 240

Met Ile Cys His Leu Ala Val Phe His Pro Pro Asp Leu Leu Gln Ile
                245                 250                 255
```

```
Arg Val Leu Thr Glu Asp Pro Glu Asp Pro Asp Trp Ser Trp Leu Lys
            260                 265                 270

Trp Leu Pro His Val Gln His Gln Thr Glu Thr Asp Gly Ala Gly Pro
        275                 280                 285

Val Arg Met Ile Ser Thr Arg Pro Asp Gly Leu Ala Asp Leu Ala Ala
    290                 295                 300

Arg Gly Pro His Ala Pro Asp Thr Leu Pro Thr Gly Pro Tyr Val Val
305                 310                 315                 320

Val Leu Asp Leu Thr Gly Gly Lys Ala Gly Phe Pro Pro Asp Gly Arg
                325                 330                 335

Ala Gly Val Thr Val Ile Thr Leu Gly Asn His Arg Gly Ser Ala Tyr
            340                 345                 350

Arg Ile Arg Val Ala Glu Asn Gly Thr Ala Asp Asp Arg Leu Pro Gly
        355                 360                 365

Gln Gln Phe Arg Leu Val Thr Ala Ala Ala Asp Ser Met Thr Pro Gln
    370                 375                 380

Glu Ala Thr Arg Leu Ala Arg Lys Leu Ala Gly Trp Ser Ile Thr Gly
385                 390                 395                 400

Thr Ile Leu Asp Lys Thr Gln Arg Ile Gln Lys Lys Val Ala Thr Glu
                405                 410                 415

Phe His Gln Leu Val Asn Ala Lys Ser Val Glu Asp Ile Thr Pro Gly
            420                 425                 430

Arg Trp Arg Met Tyr Thr Asp Thr Asp Arg Asp Arg Leu Lys Ile Pro
        435                 440                 445

Phe Gly His Glu Leu Lys Thr Gly Asn Val Met Tyr Leu Asp Ile Lys
    450                 455                 460

Glu Gly Ala Glu Phe Gly Gly Gly Pro His Gly Met Leu Ile Gly Thr
465                 470                 475                 480

Thr Gly Ser Gly Lys Ser Glu Phe Leu Arg Thr Met Ile Leu Ser Leu
                485                 490                 495

Val Ala Met Thr His Pro Asp Gln Val Asn Leu Leu Leu Thr Asp Phe
            500                 505                 510

Lys Gly Gly Ser Thr Phe Leu Gly Met Glu Lys Leu Pro His Thr Ala
        515                 520                 525

Ala Val Ile Thr Asn Met Ala Glu Glu Ala Glu Leu Val Ser Arg Met
    530                 535                 540

Gly Glu Val Leu Thr Gly Glu Leu Asp Arg Arg Gln Ser Ile Leu Arg
545                 550                 555                 560

Gln Ala Gly Met Lys Val Gly Ala Ala Gly Ala Leu Ser Gly Val Ala
                565                 570                 575

Glu Tyr Glu Lys Tyr Arg Glu Arg Gly Ala Asp Leu Pro Pro Leu Pro
            580                 585                 590

Thr Leu Phe Val Val Val Asp Glu Phe Ala Glu Leu Leu Gln Ser His
        595                 600                 605

Pro Asp Phe Ile Gly Leu Phe Asp Arg Ile Cys Arg Val Gly Arg Ser
    610                 615                 620

Leu Arg Val His Leu Leu Leu Ala Thr Gln Ser Leu Gln Thr Gly Gly
625                 630                 635                 640

Val Arg Ile Asp Lys Leu Glu Pro Asn Leu Thr Tyr Arg Ile Ala Leu
                645                 650                 655

Arg Thr Thr Ser Ser His Glu Ser Lys Ala Val Ile Gly Thr Pro Glu
            660                 665                 670

Ala Gln Tyr Ile Thr Asn Lys Glu Ser Gly Val Gly Phe Leu Arg Val
```

675 680 685

Gly Met Glu Asp Pro Ile Lys Phe Ser Thr Leu Tyr Ile Ser Gly Pro
690 695 700

Tyr Val Pro Pro Ala Thr Ala Glu Thr Asn Gly Asp Gly Ser Gly Pro
705 710 715 720

Ser Thr Gln Phe Ala Lys Arg Ala Leu Gln Ile Arg Glu Phe Thr Ala
725 730 735

Ala Pro Val Leu Glu Glu Ala Leu Thr Pro
740 745

<210> SEQ ID NO 19
<211> LENGTH: 591
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5446

<400> SEQUENCE: 19

Met Thr Ala Glu Pro Glu Val Arg Thr Leu Arg Glu Val Ile Leu Asp
1 5 10 15

Gln Leu Ser Thr Val Glu Ser Arg Ala Tyr Lys Met Trp Leu Pro Pro
20 25 30

Leu Val Asp Pro Thr Pro Leu Asp Glu Leu Val Ala Arg Asp Arg Arg
35 40 45

Gln Pro Leu Arg Phe Ala Leu Gly Ile Met Asp Glu Pro Arg Arg His
50 55 60

Leu Gln Asp Val Trp Gly Val Asp Val Ser Gly Ala Gly Gly Asn Ile
65 70 75 80

Gly Ile Gly Gly Ala Pro Gln Thr Gly Lys Ser Thr Leu Leu Gln Thr
85 90 95

Leu Val Met Ser Ala Ala Ala Thr His Ser Pro Arg Lys Val Gln Phe
100 105 110

Tyr Cys Ile Asp Leu Gly Gly Gly Gly Leu Ile Tyr Leu Glu Asn Leu
115 120 125

Pro His Val Gly Gly Val Ala Gly Arg Ser Glu Pro Asp Lys Val His
130 135 140

Arg Val Val Ala Glu Met Gln Ala Val Met Arg Gln Arg Glu Ala Thr
145 150 155 160

Phe Lys Glu His Arg Val Gly Ser Ile Ala Met Tyr Arg Gln Leu Arg
165 170 175

Asp Asp Pro Asn Gln Ala Val Ala Ser Asp Pro Tyr Gly Asp Val Phe
180 185 190

Leu Ile Ile Asp Gly Trp Pro Ala Phe Val Ser Glu Phe Pro Asp Leu
195 200 205

Glu Gly Gln Val Gln Asp Leu Ala Ala Gln Gly Leu Ser Phe Gly Val
210 215 220

His Thr Ile Leu Ser Thr Pro Arg Trp Thr Glu Leu Lys Ser Arg Val
225 230 235 240

Arg Asp Tyr Leu Gly Thr Lys Ile Glu Phe Arg Leu Gly Asp Val Asn
245 250 255

Glu Thr Gln Ile Asp Arg Ile Thr Arg Glu Ile Pro Ala Asn Arg Pro
260 265 270

Gly Arg Ala Val Ser Met Glu Lys His His Leu Met Ile Gly Val Pro
275 280 285

-continued

Arg Leu Asp Gly Val His Ser Ala Asp Asn Leu Val Glu Ala Ile Thr
    290                 295                 300

Ala Gly Val Ala Gln Ile Ala Ala Gln His Thr Asp Lys Ala Pro Pro
305                 310                 315                 320

Val Arg Thr Leu Pro Glu Arg Ile His Leu His Glu Leu Asp Pro Asn
                325                 330                 335

Pro Pro Gly Pro Glu Ser Asp Tyr Arg Thr Arg Trp Glu Ile Pro Ile
            340                 345                 350

Gly Leu Arg Glu Ser Asp Met Glu Val Ala Tyr Ser His Met His Thr
        355                 360                 365

Asn Pro His Leu Leu Ile Phe Gly Ala Ala Lys Ser Gly Lys Thr Thr
    370                 375                 380

Ile Ala His Ala Ile Ala Arg Ala Ile Cys Ala Arg Asn Ser Pro Asp
385                 390                 395                 400

Gln Val Arg Phe Met Leu Ala Asp Tyr Arg Ser Gly Leu Leu Asp Ala
                405                 410                 415

Val Pro Asp Thr His Leu Leu Ser Ala Gly Ala Ile Asn Arg Asn Ser
            420                 425                 430

Ala Thr Leu Asp Glu Ala Val Lys Ala Leu Ala Ala Asn Leu Lys Asn
        435                 440                 445

Arg Leu Pro Pro Ala Asp Leu Thr Thr Ala Gln Leu Arg Ser Arg Ser
    450                 455                 460

Trp Trp Ser Gly Phe Asp Val Val Leu Leu Val Asp Asp Trp His Met
465                 470                 475                 480

Ile Val Gly Ala Ala Gly Gly Met Pro Pro Met Ala Pro Leu Ala Pro
                485                 490                 495

Leu Leu Pro Ala Ala Thr Asp Ile Gly Leu His Ile Ile Val Thr Cys
            500                 505                 510

Gln Met Ser Gln Ala Tyr Lys Ala Thr Met Asp Lys Phe Val Gly Ala
        515                 520                 525

Ala Phe Gly Ser Gly Ala Pro Thr Met Phe Leu Ser Gly Asp Lys Gln
    530                 535                 540

Glu Phe Pro Ser Ser Glu Phe Lys Val Lys Arg Arg Pro Pro Gly Gln
545                 550                 555                 560

Ala Phe Leu Val Ser Pro Asp Gly Lys Glu Val Ile Gln Ala Pro Tyr
                565                 570                 575

Ile Glu Pro Pro Glu Glu Val Phe Ala Ala Pro Pro Ser Pro Gly
            580                 585                 590

<210> SEQ ID NO 20
<211> LENGTH: 98
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5447

<400> SEQUENCE: 20

Met Glu Gln Lys Ser His Gly Ala Ala Ile Ala Asp Ile Gly Thr Leu
1               5                   10                  15

Leu Ser Gly Asn Ala Arg Ile Gly Val Thr Ser Asp Ala Ala Ala Leu
            20                  25                  30

Ala Ser Val Thr Gly Val Val Pro Ala Gly Ala Asp Glu Val Ser Thr
        35                  40                  45

Gln Ala Ala Thr Ala Phe Ala Ala Glu Gly Ala Gln Leu Leu Ala Ser
    50                  55                  60

Ser Ser Ala Ala Gln Arg Glu Ile His Arg Ala Gly Glu Ser Pro His
65 70 75 80

Arg Ile Ala Pro Asn Pro Ala Glu Val Ser Asp Gly Ala Ala Ser Val
85 90 95

Ile Val

<210> SEQ ID NO 21
<211> LENGTH: 367
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5448

<400> SEQUENCE: 21

Met Leu Trp His Ala Met Pro Pro Glu Leu Asn Thr Ala Arg Leu Met
1 5 10 15

Ala Gly Ala Gly Pro Ala Pro Met Leu Ala Ala Ala Ala Gly Trp Glu
20 25 30

Ala Leu Ala Ala Ala Leu Asp Ala Gln Ala Val Glu Leu Thr Ala Arg
35 40 45

Leu Asn Ser Leu Gly Glu Ala Trp Thr Gly Gly Gly Ser Glu Lys Ala
50 55 60

Leu Ala Ala Ala Leu Pro Met Val Thr Trp Leu Gln Thr Ala Ser Thr
65 70 75 80

Gln Ala Lys Thr Arg Gly Leu Gln Ala Gly Ala Gln Ala Ala Ala Tyr
85 90 95

Met Gln Ala Met Ala Thr Thr Pro Ser Leu Pro Glu Ile Phe Ala Asn
100 105 110

His Ile Thr Asn Val Ile Leu Asn Ala Thr Asn Phe Phe Gly Ile Asn
115 120 125

Thr Val Pro Ile Ala Phe Asn Glu Met Asp Tyr Phe Val Arg Met Trp
130 135 140

Asn Gln Ala Ala Leu Ala Met Asp Val Tyr Gln Ala Glu Thr Thr Ala
145 150 155 160

Asn Thr Leu Phe Glu Gln Leu Glu Pro Met Thr Ser Ile Leu Asp Pro
165 170 175

Ala Thr Ala Gln Ser Met Pro Thr Ser Ser Thr Pro Leu Leu Asp Met
180 185 190

Ala Ser Gln Val Thr Gly Ile Pro Ser Ser Glu Leu Gln Gln Thr Ala
195 200 205

Thr Gln Val Ala Glu Ala Ser Gly Pro Met Gln Gln Leu Ala Gln Pro
210 215 220

Ala Gln Gln Met Thr Ser Ala Phe Ser Asn Thr Gly Ser Ser Gly Asn
225 230 235 240

Gly Ala Asp Glu Glu Gly Phe Arg Met Gly Leu Leu Gly Ala Gly Ala
245 250 255

Leu Ser Asn His Pro Leu Ala Gly Gly Ser Gly Pro Thr Thr Gly Ala
260 265 270

Gly Leu Leu Arg Gly Glu Ser Leu Pro Gly Ala Gly Gly Thr Leu Thr
275 280 285

Arg Thr Pro Leu Ile Ser Glu Leu Val Glu Lys Pro Met Gly Pro Ser
290 295 300

Val Gln Pro Ala Ala Ala Ala Gly Ser Ser Ala Ser Ser Gly Ala Ala
305 310 315 320

```
Pro Val Gly Ala Gly Gly Met Gly Ala Gly Ala Gly Ala Gly Ala Gly
                325                 330                 335

Gly Ser Ser Arg Pro Gly Met Ala Ala Pro Ala Thr Leu Thr Gln Glu
            340                 345                 350

Arg Asp Glu Ala Asp Glu Asp Asp Trp Asp Asp Glu Asp Asp Trp
        355                 360                 365


<210> SEQ ID NO 22
<211> LENGTH: 100
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5449

<400> SEQUENCE: 22

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Ala Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Ala Glu Leu Asp Glu Ile Ser Thr Asn Ile Arg Gln Ala Gly
65                  70                  75                  80

Val Gln Tyr Ser Arg Ala Asp Asp Glu Gln Gln Gln Ala Leu Ser Ser
                85                  90                  95

Gln Met Gly Phe
            100


<210> SEQ ID NO 23
<211> LENGTH: 95
<212> TYPE: PRT
<213> ORGANISM: Mycobactrium marinum
<220> FEATURE:
<221> NAME/KEY: MISC_FEATURE
<223> OTHER INFORMATION: M. marinum MMAR_5450

<400> SEQUENCE: 23

Met Thr Glu Gln Gln Trp Asn Phe Ala Gly Ile Glu Ala Ala Ser Ser
1               5                   10                  15

Ala Ile Gln Gly Asn Val Thr Ser Ile His Ser Leu Leu Asp Glu Gly
            20                  25                  30

Lys Gln Ser Leu His Lys Leu Ala Ala Ala Trp Gly Gly Ser Gly Ser
        35                  40                  45

Glu Ala Tyr Arg Gly Val Gln Gln Asn Trp Asp Ser Thr Ala Gln Glu
    50                  55                  60

Leu Asn Asn Ser Leu Gln Asn Leu Ala Arg Thr Ile Ser Glu Ala Gly
65                  70                  75                  80

Gln Ala Met Ser Ser Thr Glu Gly Asn Val Thr Gly Met Phe Ala
                85                  90                  95


<210> SEQ ID NO 24
<211> LENGTH: 879
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5451
```

<400> SEQUENCE: 24

```
Met Pro Ala Asp Tyr Asp Glu Leu Phe Gln Pro Ala Glu Gly Ser Gly
1               5                   10                  15

Pro Pro Asp Asp Glu Thr Gly Gln Thr Phe Phe Asp Pro Gly Thr Ala
            20                  25                  30

Tyr Pro Pro Pro Val Lys Pro Asn Gly Asp Gly His Ser Ala Pro Lys
        35                  40                  45

Asp Trp Ser Arg Ala Phe Pro Pro Ala Glu Asp Glu Ser Pro Ser Asp
    50                  55                  60

Ser Ala Glu Pro Ala Ala Gly Pro Ala Lys Ser Pro Leu Pro Pro Met
65                  70                  75                  80

Pro Ile Gly Gly Pro Ala Pro Thr Pro Pro Glu Pro Pro Pro Ala Pro
                85                  90                  95

Pro Glu Leu Pro Pro Ala Pro Pro Glu Pro Pro Pro Ala Arg Pro Glu
            100                 105                 110

Ala Pro Pro Gln Ala Pro Thr Ala Glu Ala Glu Pro Pro Asp Glu Ala
        115                 120                 125

Ile Pro Val Ser Gly Pro Pro Pro Gly Gly Lys Ser Pro Leu Pro Pro
    130                 135                 140

Met Pro Ile Gly Gly Pro Pro Pro Ala Ser Pro Glu Pro Pro Ala Ala
145                 150                 155                 160

Pro Pro Glu Pro Thr Ala Pro Ala Glu Pro Pro Gln Pro Pro Glu Ala
                165                 170                 175

Ala Ala Gln Pro Pro Gln Ala Val Glu Glu Gln Ala His Ala Thr Ala
            180                 185                 190

Glu Pro Pro Ala Ala Pro Asn Pro Pro Arg Pro Pro Met Pro Ile Gly
        195                 200                 205

Gly Pro Pro Pro Thr Pro Pro Ala Ala Pro Glu Pro Gln Gln Asp Ile
    210                 215                 220

Ala Glu Glu Pro Ala Pro Ala Ala Ala Glu Ala Pro Ala Ala Pro Pro
225                 230                 235                 240

Lys Ser Pro Leu Pro Pro Met Pro Val Ser Gly Pro Pro Pro Glu Pro
                245                 250                 255

Pro Glu Leu Pro Pro Ala Pro Pro Glu Pro Thr Ala Ser Ala Glu Pro
            260                 265                 270

Pro Gln Pro Pro Gln Ser Val Glu Glu Gln Ala His Ala Thr Ala Glu
        275                 280                 285

Pro Pro Ala Ala Pro Lys Pro Thr Arg Pro Pro Met Pro Ile Gly Gly
    290                 295                 300

Pro Pro Pro Thr Pro Glu Pro Gln Gln Gly Ala Pro Gln Pro His Gln
305                 310                 315                 320

Asp Ile Ala Glu Glu Pro Asn Pro Ala Ala Ala Glu Ala Pro Ala Ala
                325                 330                 335

Pro Pro Lys Ser Pro Arg Pro Pro Met Pro Val Asn Gly Pro Ala Pro
            340                 345                 350

Thr Arg Pro Glu Pro Pro Leu Pro Pro Gly Pro Pro Arg Arg Arg Ala
        355                 360                 365

Gln Pro Pro Thr Ala Pro Pro Asn Gln Pro Gly Gln Pro Lys Pro Ile
    370                 375                 380

Ser Gly His Pro Pro Pro Pro Pro Arg Pro Ala Ala Phe Ala Pro Pro
385                 390                 395                 400

Ala Arg Gly Ala Thr Pro Asn Arg His Glu Ser Ala Glu Pro Pro Pro
```

-continued

```
                405                 410                 415

Pro Arg Arg Val Arg Ile Gly Gly Pro Pro Gln Pro Pro Gly Pro Pro
            420                 425                 430

Glu Ala Glu Ser Glu Ala Pro Arg His Ser Arg His Ala Arg Arg Thr
        435                 440                 445

His Arg Tyr Arg Pro Glu Pro Glu Thr Asp Asp Leu Glu Ala Thr Ala
    450                 455                 460

Val Arg Pro Leu Pro Thr Arg Glu Pro Met Arg Arg Asn Gly Pro Ala
465                 470                 475                 480

Ala Asp Glu Ser Ser Thr Ala Ser Phe Ala Trp Leu Gln Gln Ser Gln
                485                 490                 495

Pro Thr Leu Asp Arg Pro Ser Gly Pro Met Pro Ala Ala Pro Gly Ala
            500                 505                 510

Pro Val Glu Ser Ala Pro Gly Arg Ala Asp Gly Arg Arg Ala Arg Arg
        515                 520                 525

Arg Ala Glu Ser Arg Thr Ser Ala Ala Ser Thr Pro Ser Pro Leu Val
    530                 535                 540

Pro Thr Arg Ala Gln Pro Pro Gly Pro Thr Arg Ala Gln Pro Pro Arg
545                 550                 555                 560

Thr Ala Ala Pro Ala Gln Pro Ala Thr Glu Pro Leu Pro Asp Ala Gly
                565                 570                 575

Ala Pro Ala Glu Gln Ser Lys Lys Pro Asn Lys Pro Val Pro Gln Arg
            580                 585                 590

Gly Trp Arg Arg Trp Val Tyr Ala Val Thr Arg Ile Asn Phe Gly Leu
        595                 600                 605

Ser Pro Asp Glu Lys Tyr Glu Leu Asp Leu Arg Thr Arg Ile Gly Arg
    610                 615                 620

Lys Pro Arg Gly Ser Tyr Gln Ile Ala Ile Leu Gly Leu Lys Gly Gly
625                 630                 635                 640

Ala Gly Lys Thr Thr Thr Thr Val Thr Leu Gly Thr Thr Leu Thr His
                645                 650                 655

Val Arg Gly Asp Arg Ile Leu Val Leu Asp Ala Asp Pro Gly Ala Gly
            660                 665                 670

Asn Leu Ala Glu Arg Ser Gly Arg Ser Ser Pro Ser Ser Ile Ala Asp
        675                 680                 685

Leu Leu Ala Asp Pro Arg Leu Ser His Tyr Asn Asp Val Arg Ala His
    690                 695                 700

Thr Ser Val Asn Ala Ala Asn Leu Glu Ile Leu Pro Thr Ala Glu Tyr
705                 710                 715                 720

Thr Ser Ala Gln Arg Gly Leu Ser Gly Glu Asp Leu Arg Ser Ala Val
                725                 730                 735

Asp Thr Val Ser Lys Phe Tyr Asn Leu Val Leu Ala Asp Cys Gly Ala
            740                 745                 750

Gly Leu Phe Asp Pro Val Thr Leu Gly Val Leu Asp Thr Ala Ser Ala
        755                 760                 765

Ile Val Ile Leu Thr Asn Val Ser Ile Asp Ser Ala Arg Gln Ala Ala
    770                 775                 780

Ile Ala Leu Asp Trp Leu Arg Lys His Gly Tyr Gln Asp Leu Ala Ser
785                 790                 795                 800

Arg Ala Cys Val Ala Ile Asn His Val Ala Val Gly Glu Thr Asn Val
                805                 810                 815

Ser Glu Gln Gln Leu Val Arg Asp Phe Glu Gln Gln Leu Gln Pro Gly
            820                 825                 830
```

Arg Val Val Val Leu Pro Trp Asp Arg His Ile Ala Ala Gly Thr Glu
835 840 845

Ile His Leu Asp Gln Leu Gly Pro Val Tyr Arg Arg Arg Val Leu Glu
850 855 860

Leu Ala Ala Ala Leu Ser Asp Asp Phe Glu Arg Ala Gly Arg Arg
865 870 875

<210> SEQ ID NO 25
<211> LENGTH: 479
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5452

<400> SEQUENCE: 25

Met Thr Asp Leu Val Leu Pro Ala Ala Ala Pro Met Glu Ser Tyr Val
1 5 10 15

Asp Glu Thr Val Ala Ile Leu Ala Asp Leu Leu Glu Asp Thr Pro Ala
20 25 30

Glu Val Leu Ala Gly Phe Asp Phe Glu Ala Gln Gly Val Trp Thr Phe
35 40 45

Ala Arg Pro Gly Phe Pro Pro Leu Lys Leu Asp Gln Ser Leu Asp Glu
50 55 60

Ala Gly Val Val Asp Gly Ser Leu Leu Thr Leu Val Leu Ala Ser Arg
65 70 75 80

Thr Glu Arg Tyr Arg Pro Leu Val Glu Asp Val Ile Asp Ala Ile Ala
85 90 95

Val Leu Asp Glu Ser Pro Glu Phe Asn Arg Thr Ala Leu Glu Arg Phe
100 105 110

Leu Ala Val Ala Ile Pro Leu Phe Ala Leu Pro Ile Thr Ala Val Ala
115 120 125

Met Arg Ala Trp Trp Gln Thr Gly Arg Ser Val Phe Trp Pro Leu Ala
130 135 140

Ile Gly Leu Ile Gly Leu Ala Ala Leu Ala Gly Ser Phe Val Ala Lys
145 150 155 160

Arg Phe Tyr Gln Asn Ser Arg Leu Ala Glu Ser Leu Leu Val Thr Ser
165 170 175

Tyr Gly Val Ile Ala Ala Ala Ala Ala Ile Ala Val Pro Leu Pro Arg
180 185 190

Gly Phe His Ser Leu Gly Ala Pro Gln Leu Ala Ala Ala Ala Thr Ala
195 200 205

Val Leu Phe Ile Thr Leu Met Met Arg Gly Gly Pro Tyr Lys Arg His
210 215 220

Asp Ile Ala Ala Phe Val Val Ile Thr Ser Ile Ala Val Ile Ser Ala
225 230 235 240

Ala Val Ala Phe Gly Tyr Gly Tyr Gln Gln Trp Val Pro Ala Gly Ala
245 250 255

Ile Ala Phe Gly Leu Phe Ile Val Thr Asn Ala Ala Lys Leu Thr Val
260 265 270

Ala Val Ala Arg Ile Ala Leu Pro Pro Ile Pro Val Pro Gly Glu Thr
275 280 285

Val Asp Asn Glu Glu Leu Leu Asp Pro Ile Thr Ala Gln Asp Ala Thr
290 295 300

Asn Glu Glu Thr Pro Thr Trp Gln Ala Ile Ile Ala Ser Ala Pro Ala 305 310 315 320

Ser Ala Ala Arg Leu Thr Glu Arg Ser Lys Leu Ala Lys Gln Leu Leu
325 330 335

Val Gly Tyr Val Thr Ala Gly Thr Leu Ile Leu Ala Val Gly Ser Ile
340 345 350

Ala Val Val Val His Gly His Phe Phe Ile His Ser Met Ile Val Ala
355 360 365

Gly Leu Ile Thr Val Ile Cys Ser Phe Arg Ser Arg Leu Tyr Ala Asp
370 375 380

Pro Trp Cys Ala Trp Ala Leu Leu Ala Ala Thr Val Ala Ile Pro Thr
385 390 395 400

Gly Leu Ala Val Lys Leu Ser Leu Trp Tyr Pro His Tyr Ala Trp Leu
405 410 415

Leu Leu Thr Ile Tyr Leu Ala Ala Ala Leu Val Thr Leu Ile Ser Val
420 425 430

Gly Ala Met Asn Gln Val Arg Arg Val Ser Pro Val Met Lys Arg Ala
435 440 445

Leu Glu Leu Phe Asp Gly Ala Met Val Ala Ser Ile Val Pro Leu Leu
450 455 460

Leu Trp Ile Thr Gly Val Tyr Asp Leu Val Arg Asn Ile Arg Phe
465 470 475

<210> SEQ ID NO 26
<211> LENGTH: 278
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5453

<400> SEQUENCE: 26

Met Ala Glu Pro Leu Ala Val Asp Pro Ala Arg Leu Ile Ala Ala Gly
1 5 10 15

Ser Lys Leu Ala Glu Leu Val Phe Pro Ala Pro Pro Ala Pro Ile Ala
20 25 30

Ala Thr Gly Gly Asp Pro Val Ser Ala Ala Ile Asn Asp Thr Met Pro
35 40 45

Gly Ile Glu Ser Leu Val Ser Asp Gly Met Pro Gly Val Thr Ala Ala
50 55 60

Leu Lys Arg Thr Ala Ser Ser Met Ser Thr Ala Ala Asp Ile Tyr Ala
65 70 75 80

Lys Ala Asp Gln Ala Leu Gly Asp Ala Leu Thr Gln Tyr Gln Phe Gly
85 90 95

Gly Asp Gly Gln Ala Leu Gly Ala Ser Gly Ala Asn Ala Val Ala Gln
100 105 110

Ser Gln Ala Gly Gln Thr Val Gln Ser Leu Ala Ala Pro Ala Ala Gly
115 120 125

Leu Leu Gly Ala Pro Val Ala Gln Ala Leu Ala Ala Pro Ala Thr Gly
130 135 140

Leu Leu Gly Val Pro Ala Ala Ala Ala Thr Gln Ile Gly Glu Ala Val
145 150 155 160

Ser Ala Gln Ala Glu Ala Leu Ser Pro Arg Val Ala Ala Thr Ile Pro
165 170 175

Gln Leu Val Gln Leu Ala Pro Gln Ala Gly Gln Met Ala Gln Gln Ala
180 185 190

-continued

```
Ser Pro Ile Ala Gln Thr Ile Ser Gln Ser Ala Gln Gln Gly Ser Ser
        195                 200                 205

Gln Gly Gly Ala Ala Pro Ala Gln Leu Val Ser Asp Thr Lys Pro Asp
    210                 215                 220

Glu Asp Ala Glu Leu Ala Asp Glu Thr Lys Glu Gly Glu Glu Asp Ala
225                 230                 235                 240

Met Ala Ala Ala Gly Ala Glu Gly Ala Ala Ala Gly His Ala Thr Leu
                245                 250                 255

Val Ser Ala Pro Val Glu Ser Thr Gly Gly Gly Glu Thr Ser Thr Gly
            260                 265                 270

Ser Val Ser Ala Pro Ile
        275


<210> SEQ ID NO 27
<211> LENGTH: 298
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5454

<400> SEQUENCE: 27

Met His Pro Asp Glu Ala Ala Thr Tyr Asp Arg Met Leu Asp Asp Leu
1               5                   10                  15

Leu Asn Arg Phe Ala Pro Asp Ala Gly Pro Phe Glu Pro Asp Gly Phe
            20                  25                  30

Glu Ser Asp Ala Trp Glu Thr Gln Phe Asp Gly Phe Glu Ser Asp Ala
        35                  40                  45

Gly Glu Ile Glu Arg Glu Ala Glu Ala Gly Ala Ala Asp Asn Pro His
    50                  55                  60

Glu Leu Cys Arg Gly Thr Val Val Cys Ala Ser Thr Leu Thr Ile Leu
65                  70                  75                  80

Gly Val Met Trp Gly Trp Leu Gly Asp Ser Pro Pro Glu Gln Gly Asp
                85                  90                  95

Arg Leu Ala Ser Ser Gly Ser Leu Phe Asp Asp Val Gly Ala Gln Val
            100                 105                 110

Ala Ala Leu Asp Pro Asp Gly Gly Trp Arg Gly Asn Ala Ala Gln Ala
        115                 120                 125

Tyr Trp Val Gln Asn Leu Ala Gln Ser Arg His Ala Thr Leu Met Ala
    130                 135                 140

Glu Leu Asp Arg Leu Thr Ala Gly Leu Val Ser Ser Gln Ala Asp Ala
145                 150                 155                 160

Val Lys Gln Ala Arg Glu Arg Leu Ser Val Leu Ile Ala Val Val Leu
                165                 170                 175

Gly Val Leu Met Val Cys Ala Gly Leu Glu Leu Gly Gly Pro Glu Gly
            180                 185                 190

Gln Leu Pro Ser Phe His Ile Ala Val Ala Ala Cys Gly Val Val Gln
        195                 200                 205

Val Ala Ala Ala Ala Thr Leu Ile Gly Leu Ala Asn Lys Thr Ser Ser
    210                 215                 220

Asn Ala Ser Ser Leu Arg Ala Ala Thr Gln Arg Ala Thr Glu Met Leu
225                 230                 235                 240

Ala Ala Arg Ser Ala Arg Leu Asp Ala Ile Pro Gly Pro Ala Gly Met
                245                 250                 255

Thr Ala Pro Asp Val Gly Thr Pro Pro Ser Gly Ala Arg Pro Arg Leu
            260                 265                 270
```

```
Asp Val Ala Gly Asn Thr Ala Arg Ser Arg Arg Thr Pro Asp Arg Gly
        275                 280                 285

Ala Ala Phe Ala Glu Leu Ser Asp Arg Ser
    290                 295


<210> SEQ ID NO 28
<211> LENGTH: 776
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5455

<400> SEQUENCE: 28

Met Gly Ile Pro Arg Pro Thr Gly Glu Tyr Ala Gly Arg Met Leu Glu
1               5                   10                  15

Ala Gly Gly Trp Pro Asp Ala Asp Glu Asp Ile His Tyr Asp Arg Ala
            20                  25                  30

Arg Glu Tyr Asn Arg Val Leu His Leu Phe Thr Asp Val Met Asp Ala
        35                  40                  45

Cys Arg His Gln Gln Val Glu Val Phe Asp Gly Gly Val Trp Ser Gly
    50                  55                  60

Gly Ala Ala Ser Ala Ala Asn Gly Ala Leu Gly Gly Asn Leu Glu Gln
65                  70                  75                  80

Met Ser Thr Leu Gln Asp Tyr Leu Ala Thr Val Ile Thr Trp His Gln
                85                  90                  95

His Val Ala Gly Leu Ile Ala Glu Ala Lys Ala Asn Ile Asp Asn Asn
            100                 105                 110

Val Asp Gly Ala His Arg Glu Ile Arg Val Leu Glu Gly Asn Ala Asp
        115                 120                 125

Leu Asp Pro Glu Glu Arg Lys Ala Ala Ile Ala Ser Leu Ile Arg Ser
    130                 135                 140

Ala His Glu Ala Asn Ser Gly Leu Val Ala Glu Ala Ala Glu Gln Val
145                 150                 155                 160

Leu Ala Ser Arg Asn Trp Lys Pro Pro His Asn Ala Leu Lys Asp Leu
                165                 170                 175

Leu His Gln Val Thr Pro Pro Ala Pro Gly Ile Pro Ser Val Thr Val
            180                 185                 190

Pro Thr Pro Gly Gln Pro Ala Pro Arg Pro Pro Gly Pro Lys Pro Phe
        195                 200                 205

Glu Pro Thr Pro Val Asn Pro His Lys Pro Val Thr Pro Gly Gly Pro
    210                 215                 220

Gly Thr Pro Val Asn Pro Lys Pro Gly Ala Pro Val Val Pro Thr Pro
225                 230                 235                 240

Gly Gly Pro Thr His Pro Val Thr Pro Gly Ile Pro Gly Thr Pro Gly
                245                 250                 255

Thr Pro Gly Ile Pro Gly Ile Pro Gly Thr Pro Ile Thr Pro Gly Thr
            260                 265                 270

Pro Ile Thr Pro Gly Lys Pro Val Thr Pro Val Thr Pro Gly Lys Pro
        275                 280                 285

Lys Pro Gly Lys Pro Asp Thr Pro Val Leu Pro Val Glu Pro Thr Pro
    290                 295                 300

Ala Pro Ala Pro Ala Pro Ala Pro Ala Pro Ala Pro Ala Pro Ala Pro
305                 310                 315                 320

Ala Pro Ala Pro Ala Pro Ala Pro Ala Pro Gln Pro Ala Pro Ala Pro
```

```
                325                 330                 335

Gly Pro Gly Pro Gln Pro Gly Pro Ala Asp Pro Gly Ala Ser Pro Gln
            340                 345                 350

Pro Ala Pro Ser Gln Pro Gly Ser Pro Ser Thr Pro Gly Gln Pro Ser
        355                 360                 365

Thr Asp Pro Ala His Val Lys Pro Ala Ala Ala Thr Glu Thr Ser Thr
    370                 375                 380

Ala Pro Ser Thr Gln Pro Ser Gly Pro Ser Gly Pro Ala His Gly Asp
385                 390                 395                 400

Asp Ser Ser Gly Gly Gly Ala Ala Ala Pro Ala Ala Ser Ala Met Pro
                405                 410                 415

Gly Gly Gly Arg Gly Val Ser Ala Gly Ser Ser Ser Gly Leu Ser Ser
            420                 425                 430

Ala Gly Ala Ser Ser Ser Thr Ser Gln Ser Ala Ala Ser Gly Ala Gly
        435                 440                 445

Ser Arg Ala Ala Ser Gly Arg Ala Pro Val Glu Ser Gly Gly Arg Gly
    450                 455                 460

Pro Asn Thr Ala Ala Pro Arg Pro Ala Ala Ala Arg Thr Ala Ser Pro
465                 470                 475                 480

Thr Arg Pro Ala Pro Glu Arg Pro Lys Pro Asp Glu Lys Glu Lys Ser
                485                 490                 495

Glu Ala Pro Asp Ala Val Thr Pro Ser Pro Met Val Pro Val Ser Ala
            500                 505                 510

Ala Arg Ala Ala Arg Asp Ala Ile Ala Ser Ala Ser Arg Arg Ser Gln
        515                 520                 525

Lys Lys Asp Pro Leu Arg Leu Ala Arg Arg Ile Ala Ala Ala Leu Asn
    530                 535                 540

Ala Pro Asp Thr Tyr Asn Lys Gly Asp Tyr Gly Phe Phe Trp Ile Thr
545                 550                 555                 560

Ala Val Thr Thr Asp Gly Asp Ile Val Val Ala Asn Ser Tyr Gly Leu
                565                 570                 575

Ala Tyr Ile Pro Glu Asn Val Glu Leu Pro His Lys Val Tyr Met Ala
            580                 585                 590

Ser Ala Asp His Ala Ile Pro Ala Asp Glu Gln Ala Arg Phe Ala Thr
        595                 600                 605

Tyr Pro Val Leu Ala Val Gln Gly Trp Ala Ala Phe His Asp Leu Lys
    610                 615                 620

Leu Arg Ala Val Ile Gly Thr Ala Glu Gln Leu Ala Asn Ser Asp Ala
625                 630                 635                 640

Gly Ala Ala Lys Ile Ile Leu Glu Ala Asp Asp Ile Pro Glu Ser Gly
                645                 650                 655

Lys Met Thr Gly Arg Pro Arg Leu Glu Val Val Asp Pro Ser Ala Ala
            660                 665                 670

Ala Gln Leu Ala Glu Thr Glu Asp Leu Arg Leu Leu Glu Leu Leu Pro
        675                 680                 685

Pro Ala Pro Ala Asp Ala Asn Pro Pro Asp Asp Glu Arg His Met Phe
    690                 695                 700

Trp Phe Asp Leu Met Lys Pro Met Thr Ser Asn Ala Thr Gly Arg Glu
705                 710                 715                 720

Val Ala His Leu Arg Ala Phe Arg Ala Tyr Ala Glu His Cys Gln Glu
                725                 730                 735

Ile Ala Leu His Gln Ala Tyr Ser Ala Ala Asp Ala Glu Ala Gln Arg
            740                 745                 750
```

Pro Ala Val Ala Asp Trp Leu Tyr Trp Arg Tyr Val Ala Gly Leu Leu
755 760 765

Ala Asn Ala Leu Ala Asp Ala Ser
770 775

<210> SEQ ID NO 29
<211> LENGTH: 115
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5456

<400> SEQUENCE: 29

Met Thr Ser Met Glu Met Asp Pro Gln Val Ala Gln Val Leu Ala Leu
1 5 10 15

Ala Ala Arg Phe Gln Ser Ala Leu Asp Gly Thr Leu Asn Gln Met Asn
20 25 30

Thr Gly Asn Phe Arg Gly Lys Asp Asp Thr Glu Thr Val Glu Val Thr
35 40 45

Ile Asn Gly His Gln Trp Leu Thr Ala Val Arg Ile Asp Asp Gly Leu
50 55 60

Leu Lys Glu Val Gly Pro Glu Val Val Ser Ala Arg Val Asn Gln Ala
65 70 75 80

Leu Lys Asn Ala Gln Ala Ala Ala Ser Lys Tyr Asn Asp Ala Ala Gly
85 90 95

Glu Lys Leu Thr Ala Val Leu Ser Ser Met Ser Gln Thr Met Asn Asn
100 105 110

Gly Met Val
115

<210> SEQ ID NO 30
<211> LENGTH: 454
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5457

<400> SEQUENCE: 30

Met Ser Gln Pro Gln Thr Val Thr Val Asp Gln Gln Glu Ile Leu Asn
1 5 10 15

Arg Ala Asp Glu Val Glu Ala Pro Met Ala Thr Pro Pro Thr Asp Val
20 25 30

Pro Gln Ala Pro Ser Gly Leu Thr Ala Ala Asn Asn Ala Ala Glu Gln
35 40 45

Leu Ala Val Ser Ala Asp Asn Val Arg Leu Tyr Leu Gln Ala Gly Glu
50 55 60

Arg Glu Arg Gln Arg Leu Ala Thr Ser Leu Arg Asn Ala Ala Ala Ala
65 70 75 80

Tyr Gly Glu Val Glu Asp Glu Ser Ala Thr Ala Leu Asp Asn Asp Gly
85 90 95

Asn Gly Glu Val Asp Ala Gln Ser Ala Gly Gly Ala Gly Ala Gly Gln
100 105 110

Thr Glu Ser Leu Glu Glu Thr Pro Lys Val Ala Ala Ala Gly Glu Ser
115 120 125

Asp Phe Thr Asp Leu Lys Thr Ala Ala Thr Lys Leu Glu Ser Gly Asp
130 135 140

Gln Gly Thr Ser Met Val Asn Phe Ala Asp Gly Trp Asn Asn Phe Asn
145 150 155 160

Leu Ser Leu Gln Arg Asp Ile Lys Arg Phe Arg Ile Phe Glu Asn Trp
165 170 175

Glu Gly Asp Ala Ala Thr Ala Cys Glu Ala Ser Met Asp Gln Gln Lys
180 185 190

Glu Trp Ile Leu His Met Ala Lys Leu Ser Ala Ser Leu Ala Lys Gln
195 200 205

Ala Asn Phe Met Ala Gln Leu Gln Leu Trp Ala Arg Arg Gly His Pro
210 215 220

Thr Leu Ala Asp Ile Val Glu Leu Glu Arg Leu Ala Lys Asp Pro Asp
225 230 235 240

Tyr Gln Glu Gln Ala Ile Lys Leu Tyr Ala Glu Tyr Gln Glu Thr Ser
245 250 255

Glu Lys Val Leu Ser Glu Tyr Asn Thr Lys Ala Asp Leu Glu Pro Val
260 265 270

Asn Pro Pro Lys Pro Pro Ala Ala Ile Lys Ile Asp Pro Pro Pro Pro
275 280 285

Ala Gln Pro Gln Gly Leu Ile Pro Gly Phe Leu Met Pro Pro Gly Asp
290 295 300

Gly Ser Thr Gly Leu Ala Ser Gly Met Thr Pro Pro Met Ile Pro Pro
305 310 315 320

Thr Gly Gly Ala Gly Gly Thr Pro Asp Val Asn Thr Ala Glu Leu Thr
325 330 335

Ser Ala Gly Arg Glu Ala Ala Ser Asn Leu Ser Lys Gly Leu Gly Val
340 345 350

Lys Pro Met Ser Leu Gly Gly Gly Gly Gly Gly Leu Gly Gly Met Pro
355 360 365

Met Gly Asp Ala Ala Leu Ala Gly Gly Glu Ser Val Arg Pro Ala Ala
370 375 380

Ala Gly Asp Ile Ala Gly Ala Gly Gln Gly Gly Gly Ala Ala Gly Arg
385 390 395 400

Gly Met Ala Gly Gly Gly Met Gly Met Pro Met Gly Gly Ala Gly Gln
405 410 415

Gly Gln Gly Gly Ala Lys Ser Lys Gly Ala Gln Gln Asp Glu Glu Ala
420 425 430

Leu Tyr Thr Glu Asp Arg Glu Trp Thr Glu Ala Val Ile Gly Asn Arg
435 440 445

Arg Arg Gln Asp Asn Lys
450

<210> SEQ ID NO 31
<211> LENGTH: 465
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5458

<400> SEQUENCE: 31

Met Arg Asn Pro Phe Ser Ser Ile Arg Phe Arg Val Ser Thr Gly His
1 5 10 15

Thr Leu Val Val Ala Val Leu Ala Pro Pro Cys Ile Met Met Phe Leu
20 25 30

His Met Arg Tyr Trp Trp Val Gly Ile Ala Leu Val Ala Leu Gly Val

-continued

```
        35                  40                  45

Ile Val Ala Thr Val Thr Phe Ser Gly Arg Arg Val Thr Gly Trp Val
    50                  55                  60

Ala Thr Val Phe Ala Trp Leu Arg Arg Arg Arg Arg Pro Pro Asp Val
65                  70                  75                  80

Pro Ser Glu Pro Val Val Gly Ala Thr Val Lys Pro Gly Asp His Val
                85                  90                  95

Ala Val Arg Trp Arg Arg Asp His Leu Ile Ala Val Ile Glu Leu Lys
            100                 105                 110

Pro Arg Pro Phe Thr Pro Thr Val Ile Val Asp Gly Lys Ala His Thr
        115                 120                 125

Asp Asp Val Leu Asp Thr Arg Leu Leu Glu Asp Leu Leu Ser Val His
    130                 135                 140

Cys Pro Asp Leu Glu Ala Asp Val Val Ser Ala Gly Tyr Arg Val Gly
145                 150                 155                 160

Asn Thr Ala Ser Glu Glu Val Val Ser Leu Tyr Gln Arg Val Ile Gly
                165                 170                 175

Ala Asp Pro Ala Pro Ala Asn Arg Arg Thr Trp Ile Met Leu Arg Ala
            180                 185                 190

Asp Pro Glu Gln Thr Arg Lys Ser Ala Gln Arg Arg Glu Ala Gly Leu
        195                 200                 205

Ala Gly Leu Ala Arg Tyr Leu Val Ala Ser Ala Thr Arg Ile Ala Asp
    210                 215                 220

Gly Leu Ala Ser Asn Gly Val Asp Ala Val Cys Gly Arg Ser Phe Asp
225                 230                 235                 240

Asp Tyr Asp Arg Ala Thr Asp Ile Gly Tyr Val Arg Glu Lys Trp Ser
                245                 250                 255

Met Ile Lys Gly Ala Asp Ser Tyr Thr Ala Ala Tyr Thr Ala Pro Gly
            260                 265                 270

Gly Pro Asp Leu Trp Trp Ser Ala Arg Ala Asp His Thr Ile Thr Arg
        275                 280                 285

Val Arg Ile Ala Pro Gly Met Pro Pro Arg Ser Thr Val Leu Leu Thr
    290                 295                 300

Thr Val Gly Lys Pro Lys Thr Pro Arg Gly Phe Ser Arg Leu Phe Gly
305                 310                 315                 320

Ser Gln Arg Pro Ala Leu Glu Gly Gln Thr Leu Val Ala Asn His His
                325                 330                 335

Cys Gln Leu Pro Ile Gly Ser Ala Gly Val Leu Ile Gly Glu Thr Val
            340                 345                 350

Asn Arg Arg Pro Val Tyr Met Pro Phe Asp Asp Val Asp Ala Thr Val
        355                 360                 365

Asn Leu Gly Asp Ala Gln Thr Phe Thr Gln Phe Ala Val Arg Ser Ala
    370                 375                 380

Ala Ala Gly Gly Val Val Thr Val Gly Pro His Phe Glu Gln Phe Ala
385                 390                 395                 400

Gly Leu Ile Gly Ala His Val Gly Ala Glu Ala Lys Val Val Trp Pro
                405                 410                 415

Asn Ala Thr Thr Tyr Leu Gly Ala His Pro Gly Ile Asp Arg Val Ile
            420                 425                 430

Leu Arg His Asn Leu Val Gly Thr Pro Arg His Arg Lys Leu Pro Ile
        435                 440                 445

Arg Arg Val Ser Pro Pro Glu Glu Ser Arg Phe Gln Met Ala Leu Pro
    450                 455                 460
```

Lys
465

<210> SEQ ID NO 32
<211> LENGTH: 468
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5459

<400> SEQUENCE: 32

Met Gln Ala Gly Leu Thr Arg Ala Cys Gln Ser Phe Thr Ala Ala Arg
1 5 10 15

Glu Arg Ser Asp Ser Gly Val His Arg Thr Leu Leu Thr Met Val Ala
20 25 30

Leu Ala Leu Leu Thr Ala Pro Pro Ala Leu Ala Ile Asp Pro Pro Ser
35 40 45

Ile Asp Pro Gly Ala Val Pro Pro Asp Val Thr Gly Pro Asp Gln Pro
50 55 60

Thr Glu Gln Arg Val Leu Cys Thr Ser Pro Thr Thr Leu Pro Asp Ser
65 70 75 80

Ser Phe His Asp Pro Pro Trp Ser Asn Ala Tyr Met Gly Val Gly Glu
85 90 95

Ala His Lys Phe Ala Thr Gly Ala Gly Val Thr Val Ala Val Ile Asp
100 105 110

Thr Gly Val Asp Ala Ser Pro Arg Val Pro Ala Glu Pro Gly Gly Asp
115 120 125

Phe Val Asp Gln Ala Gly Asp Gly Leu Ser Asp Cys Asp Ala His Gly
130 135 140

Thr Leu Thr Ala Ser Ile Ile Gly Gly Arg Pro Ala Pro Thr Asp Gly
145 150 155 160

Phe Val Gly Val Ala Pro Asp Val Arg Leu Leu Ser Leu Arg Gln Thr
165 170 175

Ser Glu Ala Phe Glu Pro Val Gly Ser Gln Pro Asn Pro Asn Asp Pro
180 185 190

Asn Ala Thr Pro Ala Ala Gly Ser Ile Arg Ser Leu Ala Arg Ala Val
195 200 205

Val His Ala Ala Asn Leu Gly Ala Gly Val Ile Asn Ile Ser Glu Ala
210 215 220

Ala Cys Tyr Lys Val Ser Arg Pro Ile Asp Glu Ile Ser Leu Gly Ala
225 230 235 240

Ala Ile Asp Tyr Ala Val Asn Ala Lys Asn Ala Val Val Val Val Ala
245 250 255

Ala Gly Asn Thr Gly Gly Asp Cys Ser Gln Asn Pro Met Pro Asp Ala
260 265 270

Ser Thr Pro Asn Asp Pro Arg Gly Trp Asn Lys Val Gln Thr Val Val
275 280 285

Thr Pro Ala Trp Tyr Ala Pro Leu Val Leu Thr Val Gly Gly Ile Gly
290 295 300

Gln Asn Gly Val Pro Ser Ser Phe Ser Met His Gly Pro Trp Val Gly
305 310 315 320

Val Ala Ala Pro Ala Glu Asn Ile Ile Ala Leu Gly Asp His Gly Glu
325 330 335

Pro Val Asn Ala Leu Gln Gly Arg Glu Gly Pro Val Pro Ile Ala Gly 340 345 350

Thr Ser Phe Ala Ala Ala Tyr Val Ser Gly Leu Ala Ala Leu Val Arg
355 360 365

Gln Arg Phe Pro Glu Leu Thr Pro Val Gln Val Met Asn Arg Ile Thr
370 375 380

Ala Thr Ala Arg His Pro Gly Gly Gly Ile Asp Asn Leu Val Gly Ala
385 390 395 400

Gly Val Val Asn Ala Val Ala Ala Leu Thr Trp Asp Ile Pro Pro Gly
405 410 415

Pro Ala Ser Val Pro Pro Ser Val Arg Arg Leu Pro Pro Pro Arg Ile
420 425 430

Glu Pro Gly Pro Asp His Arg Pro Ile Thr Met Val Ala Val Ser Val
435 440 445

Leu Gly Leu Thr Leu Val Leu Gly Leu Gly Thr Leu Ala Ala Arg Ala
450 455 460

Leu Arg Arg Arg
465

<210> SEQ ID NO 33
<211> LENGTH: 186
<212> TYPE: PRT
<213> ORGANISM: Mycobacterium marinum
<220> FEATURE:
<221> NAME/KEY: MISC_FEATURE
<223> OTHER INFORMATION: M. marinum MMAR_5460

<400> SEQUENCE: 33

Met Lys His Glu Phe Tyr Ser Leu Val Glu Arg His Gln Asp Gly Thr
1 5 10 15

Pro Asp Met Ile Gly Met Glu Ala Val Asn Gln Leu Leu Val Lys Leu
20 25 30

Glu Thr His Arg Phe Asp Phe Cys Phe Ile Gly Ala Gly Tyr Glu Asp
35 40 45

Gln Val Asp Glu Phe Leu Ser Val Asn Pro Gly Leu Ala Gly Arg Phe
50 55 60

Asn Arg Lys Leu Arg Phe Glu Ser Tyr Ser Pro Thr Glu Ile Val Glu
65 70 75 80

Ile Gly Gln Arg Tyr Ala Ala Pro Arg Ala Ser Leu Leu Asp Glu Ala
85 90 95

Ala Arg Glu Thr Phe Leu Asp Ala Ala Thr Thr Ile Arg Asn Tyr Thr
100 105 110

Thr Pro Gly Gly Gln His Gly Ile Asp Ala Met Gln Asn Gly Arg Phe
115 120 125

Ala Arg Asn Val Ile Glu Arg Ala Glu Gly Tyr Arg Asp Thr Arg Val
130 135 140

Val Ala Gln Lys Arg Ala Gly Arg Ala Val Ser Val Glu Asp Leu Gln
145 150 155 160

Met Ile Ala Ala Gly Asp Val Glu Ala Ala Val Arg Ser Val Cys Ala
165 170 175

Asp Asn Arg Asp Met Ala Ala Ile Val Trp
180 185

<210> SEQ ID NO 34
<211> LENGTH: 291
<212> TYPE: PRT
<213> ORGANISM: Mycobacterium marinum
<220> FEATURE:

<221> NAME/KEY: MISC_FEATURE
<223> OTHER INFORMATION: M. marinum MMAR_5461

<400> SEQUENCE: 34

```
Met Thr Asp Pro Leu Ile Leu Gln Thr Leu Ala Thr Leu Ser Arg Gly
1               5                   10                  15

His Gly Leu Phe Ala Gly Arg Leu Val Asp Glu Arg Ser Arg His Glu
            20                  25                  30

Pro Gln Leu Gln Ala Leu Ala Asp Ser Val Ser Gln Thr Arg Gly Asp
        35                  40                  45

Arg Leu Pro Asp Arg Ala Ala Ala Arg Ser His Ala Val Val Gln Ala
    50                  55                  60

Val Arg Arg Ser Ile Asp Thr Asp Arg Glu Leu Ala Gln Ile Met Ser
65                  70                  75                  80

Ile Ala Gln Thr Asp His Ala His Ala Arg Arg Ala Thr Arg Ala Ile
                85                  90                  95

Leu Gln Ala Ala His Ala Asp Ser Gly Leu Ala Ala Asp Thr Pro Leu
            100                 105                 110

Gly Arg Arg Glu Ala Met Val Arg Met Ala Ala Arg Leu Arg Ala Gln
        115                 120                 125

Arg Arg His Ile Val Arg Ser Arg Val Arg Ala Arg Gln Leu Val Leu
    130                 135                 140

Arg Leu Arg Arg Leu Arg Tyr Arg Gln Ala Ala Ala Arg Arg Gln His
145                 150                 155                 160

His His Val Pro Pro Thr Gly Arg Pro Ala Val Leu Ala Ala Ile Arg
                165                 170                 175

Lys Ala Leu Asp Ile Glu Gly Ile His Asp Pro Ala Ala Arg Ala Arg
            180                 185                 190

Trp Thr Arg Gly Met Asp Leu Val Ala Arg Arg Glu Ser Gly Tyr Asn
        195                 200                 205

Ala Ser Ala Val Asn Asp Trp Asp Ala Asn Ala Ser Gln Gly Thr Pro
    210                 215                 220

Ser Arg Gly Ala Trp Gln Phe Ile Ala Pro Thr Phe Ala Ala Tyr His
225                 230                 235                 240

Gln Leu Gly Thr Ser Thr Asn Ile Thr Asn Leu Val Ala Gln Ala Cys
                245                 250                 255

Ala Phe Ile Asn Tyr Ala Gln Gly Arg Tyr Gly Val Ala Ala Asp Ala
            260                 265                 270

Ser Asn Leu Ala Asp Arg Ile Gln Gln Ala Asp Pro Arg Arg Ser Pro
        275                 280                 285

Arg Gly Tyr
    290
```

<210> SEQ ID NO 35
<211> LENGTH: 1158
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5429

<400> SEQUENCE: 35

```
atgcaagacc tttctcagcg agtgctcgac gagctcaacg ccgcacaggc gaatccgcca      60

gcggcggaag aggagttgac cgatagtttc ctttcgaagc atcgaggaag cgttgtttgc     120

ttggggaccg acggcatcct tggtggcttg ctggcatggc ttggacatga gttccccgac     180
```

-continued

```
caggggggacc gcctggacag cagtgggtcg atgttcgacg gtgtcattgc ccagatcgcg    240

gcccttggtc ccgacggcgg ttggcagggc agcgcggccc gcgcctatgg ggctcgcaac    300

ctcgcccaat cccagcacac ggggctgatg gcggatctgg accgactcgc cgccgagctg    360

gtgtcagccc aagccgatga cgtgcacaaa gtgcgctcca ccctgtgggc actagtagcg    420

attgtgtcgg tcttgcttgt ggtttgcatt ggtttggaac tgcaggggcc cgagggccaa    480

cttgtgtcct tctattccgc actacccata tgcggtaccg cgttgtttgt cgccgctgtc    540

gccctgacct tcttggcggt cacgacgtcg cggaatgcca gcgccgtgca ggcggcgacg    600

cagcgattga ccgccatggt ggcggccctg accaccggcc ccgacgcagt tcccggttcg    660

cccgaaatgc ctactccccc aaaatattgc ctctcggagt tcgatctcgc cgaggacacc    720

gggcccaccc caccgcagct gcccgatctg ggctcggctt tcaccgactt acccggcgcc    780

cccgaatttc acctggccac cggaaccggc gcgggcctcc ccgacttcgg cgcaccgcag    840

ttacccatcc ccgcgctgac cggcctgcca accctgcccg gacccacaaa cctgaccgac    900

ctaaccagcg tcctagccgg cctgcccacg atcgctcaac tcagcaccac cctgagccaa    960

ctcaccaacc tcgccggacc caccagcacc accacccaac cggcccaaca gcacaccacc   1020

ccggccgacc accccaccca ggacgacgcc accgacacac ccgacaccgc cgccgcagcc   1080

accaccacca gcggcgagcg cgcacccctg ggcagcacaa cccgccccac ccaacaaaac   1140

caagacctcg tcgtgtga                                                  1158
```

<210> SEQ ID NO 36
<211> LENGTH: 1194
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5430

<400> SEQUENCE: 36

```
atgaacctca acggaacaat gaggaatctg attcgacgac taatcgcaga agacccagag     60

gggaacgaag aaaatcccca atggctgcgc cgaggcagcg ttgtttgcct ggtgaccgac    120

tgcatccttg gcggcgaact ggcatggctt ggacatgcgt cccccgacca aggtggttgc    180

ctggtcaaag gcgcggcgat gttcgacgac ctcggcgccc agatcgccgc tcttgttccc    240

gatagcggtt ggcagggcag cgcggcccgc tcctatgggg cccacaccct cgcccagtcc    300

cgacactcca cgctgatggc tgatctggac cggctcgccg ccgagctggt gtcatcccaa    360

gccgacgacg tgaagcaagc gcgcaccgca ctgtgggcag caatcggctt tgtctcggtc    420

tacctattga tttgcctcgg catagaactt caggggcccg agggccagct actctccttc    480

aacttcgccg tagtcgtatg cggtgccgtg ctaggtatct ctgctctcgt tctgcacgac    540

ttggcgaaga agacgtcgcg cagggccagc agtctgcaga cgactacgca gcgactgtcc    600

gacatggtgg cgggcctggc tacacggtcg gacatgattc ccggctcacc cgaaatgagc    660

ctgcccccag cgcattccct gtcagagttc catctcaccg atagcagcgc cgcctccccg    720

ccgcacctcc ccgatctgga ctcggctttc gccgacctac ccggcgcccc cgaatttcac    780

ctgcccaccg cggccggcgc cggcttgccc gacttcggcg caccgcagct gcccatcccc    840

gcgctgagcg gcctaccaac cctgcccgat ccgacagacc cgaccgacct atccagcatg    900

ctggccggcc tgcccacgat cacccagctg cccgccatcc tcagtcaact caacaacctc    960

gccgggccaa ccagcgccgt gagccaactg gccaacaccg ccacccaaca cgcacaaatg   1020
```

atctccaccc tggcccaaca gggcgcccat ccgcacacca ccctgaccga tcaccacacc 1080
acagacgaaa cccccgacac cgacgccgcc accgcagcca ccagcagcgg cgaacgcgca 1140
cccctggaca ccacaaccca ccccacccaa caccgcctag accacatcgt gtga 1194

<210> SEQ ID NO 37
<211> LENGTH: 1206
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5431

<400> SEQUENCE: 37
atgtatctca gtcaacttca gcgtttggtt cagcaaatct cgcgatgggt acgcggagat 60
ggaaatctgc agaacttcca agacatccaa gagggaggcg gaaatccgcc gccggcgcag 120
gagggggcgc ccgacaattc cccttgggcg cgtcgaggaa gcgttgtttg cggggtgacc 180
gagggcatcc tcggccttct actggcattg cttggagagg ccgtcccatc ccggggcgaa 240
tccctggacc gcagtggatc gatgttcgac ggtgtcagca cccagatcgc gacccttgat 300
cccgacggcg gttggcgggg caacgcagcg cgggcctacg ggccaagaa cctcgcccaa 360 tcccaacaca ccacgctgat cgctgatctg gaccggctca ccggcgagct ggtgtcatcc 420
caggccgacg ccgtgaagcg ggcacgcgac ctgctatcgg ccgaaatttg gattgtcttg 480
gtcttgcttg tggtttgcat tggcttggag ttgcacgggc ccgagggcca aatcctgtcc 540
ttccatatcg caatacccat atgcactatg gcggtgttta cggccgctac cgccctgggc 600
gtgttggcgg ccacgacgtc gcagaatgcc agcgccgtgc aagcggcgac gcagcgattg 660
accgccatgg cggcggccct gaccaccggg gcggacacag ttcccagttc gcccaaaatg 720
acctttccac caatacattc cctgtcggag ttcgatctca ccgaggccac cggccccacc 780
ccaccgcagc ttcccgatct gcagtcgacg ttggccgagt tacccggtgc cccgagttt 840 cacctggcca ccagggccgg cgcgggcttc cccgacttcg gcgcaccgca gctgcccatc 900
accgaattga ccggcctgcc aaccctgccc gatcccacaa acctgaccga cccaaccagc 960
atgctggccg acctgcccac gatcgcgcaa ctcagcacca ccctgagcca actcaccaac 1020
ctcgccggac ccaccagcgc caccacccaa ccggcgcaac agcacaccac cccggccgat 1080
caccgcaccc aagacgacgc caccaacacc cccgacaccg ccaccgccac tgcagccacc 1140
agcagcagtg aacgcgcacc gctggacacc caaacccacc cccaccggca gcgcctactg 1200
acttga 1206

<210> SEQ ID NO 38
<211> LENGTH: 537
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5432

<400> SEQUENCE: 38
atgaccgacc agcccgggta cgacgcccat aactatctag cgggactggg tttctccggc 60
cccgcaaccg gagagaccga ctccgccatc gacgcgttgc tcagctacgc accggcccaa 120
cccgaggaca ccggatccga catgtcagca atccttgggg cgaccgagga ggacaaaacc 180
gatgagtgcg aactgttcac ggtaaccaat cctcaaggga gcgtttcggt gtcggccgtc 240
atgggcgggg acatccaccg ggtcgagctg tcggacaagg tcgacaacat gtccgaaccg 300
aggcttgccg aggagatatt tgttcttgcg gacctggccc ggcagaaggc gcgggccgcg 360
cagcacgcct tcatgctcca aggcatggat gaagtggacg acgaagagca acgcgccgtg 420
ctgcgcgaaa tcgtcgagaa gacaatgaac ttgccgacgc ccgagcaggc ggccgcggca 480
gaagaagagg tgttcgccac ccgatacaag aacgacttca ctgcaacaac tggctag 537

<210> SEQ ID NO 39
<211> LENGTH: 315
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5433

<400> SEQUENCE: 39
atgaatgaca tgttgacgtt gcagcccgac gtcgtgaacc ggcttgccag tgggcacgac 60
gccaccgcaa caagtctgcg ggcagcgacg gcggcgcccg ccgggatcgg tgcgacagtc 120
gccgagaccc acggcccatt cacgtcgacc ttcaacaatg cactaagcgc ctacgaggca 180
gtccgcgcta gcgcggggcg agccctggag ggggtcgctg atgggctttc cacgaatctg 240
acccgggccc tcgccgccta caccgatacg gaccaacgtg gcgccgagat cctcgacgag 300
cagattgaca actga 315

<210> SEQ ID NO 40
<211> LENGTH: 339
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5434

<400> SEQUENCE: 40
atgaacctcg accccaccgc cgcacacctg ctcgcagggc tcacccaatt ccacaccgcc 60
ctgcaaaacc gcttccacca aatgaacgcc ggcaacttca aagcctcaga caacacccac 120
accgtgcagg tcaccctcaa cggatacaac tggctcaccg gcatccgcat ccaagacggc 180
ctcctcaaac aactcggctc ccaaggcgtc gcccaccgcg tcaaccaagc cctccacaac 240
gccaaacaag ccgtccacgc ctacgacaac gccgccaacc acgccctggc caccaccctg 300
gccaccctct ctgccgccat caaccaaacc cacccctaa 339

<210> SEQ ID NO 41
<211> LENGTH: 1347
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5435

<400> SEQUENCE: 41
atgtcgcagc cgtggatgct ggcggtggat cccagcgaga tcgtggccag ggccaccgag 60
gtggaagccc cgatcgctga tccgcccggc ggtgcggtgt tggccgcgtg cgccctggac 120
ccggcggttg cgggggccac acaactggcg ttgtcggccg agagcatgcg cgcttatctg 180
cagtcgggcg cccaagcgcg gcaacggctt gcgaagttca tgcgggacgc ggccaaggcc 240
tacgaacaga tcgacgaagg cgcggcaacg gctttgggca ccaacggcca cggcatcgga 300
gcaccgccgg tacccgcggg tacggacctg gctccggtcg cgctgagcga taccccctacc 360 gcgccagcag cgcctccgtt tccatatacc ggtgtcaaac tggccgcgat caacctcaac 420
aagcccgacc agggtgtatc gctgaagaag ttcgcccatg actggaatgc ctacaacctg 480
acaattcagc aggccctggg ccggttccgt gacttcgagg attgggaagg tgaagcggcc 540
gccgcggtgc aggccgcatt cgatcaacac cgggactggc tgcgcctgat ggcgcggttg 600
agtaccacga tggccaaaca agcctcaggc ctcgaacaag cccaccactg ggccattggt 660
caacacccga cattggcgga tatcaccacg ctagaagaac tccttcgtga ccccagagtg 720
cccgataaaa aaccgttaat gaaggtctac gcgcaatgtc agaagaaatc cgaggaagtg 780
ctgaccggat acgccaccag gacaatcacc gagcccgtgc aaccaccccg accaccggca 840
gcccccaccc acaacgaccc caaaccccca ccgccgctac caccgctacc gcccggcggg 900
gaccccacac tgcccttcac cggcacacca ccgatgccga cgatgccgtt caccccaccc 960
cccgccgcaa cccccgacac cactgaagcc gcccgcgccg cggccacact cgccaccggc 1020
cccaccgtca aacccgccgc actcggcggg ggcgccggcg ccgccatccc cttgaccgcc 1080
cccctgggcg cgggccccac acccccgagt gcgccaggcg ccctgggccc cggcaccgcg 1140
cccaccggcc gcccccctggg cgcgggcccc atggggggca tgcccatggg ggcaaacggg 1200
caagcccaaa acgccaaaac caaacgcacc cagcaagacg accgagccct ctacaccgaa 1260
caacgaccct ggaccgaagc gctcatcggc cccgcccgac cccacctcac cacccccaac 1320
agcaccaaca cggagcacca accatga 1347

<210> SEQ ID NO 42
<211> LENGTH: 1314
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5436

<400> SEQUENCE: 42
atgaacgaac gcgaggagtt tctgcgagac cgggtccggc cggaccagcc cagcgttccc 60
gacgcgagtc ggtctcatca gcgttccggt atgcaccgga cggcgacgga cgcgtcaggc 120
cctccggtag cgcccactca ccaacctcgg cccgccccgc cccgtccgcc gactccgcag 180
ccttcacccg ttccaccgcg gggggccaac ccgcatcccc cgccgccacc ggcgccacct 240
tcggtcccgg cgccgccgcc cccaccggtg gcgcatccac ccaacgggca caactcgccg 300
ccacaagctg ccccacacga accgatgccg gaggttccac cgccaagcct ttgggccgag 360
cccacaccgg cgcgcacccc cggcgagcct ccatccaccg accacggctg gcgccacatc 420
attcgggtcg cgtcgttcgg gctgatcaac ccacgcccat cggcggcgca gcgcgatgcc 480
gccgaattcg aagcggccat tcgagccccg ttgcgcggca cccacaaggt tggtgtgctg 540
ggcaagggcg gcgtcggcaa gacgtcagtc gccgccagca tcgggtcact cctggccgaa 600
ttgcgacagc aggaccgcat cgtggcagtc gacgccgata ccgcttttgg ccggttgagc 660
agcaggatcg atcccacggc gcgtggctcg ttctgggacc tgaccgccga taggaatctg 720
gcgtcgttcg ccgatgtggt tgcccgcttg ggccgaaacg ctgcgggcct gcacgttttg 780
cccggcgagg cggccgtcgg tggtcgccgg ttacttgacc ccgcgattta tcgcgaagcg 840
gcgctacgac tcgaccgcca tttcaccatc tcgatcattg actgcggctc cacgatggac 900
gcgcccctaa ctcaggaagt gttgcgcgac ctagacgcgc ttatcgtggt gtcctccccc 960
tgggcggacg gtgcctcggc ggccgccaag acaatggaat ggctcgcgga ccgcaaactc 1020
agcggcttgc tgcggcgcag cgtcgtggtg ctcaacgatt cggacgggca ttccgacaag 1080
cgcacgcgtt cagtgcttgc gcgcgagttc gtcgaccatg gacagcaggt tgtcgaggtg 1140
ccttttgatc cgcatctgcg ccccggcggt gttatcgatg tgagccatga gttggagccg 1200
ggaacgcggc tgaagtttct gcaaatcgcc gcaacgatta ccggacactt cgccgcgcgg 1260
tccgctgccg acgacgaccc ccgtcccacc gaaaacgtag cgtctgagac ctag 1314

<210> SEQ ID NO 43
<211> LENGTH: 288
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5437

<400> SEQUENCE: 43
atgactgcaa ctgctctgta cgagattccg ctgggcgttt gcacgcagga ccccgaccgt 60
tggacgacaa cgcccgacga ggaggccaag acgctgtgtc gcgcgtgccc gcgtcggtgg 120
gcgtgtgcgc gggacgcggt tgagtcgccg ggtgcggaag gactttgggc gggtgttgtg 180
attccggaag caggccgggc gcgggcgttc gcgttgggcc aacttcggtc gctggcagag 240
cgcaacggtt tcccggcgcg cgagcggatc accgcccaat cggcatga 288

<210> SEQ ID NO 44
<211> LENGTH: 1158
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5438

<400> SEQUENCE: 44
atgttggtca gcggaacgcg cgccttgcca cccgcctcag tagccgcgag cgaggaatcg 60
acgtacatgc ccgacgccga atcgactgct cggccggccc tgcgagtcgc ccgtggcggc 120
gactcaccgg gcctggtaac gcccggtcac cgacccgtcg gccgcggcgc gctgaccaac 180
gcacgactgg atgatcccgt gttatcgcag acacatgtgc gagcggtttc cgatggtggg 240
cagcggcgga tcgtcaccaa cagcccaaac ggtatgttcg tcgacggaac acggaaaagt 300
tctgtggctg tcagcgacaa gaccattgtc cggttcggcg atcccactgg aggcaaggcg 360
ttgacgttcg aagtcgtcag gccctcgaat tcgcctgaag aagacagccg tgaacagcga 420
ccggccgagc aatcggactc tcagaccaac gaagccgatc ctggtgtggt tcgcgccggg 480
gccgccgccg cggcacgacg ccgagagctc gacatcagtc agcgcagcct ggcagccgac 540
gggatcatca acgccggcgc actgatcgcg ttcgagaagg gccgcagctg gccacgcgaa 600
cgcacccgcg ccaagctgga agaagtcctg cagtggcccg cgggaaccat cgcgcggata 660
cgccagggcg agtccgttgc gccagagccc gctcccgaag ccagcgtgga ggcgccgacc 720
tccgacggcc cagcgtcgct gatcgcgcag gcggttgccg ccgcggtcga tacctgcagc 780
ctcgcgatcg ccgcattgcc cgcacccgag gaacctgact tcaccgagcg ggccgcaccg 840
atccttgccg atttgcgcca gctcgagggc atcgccgtcc aggcgacccg catcagccgc 900
atcacaccgg aactgatcaa ggcgcttggt gctgttcggc gctatcacga caaattgatg 960
acgctcagcg caaccgcacc aggagccaca ctggcgcagc gtttgtatgc cgcccggcgg 1020
cgggcgaatc tgtccacttc ggaaaccgcg caagccgccg gagtgaccga agaattgatc 1080
gtccgcgcgg aagccgagga agctttgcat gccgaagccg ccgaggctat tgaagcgctc 1140
atccgtcaaa tcaattga 1158

<210> SEQ ID NO 45
<211> LENGTH: 1257
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5439

<400> SEQUENCE: 45
atggtgccaa agggaagcgg tctttgcaag acaacaagta atttcatttg gggtcagttg 60
cttttgcttg gagaaggcat ccccgacccg ggcgatatct tcaacaccgg ttcgacgctc 120
ttcaaaggaa tcgccgacaa gatgggtctg gcgattccgg gcaccaactg gctcggccag 180
gcggcggacg cctatttgaa ccagaacatc gctcaagaac ttcgcgcgaa ggtgatgggt 240
gacgtcgact atctgaccgg caacctgatt tcgaatcagg ccgaatatgt gtcgaacacc 300
cgcgacgtgc tgcgcgcgat gaagaagatg atcgacggcg tctacaaggt ctgcaaaggc 360
ctcgaaaagg tgccgatact cggctggttg tggtcgtggg agctcgccct gccgatgtcg 420
ggcattgcga tggccaccgt cggcggcgcg ctgctttacc tgaccatcat gacgttgatg 480
aacctgacca acctgaaggg cctgctcggc aggttggtcg aaatgttggc cagcctgcca 540
tcgctgatcg gcggcctact cccgaacatt ccgggcatca tcgacgacct gtggccgccc 600
aagttgcccg accttcccat cccgggtctg ccgaacatcc cgggcctgcc cgatttcacc 660
tggccaccca agatcgacat tccggattgg aacttgccga tcccggggct ccccggtttc 720
gaattcccgc cgacctcggg aatccccggc atcgacttcc cgttccccaa catcccgggc 780
ttgcccagct tccccagcct tcctgggttg ccgagcatcc cggacctgtt ccccggcttg 840
cccggcctgg gtgacctgtt ctccgggatc gggaaatggg gcacgttgcc cacctggacc 900
gacttggcgg ccctacccga cttcttgggt ggcttcgccg ggctacccag cctgagcttc 960
tccaacctgc tcggcttcgc ccaattgccc aacgtcggtt cgctgaccgc gacgatgggc 1020
cagctgcaac acctggtctc ggccgctggc ggacctggcc aactgggcag tatggcgggc 1080
cagcaggcca gcatgatctc gtcgcaggct tcccaaggcg gtcaacaggc caccctggtg 1140
agcgacaaga aggaagacga cgaagacggt gcggccgcgg gcagcgccgg tgcggaacgc 1200
gctcccatcg atgcgggaag caacacaggg caaggcaacg aggggaccct cctctag 1257

<210> SEQ ID NO 46
<211> LENGTH: 312
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5440

<400> SEQUENCE: 46
atgacaggac tactgaacgt cgtgccttca ttcttgaagg tgctggcggg catgcacaac 60
gagatagtcg gcgaactcaa atcggcgacc aacgtcgtga gcggaatcgg ctcgcgggtc 120
cagctgaccc acggctcatt cacctcgaat ttcaacgaca cgctcgtcga gttcgaaacc 180
acccgcaaca gcgccgggac aggcctgcag ggcgtcacgg gcaagttggc caacaatctg 240
atctcggccg ctggcgccta tctgaactcc gacgaagggc tcgctggcat catcgacaag 300
atttttggct ga 312

<210> SEQ ID NO 47
<211> LENGTH: 840
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5441

<400> SEQUENCE: 47
atgaccggtc cgctcgctac cggtcgcgcg ggcaccggtg acgatgtcgt cggagtcgag 60
gtaaccatcg acggcatgct ggtgatcgcg gaccggttac acctggtcga tttccctgtc 120
acgcttggga tccggccgaa catcccgcaa gaggatctgc gagagatcgt ctgggaccag 180
gtggcgcgcg accttactgc gcagggcgtg ttggaccaca atggccagcc gcatccggcg 240
gttgcggcga tggtcgacac gctcagcagg gcggaccgca ccttggaagg tcgctggtgg 300
cgccgcgacg ttggcggcgt gatggtgcgg ttcgtggtat gccgcaaggg cgaaagacat 360
gtcatcgcag ttcgcgatgg cgacatgctg gtactgcagc tggtggctcc gcgggtcggc 420
ctggcaggca tggtgacggc cgtgctgggc accgcggaac ccgccaatgt cgaaccgctg 480
accggcattg ccagcgaact gggtgagtgc accaacgccg cacagctgac ccgatatggg 540
ctcacgccga ccaccgcccg cctgtacacc gaaatcgtca ccaatccgaa gagctgggtg 600
gaaatcgtcg ccagcgaacg ccatccgggc ggtacgacca cccacaccaa ggctgccgcg 660
ggggtcttgg attcagcaca tggcaggctt gtctcgcttc cccgccaagt tggcggggaa 720
ctgtacggca gcttcctccc cggtaccgag cagaatctcc agcgggcgct ggacagtctg 780
ctcgaactac ttccgtcagg ctcgtggttg gatcgcgccg acgccaccgc ccgaggttga 840

<210> SEQ ID NO 48
<211> LENGTH: 558
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5442

<400> SEQUENCE: 48
gtggacctgc ccgggaacga cgactacaac caagatctcg gcgccctaga tttctccggc 60
ggcggtacgt ctgaggactc tggactcggt gcactcgacg agtacgcgcc ccccgagccc 120
caggaaaccg agcaagccgg agccgacctg gatgcacttc acgggctgac cgagaaggaa 180
gacgagcccg acattgcgat gttcaccgtg accaacccgc aagggagcgt gtcggtcacc 240
accatgatgg gtggcatcgt ccagcaagtt acggtgaccg acaaggctgc gaacatgtcg 300
gaatccgctc tggccgaaga gatctttgtc atcgctgatc tggcccgcca aaaggcgcgc 360
gccgcacaac acacgttcat ggtggaagcc atggccagcg aactgagcga cgagaccgaa 420
gaagaaggtg cgctgttgcg cgagttcgtc ggtatgacgc tcaacttgcc gacgccggag 480
gaagcagaag cggccgaagc cgaggtattc gccacccgct acgaggtcga ctacacctct 540
cgttacaacg aacggtga 558

<210> SEQ ID NO 49
<211> LENGTH: 1722
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5443

<400> SEQUENCE: 49
atgactgatc gcctggccgg tttgttcgaa agtgccgtca gcatgcttcc gctgtcggag 60
tcaaggtcca tggacctatt caccgagatc acaaactatg acgaatcagc gtgcgatgct 120
tgggtcggcc ggatccgatg tggcgatgtc gaccgggtga ctttgttccg tgcctggtac 180
tcgcgccgca acttcggtca gctggcaggc acggcgcaga tctcgatgag caccctcaac 240
gccagggtcc ccataggtgg tttgtacgga gacatcacct accccgttac ctcccccctg 300
gccatcacca tgggcttcgc cgcatccgaa gccgcgcagg gcaactacgc ggacgcgatg 360
gaggccatcg acgctggcgc ggtcaccggt tcggagcatc tggtgtcgtg gctcaaggcg 420
gtcatcttcg gcgctgccga gcgctggacc gacgttatcg atgaagtcaa gggtgccggg 480
aagtggccgg acaagttcct ggccggagcc gccagcgtcg cccatggggt tgcggcggcc 540
agccttggcc tgttcaccga agccgaacgc agactgaccg aagccaatga ctcaccggcc 600
ggcgaagcct gcgcgcaggc catcgcgtgg tatctggcca tggcccggcg gggccaaggc 660
aacgaggaag ccgcggtggc actgctggaa tggttgcaga ccacgcatcc ggctccgaaa 720
gtctctgctg cgttgaagga tccgtcctac cggctcaaga cgaccaacgc cgaacagatt 780
gcgtcccgtt cggatccatg ggatccgacc agcgtggtga ccgacaattc cggtcgcgaa 840
aagttgttgg ccgaagccca agaagaactc gaccgccaaa tcggattatc ccgggtaaaa 900
agccagctcg agcggtaccg cgcggcgacc atgatggctc gtatccgcga ggccaaaggc 960
atgaaagtcg cacagcccag caagcacatg atctttaccg ggccccctgg caccgggaag 1020
accacgatcg cgcgggtggt cgccaacatg ctcgccggac taggcgtcat cgccgaaccc 1080
aagctggtcg agacgtcacg taaagacttc gttgccgagt acgagggcca gtcagcagcc 1140
aagaccgcca agacgatcga tcaggctcta gggggcgtgc tgttcatcga cgaggcttac 1200
gccctcgtgc aggagcgcga cggacgcacc gacccgttcg gccaggaagc gatggatacc 1260
ctgctggccc ggatggagaa cgaccgcgat cgcttggtgg tcatcatcgc cggctacagc 1320
tccgacatcg atcggctgct ggaaaccaac gagggtctac gctcgcgatt tgccacccgt 1380
atcgaattcg acacctacag cccggaagag ctcctcgaga tcgcgaaagt cattgcggct 1440
gggaatgact cgacgctgag cacggcggcc gcggatgaac tcctgcaggc agccaaaacg 1500
ctgcacgaac gtacgttgcg ggccgtccg gctctcgaca tcgccggcaa cggccgatat 1560
gcgcgacaat tggttgaggc ctctgagcag taccgtgaca tgcggctagc acagggcctc 1620
gacatcgagg ccctcgatgt ggacagactg caagagatca acggcgcgga catggccgag 1680
gcaatcgcca cggtgcatgc acacctcaat atgagagagt ga 1722

<210> SEQ ID NO 50
<211> LENGTH: 1446
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5444

<400> SEQUENCE: 50
atggggcttc gcctgaccac caaggttcag gtaagcggct ggcgcttcct gcttcgccga 60
gtcgagcatg ccatcgtgcg gcgcgacacc cgcatgttcg atgatccgct gcagttctac 120
agccgctcga tagcgctggg catcgttgtc gccgtattga tcttggccgg tgccggcctg 180
ctggcctact tcaaaccagc tggaaaactt ggtggcagca acctgctgac cgaccgcgcg 240
actaaccagc tctatgtact gctgtccggg cagttgcacc ctgtctacaa cctcacctcg 300
gcgcgcctcg tgttgggcac ccctgccgcc cccgtcaccg tcaagtcctc cgaattgagc 360
cagttgccct tgggccaaac catcggaatc cccggcgccc cctacgccac cccggtttcc 420
ggggacacca cttcaacctg gaccctttgc gacaccgtca gccgggcggg taccgcctcc 480
gcctcggtcg agacatcgct gctggtgatg ccgctgcgga tcgatgccgc gatcgatccg 540
atcgagccca acgaggcgat gctggcggac tatcacggcc agacctggat cgtcacatca 600
aagggacgcc actcgatcga cctcaacgat cgtgcgctca catcggccgt gggcatcccc 660
atcaccgccc agacggtccc catttccgag ggaatgttca atgcgcttcc ggccaggggc 720
ccctggcaat tgccacccat ccccgccgcc ggagagccaa acaccctcgg gcttccggaa 780
gatttggtaa tcggatcggt gtttcaaatc cacaccgaca aggggccgca atattacgta 840
gtgctgaccg acggcatcgc cgcggtaaat ggcaccactg ccgcggcact gcgcgccact 900
cagtcccatg ggctggtggc gccgcccgcg gtggtgccga gcctggtcgt caggatcccc 960
gaacgggttt actcatcacc gctgcccgac gagaccctca acctcatgtc ccggccggac 1020
gacccggtct tgtgttggga atgggagcgt agcgctgggg accaggcccc caatacgacg 1080
gttctcaccg gacggcactt gcccatcccg ccctcggcca tgaagaccgg cctcaagcag 1140
attcagggca ggtcaaccgt ctatatcgac ggcgggaaat ttgttcagtt gcagtcaccc 1200
gatccccgat acggcgaatc gatgtactac atcgacccgg aaggggtgcg ctacggggtg 1260
cccgacgccg actcggccaa ggcgctgggc ctgggcatgc cgaagacggc gccgtgggag 1320
atcgttcgcc tcctggtgga cggtccagtg ttatccaaag acgccgctct gctcgaacac 1380
gaaacgttgc cctccgaccc caatcctcga aaagttccag ctgggacacc cggagcacct 1440
caatga 1446

<210> SEQ ID NO 51
<211> LENGTH: 2241
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5445

<400> SEQUENCE: 51
atgacgacaa agaaattcac cccaacgatc acccgtggcc cccggctcac cccgggcgag 60
atcagcctca cgccaccgga tgatctcggt atcgacatcc cgccgtcggg cgtgcagaag 120
atcctgccct acgtcatggg cggcgcgatg ctgggcatga tcgtgatcat ggttgccggc 180
ggcaccagac agctatcgcc atacatgctg atgatgcccc tgatgatgat cgtgatgatg 240
gtgggcacac tcgccggggg cagcggcggc ggcagcaaga aggtgcccga gatcaatgcg 300
gaccgcaagg agtacttgcg gtatctcgcc ggcctgcgcg gccgcgtaac gacgtcggcc 360
acctcccagg tctcgttctt cggctaccac gcgccccatc ccgacgatct tctgtccatc 420
gtcggcaccc agcggcagtg gtcgaggccg gccaacagcg acttctatgc ggcagcccgc 480
atcgggatcg gcgaccagcc ggcggtggac cggctactga agccggcggt cggcggcgag 540
ctggcggcca gcagcgcggc cccccagccc tatctcgagc cggtaagcca catgtgggtg 600
gtcaagttcc tgcgtaccca cgggttgatc cacgactgcc cgaaactcgt gcagctgcgc 660
agttttccaa cgatcgcgat cggcggtgat cgaccgggag ccgatcgact gttgaccgcg 720
atgatctgcc acctggcggt cttccatccg cccgacctgt tgcagatccg cgtcctcacc 780
gaggaccccg aggatcccga ctggtcctgg ttgaaatggc tgccacacgt ccagcaccag 840

```
accgaaaccg acggggccgg gccggtccgg atgatctcca cgcgcccgga cggcctcgcc    900
gacctggccg cccggggacc ccacgcgccc gacactctcc ccaccggtcc ctacgtcgtg    960
gtcctcgacc tgaccggcgg caaggcgggc ttcccgccag acggcagggc cggggtgacg   1020
gtaatcacgc tgggcaacca tcgcgggtcc gcctatcgca tcagagtggc cgagaacggc   1080
accgccgacg accggctgcc tgggcagcag ttccggctgg tgaccgcggc cgccgacagc   1140
atgacgccgc aggaggccac ccgcctcgcc cgcaagttgg ccggatggtc gatcaccgga   1200
accatcctcg acaagaccca acgtatccag aagaaggtcg cgaccgagtt ccatcagttg   1260
gtcaacgcca agagcgtcga ggacatcacc ccgggccgtt ggcgcatgta caccgacacc   1320
gatcgagacc ggctcaagat cccgttcggt cacgaactca agaccggcaa tgtcatgtac   1380
ttggacatca aggaaggtgc ggagttcggc ggcgggccgc acggcatgct catcggcacc   1440
accggttccg gcaaatccga gttcctgcgc accatgatcc tgtcgttggt ggcgatgacc   1500
caccccgatc aggtgaacct gctgcttacc gacttcaagg gcggctcgac atttctgggg   1560
atggagaagc tcccgcacac cgcggctgtg atcaccaaca tggccgagga agccgagctg   1620
gtaagccgga tgggcgaggt gctgaccggc gaactggacc gccgccagtc gatcctgcgt   1680
caggcgggga tgaaggtcgg cgcggccggc gcgctgtccg gcgtggccga gtacgagaag   1740
taccgcgaac gcggcgctga cctcccgccg ctgccgacac ttttcgttgt ggtggacgag   1800
tttgccgaac ttctgcagag tcacccggat ttcatcggcc tgttcgaccg aatttgccga   1860
gtcgggcgat cattgcgggt gcacctgcta ctggccaccc agtcactaca aaccggcggt   1920
gtccgcatcg acaagctcga acccaacctg acgtatcgca tcgcgttgcg taccaccagc   1980
tctcatgaat ccaaagcggt gatcggaacc ccggaggccc agtacatcac caacaaggaa   2040
agcggtgtcg gctttctccg ggtcggcatg gaggacccca tcaagttcag cacgctctat   2100
atcagtgggc catacgttcc gccggcgacc gctgaaacca acggcgatgg cagcggaccc   2160
agtacccagt tcgccaagcg agccttgcag atccgcgagt tcaccgcggc tccggttctc   2220
gaggaagcgc tgacaccatg a                                             2241
```

<210> SEQ ID NO 52
<211> LENGTH: 1776
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5446

<400> SEQUENCE: 52

```
atgactgccg aacctgaagt acggacgttg cgtgaggtca tcctcgacca gctcagcacc     60
gtcgagtcac gcgcctacaa gatgtggttg ccgccgctgg ttgatccgac cccgctcgac    120
gagctggtcg cccgcgatcg gcgacaacca cttcgcttcg cgctgggaat catggacgag    180
ccgcgccgcc acctgcagga cgtttggggc gtcgacgtgt cgggcgctgg cggaaacatc    240
ggtatcggcg gtgcccccca gaccggcaag tcgacactgc tgcagacgtt ggtcatgtcg    300
gccgctgcca cgcactcgcc gcgcaaggtc cagttctatt gcatcgacct cggtggtggc    360
ggcctgatct atctggagaa cctgccccat gtgggcgggg tcgcgggccg gtccgaaccc    420
gacaaagtcc accgggtggt cgcggagatg caagccgtga tgcgacaacg agaggccacc    480
ttcaaggaac accgggtcgg ctcgatcgcg atgtatcgcc agctgcgtga cgaccccaac    540
caggccgtcg cctcagaccc ctacggcgat gtattcctga tcatcgatgg atggcccgcc    600
```

ttcgtcagtg agtttcccga cctcgaaggc caggtccagg acctggccgc acaggggctg 660
tcctttggtg tgcacacgat tctgtccacg ccgcggtgga cggaattgaa atcacgtgtc 720
cgcgactacc tgggcaccaa gatcgaattc cggctcggcg acgtcaacga aacccagatc 780
gaccgcatca cccgggagat cccggcgaac cgcccgggtc gggcggtgtc catggaaaag 840
caccacctga tgatcggggt gcccaggctc gacggtgtgc acagcgccga caacctggtg 900
gaggcgataa cggcgggcgt agctcaaatc gcagcccagc acacggacaa ggcacctccg 960
gtacgaaccc tgccggaacg catccacctc cacgagctgg atcccaaccc tcccgggccc 1020
gaatccgact accgcacccg ctgggagatc ccgatcggat tgcgcgaatc cgacatggaa 1080
gtggcttaca gccacatgca caccaacccg cacctgctca tcttcggtgc cgccaagtcg 1140
ggcaagacga ccattgccca cgcgatcgca cgcgccatct gcgctcgaaa cagccccgac 1200
caggtgcggt tcatgctcgc cgactatcgc tccggactcc tcgatgcggt gcccgacaca 1260
cacctgctct cggccggagc catcaaccgc aacagcgcga cgttggacga ggccgtcaaa 1320
gccctggccg ccaacttgaa gaatcggctg cccccagccg acctcacgac ggctcaactg 1380
cgctcgcgtt cgtggtggag cggattcgac gttgtgctgc tcgtcgacga ctggcacatg 1440
attgtcggcg ctgccggcgg catgcccccg atggcgccac ttgcgccctt attgccggcg 1500
gcgaccgata tcggcttgca catcattgtg acctgtcaga tgagccaggc ctacaaggcg 1560
accatggaca agttcgtcgg tgccgcattc ggttcgggcg ctccaacaat gttcctttcc 1620
ggtgacaagc aggaattccc ctccagcgag ttcaaggtca agcggcgccc ccccggccag 1680
gcgtttctgg tctcgcccga cggcaaagag gtcatccagg cccccttacat cgagccgcca 1740 gaagaagtgt tcgcagcacc cccaagcccc ggttag 1776

<210> SEQ ID NO 53
<211> LENGTH: 297
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5447

<400> SEQUENCE: 53
atggaacaaa agtcacacgg cgcggcgatc gccgacatcg gcacactatt gagcggcaac 60
gctcgcattg gtgtgacctc cgatgcggca gcgttggcgt cggtgaccgg ggtggttcca 120
gctggagcag acgaggtgtc gacgcaagcg gccacagcct tcgccgccga gggcgcccag 180
ttgctggctt cgagctcggc ggctcagcgg gagatccacc gagccggcga atcgccccac 240
cgtatcgccc ctaaccctgc agaagtcagc gacggcgcag ccagcgtcat cgtgtag 297

<210> SEQ ID NO 54
<211> LENGTH: 1104
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5448

<400> SEQUENCE: 54
atgctgtggc acgcaatgcc accggagctg aataccgctc gcctgatggc cggcgcgggc 60
ccggccccga tgctggccgc ggccgccgga tgggaggctc tggcagccgc cttggacgct 120
caggccgtcg aattgaccgc gcgcttgaac tcgctcggcg aagcgtggac cggaggcggc 180
agcgagaaag ccctggcggc cgccctgccg atggtgacct ggttgcagac cgcctcgacc 240
caggccaaga cgcgtggcct ccaagccggc gcccaggccg ctgcatacat gcaggccatg 300
gccacaacgc cttcgctacc cgagatcttt gccaaccaca tcaccaacgt gatcctcaac 360
gcgaccaact tcttcggcat caacacggtt cccatcgcct tcaacgagat ggattacttc 420
gtccgcatgt ggaatcaggc ggcgctggcg atggatgtct accaggccga gacgacggcc 480
aacacgctgt tcgaacagct cgagccgatg acgtcgatcc tcgatcccgc cactgcacag 540
agcatgccga cttcgtcgac tccgctgctg gacatggcgt cacaggtcac cggcataccg 600
agcagtgagc ttcagcagac cgccacgcag gtcgccgagg cgagtggccc catgcagcag 660
ctggcacaac cggcgcagca gatgacgtcg gcgttcagca acaccggcag ctcgggcaac 720
ggcgcggacg aagaaggctt ccggatgggc ctgctcggcg ccggcgcgct gtccaatcac 780
ccgctggcgg gtgggtcagg cccgaccacc ggcgcgggcc tgctgcgcgg tgaatcgctg 840
cccggcgccg gcgggaccct gacccgcacg ccactgatca gcgaactcgt cgaaaagccg 900
atgggtccgt cagtgcagcc ggctgcggct gccggatcgt cggcaagcag tggcgccgcc 960
ccggtgggcg ccggcggaat gggggcagga gctggcgccg gtgctggcgg ttcgtcgcgg 1020
ccaggcatgg ccgccccggc gacgctgacc caggagcggg acgaggccga cgaagacgac 1080
tgggatgacg aggacgactg gtga 1104

<210> SEQ ID NO 55
<211> LENGTH: 303
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5449

<400> SEQUENCE: 55
atggcagaga tgaagaccga tgccgctacc ctcgcgcagg aggcaggtaa tttcgagcgg 60
atctccggtg acctgaagac ccagatcgac caggttgagt cgaccgccgg ttcgctgcag 120
gcccagtggc gcggtgcggc tggtaccgcc gctcaggctg cggtggtccg tttccaggaa 180
gccgccaaca agcagaaggc cgaactcgac gagatttcga cgaacatccg tcaggccggt 240
gtccagtact cccgggccga cgacgagcag cagcaggcgc tgtcctcgca aatgggcttc 300
tga 303

<210> SEQ ID NO 56
<211> LENGTH: 288
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5450

<400> SEQUENCE: 56
atgacagaac agcagtggaa tttcgccggc attgaggcag catccagcgc aattcaggga 60
aatgtcacca gcattcattc ccttctggat gagggcaagc agtcgctgca caagctggcc 120
gcagcctggg gtggtagcgg ttcggaggcc taccggggtg tgcagcagaa ttgggactcc 180
accgcgcagg agctcaacaa ctcgctgcag aacctggctc gcaccatcag cgaggccggt 240
caggcaatgt cctccaccga gggcaacgtc acggggatgt ttgcttaa 288

<210> SEQ ID NO 57
<211> LENGTH: 2640

-continued

<212> TYPE: DNA
<213> ORGANISM: Mycobacterium marinum
<220> FEATURE:
<221> NAME/KEY: misc_feature
<223> OTHER INFORMATION: Nucleotide sequence MMAR_5451

<400> SEQUENCE: 57
atgccggcgg actacgacga gctatttcag cccgccgagg gttccggacc tccagatgac 60
gaaactgggc aaaccttctt tgatcctggt accgcgtatc cgccgcccgt gaaacccaac 120
ggcgacgggc actcggcgcc taaggactgg tcgcgcgcat ttccaccggc ggaagatgag 180
tcgccgtcag actccgcaga accggcagct ggccccgcca agtcgccgtt gccccccatg 240
cccatcggcg ggcctgcgcc gacaccccca gaaccaccac cggccccccc ggagctacca 300
ccggcacccc cggaacctcc accggctcgt ccggaggcac ctccgcaagc gccgacagcc 360
gaggctgaac ctccggacga ggcaataccc gttagcgggc cccgcctggc cggcaagtcg 420
ccgctgcctc cgatgcctat cggtgggccg ccaccggcat ctccggagcc acctgcggct 480
ccaccggaac cgacggcgcc agcagaacca ccgcagccgc cggaggctgc tgcacaaccg 540
ccgcaggccg tcgaggaaca ggcccacgca accgccgaac ccccagcggc accaaacccg 600
ccgcgtcccc ccatgcccat cggcgggccc ccacccacac ccccggccgc accggaacca 660
caacaggaca tagcagaaga accggcgccg gcggccgccg aagccccagc ggcaccaccg 720
aagtcaccgc taccgcccat gccggtcagc ggaccgccac cggaaccgcc cgaactgcca 780
ccggctccac cggaaccgac ggcctcagca gagccaccgc agccgccgca gtccgtcgag 840
gaacaggccc acgcaaccgc cgaaccccca gcggcaccaa aaccgacgcg tccccccatg 900
cccatcggcg ggcccccacc cacaccggaa ccacaacagg gcgcgccgca accacaccag 960
gacatagcag aagaaccgaa cccggcggcc gccgaagccc cagcggcacc accgaaatca 1020
ccgcggcccc ccatgccggt caacgggccg gcacccaccc ggcccgagcc accgctacca 1080
ccgggccccc cgcgtcgccg cgctcaaccg ccaacggcgc caccgaacca gcccgggcaa 1140
ccgaagccca tcagcggaca cccgccgccc ccaccgaggc cagcggcgtt cgcgccccca 1200
gcacgcggcg ccacgccaaa ccggcatgaa tcggccgaac ctccgccacc gcgccgggtc 1260
cggatcggtg gcccgcctca gcctccaggg ccaccggagg ctgaatccga ggctcctcgg 1320
cactcgcggc atgcccgacg gacgcatcgt tatcggcccg agcccgaaac cgatgacctc 1380
gaggccacgg cggtacggcc gcttccgacg cgcgagccga tgaggcgaaa cggacccgcg 1440
gcggacgaaa gctcaaccgc gtccttcgcg tggctgcagc agagccagcc gaccctcgat 1500
cggccttctg gacccatgcc cgccgcccct ggggcccccg tcgagtccgc gccgggtcgc 1560
gctgatggtc gtagggccag gcggcgcgcc gaatcccgga cttcggccgc ttcgacgcca 1620
tctccgctgg tgccaaccag ggctcaaccg ccgggcccca ccagggctca gccgccgcgc 1680
accgccgccc cggctcaacc cgctactgag cccctgccgg acgccggcgc cccggccgag 1740
cagtcgaaga agccgaataa gccggtgcca caacggggtt ggcggcgttg ggtttacgcg 1800
gtcacgcgga taaacttcgg tctttctccc gatgagaagt atgaattgga cctgcgcacg 1860
cggatcggtc gaaagccccg cggctcgtat cagatcgcga tcttgggcct caagggcggc 1920
gccgggaaga cgaccacgac ggtcactctt ggcaccacac tgacgcacgt gcgcggggat 1980
cggatcctgg tgcttgacgc cgatccgggc gccggaaatc tcgccgaacg ttcgggacgt 2040
tcgtcgccat catcgattgc cgatctgctg gcggatccgc ggctgtcgca ctacaacgat 2100
gtccgcgcac acaccagcgt caatgccgcc aatctcgaaa ttctccccac cgcggaatac 2160
acctccgcgc agcgcgggct cagcggcgaa gacttgcgat cggccgtcga taccgtgtcg 2220
aagttctaca acctggtcct ggccgattgc ggggcagggc tattcgatcc ggtgacactg 2280
ggtgtgctcg ataccgcctc agcgatcgtg atcttgacta acgtttccat cgacagtgcg 2340
cgccaagccg caatcgcact ggactggttg cgcaaacacg gttaccagga tttggcgagc 2400
cgcgcatgcg tagcgataaa ccatgtcgcc gttggcgaaa ccaacgtgtc ggaacagcag 2460
ttggtccggg actttgaaca gcagctccaa cccgggcgcg tggtggtctt gccatgggac 2520
cggcacatcg cggccggcac cgaaattcat ctcgaccagc ttggccccgt ctaccgacga 2580
cgggttctcg agctggccgc ggctctgtcc gacgattttg aaagggctgg acgtcgttga 2640

<210> SEQ ID NO 58
<211> LENGTH: 1440
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5452

<400> SEQUENCE: 58
atgacagatc tagtgctgcc cgcggcggca cccatggaga gctatgtcga cgagaccgtc 60
gcgatcttgg ccgatctgct cgaagacact cccgcggagg tgctggccgg cttcgacttc 120
gaagctcagg gcgtttggac gttcgcgcgg cccggattcc cgccgctgaa gctcgaccag 180
tccctcgatg aggccggcgt tgtcgacgga tcgctgctga ccttggtctt ggccagtcgc 240
accgagcggt atcggcccct cgtcgaggac gtcatcgacg cgatcgcggt gctcgacgag 300
tcgcccgagt tcaaccgcac cgctctggaa cgcttcctcg ccgtggcaat ccccctcttc 360
gccctgccca tcacggccgt tgccatgcgg gcctggtggc aaactgggcg cagcgtgttc 420
tggccgctgg cgatcggcct aattgggctc gccgccttgg ccggttcctt cgtcgcaaaa 480
cggttctacc aaaactcgcg gctcgccgag agcctgctgg tgacgtcgta cggcgtcatc 540
gccgcggcgg cagctatcgc cgttccgctg ccgcgcgggt tccattcgct gggggcgccc 600
cagctcgccg ccgccgccac agcggtgttg ttcatcacct tgatgatgcg cggcgggccg 660
tacaaacgcc acgacatcgc ggcgtttgtg gtgattacat cgatcgcggt catttcggcg 720
gcggtcgcct tcggatacgg atatcagcaa tgggtgccgg ccggggcgat tgcgttcggg 780
ttgttcatcg tgacgaacgc ggccaaactg actgtcgccg tcgcgcggat cgcgctgccg 840
cccatccccg ttcccggaga gaccgtggac aacgaggaac tgctcgatcc catcaccgcc 900
caagacgcga ccaacgaaga gacaccgacc tggcaagcca tcatcgcctc cgccccggcg 960
tcggcagccc ggctcactga gcgcagcaaa ttggctaagc agctgctcgt cggctacgtc 1020
accgcgggaa cgctgattct tgcggtcggt tcgatagccg tggtggtaca cggccacttc 1080
ttcatacaca gcatgattgt ggcgggtctg atcacggtga tctgttcgtt ccgatcgcgg 1140
ctgtacgcgg atccgtggtg cgcatgggcg ctgctggcgg cgaccgtcgc catcccgacc 1200
gggcttgccg tgaagctgag cctttggtac ccccactatg cctggctgtt gttgacgatc 1260
tacctcgcgg cggccctcgt tacgctcatc tcggtcggcg cgatgaacca ggtacgtcgc 1320
gtttcgccag tcatgaaacg ggccctggaa ttgttcgatg gcgcgatggt cgcgtcaatc 1380
gtcccgctgc tgctgtggat taccggcgtc tatgacctgg ttcgaaacat ccgattctga 1440

<210> SEQ ID NO 59
<211> LENGTH: 837

<212> TYPE: DNA
<213> ORGANISM: Mycobacterium marinum
<220> FEATURE:
<221> NAME/KEY: misc_feature
<223> OTHER INFORMATION: Nucleotide sequence MMAR_5453

<400> SEQUENCE: 59

```
atggctgagc ctctggccgt cgatcccgcc cgtctgattg ctgcgggaag caagctcgcc     60

gagctggttt ttccggcgcc accagcgccg atagcagcaa ctggagggga tccggtttcg    120

gctgcaatca acgacacaat gcctggcatc gagtccttgg tatccgacgg gatgcccggt    180

gtaaccgccg ccttgaaacg aaccgcttcc agcatgtcga ctgccgcaga catctacgcg    240

aaagccgacc aagcccttgg cgatgcattg acgcagtacc aattcggcgg cgacggccaa    300

gcgctaggcg caagcggtgc aaacgctgtg gcacagagcc aggccggaca gaccgtgcaa    360

tcattggccg cgcccgccgc ggggctattg ggcgcgcccg tggcgcaagc attggccgcg    420

cccgcgaccg ggctgctggg tgtacccgcg gcggccgcga cacagatcgg cgaggcggtc    480

agcgctcagg cggaagccct gtcgccccga gtggccgcca caattcccca gctggtgcaa    540

ctggccccgc aagccggtca gatggcgcag caggcctcac cgatcgcgca gaccatcagt    600

cagtcggccc aacaggggtc ctcgcagggc ggcgcagcgc cggcacagct cgtctcggac    660

accaaacccg acgaagacgc ggagctggct gacgagacca aagagggcga ggaagacgcc    720

atggcagcgg ccggtgcaga aggcgccgcg gccggccacg ccacactggt gagcgctccc    780

gtcgaaagca ccggcggtgg cgagacgtcg acgggttcgg tctcagctcc gatctga       837
```

<210> SEQ ID NO 60
<211> LENGTH: 897
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5454

<400> SEQUENCE: 60

```
atgcacccgg atgaagcggc cacatatgac cgaatgcttg acgatttact caaccgcttc     60

gcgccggacg caggaccgtt tgaacctgac ggattcgaat cggacgcatg ggagacccaa    120

tttgacggat tcgaatcgga cgcaggggag attgagcgag aagcggaagc gggggcggcc    180

gataatcccc acgagctatg ccgaggaacc gttgtttgcg cgtcgaccct gaccatcctt    240

ggtgtcatgt ggggatggct tggagattcg ccacccgagc agggtgatcg cttggcgagc    300

agtgggtcat tgttcgacga cgtcggcgcc caggtcgccg cccttgatcc ggacggcggt    360

tggcggggca atgcggcgca ggcctattgg gttcagaacc tcgcacagtc gcggcacgcc    420

acgctgatgg ctgagctgga ccggctcacc gccgggctgg tgtcctccca agccgatgcc    480

gtcaagcaag cccgcgagcg gctgtcggta ctgatcgcgg tagtcctggg tgtgctgatg    540

gtttgtgctg gcctggaact aggggggccc gagggccagc tcccgtcctt ccacattgcg    600

gtcgccgcat gcggtgttgt gcaggttgcc gccgccgcca ccctgatcgg gttggcgaac    660

aagacctcct cgaacgccag cagcctgcgg gcggcgacac agcgagcgac cgaaatgttg    720

gcggcacggt cggcacgctt ggacgcgatc cccgggccgg ccggtatgac ggcgcccgat    780

gtgggcacgc ccccgtccgg cgcccggccg cggttggatg tcgccggtaa caccgcgcgt    840

agccgccgta cgcccgatcg gggtgcggct ttcgccgaat tatcagatcg gagctga       897
```

<210> SEQ ID NO 61

<211> LENGTH: 2331
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5455

<400> SEQUENCE: 61

```
atgggtattc cgaggccgac gggggagtac gccgggcgga tgctcgaggc gggtgggtgg     60
cccgacgctg acgaggacat ccactacgac cgggctcgcg agtacaaccg ggtcctgcac    120
ctgtttaccg atgtgatgga cgcctgtcgg caccagcagg tcgaggtctt cgacggtggt    180
gtctggtccg gtggtgccgc cagtgcggcc aacggtgcgc tgggcggcaa tctcgagcaa    240
atgagcacgc tgcaggacta tctcgccacg gttattacct ggcaccagca tgtggctggg    300
ttgatcgccg aggcgaaggc aaacattgac aacaacgtgg acggtgctca tcgcgaaata    360
cgggttctgg agggcaacgc cgaccttgac cccgaggagc gcaaggcggc gatcgcatcc    420
ctgatccgct cagctcacga ggccaactcg ggtctggtgg ccgaagccgc tgagcaggtt    480
ctggcatcca gaaactggaa gccgccgcac aatgcgctca aggatctgct gcaccaggtg    540
acgcctccgg ccccgggcat tccgtcggtg accgtgccga cgccaggtca gccagccccg    600
aggccaccgg gaccgaagcc gttcgaaccc acgccggtca acccgcacaa gccggttacc    660
ccgggcggac cgggcacgcc ggtgaacccg aagccgggtg ctccggtggt tccgacaccc    720
ggcgggccaa cgcacccggt taccccgggt atcccgggta ccccggggac cccgggtatc    780
ccgggtatcc cgggtactcc gatcacccca ggtactccga tcaccccggg caagccggtg    840
acgccggtca ccccgggcaa gccgaagcca gggaagcccg acaccccggt cttgccggtc    900
gagccaaccc ctgcaccagc gccggcccca gcgccggccc cagcgccggc ccctgcgccc    960
gccccggcac ctgccccagc gccggcaccg cagcccgcgc cagctccggg gcccggtccg   1020
cagccggggc ccgccgaccc gggcgcgagt ccgcagcccg cgccatcgca gccggggtcg   1080
ccgtccacgc cggggcagcc gtcaaccgac ccggctcacg tgaagccggc agcggcaacg   1140
gagacgtcca cggcaccgtc aacccagccg tcgggacctt cgggccctgc gcacggcgac   1200
gactcgtcgg gagggggcgc ggccgcacct gccgccagcg cgatgccggg cggcggtcga   1260
ggagtgtccg caggatcaag ctcgggcctg tcctcggccg gagcgagttc gagcacaagc   1320
cagtcagcgg cctcgggtgc cggctcgcgt gccgcctcgg ggcgcgcacc ggtggagtcg   1380
ggcggccggg gccccaatac ggccgcgccg cgcccggcgg cggctcgcac cgcatcgccg   1440
acccgtccgg ctccggagcg acccaagccg gacgaaaaag agaagtccga agcgcccgat   1500
gccgttacgc catcgccgat ggttccggtc tcggcggcgc gggccgcgcg cgatgccatc   1560
gcttcggcgt ctcgtcgcag tcaaaagaag gaccccttgc ggttggcgcg acgcatcgcg   1620
gccgcgttga acgcgcccga cacctacaac aagggcgact acgggttctt ctggatcacc   1680
gcggtgacca ccgacggcga catcgtggtg gccaacagtt atgggctggc ctacataccc   1740
gagaatgtcg agctaccgca caaggtctac atggccagcg ctgaccatgc gatcccggcc   1800
gatgagcagg cccggttcgc cacctacccg gtgttggccg tgcagggttg ggcggcgttt   1860
cacgacttga agctgcgcgc ggtgatcggg acggccgaac aattggccaa ctcggacgcg   1920
ggcgcggcca agatcatcct ggaagccgac gacattccgg agagcggcaa gatgaccgga   1980
cgtccgcggc tcgaggtggt agacccctcg gcggcggccc agctggcaga gaccgaagat   2040
ctgcggctgc tggagttgct gccgccggcg ccggccgacg ccaatccgcc agacgacgag   2100
```

-continued cggcacatgt tctggttcga cctgatgaag ccgatgacga gtaacgccac cggacgcgag 2160
gtcgcgcacc tgcgggcatt ccgcgcctat gccgaacatt gccaggagat cgcgctgcac 2220
caggcataca gcgcggcaga cgctgaagcc cagcggcccg cggtcgccga ctggctgtac 2280
tggcgttatg tcgccgggct gcttgccaac gctttggcgg acgcgtcctg a 2331

<210> SEQ ID NO 62
<211> LENGTH: 348
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5456

<400> SEQUENCE: 62
gtgaccagca tggagatgga cccccaagtc gcgcaggtgt tggcgttggc ggcacggttc 60
cagtcggcct tggacggaac gctgaaccaa atgaataccg gcaatttccg tggcaaagac 120
gacaccgaga cggtcgaggt gacgatcaat gggcaccagt ggctcaccgc tgtgcgcatc 180
gacgacggcc tgctgaagga agttggtccg gaggtcgtta gtgcgcgggt caaccaggcg 240
ttgaagaacg cccaggccgc cgcatccaaa tacaacgacg cggcgggaga aaagctgacc 300
gcggtgttgt cctcaatgtc tcaaacaatg aacaacggga tggtctga 348

<210> SEQ ID NO 63
<211> LENGTH: 1365
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5457

<400> SEQUENCE: 63
atgagccagc cgcagaccgt cacggtggat cagcaggaaa tcttgaacag ggcagacgag 60
gtggaggcgc cgatggcgac tccgcccact gatgtgcccc aggcaccgtc cggcctcacg 120
gcagccaaca acgcggccga acaactggcc gtctccgccg acaacgtccg cctatacctg 180
caggcaggcg agcgggagcg gcaacgtctg gcgacgtcgc tgcgcaacgc tgccgcggct 240
tatggcgagg tcgaggacga gtcggcaacc gcgctcgata acgacggcaa cggtgaggtc 300
gacgcccaat cagcgggcgg tgccggcgcc ggccagaccg agtctctgga ggaaaccccc 360
aaggtggcgg ccgcgggtga atcagacttc accgacctca agaccgcggc gacaaagctc 420
gaatccggtg accagggcac gtcgatggtc aacttcgctg acgggtggaa caacttcaac 480
ctgtcgctgc aacgcgacat caagcggttc cggatcttcg agaactggga gggtgacgcc 540
gctaccgcct gcgaggcctc gatggaccag cagaaggagt ggatactcca catggccaag 600
ctgagtgcat cgctggccaa gcaggccaat ttcatggcgc aactgcagct gtgggccagg 660
cgggggcacc ccaccctggc cgacatcgtc gaactcgaga gactggcgaa agacccggac 720
tatcaagagc aagccatcaa gctctacgcc gagtatcaag agacctcgga gaaggtgttg 780
agcgaataca acaccaaggc tgatctggag ccggtgaatc cgccgaagcc tccggcggcg 840
atcaagatcg acccgccgcc acccgcgcaa ccgcagggcc tgatcccggg cttcttgatg 900
ccgcccggcg acggttccac cgggctggcc tcgggaatga cgcccccgat gattccgccc 960
accggtggag cgggcggcac acccgacgtc aacaccgccg agctcacctc ggcgggtcgc 1020
gaggcggcgt ccaacctgtc caagggcctc ggcgtcaaac cgatgtcttt gggcggcggc 1080
ggtggtggtc tcggcgggat gccgatgggt gatgcggccc tggccggcgg cgagtccgtg 1140

```
cgaccggccg cggcagggga catcgccggt gccggccagg gtggtggtgc cgcaggtcgc   1200

ggaatggccg gaggcggcat gggaatgccg atgggcggcg ctggccaggg ccagggcggc   1260

gccaagtcca agggcgctca acaagacgag gaagcgctct acaccgagga ccgcgagtgg   1320

accgaggccg taatcggtaa ccgccgccgt caggacaaca agtag                   1365
```

<210> SEQ ID NO 64
<211> LENGTH: 1398
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5458

<400> SEQUENCE: 64

```
atgaggaacc ccttcagttc aatacggttc cgggtcagca ccggtcacac acttgtcgtc     60

gcggtgctgg cgccgccctg catcatgatg ttcctgcaca tgcgctactg gtgggtgggc    120

atcgcgctgg tagcgctggg cgtcatcgtg gcgacggtga ctttctccgg tcgtcgggtc    180

accgggtggg tggccaccgt gttcgcctgg ctgcgtcggc gtcgccgacc gccggatgtg    240

ccgtccgaac cggtggtcgg tgccaccgtg aagccgggtg atcacgttgc ggtgcgttgg    300

cgacgcgacc acctgattgc ggtgatcgag ctcaagcccc gcccgtttac cccgacggtc    360

atcgtcgacg gcaaggctca caccgacgac gtgctggaca cccgcctact cgaggacctg    420

ctgtcggtgc attgcccgga cctggaagca gatgtggtct cggcgggcta ccgcgttggc    480

aacaccgcct ccgaagaggt ggtgagcctt taccagcggg tgatcggcgc cgatccggct    540

ccggcaaacc ggcggacctg gatcatgctg cgagccgacc cggaacaaac ccgcaagtct    600

gcgcagcgtc gcgaggccgg cctcgccggt ttggctcgct atctggtggc gtcggcgact    660

cgcatcgccg atggcctggc cagcaacggc gtcgacgcag tatgcggccg cagcttcgac    720

gactacgacc gcgccaccga catcggttat gtgcgggaaa aatggtcgat gatcaagggc    780

gctgacagct acaccgccgc ctacaccgcg cccggcggcc cggatttgtg gtggtccgca    840

cgagcagatc acaccattac cagggtccgg attgcgcccg ggatgccgcc gcggtccaca    900

gtgttgttga ccacagtggg aaagcccaag actccccggg gcttctcgcg cctgttcggc    960

agccagcggc cggcgttgga agggcagacc ctggttgcca atcaccactg ccaactgcca   1020

atcggatcag cgggcgtgtt aatcggcgag accgtgaacc gccgcccggt gtacatgccg   1080

ttcgatgatg tggacgcgac cgtcaacctg ggggacgccc agacgttcac ccagttcgcc   1140

gtgcgttcgg cggctgccgg cggcgtggtc accgtgggac cacacttcga acagttcgcc   1200

gggctcatcg gtgcccatgt cggcgcggag gccaaggtgg tgtggccgaa cgcgacgacc   1260

tatctgggcg cgcaccctgg tatcgaccgg gtgatcctgc gtcacaactt ggtcggcacc   1320

ccgcgacacc gcaagttgcc gatccggcgg gtctctccac cggaggaaag tcgcttccag   1380

atggccctgc ccaagtag                                                 1398
```

<210> SEQ ID NO 65
<211> LENGTH: 1407
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5459

<400> SEQUENCE: 65

-continued

```
atgcaggcag gactgacacg agcgtgccag agcttcactg cggctagaga acggagtgat      60

tccggggtgc accggacctt gctgacgatg gtcgcgctgg cgttgctgac cgcaccgccg     120

gctttggcaa tcgatcctcc ctcgattgat cccggcgcgg taccgccgga tgtaaccggt     180

cccgaccaac ccaccgagca gagagtgctc tgtaccagcc ccacgacgct gcccgattcc     240

agctttcacg atccgccgtg gagtaacgcc tatatgggtg tcggagaggc ccacaagttt     300

gcgaccgggg ccggcgtcac ggtggcggtg atcgataccg gcgtggacgc ctcaccacgg     360

gtcccggccg agccgggcgg ggacttcgtc gatcaggccg gcgacggact gtcggactgt     420

gatgcgcacg gcacgctcac ggcctcgatt atcggcgggc gccccgcacc gacggatggt     480

ttcgttggcg ttgcccccga cgtgcgactg ctttcgttgc gccagacatc ggaggccttc     540

gaaccggttg gctcgcaacc caaccccaat gatcccaacg cgacgccggc ggccgggtcc     600

atccgcagtc ttgcccgtgc ggtggtgcat gcggccaacc tcggggcggg agtgatcaac     660

atcagcgagg cggcgtgtta caaggtgagc aggccgatcg acgaaataag tctgggcgcg     720

gccatcgact atgcggtcaa cgccaagaac gccgtggtgg tcgtcgccgc gggtaacacc     780

ggcggcgact gctcgcagaa tccgatgccc gacgcgtcga cacccaatga tccccggggc     840

tggaacaagg tgcagacggt ggtcacaccg gcttggtatg cgcccttggt gctgactgtc     900

gggggcatcg gccagaatgg ggtgccgagt tcgttttcca tgcacggacc gtgggtgggg     960

gtagcggcac ccgcggagaa catcatcgcg ctcggtgatc acggcgaacc ggtcaacgcc    1020

ctgcaaggtc gagaaggacc cgtcccgatc gccggcacct cgtttgcggc ggcctatgtc    1080

tcgggtctgg ccgcgctggt ccggcaacgg tttccggagc tgacgccggt gcaggtgatg    1140

aaccggatca ccgctaccgc gcgacatccc ggaggcggta tcgacaatct cgtcggcgcc    1200

ggggtggtca atgctgtcgc ggcgctgacg tgggatatcc cgccgggccc ggcgtcggtg    1260

ccccccagcg tcagacgact accgccccca cgcatcgaac ccggcccgga tcaccgcccg    1320

atcacaatgg tggcggtgtc ggtactgggg ctgacgctgg tgctcggatt gggcacgttg    1380

gccgcccggg cgctgaggcg ccgatga                                        1407
```

<210> SEQ ID NO 66
<211> LENGTH: 561
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5460

<400> SEQUENCE: 66

```
atgaaacacg agttttactc actggtggaa cgtcaccagg acggaacacc ggacatgatt      60

ggcatggagg cggtcaacca gctcctggtc aagttggaga cccaccgatt cgatttctgt     120

ttcatcggtg cgggctatga ggatcaggtc gacgaattcc tcagcgtgaa tccgggtttg     180

gccggccgat tcaatcgcaa gctgcgcttt gagtcctatt cgccgacgga aatcgtcgag     240

atcgggcagc gctatgccgc gccgcgcgcc agcctgctcg atgaggcggc gcgcgagacc     300

tttttggatg cggccaccac catccgcaac tacaccaccc cgggtgggca acacgggatc     360

gatgccatgc agaacgggcg gttcgcgcgc aacgtcatcg agcgcgccga gggatatcgg     420

gacactcgag tggtcgccca gaagcgagcg gggcgagcgg tgtccgtcga ggatcttcag     480

atgatcgccg ctggtgatgt cgaagccgcg gtgcgcagcg tgtgcgcgga caaccgtgac     540

atggccgcca tcgtttggtg a                                              561
```

<210> SEQ ID NO 67
<211> LENGTH: 876
<212> TYPE: DNA
<213> ORGANISM: Mycobacterium marinum
<220> FEATURE:
<221> NAME/KEY: misc_feature
<223> OTHER INFORMATION: Nucleotide sequence MMAR_5461

<400> SEQUENCE: 67
ttgactgatc cgctgatcct tcagacgctg gcgaccttgt cccgcgggca cgggctgttc 60
gccggtcgct tagtcgacga aagaagccgc cacgagccgc agcttcaggc actggccgac 120
tccgtatcgc agacaagagg ggaccggctt cccgatcggg ccgcagcgcg atcgcacgcc 180
gtcgtccagg ccgtacgacg gtccatcgac accgaccggg aactcgcaca gatcatgtcg 240
atagcccaga ccgatcacgc gcacgcgaga agggccacgc gcgccatcct gcaggcagcc 300
cacgccgata gcgggctcgc ggccgatacg ccgcttggcc ggcgcgaagc catggtccgc 360
atggcggcaa gactgcgagc ccagcgccgc cacatcgtgc ggtcgcgcgt acgggcgcga 420
caactggtgt tgcggctgcg ccggctgcgg taccgacagg cagccgccag gcgacagcat 480
catcacgttc cacccacagg tcggcccgct gtgttggcgg cgatccgtaa agccctcgat 540
atcgagggta ttcacgaccc cgcagcacga gcacgctgga cacgcgggat ggatctggtg 600
gcccgccgag agtcgggcta caacgccagc gcggtgaacg actgggacgc taacgcgtct 660
cagggcacgc cgagtagggg agcgtggcag ttcatcgcac cgaccttcgc ggcctaccac 720
cagctgggca cctcgaccaa catcaccaac ctggtggccc aggcatgcgc gttcatcaac 780
tacgcgcagg gccgctacgg ggttgccgct gatgcatcga acctggcaga tcggatccag 840
caagccgatc cacgtcgttc cccaaggggg tactga 876

<210> SEQ ID NO 68
<211> LENGTH: 385
<212> TYPE: PRT
<213> ORGANISM: Mycobacterium marinum
<220> FEATURE:
<221> NAME/KEY: MISC_FEATURE
<223> OTHER INFORMATION: protein sequence of MMAR 5429 (partial)

<400> SEQUENCE: 68

Met Gln Asp Leu Ser Gln Arg Val Leu Asp Glu Leu Asn Ala Ala Gln
1 5 10 15

Ala Asn Pro Pro Ala Ala Glu Glu Glu Leu Thr Asp Ser Phe Leu Ser
20 25 30

Lys His Arg Gly Ser Val Val Cys Leu Gly Thr Asp Gly Ile Leu Gly
35 40 45

Gly Leu Leu Ala Trp Leu Gly His Glu Phe Pro Asp Gln Gly Asp Arg
50 55 60

Leu Asp Ser Ser Gly Ser Met Phe Asp Gly Val Ile Ala Gln Ile Ala
65 70 75 80

Ala Leu Gly Pro Asp Gly Gly Trp Gln Gly Ser Ala Ala Arg Ala Tyr
85 90 95

Gly Ala Arg Asn Leu Ala Gln Ser Gln His Thr Gly Leu Met Ala Asp
100 105 110

Leu Asp Arg Leu Ala Ala Glu Leu Val Ser Ala Gln Ala Asp Asp Val
115 120 125

His Lys Val Arg Ser Thr Leu Trp Ala Leu Val Ala Ile Val Ser Val
130 135 140

-continued

```
Leu Leu Val Val Cys Ile Gly Leu Glu Leu Gln Gly Pro Glu Gly Gln
145                 150                 155                 160

Leu Val Ser Phe Tyr Ser Ala Leu Pro Ile Cys Gly Thr Ala Leu Phe
                165                 170                 175

Val Ala Ala Val Ala Leu Thr Phe Leu Ala Val Thr Thr Ser Arg Asn
            180                 185                 190

Ala Ser Ala Val Gln Ala Ala Thr Gln Arg Leu Thr Ala Met Val Ala
        195                 200                 205

Ala Leu Thr Thr Gly Pro Asp Ala Val Pro Gly Ser Pro Glu Met Pro
    210                 215                 220

Thr Pro Pro Lys Tyr Cys Leu Ser Glu Phe Asp Leu Ala Glu Asp Thr
225                 230                 235                 240

Gly Pro Thr Pro Pro Gln Leu Pro Asp Leu Gly Ser Ala Phe Thr Asp
                245                 250                 255

Leu Pro Gly Ala Pro Glu Phe His Leu Ala Thr Gly Thr Gly Ala Gly
            260                 265                 270

Leu Pro Asp Phe Gly Ala Pro Gln Leu Pro Ile Pro Ala Leu Thr Gly
        275                 280                 285

Leu Pro Thr Leu Pro Gly Pro Thr Asn Leu Thr Asp Leu Thr Ser Val
    290                 295                 300

Leu Ala Gly Leu Pro Thr Ile Ala Gln Leu Ser Thr Thr Leu Ser Gln
305                 310                 315                 320

Leu Thr Asn Leu Ala Gly Pro Thr Ser Thr Thr Thr Gln Pro Ala Gln
                325                 330                 335

Gln His Thr Thr Pro Ala Asp His Pro Thr Gln Asp Asp Ala Thr Asp
            340                 345                 350

Thr Pro Asp Thr Ala Ala Ala Ala Thr Thr Thr Ser Gly Glu Arg Ala
        355                 360                 365

Pro Leu Gly Ser Thr Thr Arg Pro Thr Gln Gln Asn Gln Asp Leu Val
    370                 375                 380

Val
385
```

RECOMBINANT *MYCOBACTERIUM BOVIS* BCG EXPRESSING ANTIGENS OF THE *MYCOBACTERIUM MARINUM* ESX-1 SECRETION SYSTEM

INTRODUCTION

*Tuberculosis*

*Tuberculosis* (TB) represents a major public health challenge [1]. In 2012, the World Health Organization (WHO) estimates that 8.6 million people developed the disease and 1.3 million people died from TB [2]. Humans have been scourged by TB for millennia. First, PCR-confirmed cases date back to about 200 years B.C. [3] and still today approximately one third of the world population are latently infected by the bacilli. The reasons for this intriguing evolutionary success of *Mycobacterium tuberculosis* (Mtb or *M. tuberculosis*), the etiologic agent of human TB, are manifold. The slow growth of Mtb necessitates long antibiotic therapy rendering treatment susceptible to failure due to non-adherence of the patients [4]. The drugs used involve unpleasant side effects and additionally, absence from work as well as expensive travel to the treatment posts pose economical difficulties to patients, resulting in their drop out of the treatment regimen [5]. Notably, treatment failure is the major fuel for the development of drug resistances [6] with Totally Drug Resistant cases already being reported in several countries [7]. The perilous union with HIV represents a likewise challenging public health priority, as it weakens our most effective barrier against TB, our immune system [8]. A further reason for the difficult and lengthy treatment is the ability of Mtb to transform into a dormancy, or persistor state when faced with stress conditions [9]. Cellular metabolism and replication are halted to persist, and thereby escaping the host immune response and chemotherapy [10].

Mycobacteria are part of the new order Corynebacteriaceae [11] that feature an unusually complex and thick cell wall. Hallmarks are long-chain fatty acids called mycolic acids that surround the bacterial cytoplasmic membrane. These mycolic acids are covalently linked to the cell-matrix creating a second hydrophobic barrier outside the cytomembrane [12].

While mycobacteria are considered gram-positive the second membrane executes biological functions comparable to the outer membrane of gram-negative bacteria, such as the uptake of small hydrophilic nutrient via special membrane channels [13]. This protective outer membrane plays an important role in securing the *bacillus*' integrity in the face of harsh environmental conditions [14]. Yet, at the same time this complicates the secretion process of bacterial effectors across this complex barrier into the host cytosol. To this end mycobacteria employ novel secretion systems that have only recently been uncovered.

Type VII Secretion Systems

The breakthrough of discovering the Type VII Secretion Systems (T7SS) in mycobacteria resulted from the detection of unknown secreted antigens in Mtb culture filtrates [15]. Strikingly, these proteins were deficient of the conventional N-terminal signal sequence of about 20 amino acids, such as the well characterized secreted T-cell Antigen 85A, that would direct them to one of the known secretion systems (SS) [16,17]. Additionally, the genome sequence of the paradigm reference strain Mtb H37Rv [18] predicted the flanking genes of these detected secreted antigens to be trans-membrane proteins, conceivably forming chaperones and channels for their secretion [19]. This substantiated the prospect of the presence of a novel secretion apparatus.

Bacteria inherently rely on secretion of effectors into the host phagosome or cytoplasm to shape and adapt to the milieu in their in vivo niche [20]. Due to their complex membrane it was traditionally the gram-negative bacteria that attracted more attention to unravel the mechanisms of secretion [21]. Among the first SS to be characterized was the Sec pathway [22] which recognizes a specific N-terminal sequence of amino acids to guide and propel the proteins into the cytosol. Another secretion pathway employed by Mtb is the Twin-arginine Translocation that exports fully folded proteins [23]. In the past the different SS have been named I-to-VI, with the Type VI Secretion System discovered as recently as 2006 [24]. Considering the presence of the unique group of proteins without signal sequence, its occurrence only in gram-positive bacteria and the mysterious co-dependency of the different players this recently discovered novel SS was termed Type VII SS in line with the previous nomenclature [25].

The T7SS are dedicated to the secretion of low-molecular-weight proteins, notably the "6-kD Early Secreted Antigenic Target" ESAT-6, or EsxA, and its protein partner "10-kD Culture Filtrate Protein" CFP-10, or EsxB [15]. In the genome of Mtb 11 homologues with sequence similarities to the ESAT-6/CFP-10 family can be found [18,26]. In five cases these genes are encompassed by genes encoding integral inner-membrane proteins, ATP-binding proteins and cell-wall-associated mycosins [27,28], i.e. components of a putative secretion machinery, leading to the postulation that in Mtb, five T7SSs can be distinguished (FIG. 1) [29]. Subsequently, these have been named ESX-1-5 (Early Secreted Antigen 6 kD System) whereby the ESX-1 represents the paradigm T7SS.

Phylogenetically, the ESX loci are of ancient origin and have derived from gene duplication [27]. Interestingly, in silico analyses predicted that 52% of the genome of Mtb has resulted from gene duplication events suggesting this to be the major source of genetic variation [30]. The most ancient putative T7SS is ESX-4. It contains the smallest set of genes and its role in infection has not yet been established, questioning its functionality [31]. The ESX-1 locus has been most extensively studied and will be presented in more detail below.

The role of ESX-2 which encodes all core genes has not yet been described. Mutants for ESX-2 genes were shown to be viable suggesting that ESX-2 is not necessary for survival of Mtb [32]. ESX-3, like ESX-1 contains all the basic core components and is conserved in all mycobacterial genomes available today [19]. Its substrates and ESAT-6/CFP-10 homologues can be detected in culture supernatants [33] underlining the functioning of this ESX system. ESX-5 is the second most studied T7SS next to ESX-1 and its functions have recently been characterized [34-38]. It is the ESX system that has most recently evolved in mycobacteria and is only found in slow-growing mycobacteria such as Mtb, *M. bovis* and *M. leprae* [39]. In the fish pathogen *M. marinum* ESX-5 manipulates the macrophage immune response by induction of anti-inflammatory cytokines and host cell death to promote bacterial spread [36,38]. The importance of the ESX-5 system for viability and virulence in Mtb has recently been shown using ESX-5 knockout/deletion mutants [40,41].

Comparative genomics revealed the presence of T7SS also in other bacteria that could provide insights into its role and function in pathogenicity and virulence. In *Staphylococcus aureus*, failure to secrete the EsxA and EsxB homologues reduces virulence, dissemination and colonization [42]. Likewise, a distant ESX locus homologue could be identified in *Bacillus subtilis* [43]. T-cell responses against the ESAT-6 homologue in *M. leprae* [44] suggest the presence of a T7SS which is further supported by the genome sequence [45]. Yet, the un-culturable status of the *leprae* bacilli renders efforts into T7SS research difficult. Across these species the unifying feature of the T7SS is the shared amino acid (AA) motif Trp-Xaa-Gly of approximately 100 AA, therefore called WXG-100 [17,46]. This suggests that T7SS are present in many more gram-positive bacteria carrying homologues of the WXG-100 protein family and raises the question about the role of T7SS in virulence ESX-1 Locus Components The ESX-1 locus is considered the paradigm T7SS as it is partly absent in the TB vaccine strain *M. bovis* BCG contributing to its attenuation [47]. According to the recently established nomenclature for T7SS [29] genes that are present in at least four of the five ESX loci are called ESX-conserved component (Ecc), with an alphabetic suffix according to gene order in the paradigm ESX-1 system, i.e. EccA, B, C. Genes that are involved in secretion but encoded outside the ESX-1 locus are termed ESX-1 secretion-associated proteins, i.e. Esp.

TABLE 1

Core Gene names for ESX-1 in T7SS as proposed in reference [29]

| Gene Name | Gene names in Reference Strain | Other | Function |
|---|---|---|---|
| esxA | Rv3875 | ESAT-6 | Secreted Protein |
| esxB | Rv3874 | CFP-10 | Secreted Protein |
| eccA | Rv3868 | | AAA+ ATPase |
| eccB | Rv3869 | | Transmembrane |
| eccD | Rv3877 snm4 | | proteins |
| eccE | Rv3882 | | |
| eccCa | Rv3870 snm1 | | FtsK/SpoIIE-like |
| eccCb | Rv3871 snm2 | | transmembrane proteins |
| mycP | Rv3883c | | Subtilisin-like serine protease (mycosin) |
| espA | Rv3616c | Homologue of espE | Secreted protein |
| espC | Rv3615c | Homologue of espF | Secreted protein |
| espD | Rv3614c | Homologue of espH | Secreted protein |

The ESX-1 locus, in combination with the EspACD operon, consists of 23 genes (12 shown in Table 1) and is centred around esxA and B, encoding the secreted proteins ESAT-6 and CFP-10. The core genes are $eccA_1$ which encodes a putative cytoplasmic chaperone with an AAA+ ATPase domain, eccB, eccD, and eccE which encode transmembrane proteins. $EccCa_1$ and $EccCb_1$ form a FtsK/SpoIIIE-like ATPase. The mycosin MycP is a membrane associated protease. The genetic cluster encoding espA, espC, and espD, which are secreted via ESX-1 are conserved in pathogenic mycobacteria. They represent most likely gene duplicates as they are homologues of the ESX-1 genes espE, espF, and espH [19].

Mechanisms of Secretion

While the exact number of genes required for ESX-1 secretion is still under debate [48] the current working model is presented here (FIG. 2). The ESX-1 components form a multi-subunit structure spanning the cell envelope to facilitate export of bacterial effectors across the two lipid membranes [25]. ESAT-6 and CFP-10 form a 2-helix hairpin structure stabilizing each other by multiple hydrophobic interactions [49] before secretion in form of a heterodimer [50-52] (FIG. 2). This four-helix bundle is a common feature of all ESX-1 substrates and their homologues [14]. A short secretion motif on the C-terminal flexible tail of CFP-10 is uninvolved in dimerization but attaches as secretion signal to EccCb, a membrane bound ATPase [53]. The same motif has also been identified in other ESX-1 substrates [54]. To catapult the ESAT-6/CFP-10 heterodimer or other substrates into the cytosol EccCb is associated with the membrane bound EccCa [50] which subsequently assemble next to the 11 translocation channels formed by EccD [25]. Both EccCb and EccCa show similarities to SpoIIE/FtsK-like ATPase in Type IV secretion systems in gram-negative bacteria which perform an important part in directing the substrates to the transmembrane channel in an ATP dependent manner [17, 55]. EccCb/EccCa are thus predicted to provide the energy for protein export via T7SS. The pore forming channel in the outer mycomembrane has not yet been identified [14]. Data obtained from mass spectrometry analysis suggest that a single T7SS complex consists of several copies of the transmembrane proteins and ATPases [56].

Region of Difference 1

The fundamental role of a functioning ESX-1 system in virulence and pathogenicity was unravelled when the live TB vaccine *M. bovis* BCG (Bacille Calmette Guérin) was shown to have lost 38 open reading frames among which the Region of Difference 1 (RD1) of 9.5 kB, deleting essential ESX-1 components [57]. BCG is the only licensed TB vaccine and has been used in the past decades with an astonishing safety record [58,59]. Yet, its efficacy to protect against pulmonary TB remains controversial, ranging from 0-80% [60]. The absence of the RD1 is largely responsible for the reduced efficacy of BCG, and reintroduction of the ESX-1 locus into BCG restores secretion of ESX-1 immunogens, virulence and protective efficacy as vaccine [47]. In BCG, RD1 comprises nine open reading frames encoding nine genes that are deleted, among which the ESAT-6/CFP-10 partner and the EccD transmembrane channel. This results in failure to express the components of the ESX-1 secretion system and hence export its substrates, resulting in reduced virulence [61].

The deletion of RD1 and hence attenuation of BCG resulted most likely from 13 years of passaging *M. bovis* on glycerol immersed potato slices [62,63]. That RD1 is a major factor in BCG virulence could be shown as its virulence can partly be restored when complementing with RD1 [64]. Likewise, when Mtb is deleted for the RD1 region it looses its virulence [61,65]. However, BCG complemented with RD1 does not regain its complete level of virulence suggesting that there are other factors involved [47].

Comparative genomics are a powerful tool in understanding the impact of different genes on pathogenicity and to explain the variable virulence between Mtb, BCG and *M. bovis* [62,66]. The mycobacteria are an interesting target for comparative genomics as they represent a high genome homology of up to 99.9% in the *M. tuberculosis* complex, of which *M. bovis* BCG is part [67]. This allows extrapolation and interpretation of virulence factors across different mycobacteria. The mycobacterial species comprises around 80 members of mostly environmental, non pathogenic mycobacteria. While the Mtb complex is part of the more recently evolved slow-growing mycobacteria, a member of the more ancient fast-growing mycobacteria, *M. marinum*, is closely related to Mtb [39]. The agent of fish *tuberculosis* growths at 30-33° C. explaining its non-pathogenicity for humans, except for mild superficial lesions. [68]. *M. marinum* encodes the paradigm T7SS ESX-1 system which has been shown to be involved in virulence [69]. The homologies between the genome sequence of the ESX-1 system of Mtb and *M. marinum* are compelling, with the ESAT-6/CFP-10 proteins having 91% and 97% sequence homology, respectively.

There is a need in the art for new strains of *M. bovis* BCG that combine the ability to induce a greater protective immune response than that induced by *M. bovis* BCG when introduced into a subject while at the same time having a virulence equal to or lower than the virulence of *M. bovis* BCG. Such strains will find several uses, such as vaccination against and treatment of *M. tuberculosis* infections. This invention meets these and other needs in the art.

SUMMARY

This invention encompasses recombinant strains of *Mycobacterium bovis* bacille Calmette-Guérin (*M. bovis* BCG) comprising a heterologous nucleic acid sequence of *Mycobacterium marinum* (*M. marinum*). In some embodiments the heterologous nucleic acid sequence of *M. marinum* comprises a plurality of open reading frames, wherein the plurality of open reading frames comprise open reading frames that encode proteins each at least 95% homologous to the *Mycobacterium marinum* (*M. marinum*) proteins MMAR5445, MMAR5446, MMAR5447, MMAR5448, MMAR5449, MMAR5450, MMAR5451, MMAR5452, MMAR5453, and MMAR5455. In some embodiments the plurality of open reading frames further comprise an open reading frame that encodes a protein at least 95% homologous to the *M. marinum* proteins MMAR5443, MMAR5444, and MMAR5457. In some embodiments the plurality of open reading frames further comprise open reading frames that encode proteins at least 95% homologous to the *M. marinum* proteins MMAR5429, MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5454, MMAR5456, MMAR5458, MMAR5459, MMAR5460, and MMAR5461. In some embodiments the plurality of open reading frames comprise open reading frames that encode proteins at least 97% homologous to the listed *M. marinum* proteins. In some embodiments the plurality of open reading frames comprise open reading frames that encode proteins at least 99% homologous to the listed *M. marinum* proteins.

In some embodiments the plurality of open reading frames comprise open reading frames that encode *M. marinum* proteins MMAR5445, MMAR5446, MMAR5447, MMAR5448, MMAR5449, MMAR5450, MMAR5451, MMAR5452, MMAR5453, and MMAR5455. In some embodiments the plurality of open reading frames further comprise an open reading frame that encodes the *M. marinum* proteins MMAR5443, MMAR5444, and MMAR5457. In some embodiments the plurality of open reading frames further comprise open reading frames that encode the *M. marinum* proteins MMAR5429, MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5454, MMAR5456, MMAR5458, MMAR5459, MMAR5460, and MMAR5461. In some embodiments the open reading frames that encode the listed proteins have the sequence of the corresponding open reading frames present in the nucleic acid sequence of FIG. 3. In some embodiments the heterologous nucleic acid sequence comprises the nucleic acid sequence of FIG. 3.

In some embodiments the heterologous nucleic acid sequence is present on a plasmid.

In some embodiments the heterologous nucleic acid sequence is integrated into the *M. bovis* BCG chromosome.

In some embodiments the recombinant strain secretes the CFP-10 and ESAT-6 proteins of *M. marinum.*

In some embodiments, the recombinant strain induces a protective immune response greater than the parent *M. bovis* BCG when introduced into a subject, and/or the virulence of the recombinant strain is equal to or lower than the virulence of the parent *M. bovis* BCG.

In some embodiments the heterologous nucleic acid sequence comprises the *M. marinum* nucleic acid sequence inserted in the recombinant pYUB412 vector carried by the bacteria deposited at the CNCM under the reference number I-4858 on Jun. 3, 2014.

This invention also encompasses pharmaceutical compositions comprising at least one of the recombinant strains of *M. bovis* BCG of the invention. In some embodiments the pharmaceutical compositions further comprises at least one isolated recombinant protein or peptide antigen of a *mycobacterium*. In some embodiments the isolated recombinant protein or peptide antigen of a *mycobacterium* is from a strain selected from *M. bovis* BCG, *M. marinum*, and *Mycobacterium tuberculosis* (*M. tuberculosis*). In some embodiments the isolated recombinant protein or peptide antigen is selected from CFP-10 protein, ESAT-6 protein, and peptides thereof.

This invention also encompasses kits comprising at least one of the recombinant strains of *M. bovis* BCG of the invention in a container. In some embodiments the kits further comprise at least one isolated recombinant protein or peptide antigen of a *mycobacterium*. In some embodiments the isolated recombinant protein or peptide antigen of a *mycobacterium* is from a strain selected from *M. bovis* BCG, *M. marinum*, and *Mycobacterium tuberculosis* (*M. tuberculosis*). In some embodiments the isolated recombinant protein or peptide antigen is selected from CFP-10 protein, ESAT-6 protein, and peptides thereof.

The invention also encompasses methods of inducing an immune response against *M. tuberculosis* in a subject. In some embodiments the immune response is a protective immune response against *M. tuberculosis*. In some embodiments the methods comprise administering an effective dose of a pharmaceutical composition of the invention to a subject and inducing an immune response in the subject that is protective against *M. tuberculosis*. In some embodiments the methods further comprise administering at least one isolated recombinant protein or peptide antigen of a *mycobacterium* to the subject. In some embodiments the at least one isolated recombinant protein or peptide antigen is selected from CFP-10 protein, ESAT-6 protein, and peptides thereof. In some embodiments the methods further comprise administering at least one subunit vaccine to the subject. In some embodiments the methods further comprise administering at least one vaccine selected from MVA85A, rBCG30, AERAS-402, AdAg85A, M72, H1-IC31, H1-CAF01, H4-IC31 (AERAS-404), rBCGdeltaUreC:Hly (VPM1002), RUTI, and *M. vaccae* to the subject.

The invention also encompasses methods of treating an *M. tuberculosis* infection in a subject. In some embodiments the methods comprise administering an effective dose of a pharmaceutical composition of the invention to a subject and inducing an immune response in the subject that is protective against *M. tuberculosis*. In some embodiments the methods further comprise administering at least one isolated recombinant protein or peptide antigen of a *mycobacterium* to the subject. In some embodiments the at least one isolated recombinant protein or peptide antigen is selected from CFP-10 protein, ESAT-6 protein, and peptides thereof. In some embodiments the methods further comprise administering at least one subunit vaccine to the subject. In some embodiments the methods further comprise administering at least one vaccine selected from MVA85A, rBCG30, AERAS-402, AdAg85A, M72, H1-IC31, H1-CAF01, H4-IC31 (AERAS-404), rBCGdeltaUreC:Hly (VPM1002), RUTI, and *M. vaccae* to the subject.

The invention also encompasses methods of making a recombinant strain of *M. bovis* BCG of the invention. In some embodiments the methods comprise providing a vector comprising a heterologous nucleic acid sequence comprising a plurality of open reading frames, introducing the vector into *M. bovis* BCG cells, and selecting *M. bovis* BCG cells that stably maintain the heterologous nucleic acid sequence comprising the plurality of open reading frames. In some embodiments the vector is an integrating vector and the method further comprises selecting *M. bovis* BCG cells in which the heterologous nucleic acid sequence comprising the plurality of open reading frames has integrated into the host cell cell chromosome. In some embodiments the vector is the recombinant pYUB412 vector carried by the bacteria deposited at the CNCM under the reference number I-4858 on Jun. 3, 2014.

DETAILED DESCRIPTION

A. Introduction

Figure 1:
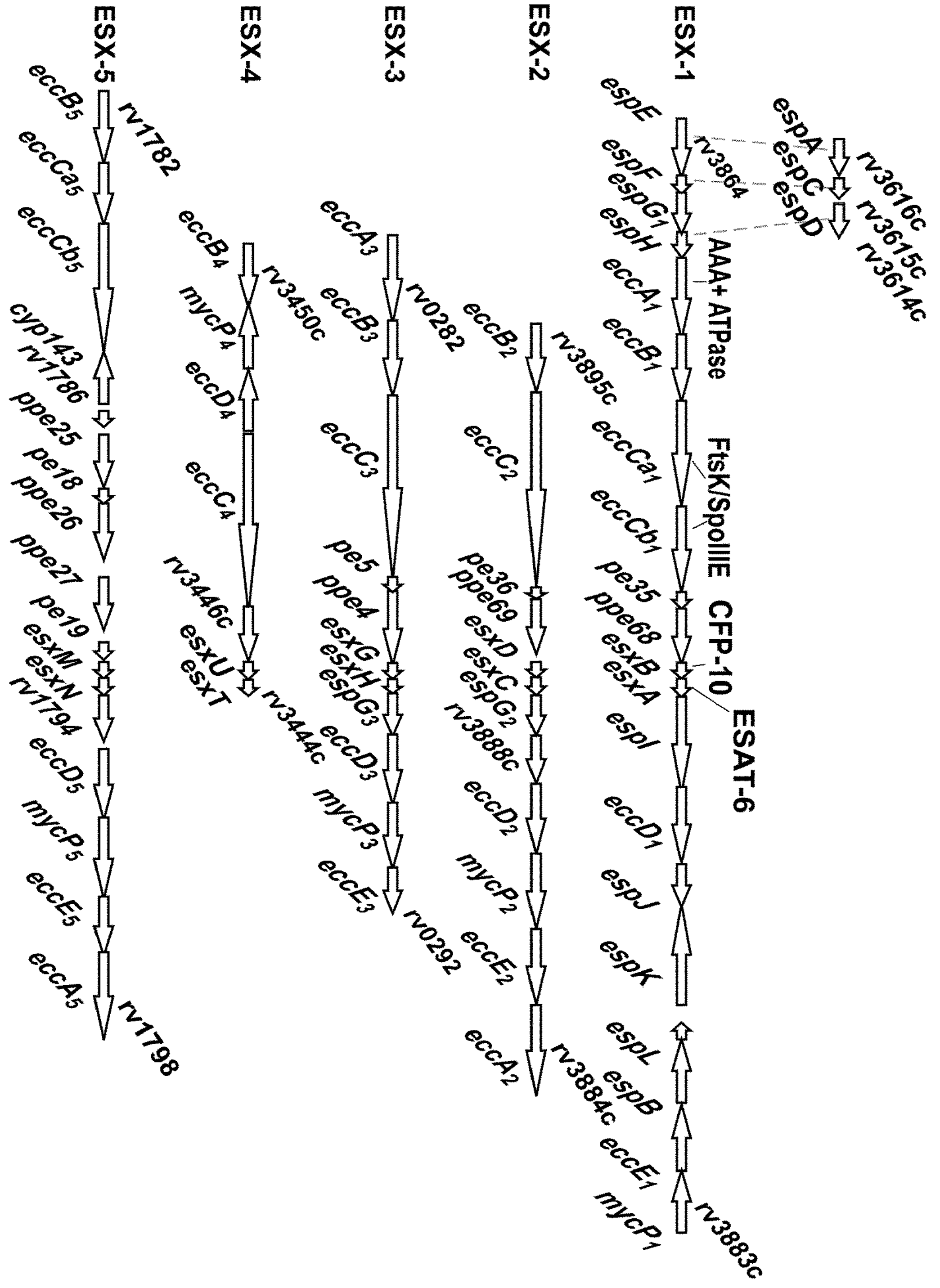
FIG. 1: The five ESX loci of Mtb as shown in reference [29]. The ESX-4 region represents the most ancient ESX system encoding supposedly the core genes required for secretion. The esxA/B family are found in all SS as well as the ATPases of the FtsK/SpoIIE family. Detailed information on mechanisms of secretion have only been described for the systems 1 and 5 [14].
Figure 2:
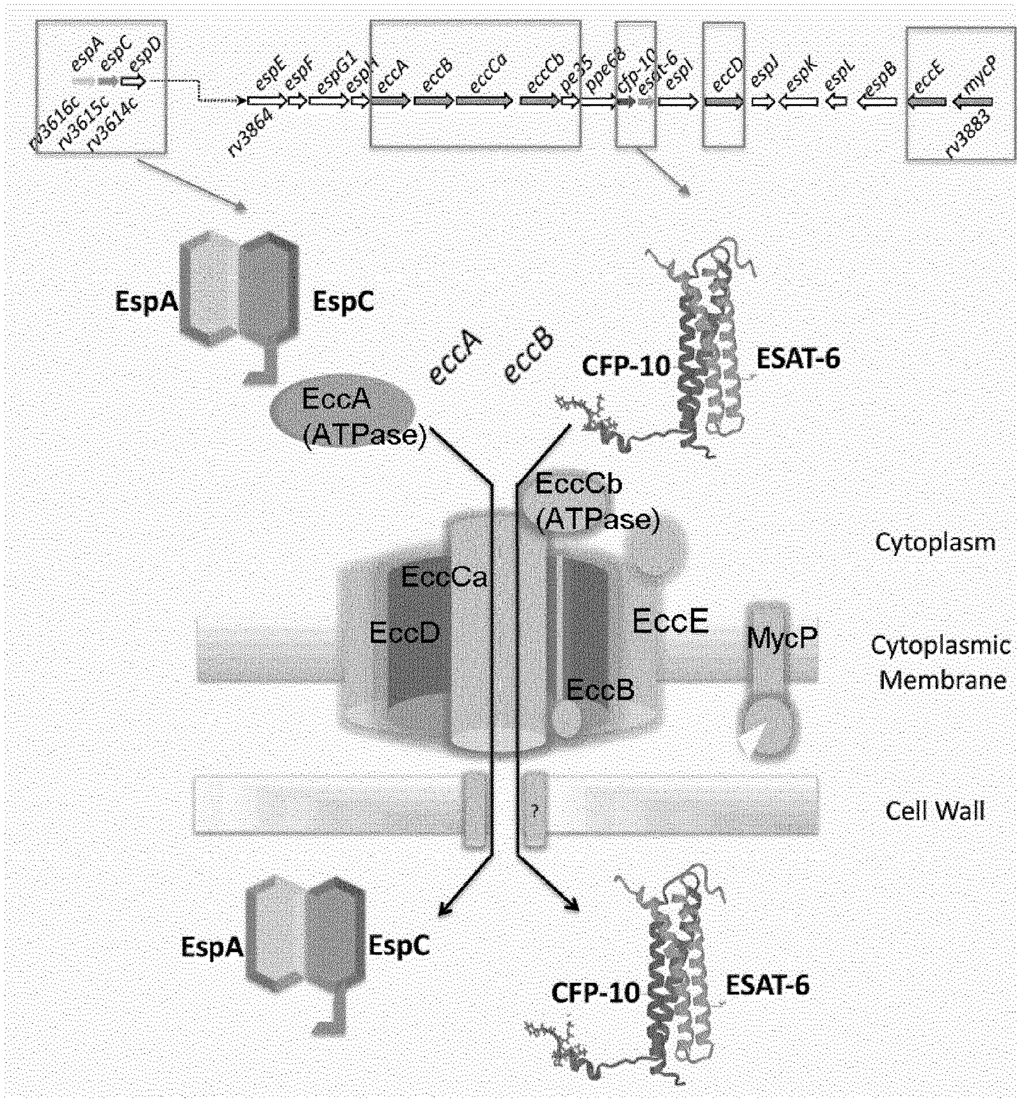
FIG. 2: The current working model of the ESX-1 SS. CFP-10 and ESAT-6 form a heterodimer and attach via the C-terminal end of CFP-10 to the ATPase EccCb. Latter interacts with EccCa which facilitates transport through the transmembrane protein EccD. How the substrates pass the outer membrane is not yet known. ESX-1 associated proteins EspA and C are secreted in the same fashion. With permission from Laleh Majlessi.

A more effective vaccine than BCG is indispensable to achieve eradication of TB by 2050, the declared goal of the Stop TB partnership [70]. In the past decade, the research pipeline has been filled with a number of encouraging TB vaccine candidates [71]. However, recent clinical evidence suggests that subunit vaccines encoding only few TB antigens do not confer adequate protection [72]. Attenuated live vaccines such as recombinant BCG may therefore present as more attractive alternative exposing a variety of antigenic epitopes to host immune cells [73,74]. The experiments reported in the examples made use of the well characterized immunogenicity of the ESX-1 encoded proteins, ESAT-6 and CFP-10, that were shown to elicit protective immunity once reintroduced into BCG [64]. While the Mtb proteins render this vaccine candidate BCG::ESX-1Mtb too virulent, the experiments reported herein heterologously expressed the ESX-1 proteins of *M. marinum* to achieve the same immunogenicity while reducing virulence. These experimental results demonstrate that the recombinant strains of *Mycobacterium bovis* bacille Calmette-Guérin (*M. bovis* BCG) comprising a heterologous nucleic acid sequence of *Mycobacterium marinum* (*M. marinum*) of this invention are promising vaccine candidates, linking the safety of BCG with the immunogenicity of ESX-1 proteins.

B. Definitions

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. Certain references and other documents cited herein are expressly incorporated herein by reference. Additionally, all UniProt/SwissProt records cited herein are hereby incorporated herein by reference. In case of conflict, the present specification, including definitions, will control. The materials, methods, and examples are illustrative only and not intended to be limiting.

The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual, 3d ed., Cold Spring Harbor Laboratory Press, Cold Spring Harbor, N.Y. (2001); Ausubel et al., Current Protocols in Molecular Biology, Greene Publishing Associates (1992, and Supplements to 2002); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976).

This disclosure refers to sequence database entries (e.g., UniProt/SwissProt records) for certain protein and gene sequences that are published on the internet, as well as other information on the internet. The skilled artisan understands that information on the internet, including sequence database entries, is updated from time to time and that, for example, the reference number used to refer to a particular sequence can change. Where reference is made to a public database of sequence information or other information on the internet, it is understood that such changes can occur and particular embodiments of information on the internet can come and go. Because the skilled artisan can find equivalent information by searching on the internet, a reference to an internet web page address or a sequence database entry evidences the availability and public dissemination of the information in question.

Before the present proteins, compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing", and is inclusive or open-ended and does not exclude additional, unrecited members, elements or method steps.

The full name of amino acids is used interchangeably with the standard three letter and one letter abbreviations for each in this disclosure. For the avoidance of doubt, those are: Alanine (Ala, A), Arginine (Arg, R), Asparagine (Asn, N), Aspartic acid (Asp, D), Cysteine (Cys, C), Glutamic Acid (Glu, E), Glutamine (Gln, Q), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), Valine (Val, V).

As used herein, the term "in vitro" refers to events that occur in an artificial environment, e.g., in a test tube or reaction vessel, in cell culture, in a Petri dish, etc., and not within an animal.

As used herein, the term "in vivo" refers to events that occur within a living animal.

As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The "isolated" products of this invention, including isolated nucleic acids, proteins, polypeptides, and antibodies are not products of nature (i.e., "non-naturally occurring"). Rather, the "isolated" nucleic acids, proteins, polypeptides, and antibodies of this invention are "man-made" products. The "isolated" products of this invention can be "markedly different" or "significantly different" from products of nature. By way of non-limiting example, the isolated nucleic acids may be purified, recombinant, synthetic, labeled, and/or attached to a solid substrate. Such nucleic acids can be markedly different or significantly different than nucleic acids that occur in nature. By way of further non-limiting example, the "isolated" proteins, polypeptides, and antibodies of this invention may be purified, recombinant, synthetic, labeled, and/or attached to a solid substrate. Such proteins, polypeptides, and antibodies can be markedly different or significantly different from proteins, polypeptides, and antibodies that occur in nature.

The term "peptide" as used herein refers to a short polypeptide that contains at least 2 amino acids and typically contains less than about 50 amino acids and more typically less than about 30 amino acids. In some embodiments a peptide consists of from 2 to 50, from 2 to 20, from 2 to 10, from 5 to 10, from 5 to 15, from 5 to 20, from 10 to 20, from 10 to 30, from 10 to 40, from 10 to 50, from 20 to 40, or from 20 to 50 amino acids. The term as used herein encompasses analogs and mimetics that mimic structural and thus biological function.

The term "polypeptide" encompasses both naturally-occurring and non-naturally occurring proteins, and fragments, mutants, derivatives and analogs thereof. A polypeptide may be monomeric or polymeric. Further, a polypeptide may comprise a number of different domains each of which has one or more distinct activities. For the avoidance of doubt, a "polypeptide" may be any length greater two amino acids. Accordingly, a "polypeptide" may be a protein or a peptide.

The term "protein" refers to a polypeptide that comprises at least 50 amino acids. A "protein" may have the amino acid sequence of a naturally occurring protein or may be a modified derivative or mutein thereof.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from a cell in which it was synthesized.

The protein or polypeptide can be purified. Preferably, the purified protein or polypeptide is more than 50%, 75%, 85%, 90%, 95%, 97%, 98%, or 99% pure. Within the context of this invention, a purified protein that is more than 50% (etc.) pure means a purified protein sample containing less than 50% (etc.) other proteins. For example, a sample of a protein comprising can be 99% pure if it contains less than 1% contaminating host cell proteins.

The term "polypeptide fragment" as used herein refers to a polypeptide that has a deletion, e.g., an amino-terminal and/or carboxy-terminal deletion compared to a full-length polypeptide, such as a naturally occurring protein. In an embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, or at least 12, 14, 16 or 18 amino acids long, or at least 20 amino acids long, or at least 25, 30, 35, 40 or 45, amino acids, or at least 50 or 60 amino acids long, or at least 70 amino acids long, or at least 100 amino acids long.

The term "fusion protein" refers to a polypeptide comprising a polypeptide or fragment coupled to heterologous amino acid sequences. Fusion proteins are useful because they can be constructed to contain two or more desired functional elements that can be from two or more different proteins. A fusion protein comprises at least 10 contiguous amino acids from a polypeptide of interest, or at least 20 or 30 amino acids, or at least 40, 50 or 60 amino acids, or at least 75, 100 or 125 amino acids. The heterologous polypeptide included within the fusion protein is usually at least 6 amino acids in length, or at least 8 amino acids in length, or at least 15, 20, or 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, a protein has "homology" or is "homologous" to a second protein if the nucleic acid sequence that encodes the protein has a similar sequence to the nucleic acid sequence that encodes the second protein. Alternatively, a protein has homology to a second protein if the two proteins have similar amino acid sequences (Thus, the term "homologous proteins" is defined to mean that the two proteins have similar amino acid sequences). As used herein, homology between two regions of amino acid sequence (especially with respect to predicted structural similarities) is interpreted as implying similarity in function.

When "homologous" or «similar» is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, Methods Mol. Biol. 24:307-31 and 25:365-89.

The following six groups each contain amino acids that are conservative substitutions for one another: 1) Serine, Threonine; 2) Aspartic Acid, Glutamic Acid; 3) Asparagine, Glutamine; 4) Arginine, Lysine; 5) Isoleucine, Leucine, Methionine, Alanine, Valine, and 6) Phenylalanine, Tyrosine, Tryptophan.

Sequence homology or similarity for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

An exemplary algorithm when comparing a particular polypeptide sequence to a database containing a large number of sequences from different organisms is the computer program BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

Exemplary parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, or at least about 20 residues, or at least about 24 residues, or at least about 28 residues, or more than about 35 residues. When searching a database containing sequences from a large number of different organisms, it may be useful to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, Methods Enzymol. 183:63-98 (1990). For example, percent sequence identity between amino acid sequences can be determined using FASTA with its default parameters (a word size of 2 and the PAM250 scoring matrix), as provided in GCG Version 6.1, herein incorporated by reference.

In some embodiments, polymeric molecules (e.g., a polypeptide sequence or nucleic acid sequence) are considered to be "homologous" to one another if their sequences are at least 80%, at least 85%, at least 90%, at least 95%, or at least 99% identical. The term "homologous" necessarily refers to a comparison between at least two sequences (nucleotides sequences or amino acid sequences).

As used herein, a "modified derivative" refers to polypeptides or fragments thereof that are homologous in primary structural sequence to a reference polypeptide sequence but which include, e.g., in vivo or in vitro chemical and biochemical modifications or which incorporate amino acids that are not found in the reference polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands that bind to labeled antiligands (e.g., antibodies), fluorophores, chemiluminescent agents, enzymes, and antiligands that can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., Current Protocols in Molecular Biology, Greene Publishing Associates (1992, and Supplements to 2002).

As used herein, "polypeptide mutant" or "mutein" refers to a polypeptide whose sequence contains an insertion, duplication, deletion, rearrangement or substitution of one or more amino acids compared to the amino acid sequence of a reference protein or polypeptide, such as a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the reference protein, and/or truncations of the amino acid sequence at either or both the amino or carboxy termini. A mutein may have the same or a different biological activity compared to the reference protein.

In some embodiments, a mutein has, for example, at least 85% overall sequence homology or similarity to its counterpart reference protein. In some embodiments, a mutein has at least 90% overall sequence homology or similarity to the wild-type protein. In other embodiments, a mutein exhibits at least 95% sequence identity, or 98%, or 99%, or 99.5% or 99.9% overall sequence identity.

As used herein, a "polypeptide tag for affinity purification" is any polypeptide that has a binding partner that can be used to isolate or purify a second protein or polypeptide sequence of interest fused to the first "tag" polypeptide. Several examples are well known in the art and include a His-6 tag, a FLAG epitope, a c-myc epitope, a Strep-TAGII, a biotin tag, a glutathione 5-transferase (GST), a chitin binding protein (CBP), a maltose binding protein (MBP), or a metal affinity tag.

As used herein, "recombinant" may refer to a biomolecule, e.g., a gene or protein, or to an organism. The term "recombinant" may be used in reference to cloned DNA isolates, chemically synthesized polynucleotides, or polynucleotides that are biologically synthesized by heterologous systems, as well as proteins or polypeptides and/or RNAs encoded by such nucleic acids. A "recombinant" nucleic acid may be a nucleic acid linked to a nucleotide or polynucleotide to which it is not linked in nature. A "recombinant" protein or polypeptide may be (1) a protein or polypetide linked to an amino acid or polypeptide to which it is not linked in nature; and/or (2) a protein or polypeptide made by transcription and/or translation of a recombinant nucleic acid. Thus, a protein synthesized by a microorganism is recombinant, for example, if it is synthesized from an mRNA synthesized from a recombinant nucleic acid present in the cell. A "recombinant" organism is an organism comprising a "recombinant" biomolecule. For example, a "recombinant" strain of *M. bovis* BCG is a strain of *M. bovis* BCG that comprises a "recombinant" nucleic acid.

The term "polynucleotide", "nucleic acid molecule", "nucleic acid", or "nucleic acid sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The nucleic acid (also referred to as polynucleotides) may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

A "synthetic" RNA, DNA or a mixed polymer is one created outside of a cell, for example one synthesized chemically.

The term "nucleic acid fragment" as used herein refers to a nucleic acid sequence that has a deletion, e.g., a 5'-terminal or 3'-terminal deletion compared to a full-length reference nucleotide sequence. In an embodiment, the nucleic acid fragment is a contiguous sequence in which the nucleotide sequence of the fragment is identical to the corresponding positions in the naturally-occurring sequence. In some embodiments fragments are at least 10, 15, 20, or 25 nucleotides long, or at least 20, 30, 40, 50, 60, 70, 80, 90, 100, 110, 120, 130, 140, or 150 nucleotides long. In some embodiments a fragment of a nucleic acid sequence is a fragment of an open reading frame sequence. In some embodiments such a fragment encodes a polypeptide fragment (as defined herein) of the protein encoded by the open reading frame nucleotide sequence.

The nucleic acid can be purified. Preferably, the purified nucleic acid is more than 50%, 75%, 85%, 90%, 95%, 97%, 98%, or 99% pure. Within the context of this invention, a purified nucleic acid that is at least 50% pure means a purified nucleic acid sample containing less than 50% other nucleic acids. For example, a sample of a plasmid can be at least 99% pure if it contains less than 1% contaminating bacterial DNA.

As used herein, an endogenous nucleic acid sequence in the genome of an organism (or the encoded protein product of that sequence) is deemed "recombinant" herein if a heterologous sequence is placed adjacent to the endogenous nucleic acid sequence. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32, and even more typically at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

"Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51. For purposes herein, "stringent conditions" can be defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

As used herein, an "expression control sequence" refers to polynucleotide sequences which affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences and fusion partner sequences.

As used herein, "operatively linked" or "operably linked" expression control sequences refers to a linkage in which the expression control sequence is contiguous with the gene of interest to control the gene of interest, as well as expression control sequences that act in trans or at a distance to control the gene of interest.

As used herein, a "vector" is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors"). The integrating cosmid vector pYUB412 is an example of a "vector".

The term "recombinant host cell" (or simply "recombinant cell" or "host cell"), as used herein, is intended to refer to a cell into which a recombinant nucleic acid such as a recombinant vector has been introduced. In some instances the word "cell" is replaced by a name specifying a type of cell. For example, a "recombinant microorganism" is a recombinant host cell that is a microorganism host cell. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "recombinant host cell," "recombinant cell," and "host cell", as used herein. A recombinant host cell may be an isolated cell or cell line grown in culture or may be a cell which resides in a living tissue or organism.

As used herein, the term "mammal" refers to any member of the taxonomic class mammalia, including placental mammals and marsupial mammals. Thus, "mammal" includes humans, primates, livestock, and laboratory mammals. Exemplary mammals include a rodent, a mouse, a rat, a rabbit, a dog, a cat, a sheep, a horse, a goat, a llama, cattle, a primate, a pig, and any other mammal. In some embodiments, the mammal is at least one of a transgenic mammal, a genetically-engineered mammal, and a cloned mammal.

C. ESX-1 Region of *M. marinum*

Figure 3:
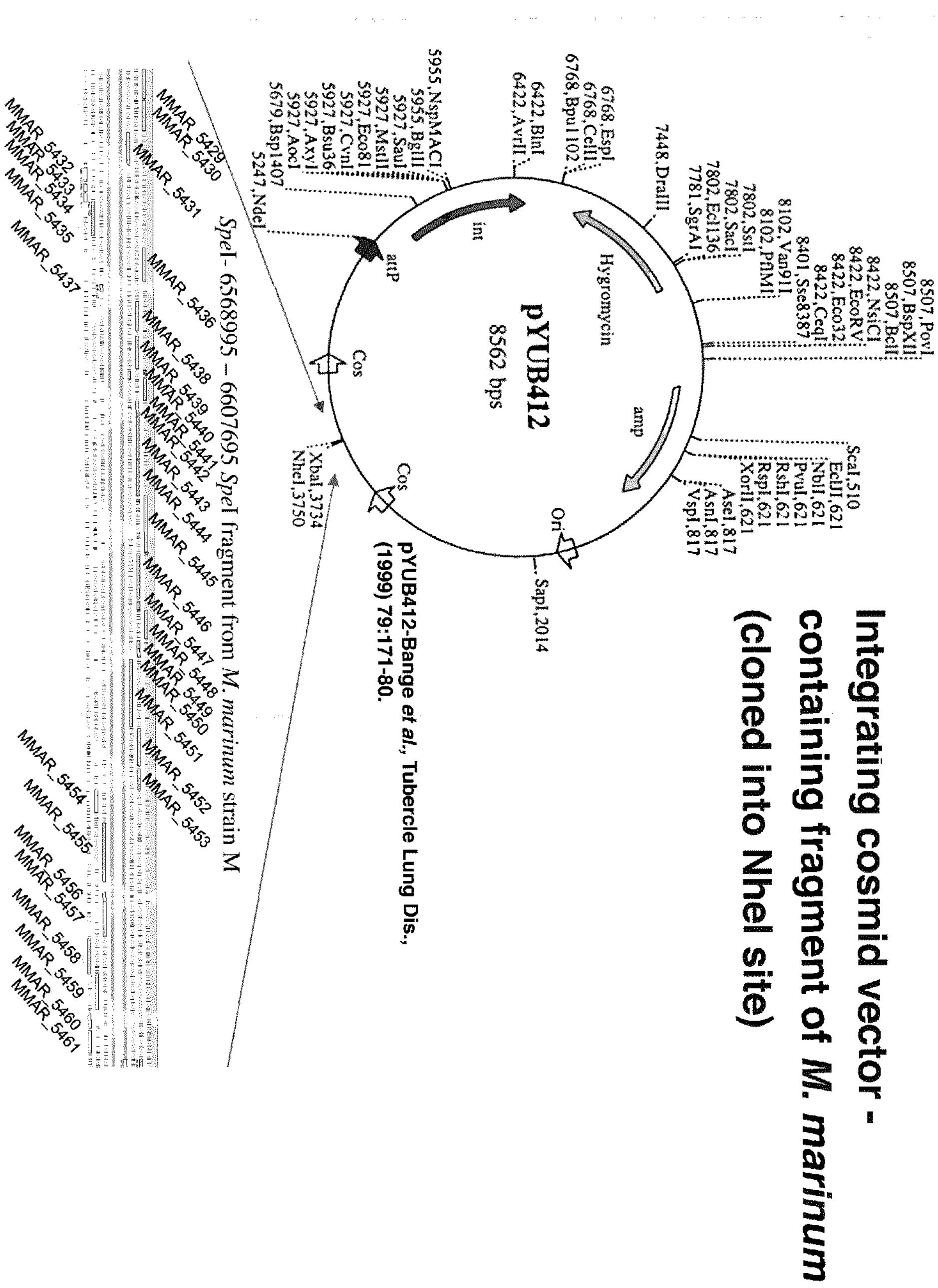
FIG. 3: A schematic drawing of the pRD 1-MAR-construct.
Figure 7:
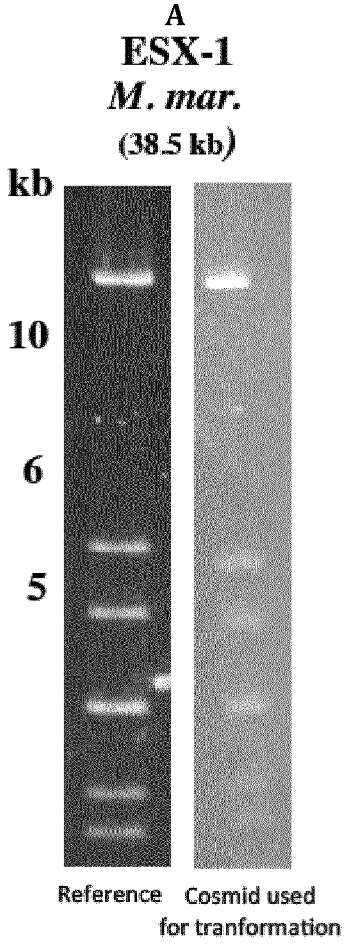
FIG. 7: The XhoI restriction profile of the cosmid vector used and PCR analysis of electroporated cells are shown. A) The restriction profile is compared to earlier profiles obtained in the laboratory. B) Two clones, A and B, were PCR positive for all three primers. BCG Pasteur was used for negative and the cosmid vector with the ESX-1 region of *M. marinum* was used as positive control.
Figure 7:
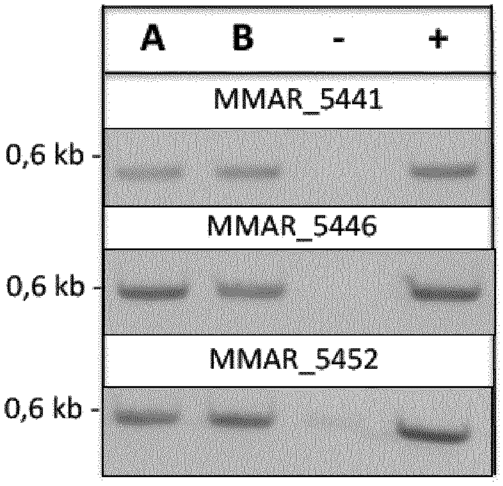
Figure 21:
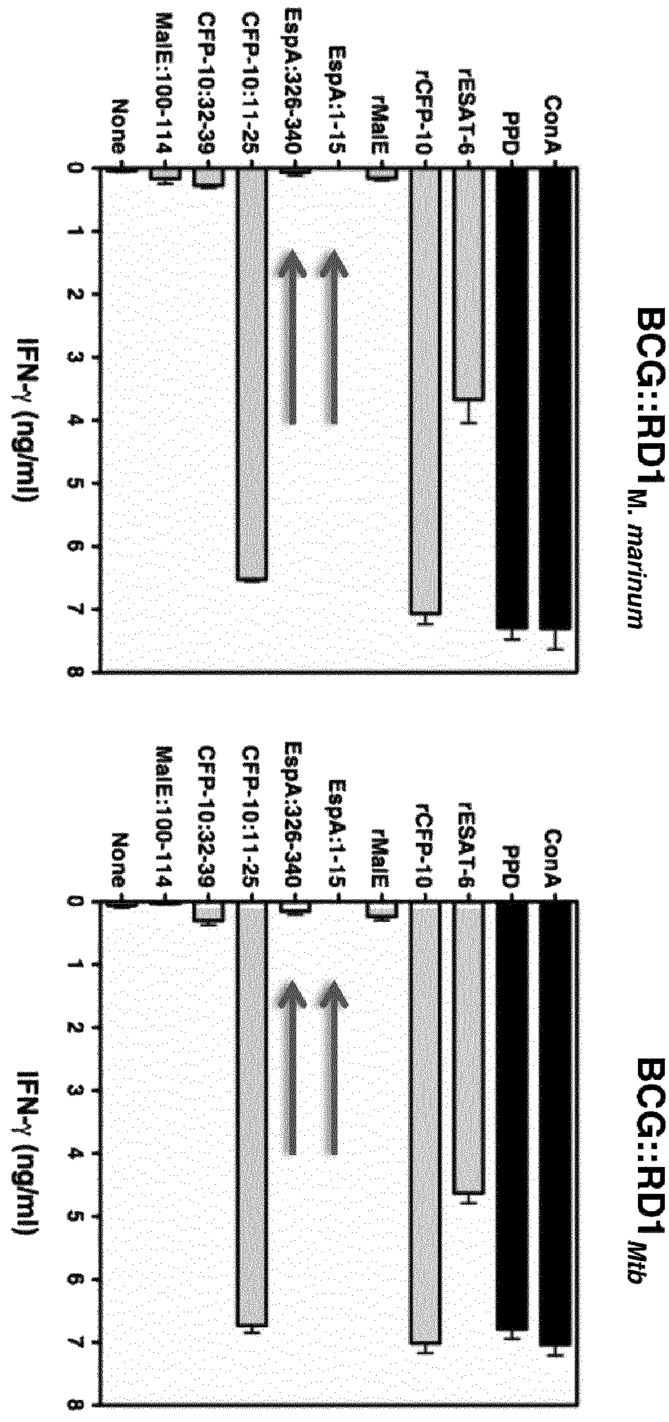
FIG. 21: Induction of CD4+ T-cell responses (as determined by IFN-gamma release by splenocytes) specific to ESX-1 substrates in CH3 (H-$2^k$) mice, immunized with BCG::pyub (vector control), BCG::RD1-*marinum* (=BCG::ESX-$1_{M.\ marinum}$), BCG::RD1-Mtb strains and *M. tuberculosis* H37Rv as control strain. The arrows point to the responses against EspA responses which were only observed for the *M. tuberculosis* control strain.
Figure 21:
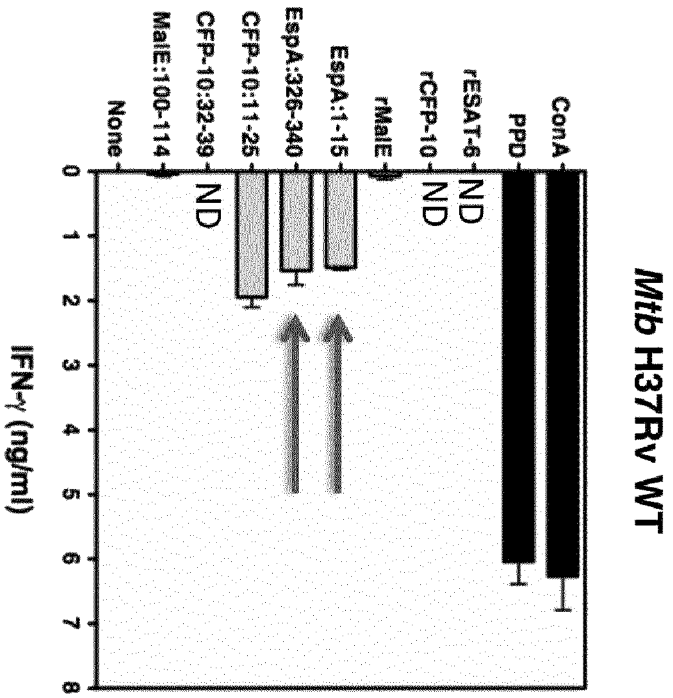
Figure 21:
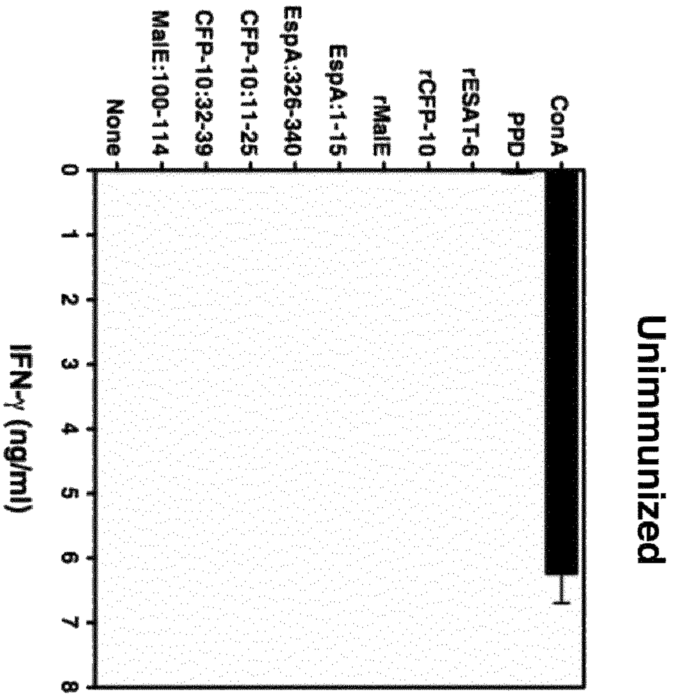
Figure 21:
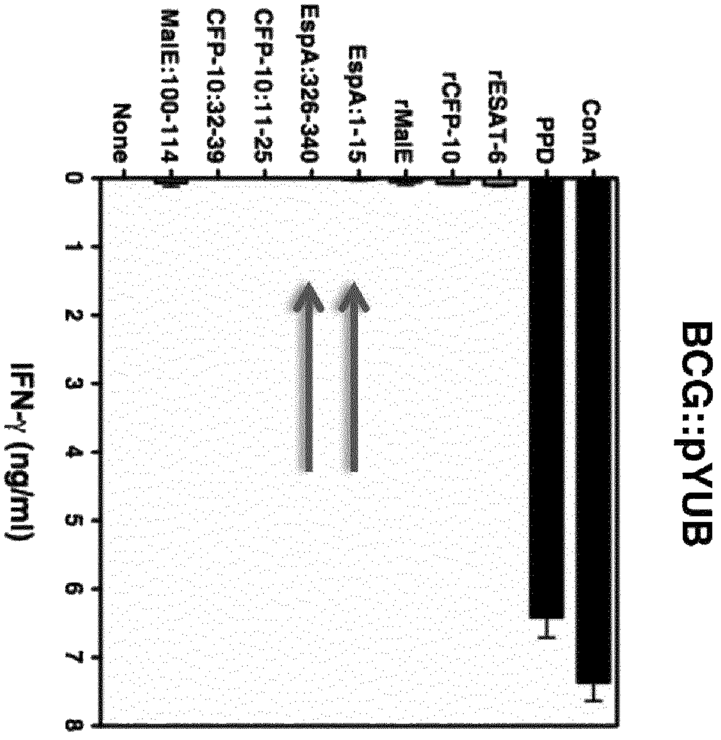

A nucleotide sequence from the ESX-1 region of *M. marinum* is provided in FIG. 3. FIG. 7 provides a map of the specific *M. marinum* nucleic acid sequence used in the Examples. FIG. 21 provides the nucleotide sequences of the open reading frames present in the nucleotide sequence shown in SEQ ID NO:1. Only part of the open reading frame for MMAR5429 is present in the sequence SEQ ID NO:1. SEQ ID NO:3-34 provides the amino acid sequences of the proteins encoded by the open reading frames present in the nucleotide sequence shown in SEQ ID NO:1.

The nucleotide sequence presented in SEQ ID NO:1 comprises open reading frames for the following *M. marinum* proteins: MMAR5429 (partial open reading frame, SEQ ID NO:68), MMAR5430 (SEQ ID NO:3), MMAR5431 (SEQ ID NO:4), MMAR5432 (SEQ ID NO:5), MMAR5433 (SEQ ID NO:6), MMAR5434 (SEQ ID NO:7), MMAR5435 (SEQ ID NO:8), MMAR5436 (SEQ ID NO:9), MMAR5437 (SEQ ID NO:10), MMAR5438 (SEQ ID NO:11), MMAR5439 (SEQ ID NO:12), MMAR5440 (SEQ ID NO:13), MMAR5441 (SEQ ID NO:14), MMAR5442 (SEQ ID NO:15), MMAR5443 (SEQ ID NO:16), MMAR5444 (SEQ ID NO:17), MMAR5445 (SEQ ID NO:18), MMAR5446 (SEQ ID NO:19), MMAR5447 (SEQ ID NO:20), MMAR5448 (SEQ ID NO:21), MMAR5449 (SEQ ID NO:22), MMAR5450 (SEQ ID NO:23), MMAR5451 (SEQ ID NO:24), MMAR5452 (SEQ ID NO:25), MMAR5453 (SEQ ID NO:26), MMAR5454 (SEQ ID NO:27), MMAR5455 (SEQ ID NO:28), MMAR5456 (SEQ ID NO:29), MMAR5457 (SEQ ID NO:30), MMAR5458 (SEQ ID NO:31), MMAR5459 (SEQ ID NO:32), MMAR5460 (SEQ ID NO:33), and MMAR5461 (SEQ ID NO:34) proteins of *M. marinum.*

The *M. marinum* genes/proteins MMAR5429, MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5443, MMAR5444, MMAR5445, MMAR5446, MMAR5447, MMAR5448, MMAR5449, MMAR5450, MMAR5451, MMAR5452, MMAR5453, MMAR5454, MMAR5455, MMAR5456, MMAR5457, MMAR5458, MMAR5459, MMAR5460, and MMAR5461 are known by various names in the art. In most cases homologues in other *mycobacterium* species are named using a different nomenclature. With reference to the *M. marinum* genes/proteins, the MMAR5429, MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5443, MMAR5444, MMAR5445, MMAR5446, MMAR5447, MMAR5448, MMAR5449, MMAR5450, MMAR5451, MMAR5452, MMAR5453, MMAR5454, MMAR5455, MMAR5456, MMAR5457, MMAR5458, MMAR5459, MMAR5460, and MMAR5461 genes/proteins the nucleotide and amino acid sequences of the genes and proteins are provided in SEQ ID NO:68, SEQ ID NO:3-34 and SEQ ID NO: 35-67, respectively.

For the avoidance of doubt, as used herein the "CFP-10" protein is coded by esxB (or Rv3874) gene in *M. tuberculosis* and the MMAR 5449 gene in *M. marinum* (SEQ ID NO:55). As used herein the "ESAT-6" protein is coded by esxA (or Rv3875) gene in *M. tuberculosis* and the MMAR 5450 gene in *M. marinum* (SEQ ID NO:56). The names are used interchangeably herein.

D. Recombinant Strains of *M. bovis* BCG

This invention encompasses recombinant strains of *M. bovis* BCG. The recombinant strains comprise a heterologous amino acid sequence that comprises a plurality of open reading frames. The plurality of open reading frames comprise open reading frames that encode proteins that are the same as or are homologous to *M. marinum* proteins. In some embodiments each of the encoded proteins are at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the corresponding *M. marinum* proteins. In some embodiments all or some of the encoded proteins are identical to the *M. marinum* proteins. In some embodiments all or some of the open reading frames are functionally linked to endogenous *M. marinum* expression regulatory sequences. In some embodiments all or some of the open reading frames are functionally linked to endogenous *M. marinum* expression regulatory sequences present in the nucleotide sequence SEQ ID NO:1. In some embodiments all or some of the open reading frames are functionally linked to heterologous *M. marinum* expression regulatory sequences.

In some embodiments the plurality of open reading frames encode proteins that comprise the *M. marinum* proteins MMAR5445 (SEQ ID NO:18), MMAR5446 (SEQ ID NO:19), MMAR5447 (SEQ ID NO:20), MMAR5448 (SEQ ID NO:21), MMAR5449 (SEQ ID NO:22), MMAR5450 (SEQ ID NO:23), MMAR5451 (SEQ ID NO:24), MMAR5452 (SEQ ID NO:25), MMAR5453 (SEQ ID NO:26), and MMAR5455 (SEQ ID NO:28) or homologues thereof. In some embodiments the plurality of open reading frames further encode proteins that comprise the *M. marinum* proteins MMAR5443 (SEQ ID NO:16), MMAR5444 (SEQ ID NO:17), and MMAR5457 (SEQ ID NO:30) or a homologues thereof. In some embodiments the plurality of open reading frames further encode at least one of the *M. marinum* proteins MMAR5429, MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5454, MMAR5456, MMAR5458, MMAR5459, MMAR5460, and MMAR5461, or homologues thereof. In some embodiments the plurality of open reading frames encode proteins that comprise the *M. marinum* proteins MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5454, MMAR5456, MMAR5458, MMAR5459, MMAR5460, and MMAR5461, or homologues thereof. In some embodiments the plurality of open reading frames encode proteins that comprise the *M. marinum* proteins MMAR5429, MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5454, MMAR5456, MMAR5458, MMAR5459, MMAR5460, and MMAR5461, or homologues thereof.

In some embodiments the plurality of open reading frames comprise open reading frames that encode *M. marinum* proteins MMAR5445, MMAR5446, MMAR5447, MMAR5448, MMAR5449, MMAR5450, MMAR5451, MMAR5452, MMAR5453, and MMAR5455. In some embodiments, the plurality of open reading frames further comprise an open reading frame that encodes the *M. marinum* proteins MMAR5443, MMAR5444, and MMAR5457. In some embodiments the plurality of open reading frames further comprise at least one open reading frame that encodes an *M. marinum* protein selected from MMAR5429, MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5454, MMAR5456, MMAR5458, MMAR5459, MMAR5460, and MMAR5461. In some embodiments the plurality of open reading frames comprise open reading frames that encode *M. marinum* proteins MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5454, MMAR5456, MMAR5458, MMAR5459, MMAR5460, and MMAR5461. In some embodiments the plurality of open reading frames comprise open reading frames that encode *M. marinum* proteins MMAR5429, MMAR5430, MMAR5431, MMAR5432, MMAR5433, MMAR5434, MMAR5435, MMAR5436, MMAR5437, MMAR5438, MMAR5439, MMAR5440, MMAR5441, MMAR5442, MMAR5454, MMAR5456, MMAR5458, MMAR5459, MMAR5460, and MMAR5461.

In some embodiments the open reading frames that encode the listed proteins have the sequence of the corresponding open reading frame presented in SEQ ID NO:35-67 (nucleotide sequence). In some embodiments the recombinant strain of *M. bovis* BCG comprises a heterologous nucleic acid sequence that hybridizes to at least one nucleic acid sequence of SEQ ID NO:35-67 (nucleotide sequence). In some embodiments the recombinant strain of *M. bovis* BCG comprises a heterologous nucleic acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to at least one of the nucleic acid sequences of SEQ ID NO:35-67 (nucleotide sequence). In some embodiments the recombinant strain of *M. bovis* BCG comprises a heterologous nucleic acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the nucleic acid sequence of SEQ ID NO:1.

In some embodiments the heterologous nucleic acid sequence is present on a plasmid. In some embodiments the heterologous nucleic acid sequence is integrated into the *M. bovis* BCG chromosome. In some embodiments the recombinant *M. bovis* BCG strain comprises a single copy of the heterologous nucleic acid sequence integrated on its chromosome. In some embodiments the recombinant *M. bovis* BCG strain comprises multiple copies of the heterologous nucleic acid sequence integrated on its chromosome.

The recombinant *M. bovis* BCG strains of the invention may be made by any suitable method known in the art. In some embodiments an integrating shuttle vector is electroporated into a strain of *M. bovis* BCG and recombinant *M. bovis* BCG cells comprising the heterologous nucleic acid sequence integrated into the host cell chromosome are identified. In some embodiments the integrating shuttle vector is a cosmid. In some embodiments the integrating shuttle vector is pYUB412.

In some embodiments the recombinant strain of *M. bovis* BCG secretes the CFP-10 and ESAT-6 proteins of *M. marinum*.

In some embodiments the recombinant strain of *M. bovis* BCG induces a protective immune response greater than the parent *M. bovis* BCG when introduced into a mammal. In some embodiments the virulence of the recombinant strain is equal to or lower than the virulence of the parent *M. bovis* BCG in a mammal. In some embodiments the recombinant strain of *M. bovis* BCG induces a protective immune response greater than the parent *M. bovis* BCG when introduced into a mammal. In another embodiment, the virulence of the recombinant strain is equal to or lower than the virulence of the parent *M. bovis* BCG in the mammal. In some embodiments the mammal is a human.

In some embodiments the recombinant strain of *M. bovis* BCG further comprises an antibiotic marker linked to the plurality of open reading frames encoding proteins that are the same as or are homologous to *M. marinum* proteins. In some embodiments the antibiotic marker is removed from the recombinant strain of *M. bovis* BCG after integration of the plurality of open reading frames, so as the recombinant strain could be used for GMP production.

E. Methods of Making Recombinant Strains of *M. bovis* BCG

The invention also encompasses methods of making a recombinant strain of *M. bovis* BCG of the invention. In some embodiments the methods comprise providing a vector comprising a heterologous nucleic acid sequence comprising a plurality of open reading frames, introducing the vector into *M. bovis* BCG cells, and selecting *M. bovis* BCG cells that stably maintain the heterologous nucleic acid sequence comprising the plurality of open reading frames. The heterologous nucleic acid sequence may be any heterologous nucleic acid sequence described in Section D above, for example. In some embodiments the vector is an integrating vector and the method further comprises selecting *M. bovis* BCG cells in which the heterologous nucleic acid sequence comprising the plurality of open reading frames has integrated into the host cell cell chromosome.

*M. bovis* BCG cells used to make a recombinant strain of *M. bovis* BCG of the invention are preferably from a commercially available BCG strain which has been approved for use in humans such as Pasteur, Frappier, Connaught (Toronto), Tice (Chicago), RIVM, Danish 1331, Glaxo-1077, Tokyo-172 (Japan), Evans, Prague, Russia, China, Sweden, Birkhaugh, Moreau and Phipps.

F. Pharmaceutical Compositions

The invention further encompasses compositions, particularly pharmaceutical compositions, comprising a recombinant strain of *M. bovis* BCG according to this disclosure and a pharmaceutically-acceptable carrier. The compositions may be, for example, for use for inducing a protective immune response against *M. tuberculosis* in a subject and/or for use for treating an *M. tuberculosis* infection in a subject.

In addition to the strains, these pharmaceutical compositions may contain suitable pharmaceutically-acceptable carriers comprising excipients and auxiliaries which facilitate processing of the living vaccine into preparations which can be used pharmaceutically. Further details on techniques for formulation and administration may be found in the latest edition of Remington's Pharmaceutical Sciences (Maack Publishing Co., Easton, Pa.). In some embodiments the pharmaceutical composition is suitable for oral and/or subcutaneous and/or intradermal and/or inhalation and/or intravesicular administration.

The determination of the effective dose is well within the capability of those skilled in the art. An effective dose refers to that amount of active ingredient, i.e the number of cells administered, which induces an immune response against *M. tuberculosis* and/or ameliorates the symptoms of *M. tuberculosis* infection. Efficacy and toxicity may be determined by standard pharmaceutical procedures in experimental animals, e.g., ED50 (the dose effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. Of course, ED50 is to be modulated according to the mammal to be treated or vaccinated. In this regard, the invention contemplates a composition suitable for human administration as well as a veterinary composition.

The invention also encompasses a vaccine comprising a recombinant strain of *M. bovis* BCG according to this disclosure and a suitable carrier. This vaccine is especially useful for preventing *tuberculosis.*

The invention therefore target said vaccine for use for preventing *tuberculosis.*

The recombinant strain of *M. bovis* BCG according to this disclosure are also useful as a carrier for the expression and presentation of foreign antigens or molecules of interest that are of therapeutic or prophylactic interest. Examples of such foreign antigens can be found in patents and patent applications U.S. Pat. No. 6,191,270 for antigen LSA3, U.S. Pat. Nos. 6,096,879 and 5,314,808 for HBV antigens, EP 201,540 for HIV-1 antigens, U.S. Pat. No. 5,986,051 for *H. pylori* antigens and FR 2,744,724 for *P. falciparum* MSP-1 antigen.

G. Kits

The invention further encompasses a kit for use for inducing a protective immune response against *M. tuberculosis* in a subject and/or for treating an *M. tuberculosis* infection in a subject. Said kit comprises a recombinant strain of *M. bovis* BCG according to this disclosure and a container. In some embodiments, said kit further comprises at least one isolated recombinant protein or peptide antigen of a *mycobacterium*. In some embodiments, said *mycobacterium* is a strain selected from *M. bovis* BCG, *M. marinum*, and *M. tuberculosis*. In some embodiments, said isolated recombinant protein or peptide antigen is selected from CFP-10 protein, ESAT-6 protein, and peptides thereof. In some embodiments, said kit further comprises at least one subunit vaccine. In some embodiments, said kit further comprises at least one vaccine selected from MVA85A, rBCG30, AERAS-402, AdAg85A, M72, H1-IC31, H1-CAF01, H4-IC31 (AERAS-404), rBCGdeltaUreC:Hly (VPM1002), RUTI, and *M. vaccae.*

H. Methods of Inducing a Protective Immune Response Against *M. tuberculosis*

The invention also encompasses methods for inducing an immune response against *M. tuberculosis* in a subject. In some embodiments, the immune response is a protective immune response. The subject may be any mammal. In some embodiments the subject is a human Generally the methods comprise administering an effective dose of a pharmaceutical composition of this disclosure to a subject and inducing an immune response in the subject that is protective against *M. tuberculosis*. In some embodiments, the methods further comprise administering at least one isolated recombinant protein or peptide antigen of a *mycobacterium* to the subject. In some embodiments, said isolated recombinant protein or peptide antigen is selected from CFP-10 protein, ESAT-6 protein, and peptides thereof. In some embodiments, the methods further comprise administering at least one *mycobacterium* subunit vaccine to the subject. In some embodiments the methods further comprise administering at least one vaccine selected from MVA85A, rBCG30, AERAS-402, AdAg85A, M72, H1-IC31, H1-CAF01, H4-IC31 (AERAS-404), rBCGdeltaUreC:Hly (VPM1002), RUTI, and *M. vaccae* to the subject.

In methods comprising administering the pharmaceutical composition of this disclosure and a second agent to the subject, the pharmaceutical composition of this disclosure and the second agent may be administered simultaneously or at separate times. In embodiments in which the pharmaceutical composition of this disclosure and the second agent are administered at separate times the order of administration may be (1) that the pharmaceutical composition of this disclosure is administered first and the second agent is administered at a later point in time; or (2) that the second agent is administered first and the pharmaceutical composition of this disclosure is administered at a later point in time. In some embodiments the second agent is administered second and is used to boost an immune response of the subject that was raised against the recombinant strains of *M. bovis* BCG present in the pharmaceutical composition of this disclosure. In some embodiments one or both of the pharmaceutical composition of this disclosure and the second agent is administered at multiple timepoints.

In some embodiments the pharmaceutical composition is administered by an oral and/or subcutaneous and/or intradermal and/or inhalation and/or intravesicular mode.

I. Methods of Treating *M. tuberculosis* Infection

The invention also encompasses methods for treating an *M. tuberculosis* infection in a subject. The subject may be any mammal. In some embodiments the subject is a human. Generally the methods comprise administering an effective dose of a pharmaceutical composition of this disclosure to a subject infected with *M. tuberculosis* and inducing an immune response in the subject that ameliorates the *M. tuberculosis* infection. In some embodiments, the *M. tuberculosis* infection is cured and the subject becomes free of *M. tuberculosis*. In some embodiments, the methods further comprise administering at least one isolated recombinant protein or peptide antigen of a *mycobacterium* to the subject. In some embodiments, said isolated recombinant protein or peptide antigen is selected from CFP-10 protein, ESAT-6 protein, and peptides thereof. In some embodiments, the methods further comprise administering at least one *mycobacterium* subunit vaccine to the subject.

In some embodiments, the methods further comprise administering at least one vaccine selected from MVA85A, rBCG30, AERAS-402, AdAg85A, M72, H1-IC31, H1-CAF01, H4-IC31 (AERAS-404), rBCGdeltaUreC:Hly (VPM1002), RUTI, and *M. vaccae* to the subject.

In methods comprising administering the pharmaceutical composition of this disclosure and a second agent to the subject, the pharmaceutical composition of this disclosure and the second agent may be administered simultaneously or at separate times. In embodiments in which the pharmaceutical composition of this disclosure and the second agent are administered at separate times the order of administration may be (1) that the pharmaceutical composition of this disclosure is administered first and the second agent is administered at a later point in time; or (2) that the second agent is administered first and the pharmaceutical composition of this disclosure is administered at a later point in time. In some embodiments the second agent is administered second and is used to boost an immune response of the subject that was raised against the recombinant strains of *M. bovis* BCG present in the pharmaceutical composition of this disclosure. In some embodiments one or both of the pharmaceutical composition of this disclosure and the second agent is administered at multiple timepoints.

In some embodiments the pharmaceutical composition is administered by an oral and/or subcutaneous and/or intradermal and/or inhalation and/or intravesicular mode.

In some embodiments the subject has an active *tuberculosis* infection. In some embodiments the subject has a latent *tuberculosis* infection.

J. Methods for Treating Other Pathologies

We hereby demonstrate that the BCG::ESX-1 *marinum* strain has a stronger immunogenicity phenotype than normal BCG. This enhanced immunogenicity could be beneficial for the treatment of other pathologies known to be cured by BCG, such as bladder cancer.

The compositions of the invention may be, for example, for use for treating bladder cancer in a subject in need thereof.

Moreover, other diseases may be cured, such as leprosy. As a matter of fact, wild-type *Mycobacterium leprae* also carries an ESX-1 cluster, so that the presence of a heterologous ESX-1 system may reinforce the immunity generated by the vaccine.

The compositions of the invention may be, for example, for use for inducing a protective immune response against *Mycobacterium leprae* in a subject and/or for use for treating an *Mycobacterium leprae* infection or leprosy in a subject in need thereof.

EXAMPLES

A. Materials and Methods

1. Generation of a Recombinant BCG a. Preparation of Cosmid DNA

A genetic construct containing the ESX-1 region of *M. marinum* integrated in the cosmid shuttle vector pYUB412 was prepared. After cloning and amplification in *E. coli* DH10B (Invitrogen Corporation, Cergy Pontoise, France) cosmid DNA was obtained. In short, the bacterial suspension was centrifuged and 250 μl of resuspension buffer (Qiagen, Venlo, The Netherlands), Lysis buffer and K+ Acetate (pH 4.8) were added to the pellet. Upon centrifugation the pellet was homogenized with 700 μl of isopropanol and incubated on ice for 1 hour. The suspension was centrifuged, washed with 70% EtOH and once more centrifuged. To verify the size and integrity of the pYUB cosmid carrying the ESX-1 region of *M. marinum* the Xhol (New England Biolabs, Ipswich, Mass.) restriction profile was compared to digestion patterns obtained earlier (R. Brosch, unpublished) on 0.8% agarose gel. Finally the DNA was dialysed to remove salts that may interfere with the electroporation.

b. Electroporation of pYUB::ESX-$1^{MM}$ into BCG.

*M. bovis* BCG Pasteur 1173P2, held at Pasteur Institute, was grown at 37° C. on Middlebrook 7H11 medium (Difco) supplemented with oleic acid-albumin-dextrose-catalse (OADC; Difco). To obtain electrocompetent cells bacteria from solid culture were transferred into 200 ml of 7H9 medium complemented with ADC (Difco) and grown for 10 days. Cells were harvested collected and washed twice with $H_2O$ and once with 10% Glycerol at room temperature. The pellet was resuspended in 2 ml of 10% Glycerol. The cell suspension was mixed with the integrative ESX-1 cosmids and electroporated using a Bio-Rad gene pulser XCell at 2500 Volt. Electroporated cells were cultured overnight at 37° C. and plated on 7H11 medium containing hygromycin 50 μg $ml^{-1}$. Antibiotic resistant colonies were collected after about 3 weeks and analysed for the presence of the integrated cosmid using PCR.

c. PCR on Resistant Colonies

Bacilli from colonies appearing on the plates were heat-killed and denaturated at 95° C. for 3 minutes to allow access to bacterial DNA. PCR reactions comprised 200 ng in 2.5 μl and were conducted according to the standard protocols in this laboratory [47]. The cyclic reactions were performed using a PTC-100 Programmable Thermal Controller (MJ Research, St. Bruno, Canada) starting with an initial denaturation step of 1 min at 95° C., followed by 30 cycles of 30 s at 94%, 1 min at 57° C., and 4 min at 72° C. Samples were transferred onto 0.8% Agarose gel and electrophoresed for 30 minutes at 135 V. Primers used were purchased at Invitrogen. Only PCR positive clones were subjected to immunoblotting analyses.

d. Immunoblotting of Recombinant BCG::ESX-$1^{MM}$

Pre-cultures of cells were grown in 7H9+ADC and transferred into Sauton Media (Institut Pasteur) at $OD_{600\ nm}$ of 0.015. Cell lysates and supernatants were obtained from early log-phase cultures indicated by reaching a $OD_{600\ nm}$ of 0.3 as follows: Cells were centrifuged 4000 r.p.m. for 10 minutes at 4° C. and the supernatant was filtered through 0.44 µm pores (Sartorius Stedim Biotech, Göttingen, Germany) The whole cell extract was washed in 50 mM sodium phosphate buffer (pH 7.0) and resuspended in 1 ml of PBS and Anti-protease mix (Complete EDTA free, Roche, Basel, Switzerland) containing 500 µm glass beads unwashed (Sigma). Cells were lysed by 10 min at level 30 in the Tissue Lyser II (Qiagen). Glass beads were washed down and whole cell lysate was aliquoted at −20° C. Samples were prepared with NuPage reducing agent and sample buffer (Invitrogen) and denatured at 70° C. for 10 ml before loading on 12% NuPage Bis-Tris gel (Invitrogen). Gels were consequently electro-blotted using Gel Transfer Stacks Nitrocellulose (Novex Life Technologies, Israel) and the iBlot apparatus (Invitrogen). Upon saturation of membranes with 5% nonfat dry milk in TBS 0.1% Tween20 (Sigma-Aldrich, St. Quentin-Fallavier, France) for 30 min the primary antibody (ESAT-6 from Antibodyshop, Lot F0703-03, CFP-10 from in house production, and Anti-GroEl (MBiosource, San Diego, Calif.) was added in TBS 0.1% Tween20 ON at 4° C. Upon 1 h of incubation with secondary antibody (ECL Anti-Mouse IgG, Amersham Biosciences, Glattbrug, Switzerland) the blot was revealed using SuperSignal West Femto Maximum Sensitivity Substrate (Thermo Scientific, IL, USA).

e. Immunogenicity and Virulence Studies

Bacterial suspensions for injection were prepared from 50 ml 7H9+ADC (Difco) liquid cultures. Bacilli were spun down, washed twice and resuspended in PBS before brief sonification. To allow residual aggregates to settle the suspensions were kept still for 1 h before aliquotation and storing at −80° C. One aliquot was used to determine the CFUs of the bacterial suspension. For immunological studies 6 week old female C3H and C57BL/6 mice (Janvier Labs, Le Genest-Saint-Isle, France) were immunized subcutaneously with $10^6$ CFUs in 200 µl PBS of BCG::ESX-$1^{MM}$ A (n=4), BCG::ESX-1Mtb (n=4) or BCG::pYUB412 (n=2). After 3 weeks mice were sacrificed and the splenocytes were obtained and cultured on 96 well plates ($1\times10^5$ cells/well) using HL-1 medium complemented with β-mercapthoethanol and 1% Streptomycin and Penicillin (Invitrogen) in the presence of various mycobacterial antigens. After 72 h of incubation IFN-γ was quantified in culture supernatants using ELISA according to standard protocols (capture and detection antibodies and streptavidin-HRP were purchased from BD, le Pont de Claix, France). For virulence studies six-week-old SCID mice (n=4 per group) (Janvier) were infected via the lateral tail vein with $10^6$ CFUs. Upon sacrifice after 3 weeks of inoculation lungs and spleens were homogenized using Tissue Lyser II (Qiagen) and plated on previously prepared 7H11 agar plates in serial dilutions and incubated at 37° C. After 2-3 weeks CFU were counted.

2. Generation of an Anti-CFP-10 and Anti-EspA T-cell Hybridoma a. T-cell Epitope Mapping of EspA A Pepscan® composed of 77 peptides of 15-mers offset by 5 amino acids scanning the complete sequence of the EspA protein (Mimotopes, Claiton, Australia) was used to identify the immunogenic regions. Female C57BL/6 (H-2b), BALB/c (H-2d) or C3H (H-2K) mice (Janvier, France) were immunized subcutaneously with 3×106 CFUs of *M. tuberculosis* H37Rv strain in 200 µl (n=2). One mouse of each strain was used as non-infected control. The MHC-II H-2K-restricted immunodominant T-cell epitoped contained in the CFP-10:11-25 peptide has been described earlier [75]. Pooled splenocytes were harvested 2 weeks post immunization and cultured at 106 cells/well in 96 well plates in RPMI 1640 Glutamax complemented with 5% FCS and 1% Penicillin-Streptomycin as duplicates in the presence of x-to-y µg/ml of individual peptides from the EspA pepscan. After 72 h of incubation at 37° C. and 5% CO2 IFN-γ was quantified in the culture supernatants using ELISA. The identified EspA immunodominant sequences were then synthetized by Polypeptide (Strasbourg, France).

b. Generation of the T-Cell Hybridoma

C3H mice (n=2) were immunized subcutaneously with 50 µg of the synthetized peptides in 200 µl in Incomplete Freuds Adjuvant (Sigma Aldrich). Two weeks post-infection splenocytes were removed, washed, pooled and cultured using complemented RPMI with 10% FCS. To verify successful immunization splenocytes were distributed in a 96 well plate (1×106 cells/well in 100 µl) and stimulated by various concentrations of the homologous peptides ranging from 5 µg/ml to 0.03 µg/ml. Culture supernatants were assessed for IFN-γ secretion after 72 h incubation at 37° C. by ELISA. The remaining splenocytes were incubated for 4 days with the homologous peptides at 10 µg/ml in 25 cm 3 flasks. The fusion partner BW5147 thymoma cells, lacking Hypoxanthine-Guanine PhosphoRibosyl Transferase activity, were cultured from stocks held at Pasteur Institut in standard medium and were centrifuged, washed twice, and counted. The re-stimulated splenocytes were enriched in live cells using 3 ml of Ficoll Hypaque solution (Lympholyte-M, Cedarlane, TEBU BIO, Le Perray-en-Yvelines, France), washed and counted. BW5147 cells and splenocytes were assembled at 1:1 ratio and washed twice at room temperature. 0.5 ml of polyethylene glycol 1500 were slowly added to the cell pellet, followed by a wash at 500 r.p.m. for 4 min Subsequently, the mix was resuspended carefully by 8 ml of complemented RPMI before adding 32 ml of medium containing 20% FCS. Upon an incubation period of 4 h at 37° C., feeder splenocytes were obtained from naive C3H mice and added at $1\times10^5$ cells/ml and the suspension homogenized. Cells were distributed in 96 well plates at 100 µl/well for incubation overnight. The next day, the HAT (Hypoxantine, Aminopterine, Thymidine) medium, blocking purine synthesis and thus eliminating the non-fused BW5147 cells, was added at 1×, thereby allowing selection of only fused BW5147-splenocytes hybrids in which the purine synthesis pathway is restored. At day 7, 100 µl of HT-complemented RPMI was added to each well and carefully monitored for appearing growth of hybridomas.

c. Detection, Quantification, and Sensitivity

The hybridomas were diluted using 100 µl of complemented RPMI with 20% FCS and 1× HT (Hypoxantine, Thymidine) before transfer into 24 well plates containing 500 µl of medium. To screen and select the hybridomas specific for the T-cell epitope, naive splenocytes were loaded with 10 µg/ml of peptide in RPMI 20% FCS. The next day the hybridomas were added and the supernatant was examined for IL-2 after overnight incubation using ELISA. The positive hybridomas were then subjected for further analyses to specify at molecular level their sensitivity. To this end, naive splenocytes were incubated with the peptide as described above, in two-fold dilutions from 5 µM to 3.9 nM. After overnight incubation the hybridomas were added and IL-2 was quantified. The most sensitive four hybridomes were named, amplified in 25m3 flasks and stored at −80° C. To determine the MHC restriction of the selected T-cell hybridomas, L fibroblasts, stably transfected with I-AK or I-EK were loaded with CFP-10:11-25 peptide or a negative control and co-cultured with the hybridomas. IL-2 was quantified in the co-culture supernatants after overnight incubation.

d. Dendritic Cell Infection Assay

Bone marrow-derived dendritic cells (BM-DC) were obtained from femurs of female 6-week-old C57BL/6 or C3H mice depending on the restriction of the epitopes to be studied. Cells were cultured in petri dishes and differentiated into DC in the presence of 10 ng/ml GM-CSF (prepared at Institut Pasteur) BM-DC were harvested, washed and distributed at 5×105 cells/well in 100 μl in a 96 well plate. The different mycobacterial suspensions were added at two fold dilutions starting at an M.O.I. of 4 in RPMI without antibiotics. Upon 24 h incubation 1×105 cells of hybridomas per well in 100 μl were added and stored at 37° C. and 5% $CO_2$. The next day IL-2 was quantified in the supernatant using ELISA.

e. FRET Assay and Flow Cytometry

Human pro-monocytic cell line THP-1 was cultured in RPMI at 10% FCS for one week. Cells were collected, washed and distributed in a 24 well plate at $5\times10^5$ cells/well in 2 ml. 20 ng/ml of PMA (Pharbol 12-myristate 13-acetate, Sigma Aldrich) was added to differentiate the cells into monocytes and incubated for 72 h. Mycobacterial strains were grown until mid-log phase in Dubos Broth (Dico) and the OD600 was determined. Differentiated THP-1 were washed twice and infected with the bacterial suspensions at an M.O.I. of 1. After 2 h of incubation the supernatant was removed and cells were washed three times with PBS. Fresh medium was added and cells were stored at 37° C. 5% $CO_2$ for 4 days. Next, cells were incubated for 2 h at RT in dark with the CCF-4 mix consisting of 50 μM CCF-4 substrate (Invitrogen) in EM buffer (120 mM NaCl, 7 mM KCl, 1.8 mM $CaCl_2$, 0.8 mM MgCl, 1.5 mM glucose and 25 mM Hepes at pH 7.3). Next, an appropriate dilution of anti-CD11b-APC (BD) was added to the wells and incubated at RT in dark for 30 min. Marked cells were washed twice and fixed with 4% Paraformadehyde and kept at 4° C. overnight. The following day the suspension was filtered using 100 μm filters (BD) and subjected to Flowcytometry analyses using the CyAn® system and the Summit Software (Beckman Coulter, Villepinte, France). Phagosomal rupture was observed when the CCF-4 signal became blue and when CCF-4 was not cleaved the signal remained green. Data were analysed with FlowJo software (Treestar, Oreg.).

f. Statistical Analyses

GraphPad Prism software (GraphPad Software, La Jolla, Calif.) was used to perform statistical analyses. The student's t and Mann-Whitney U tests were employed based on normal or skewed distribution of the data

B. Results

Example 1: Complementation of BCG with the ESX-1 Region of *M. marinum*

Figure 4:
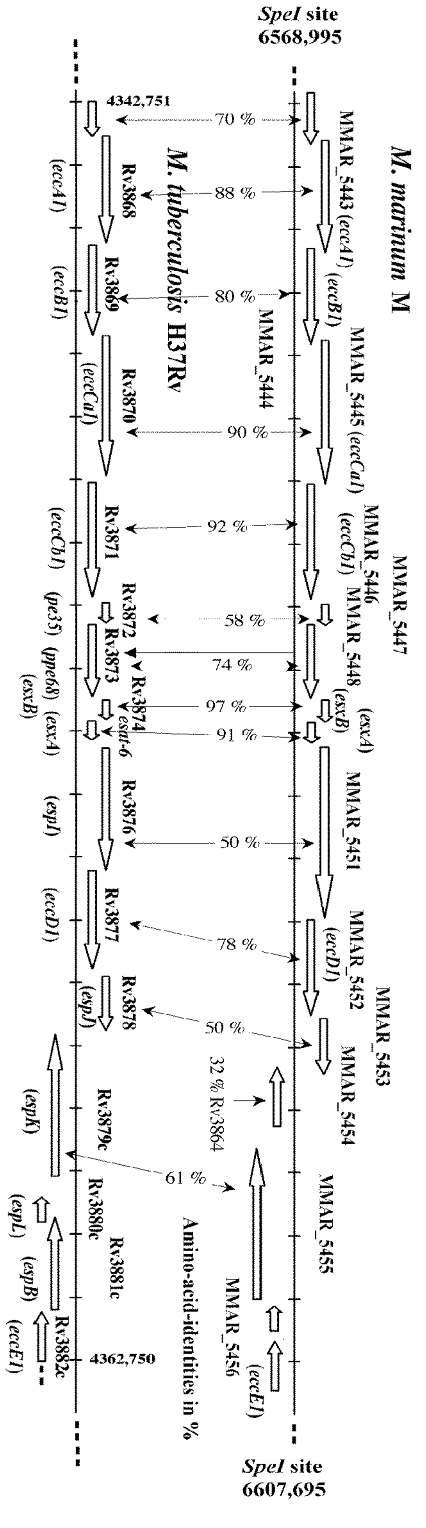
FIG. 4: Core region of insert in integrating cosmid containing the *Mycobacterium marinum* strain ESX-1 region (in comparison to the ESX-1 or RD1 region of *Mycobacterium tuberculosis* H37Rv).
Figure 5:
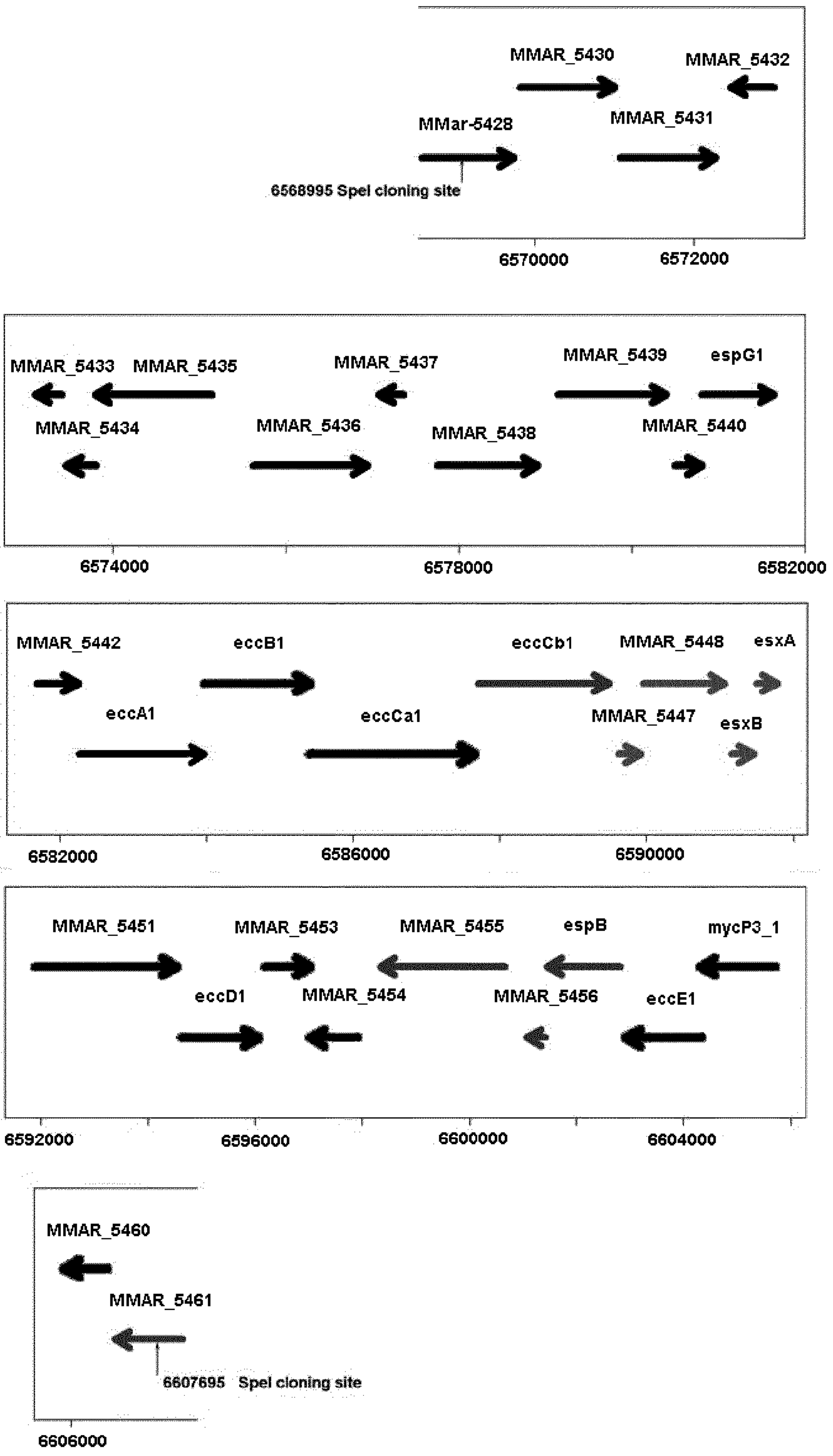
FIG. 5: ORFs comprised in the cloned fragment.
Figure 6:
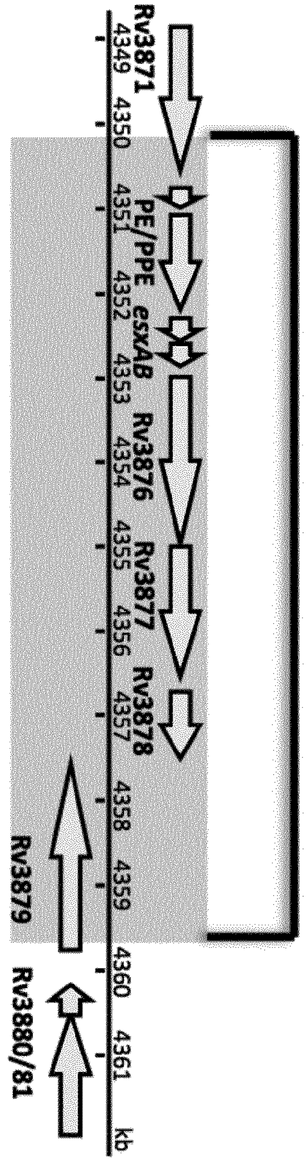
FIG. 6: The Region of Difference 1 in BCG. The genes enclosed by the black frame are absent from BCG resulting in the loss of ESX-1 function. As a result BCG is less virulent but is unable to induce adaptive immunity against ESX-1 protective antigens [62].

In order to create a recombinant BCG expressing the ESX-1 region of *M. marinum* the genetic material was introduced into BCG by electroporation. The RD1 region deletes nine coding sequences in the ESX-1 locus in BCG (FIG. 6) [64]. The integrating cosmid vector pYUB412 [76] carried the entire ESX-1 locus of *M. marinum*. The vector sequence is provided in SEQ ID NO:2 and the inserted *M. marinum* sequence in SEQ ID NO:1. A map of the vector is provided in FIG. 3. FIG. 4 shows an alignment of ESX-1 loci from *Mycobacterium tuberculosis* and *Mycobacterium marinum* species. FIG. 5 indicate the open reading frames encoded by the inserted fragment. To verify that the integrating cosmid harbours the desired ESX-1 locus a restriction profile analysis was performed using the XhoI restriction enzyme. In FIG. 7A the PCR amplified digestion profile is shown and compared to in silico prediction and earlier restriction patterns done by the laboratory. Upon electroporation of electrocompetent BCG cells the cosmid vector integrates firmly into the BCG genome. The cosmid encodes a hygromycin cassette allowing to select resistant cones on 7H11 Hygromycin agars. Seventy clones were selected for PCR analyses. Three pairs of primers specific for genes within the ESX-1 region were used to ensure the presence of the *M. marinum* fragment in the BCG::ESX-$1^{MM}$ strain: MMAR_5441 (homologue of espG1), MMAR_5446 (homologue of eccCb1), and MMAR_5452 (homologue of eccD1). Two clones, named A and B, were positive for all primers (FIG. 7B), and were chosen for further analyses. One of the strains was designated ESX-1-Mar and deposited at the Collection Nationale de Cultures de Microorganisms (CNCM), 25, Rue de Docteur Roux, F-75724 Paris Cedex 15 FRANCE on Jun. 3, 2014 under the Reference Number I-4858.

Figure 8:
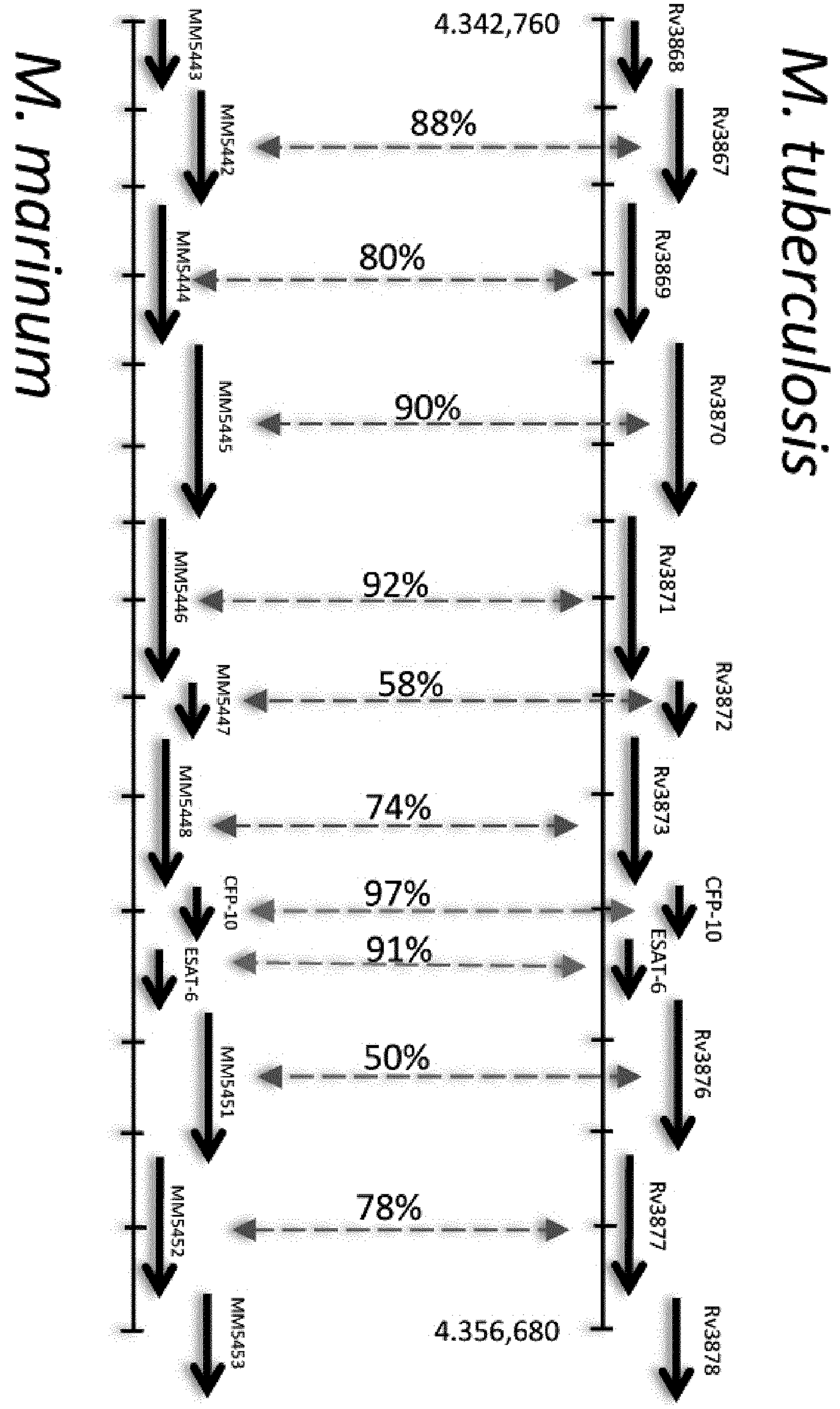
FIG. 8: Comparison of the gene homology between Mtb and *M. marinum*. The genes encoding the ESAT-6 and CFP-10 proteins show 91% and 97% sequence homology, respectively. Other genes, such as Rv3877 encoding the transmembrane channel EccD are less homologous and differs in 22% of base pairs from its *M. marinum* homologue.
Figure 9:
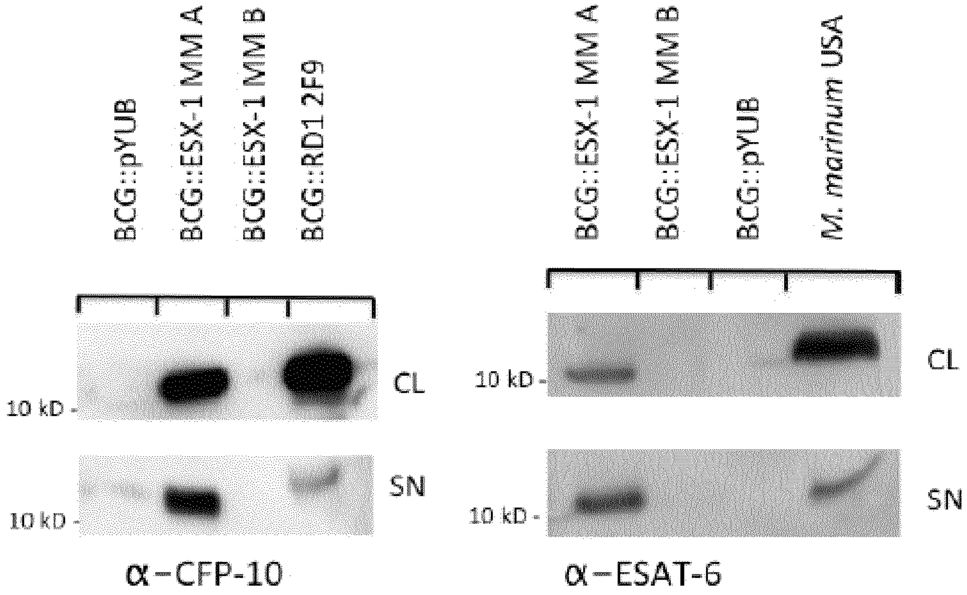
FIG. 9: Immunoblot analysis of mid-log 10 phase cultures of BCG::ESX-1MM A and B for the secreted proteins ESAT-6 and CFP-10. BCG::pYUB served as negative control not encoding and secreting these proteins. For positive control BCG::RD1 2F9 and *M. marinum* were used. CL=Cell lysate, SN=Supernatant.
Figure 10:
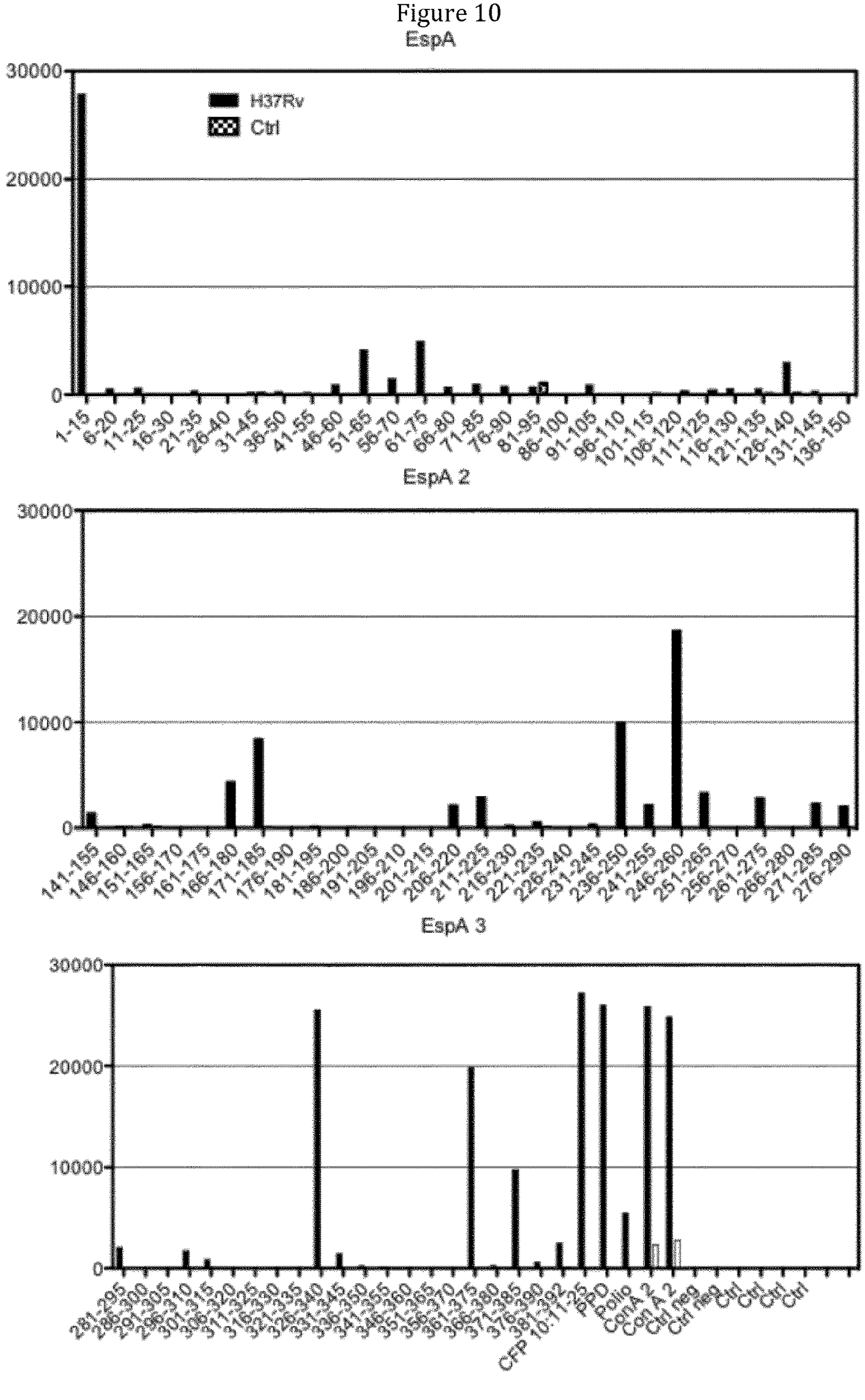
FIG. 10: T-cell epitope mapping of EspA. Splenocytes from Mtb-immunized C3H (H-2K) mice were stimulated with each of the individual 15-mer peptides of the EspA pepscan and IFN-γ was quantified in the culture supernatants using ELISA. Two immunodominant epitopes could be identified, namely the 1-15 and 326-340. Several subdominant epitopes such as 361-375 or 246-260 were not chosen for further analysis.

Example 2: Expression of ESX-1 Proteins by Recombinant BCG::ESX-$1^{MM}$ Clone A Next, the functionality of the ESX-1 secretion machinery was investigated. To this end a monoclonal antibody against ESAT-6 and a polyclonal serum against CFP-10 were used. As shown in FIG. 8, substantial homologies exist between Mtb and *M. marinum* ESX-1 genes. In particular, 91 and 97% sequence homologies are detected between the genes coding for ESAT-6 and CFP-10, respectively, leading to high sequence similarities at protein level. Therefore, antibodies specific to Mtb ESAT-6 or CFP-10 most likely will cross recognize their homologues in *M. marinum* [18]. To detect secreted ESX-1 proteins, cell lysates and supernatants from mid-log 10 phase cultures were prepared and stained with the appropriate dilutions of antibodies. FIG. 9 shows that only clone A expresses ESAT-6 and CFP-10 suggesting that the esxAB genes were heterologously expressed and exported via a functioning type VII secretion machinery. Clone B, tested positive on PCR screens, neither produces nor secretes these proteins, possibly due to incorrect integration of the cosmid into the BCG genome, or disintegration after some replication cycles. The integrated ESX-1 region contains more genes than are deleted in the RD1 region from BCG. Based on these results it cannot be inferred which proteins, apart from the RD1 deleted proteins, are BCG or *M. marinum* derived. Conventionally, an antibody staining the intracellular chaperone pro-tein GroEl-2 (Rv0440) is used to ensure that the presence of secreted proteins in the supernatant is due to actual secretion and not lysis of the cells. GroEl-2 was found in the supernatants suggesting that lysis took place and the integration of ESX-1 of *M. marinum* is toxic to the BCG cells after a number of replication cycles. Accordingly, different immunological tools were used to investigate the secretion of ESX-1 substrates from this clone in more detail.

Example 3: Search for Immunodominant Epitope in EspA

Apart from the virulence factors ESAT-6 and CFP-10, the ESX-1 region secretes other proteins encoded outside the ESX-1 locus, the ESX-1 secretion-associated proteins (Esps). In order to reveal the molecular mechanisms by which these proteins are involved in secretion and immunogenicity a powerful tool is to generate T-cell hybridomas which harbour T-cell receptors (TCR) specific to immunodominant epitopes of the secreted proteins. Upon secretion into the host cell phagosome these proteins are processed and presented by Major Histocompatibility Complex (MHC) class II molecules at the cell surface and recognized by the specific TCRs of the hybridoma. The secretion of even minute levels of proteins inside infected cells can be detected by quantifying the Interleukin-2 produced by the hybridoma using ELISA. The lab has previously generated T-cell hybridomas specific to the secreted proteins ESAT-6, EspC and to Ag85A. The latter is secreted via the conventional Sec pathway and presents therefore an internal positive control. The goal is to expand this library with hybridomas specific for EspA and CFP-10.

Figure 13:
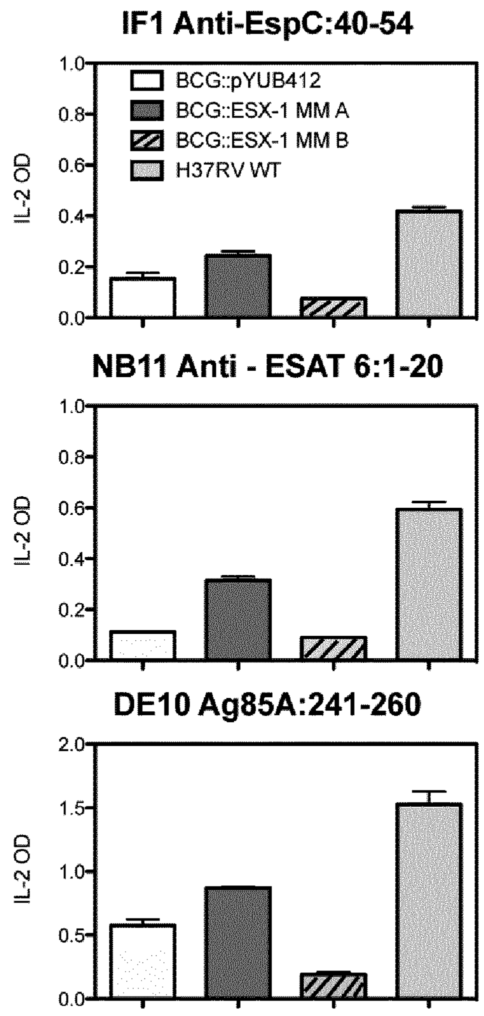
FIG. 13: Antigen presenting assay showing mycobacterial secreted pro-teins presented by BM-DCs infected at an M.O.I. of 4 with subsequent twofold dilutions. The bell-shaped curve demonstrates the lowest M.O.I. necessary to ensure presentation of antigens and the highest M.O.I. when mortality interferes with presentation.

To this end the immunodominant regions of the EspA protein were identified by epitope mapping, while the immunodominant epitope of CFP-10 has been previously described [75]. For EspA, splenocytes from Mtb-infected mice were stimulated with each of the 77 individual 15-mer peptides scanning the entire sequence of EspA. Next, the IFN-γ response was quantified to map the immunodominant epitopes of EspA. Splenocytes from Mtb-immunized C57BL/6 (H-2b), BALB/C (H-2d) (data not shown) or C3H (H-2K) mice were screeded and two immunodominant regions in C3H mice were identified (FIG. 13). Only in C3H mice two different immunodominant region for EspA could be identified. C3H mice were subsequently immunized by a mixture of CFP-10:11-25, EspA:1-15 and EspA:324-340 synthetic peptides containing these immunodominant epitopes in order to isolate from the same mice, splenocytes harbouring T-cell receptors specific to the three different epitopes. T-cell hybridomas were generated by fusing the restimulated splenocytes with BW5147 thymoma cells, as described in Methods. In a first attempt, only T-cell hybridomas harbouring TCRs specific for CFP-10:11-25 appeared after fusion, the most probably due to the strong immunodominance of the latter over the EspA epitopes.

Example 4: Generation of XE12, an Anti-CFP-10:11-25 T-Cell Hybridoma

Figure 11:
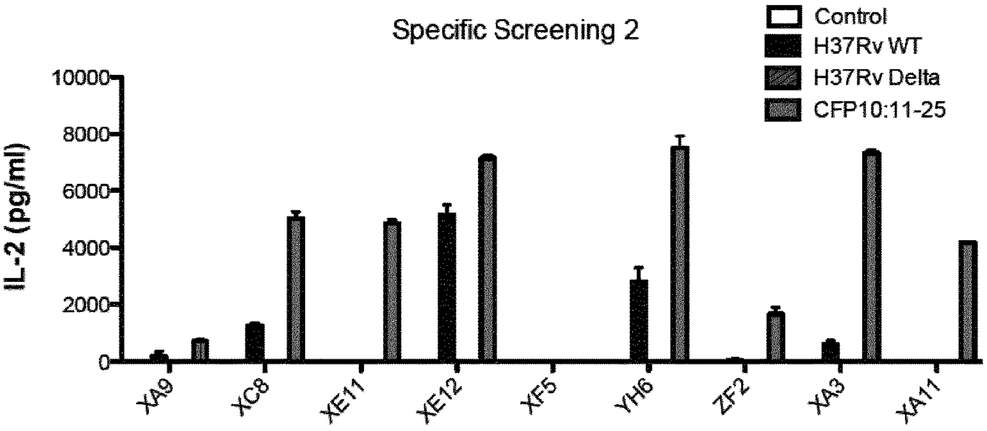
FIG. 11: Screening of T-cell hybridoms specific to CFP-10:11-25, C3H-derived BM-DC were infected with H37Rv WT, or ESX-1 deficient mutants or were loaded with the homologous peptide. After incubation overnight the hybridomas were added and IL-2 was quantified. Only the hybridoma that responded to both the peptide as well as the protein secreted by H37Rv WT were chosen, namely XC8, XE12 and YH6.
Figure 12:
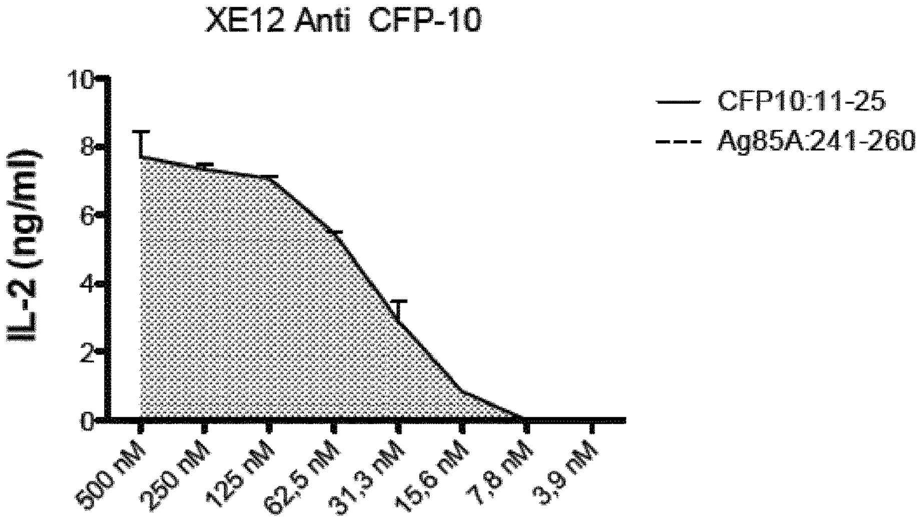
FIG. 12: The XE12 hybridoma produces IL-2 in response to CFP-10:11-25 starting at concentrations of less than 15 nM. This is more sensitive and specific than analysis using Western Blot techniques and presents a powerful tool to detect secretion of proteins at even minute levels.

The anti-CFP-10:11-25 hybridomas were named according to their position on the 96 well plates. In a first screen, all hybridoma candidates were tested for their specificity for the CFP-10:11-25 peptide when co-cultured with naïve splenocytes that were presenting the homologous peptide. Of the 38 candidates that had fused 18 were selected for further analysis. To determine their specificity in more detail the 18 candidates were co-cultured with BM-DC either loaded with homologous peptide, a negative control peptide, or infected with Mtb H37Rv WT or ΔESX-1. Two hybridomas, XE12 and YH6 appeared to produce IL-2 in response to splenocytes infected with H37Rv WT or stimulated with the peptide but not to H37Rv Δ ESX-1 which is deleted for the ESX-1 region and hence for the CFP-10 gene (FIG. 11). This is an important step as the majority of the hybridomas harbour TCRs specific for the epitope derived from the peptide but not the ordinary epitope displayed following infection with Mtb. Using this essay it was possible to select the two hyridomas, which recognize both the synthetic peptide and the native protein secreted following infection. The next step was to characterize the sensitivity of the hybridomas to determine the smallest concentration to which the hybridoma responds by IL-2 production. Here, BM-DC were cultured with different concentrations of the peptide and IL-2 was quantified after 24 h incubation with the two hybridoma candidates. XE12 appeared to be highly sensitive already responding at peptide concentrations of 15 nM.

Example 5: Analysis of ESX-1 Protein Secretion and Antigenic Presentation in Infected Dentritic Cells The Western blot analysis (FIG. 9) showed that cell lysates contain large amounts of ESAT-6 and CFP-10 indicating that the protein is properly expressed. Likewise, the proteins could be detected in the supernatant proving that the secretion machinery encoded in the ESX-1 region is functioning. To further characterize the secretion of virulence proteins bone marrow derived dentritic cells (BM-DC) from C3H mice were infected with the two BCG mutants, BCG::ESX-$1^{MM}$ A and B and detected levels of secreted ESX-1 proteins using the T-cell hybridomas. We were particularly interested in the recombinant clone BCG::ESX-1MM B that was PCR positive but showed no response on Western blotting. Notably, also the NB11 Anti-ESAT-6 T-cell hybridoma showed no secretion for this clone as opposed to the Western Blotting positive clone, BCG::ESX-1MM A and the positive control, H37Rv WT Mtb, confirming the correct integration and functioning of the ESX-1 region in the A clone (FIG. 13). Likewise, using the XE12 anti-CFP-10 hybridoma it was possible to detect secretion in the A strain compared to the B strain which further corroborates functioning integration of the genetic addition in the A strain (data not shown). Next, the protein EspC which is encoded outside the ESX-1 locus was tested for secretion. This is therefore a BCG protein (Mb3645c) that needs to be secreted via the added *M. marinum* ESX-1 encoded Type VII secretion machinery. The amino acid match between the Mtb and BCG proteins was retrieved using Genolist (http://genolist.pasteur.fr/—BoviList/genome.cgi) which showed 100% homology for EspC:40-54, the immunogenic epitope recognized by I-Ab-restricted IF1 T-cell hybridoma. Substantial secretion of EspC by BCG::ESX-1 Mtb and varying levels of the different other strains was found. Notably the BCG::ESX-1MM A had a higher secretion than BCG::ESX-$1^{MM}$ B. Lastly, the DE10 Anti-Ag85A hybridoma is used as a control for this assay as it detects a protein that is secreted via the conventional Sec pathway. Taken together these data prove the correct function and secretion, processing and antigen presentation of ESX-1 encoded proteins ESAT-6 and CFP-10 and confirms the results obtained by immunoblotting.

Example 6: Immunogenicity

Figure 14:
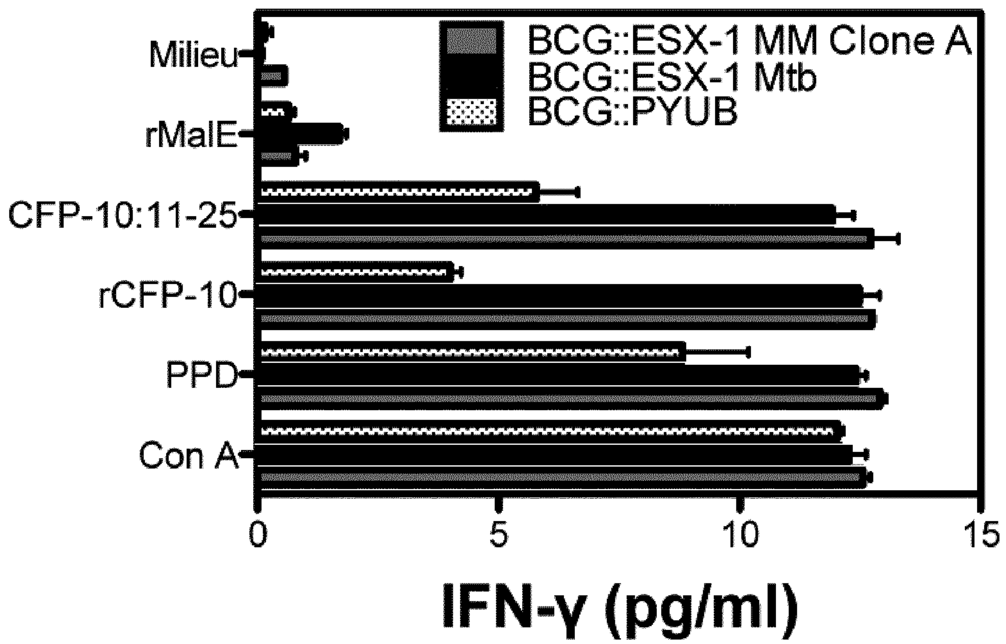
FIG. 14: Evaluation of the immunogenicity of the BCG::ESX-1MM clone A. T-cell responses of splenocytes from C3H immunized mice against PPD, CFP-10:11-25 peptide or CFP-10 recombinant protein. MalE was used as a negative recombinant control antigen. Both BCG::ESX-1Mtb and BCG::ESX-1MM clone A are able to induce strong T-cell responses against CFP-10 in vivo. It has been previously shown that the immunogenicity of ESX-1 substrates is directly proportional to their proper secretion by the ESX-1 machinery.

The two substantial characteristics a vaccine candidate must possess are its safety and its immunogenicity. While we ascertain the safety of a vaccine in severely immunosuppressed mice (SCID) we evaluated the immunogenicity of clone A in immunocompetent C3H mice in a splenocyte stimulation assay. Proper secretion of proteins is a prerequisite to elicit strong and specific T-cell responses [64]. Hence this method is a validated tool to confirm expression and secretion of the virulent factors encoded in the ESX-1 region. To this end, groups of C3H mice (H-2K) were subcutaneously immunized with BCG::pYUB, as negative control, or BCG::ESX-1Mtb, as positive control, or the BCG::ESX-1MM A strain (n=2/group). Three weeks later, T-cell immunity was assessed by comparing antigen-specific IFN-γ release by splenocytes. Concanavalin A was used to control the culturing and Purified Protein Derivative (PPD), a mix of Mtb proteins, was employed to ensure successful immunization. The results show that both the peptide CFP-10:11-25 as well as the recombinant protein CFP-10 cause IFN-γ release from splenocytes of immunized mice of the two recombinant strains (FIG. 14). The BCG::ESX-1 Mtb and BCG::ESX-1MM A exert an immunogenic response at similar level. The fact that even BCG::pYUB immunized mice react to CFP-10 stimulation, which is not encoded in this strain, is due to presence of ESX-1 components in these bacteria. PCR analysis, subsequent to these results, confirmed that the BCG::pYUB strain used in this experiment was expressing ESX-1 genes. Hence, these experiments need to be repeated using a different negative control. The use of C3H allowed us to only study for peptides restricted by MHC-II of the H-2K haplotype, further experiments to study the immunogenic potential of ESAT-6 stimulation assays on C57BL/6 mice (H-2b restricted) are planned. Taken together these results support that the ESX-1 region has integrated and functions properly to secrete the encoded proteins, such as CFP-10.

Example 7: Virulence

Figure 15:
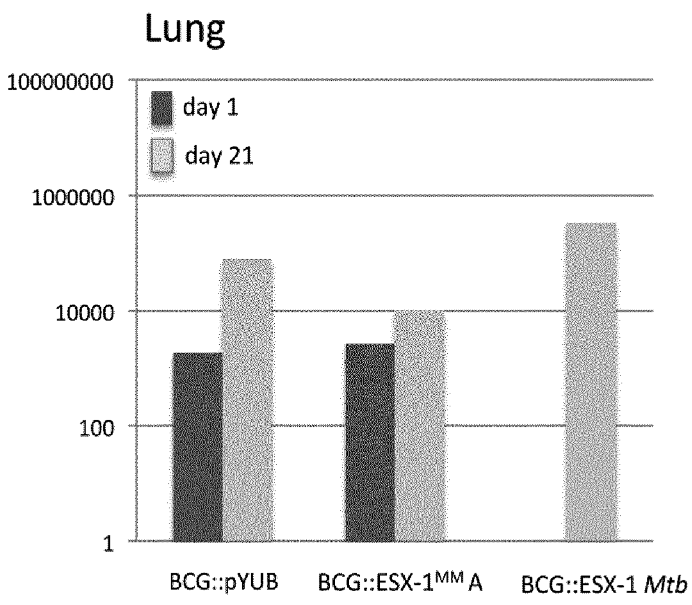
FIG. 15: Virulence studies in SCID mice suggest that the ESX-1 region of *M. marinum* is less virulent than its Mtb homologue (A in lung, B in spleen). While both BCG::ESX-1MM A and BCG::pYUB have similar levels of CFUs on day 1 the virulence of the former strain is lower as indicated by the CFUs counted on day 21. The initial CFUs for the BCG::ESX-1 Mtb strain seem to be too low but its virulence is demonstrated by high mycobacterial load on day 21 confirming earlier results [64].
Figure 15:
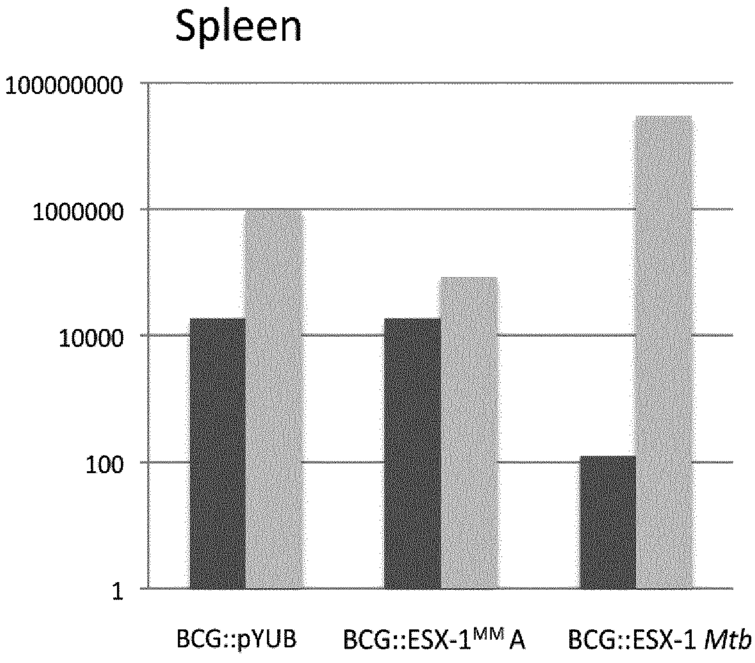

The second substantial feature of a vaccine is its safety. BCG is the most used vaccine worldwide with an astonishing safety record [59]. A potential vaccine candidate needs to as safe as BCG in order to advance to the clinical evaluation. To investigate the virulence of the A strain we infected SCID mice (n=5/group) intravenously with BCG::ESX-1$^{MM}$ A, BCG::ESX-1 Mtb and BCG::pYUB. The lungs and spleen were retrieved after 3 weeks and plated on agars to count the Colony Forming Units. While the bacteria injected were comparable for the A strain and BCG::pYUB (CFUs on day 1) the dose of BCG::ESX-1 Mtb appears to be too little (FIG. 15). The recorded virulence of this strain, however, was confirmed as on day 21 most CFUs were counted in mice injected with this strain. Interestingly, the A strain showed lower CFUs on day 21 than BCG::pYUB, suggesting that the strain undergoes a self limiting process such as lysis. This would be in line with our results obtained by immunoblotting where we continued to detect the intracellular chaperone GroEl-2 in the supernatant. It is possible that the genomic ESX-1 region from *M. marinum*, which is more distant than the respective region in Mtb, is not tolerated over a number of replication cycles in BCG and hence leads to lysis. While this could constitute a desirable feature of a vaccine, the exact process needs to be elucidated to be able to estimate the kinetics of antigenic material being presented to host cells to avoid exacerbated host immune responses [77,78].

Example 8: Induction of Phagosomal Rupture

Figure 16:
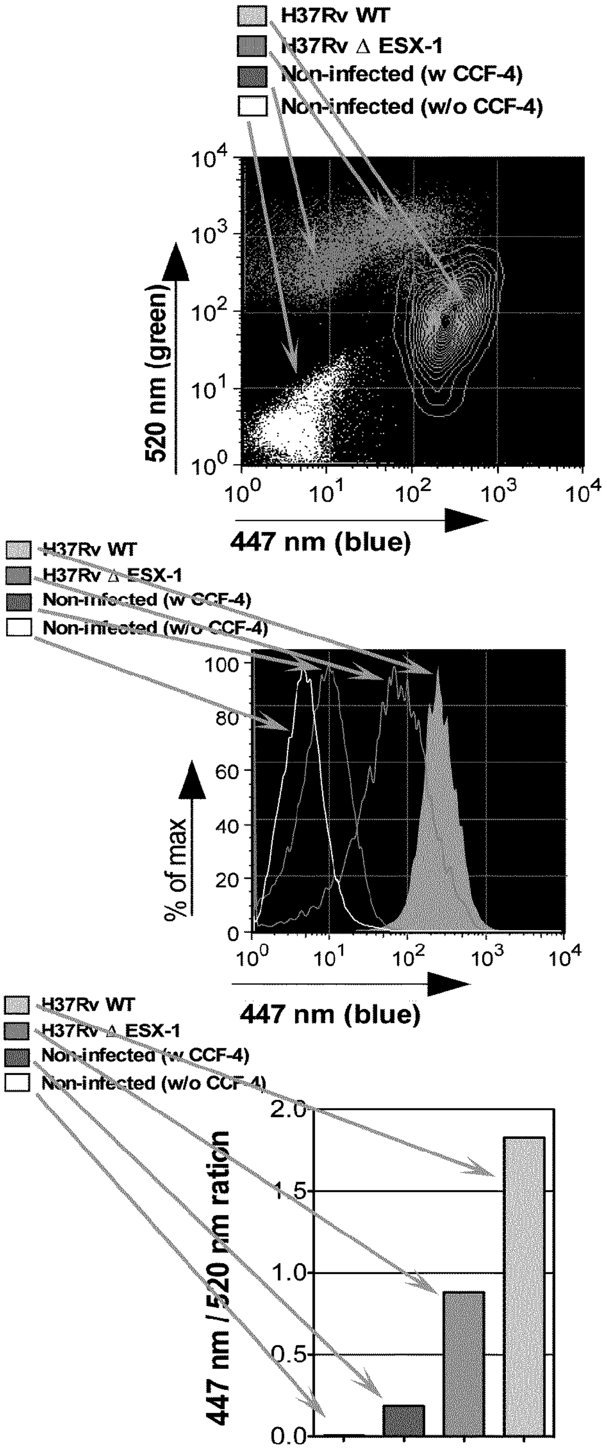
FIG. 16: FRET based study of phagosomal rupture of the different mycobacterial strains. In A, the phagosomal rupture induced by the strains H37Rv WT is evident by the increased blue (447 nm)/green (520 nm) ratio. The H37Rv Δ ESX-1 which does not encode the ESAT-6 family anymore shows a much weaker shift towards blue. Interestingly, the recombinant BCG encoding the ESX-1 *M. marinum* region is able to induce phagosomal rupture (B) compared to the negative controls, exhibiting a similar blue/green ratio as H37Rv WT. Cells were infected with an M.O.I. of 1 and analyzed 4 days after infection.
Figure 16:
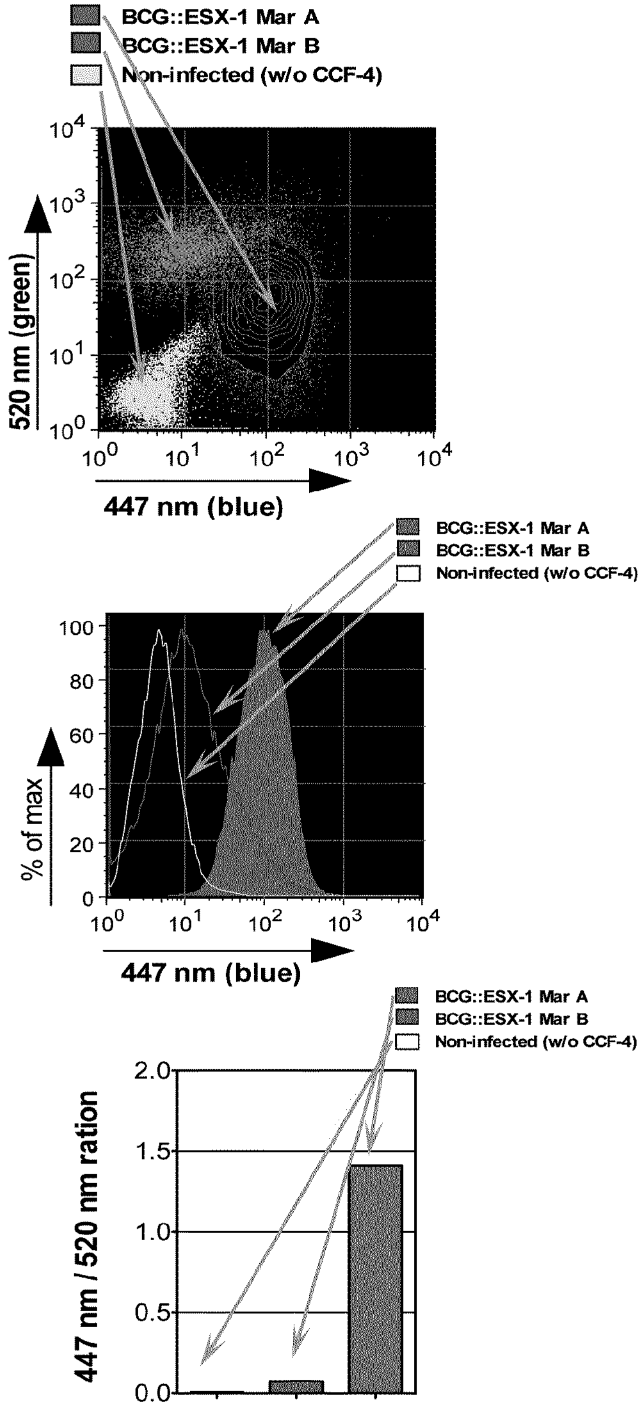

Mtb has long been thought to reside within the macrophage phagosome. This paradigm has only recently been challenged [79]. Mtb-mediated phagosomal rupture, possibly resulting in the translocation of the bacteria from the membrane-bound compartment into the host cell cytosol, correlates with virulence and pathogenicity [80]. Interestingly, this phagosomal rupture is dependant on ESAT-6 secretion and correct functioning of the ESX-1 T7SS [81]. To further characterize the pathogenic potential of the BCG:ESX-1MM A strain in terms of its ability to induce phagosomal rupture we used a fluorescence-based method where the cytoplasm of THP-1 cells, a human monocytic cell line, is loaded with a chemical probe that is sensitive to fluorescence resonance energy transfer (FRET) measurements [82]. This chemical probe, CCF-4, can be cleaved by the B1aC mediated β-lactamase intrinsic activity of Mtb and BCG [83]. In THP-1 cells infected with the different mycobacterial strains, CCF-4 diffuses freely across the cytoplasma membrane wherein it remains trapped. If the bacteria succeed in induction of phagosomal rupture, the CCF-4 is cleaved by the intrinsic β-lactamase activity of the bacteria which leads to a switch of the FRET signal from 535 nm (green) to 450 nm (blue) upon 405 nm excitation. Thus only bacteria with a functioning, ESAT-6 secreting ESX-1 system will show a FRET signal switch towards blue. The change in fluorescence can be detected using flowcytometry where gates on CD11b positive cells are used to exclude bacteria and cell debris in the flow cytometry analysis. The results show that all strains owning a functioning ESX-1 region such as Mtb induce phagosomal rupture, as evident in the FRET signal shift towards blue (FIG. 16A). Interestingly, the BCG::ESX-1$^{MM}$ A strain similarly induces a strong shift towards blue, confirming its ability to export the ESX-1 proteins and therefore the phagosomal rupture (FIG. 16B). We also tested whether the signal for the BCG::ESX-1MM B strain, that was PCR positive for ESX-1 gene primers and showed no ESAT-6/CFP-10 expression on immunoblotting, would cause a FRET signal shift towards blue. Indeed, the signal remained green similar to the negative controls BCG::pYUB and non-infected cells (FIG. 16B). These results may underline the pathogenic potential of the BCG::ESX-1MM A strain in addition to the correct and integrative functioning of the added genetic ESX-1 region.

Example 9: Evaluation of the Virulence of Strain *Mycobacterium bovis BCG::ESX*$1_{M.\ marinum}$ (Also Named BCG::RD$1_{M.\ marinum}$ or BCG::RD1-*Marinum*) in Comparison with *Mycobacterium tuberculosis* H37Rv, *Mycobacterium bovis* BCG Pasteur, and *Mycobacterium bovis* BCG::ESX-1-Mtb (Also Named BCG::RD1-2F9) in Severe Combined Immune-Deficient (SCID) Mice Two experiments of virulence test were undertaken for which the results are shown on FIGS. 17-19. In both experiments, injection of groups of mice were done intravenously (iv) and the infectious dose was determined at day 1 (mice were euthanized at day 1). The infectious dose recovered from the lungs and spleens corresponds to the mean CFU from 2 mice (a total of 12 mice was infected).

Cfu values in mice of Experiment 1 (FIG. 17):

CFU Values Per Organ at Day 1

| Strains | cfu/lungs | cfu/spleen |
|---|---|---|
| BCG::RD1-marinum | 9375 | 31250 |
| BCG Pasteur | 6250 | 25000 |
| H37Rv | 1250 | 6250 |

Cfu values in mice of Experiment 2 (FIG. 18):

| | CFU lungs at day 1 | CFU spleen at day 1 |
|---|---|---|
| BCG Pasteur | 5.31E+04 | 1.17E+05 |
| BCG::RD1-Marinum | 4.06E+04 | 2.08E+05 |

-continued

| | CFU lungs at day 1 | CFU spleen at day 1 |
|---|---|---|
| BCG::RD1-2F9 | 2.50E+04 | 9.35E+04 |
| H37Rv | 2.92E+04 | 9.37E+04 |

*M. microti* ATCC 35782 was purchased from the American Type Culture Collection (designation TMC 1608)

*M. microti* OV254 was originally isolated from voles in the United Kingdom in the 1930s (Wells, A. Q. 1937. *Tuberculosis* in wild voles. Lancet i:1221).

*M. microti* Myc 94-2272 was isolated in 1988 from the perfusion fluid of a 41-year-old dialysis patient (Van Soolingen, D., A. G. M. van der Zanden, P. E. W. De Haas, G. T. Noordhoek, A. Kiers, N. A. Foudraine, F. Portaels, A. H. J. Kolk, K. Kremer, and J. D. A. van Embden. 1998. Diagnosis of *Mycobacterium microti* infections among humans by using novel genetic markers. J. Clin. Microbiol. 36:1840-1845).

*M. microti* Maus IV is the human isolate B4 type vole obtained from the collection of the National Reference Center for Mycobacteria, Forschungszentrum Borstel, Borstel, Germany, as described in Brodin P, Eiglmeier K, Marmiesse M, Billault A, Garnier T, Niemann S, Cole S T, Brosch R. 2002. Bacterial artificial chromosome-based comparative genomic analysis identifies *Mycobacterium microti* as a natural ESAT-6 deletion mutant. Infect Immun. 70(10): 5568-78.

The *M. microti* strains were tested in the same model because some of them were meant to be vaccine strains and some of them were isolated from infected humans. These strains were control strains that were used in the same experimental setting, but they do not intervene with the testing of the BCG and recombinant BCG strains. Only the strains marked with an arrow, ie *M. microti* 2272-94, BCG::RD1$_{M.\ marinum}$ and BCG Pasteur (FIG. 17), are the main strains of interest for the vaccine testing purpose.

The virulence test corresponds to a survival experiment (time to reach the humane endpoint, which corresponds to a 20% weight loss for the mice).

For survival experiments, groups of 10 female SCID mice were subjected to intravenous challenge with a single dose of bacteria (nominally $10^6$ CFU/mouse) of the different strains and weight was controlled regularly. Upon weight loss of 20% mice were killed and the date reported in the graph.

Figure 17:
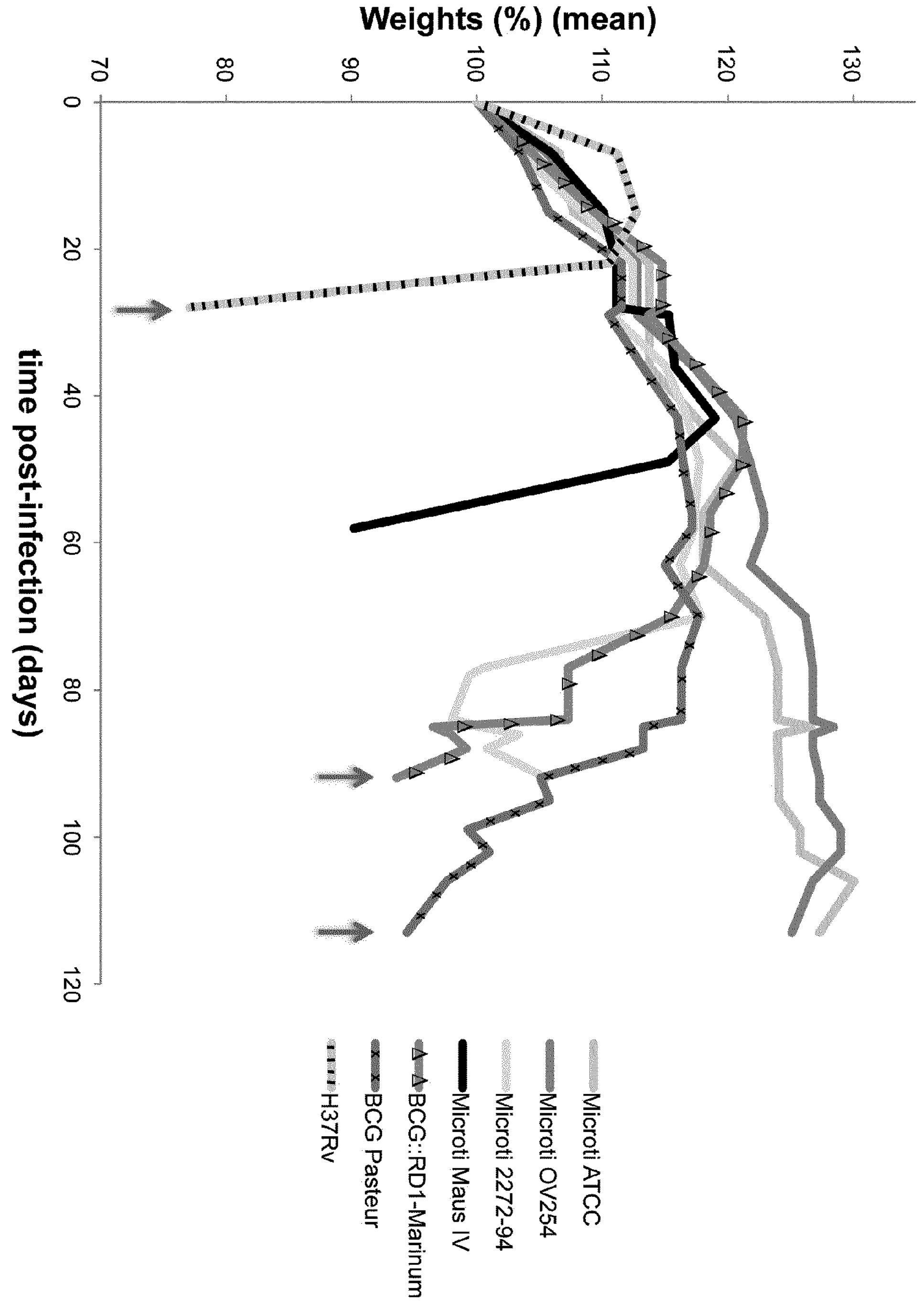
FIG. 17: Survival experiment of SCID mice that were intravenously infected with ~$10^{(6)}$ CFU per mouse. The different lines indicate the weight gain or loss of infected SCID mice over time, until they reach the humane endpoint (=20% loss of their bodyweight, when mice were killed). These virulence studies show that the ESX-1 region of *M. marinum* confers almost no additional virulence compared to the regular BCG Pasteur, particularly, as the initial dose tested (indicated on the figure) on two mice is slightly higher for BCG::RD1-*marinum* (=BCG::ESX-$1_{M.\ marinum}$). The time to humane endpoint experiment was conducted on 10 mice per group, for which the mean weight is shown here. The graphs for *Mycobacterium microti* infected mice are shown because these strains were tested in the same experiment, using the same BCG control, however, the data are not subject of this application.
Figure 18:
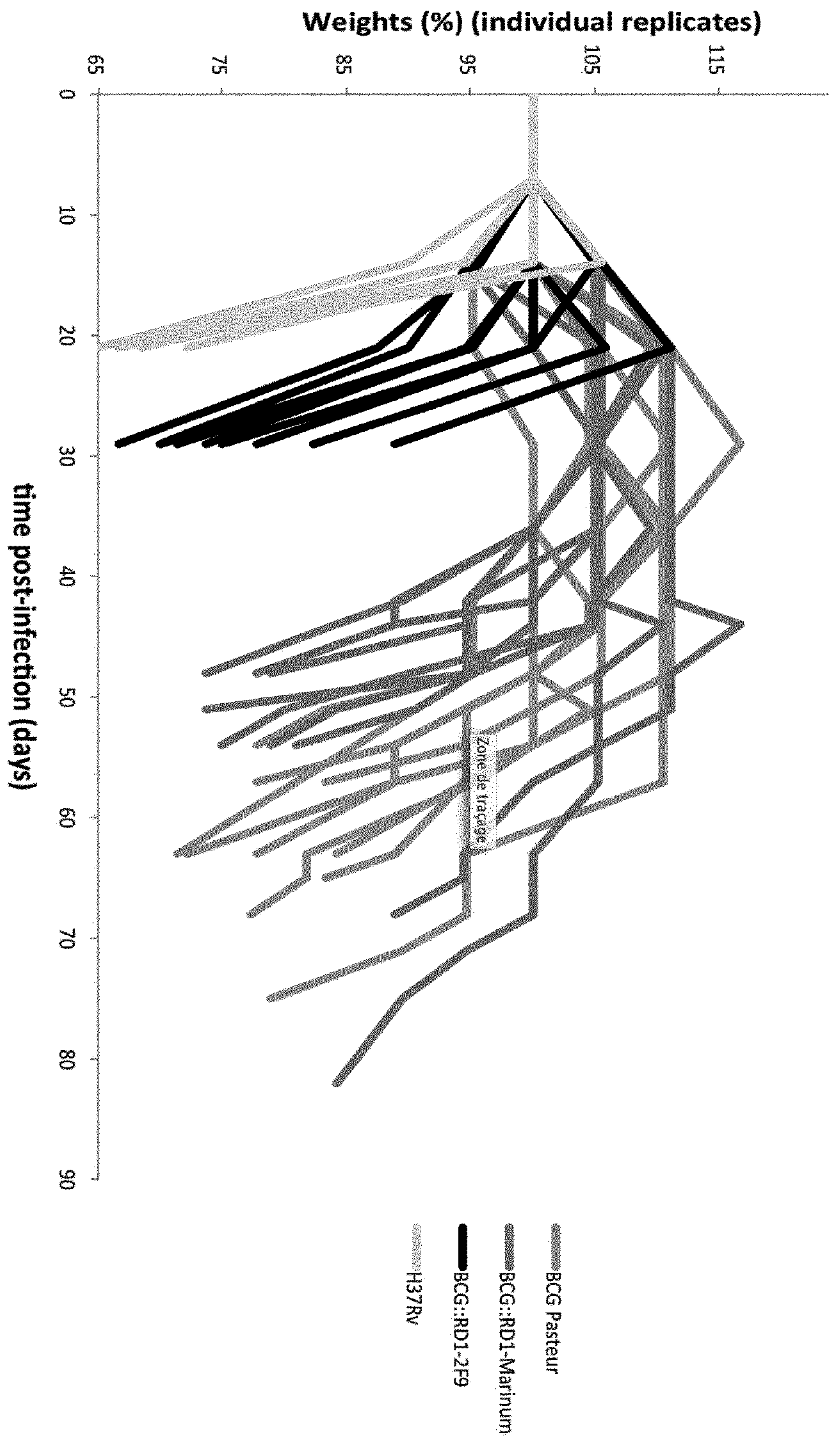
FIG. 18: Survival experiment of SCID mice that were intravenously infected with ~$10^{(6)}$ CFU per mouse. The different lines indicate the weight gain or loss of infected SCID mice over time, until they reach the humane endpoint (=20% loss of their bodyweight, when mice were killed). These virulence studies show that the ESX-1 region of *M. marinum* confers much less virulence than the one from *M. tuberculosis*. The survival of SCID mice infected with BCG::RD1-*marinum* (=BCG::ESX-$1_{M.\ marinum}$) is very similar to the survival time of SCID mice infected with BCG Pasteur. The time to humane endpoint experiment was conducted on 10 mice per group, for which the individual weight curves are shown here.
Figure 19:
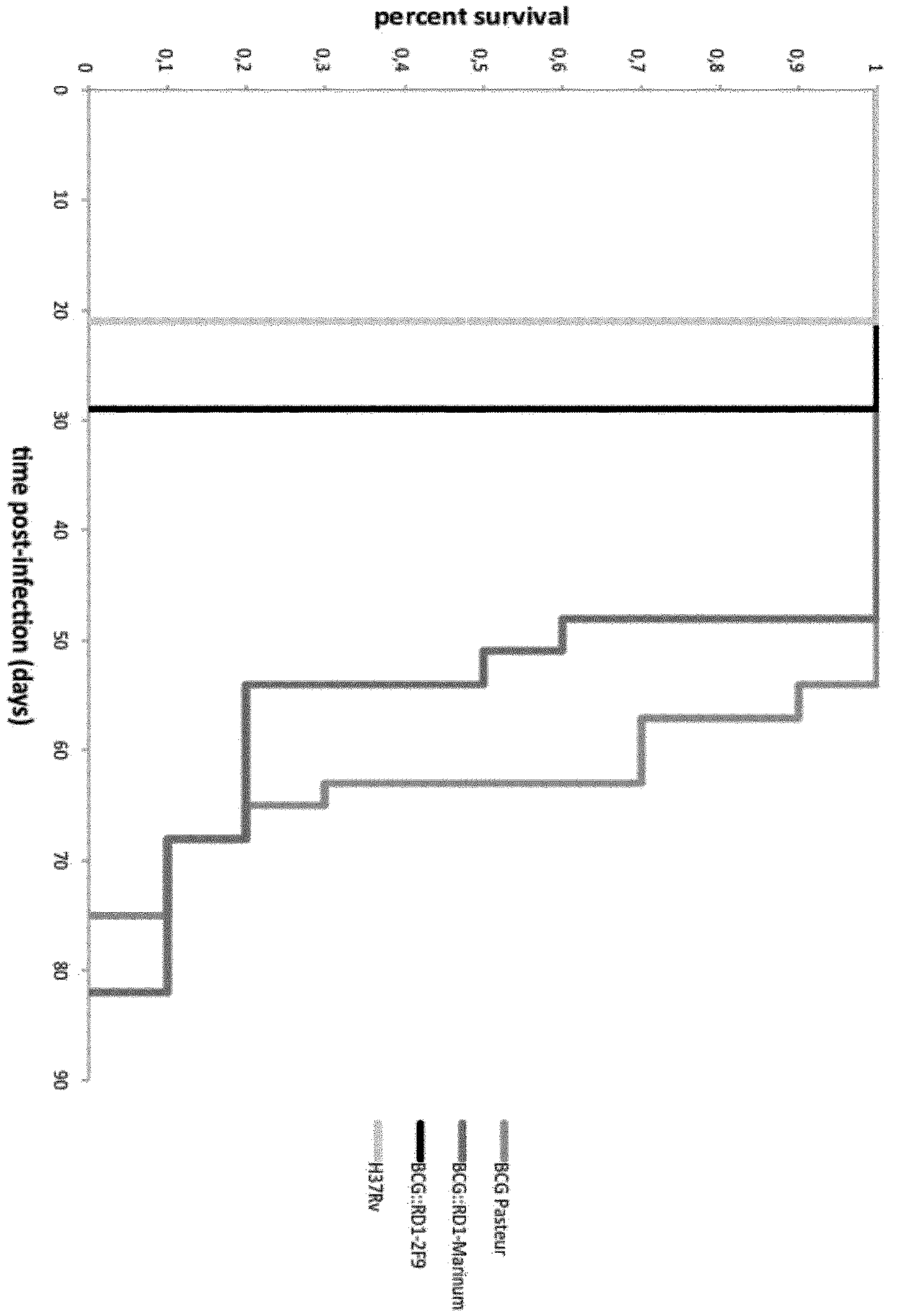
FIG. 19: Survival experiment of SCID mice that were intravenously infected with ~$10^{(6)}$ CFU per mouse. The different lines indicate the weight gain or loss of infected SCID mice over time, until they reach the humane endpoint (=20% loss of their bodyweight, when mice were killed). These virulence studies show that the ESX-1 region of *M. marinum* confers much less virulence than the one from *M. tuberculosis*. The survival of SCID mice infected with BCG::RD1-*marinum* (=BCG::ESX-1-*marinum*) is very similar to the survival time of SCID mice infected with BCG Pasteur. The time to humane endpoint experiment was conducted on 10 mice per group, for which the mean weight is shown here.

Virulence data are shown in FIG. 17 (experiment 1) and FIGS. 18 & 19 (experiment 2).

As a conclusion, SCID mice infected with the BCG::ESX1$_{M.\ marinum}$ strain survived much longer than BCG::ESX-1-mtb infected mice (until reaching the humane endpoint of loss of 20% bodyweight). Survival was very similar to mice infected with the BCG Pasteur parental strain.

Example 10: Virulence Tests of BCG::RD1$_{M.\ marinum}$ in Guinea Pigs Infected by Aerosol, Compared to BCG::RD1$_{M.\ marinum}$ and *M. tuberculosis*

Material & Methods:

Animals used in this experiment are Hartley guinea pigs (female) purchased from Charles River, 69592 L'Arbresle, France, up to 200 g at arrival in the animal house.

Twelve days after arrival, the animals were infected via aerosol using commercially available sterile nebulizers (atomizers) and bacterial solutions made from aliquots of a frozen (−80°) stock culture of Mtb H37Rv (concentration used $2.5\times10^{(5)}$ cfu/ml), BCG::RD1-*marinum* (also named BCG::ESX-1$_{M.\ marinum}$) (concentration used $3.5\times10^{(5)}$ cfu/ml), and BCG::RD1-Mtb (concentration used $2.75\times10^{(5)}$ cfu/ml). The concentration of live bacteria was verified a second time before infection, by plating out various dilutions of an aliquot of the stock culture.

Before the infection, the weight of the animals is determined (~in average 250 g). Then, animals are transferred into 500 ml plastic containers (bottles) with their nose towards the 1.5 mm opening of the container. Four such containers are then placed into each of the two aerosol chambers (340 mm long, 170 mm high and 180 mm wide), which are located in an airtight isolator that is kept under negative pressure (and which can be connected to the isolator containing the animal cages).

For each round of infection, 6 ml at the above mentioned concentration (dilution in PBS) are used to be aerosolized at 1.6 bar into each of the aerosol chambers. This procedure lasts 15 minutes until the liquid is completely aerosolized.

After infection, animals are transferred back to their cages, and the procedure is repeated until all animals have been aerosolized.

Two control animals are killed at day 1 (using CO2) after the aerosolization and their lungs are removed, homogenized and plated in different dilutions onto Middlebrook 7H11 plates containing the supplement Middlebrook OADC (Oleic Albumin Dextrose Catalase) in duplicate (1 set without antibiotics and 1 set with ampicilline as lungs of animals are often containing other bacteria) to estimate the infectious dose obtained in the lungs.

The four remaining animals per group are then kept for 6 weeks, and then killed by using increasing concentrations of CO2 (according to the recommendations of the ethics committee).

Then lungs and spleens are removed, and transferred into specific containers used for grinding the organs in the BSL3 laboratory to obtain a homogenate that is used for preparing dilutions that are plated onto 7H11 plates containing the supplement Middlebrook OADC (Oleic Albumin Dextrose Catalase) in duplicate (1 set without antibiotics and 1 set with appropriate antibiotics mix as lungs of animals are often containing other bacteria). Homogenates are kept at −80° until CFU counts have been done.

Results:

Six guinea pigs per group were infected with the different *mycobacterium* strains: BCG::RD1$_{M.\ marinum}$ (also named BCG//RD1-*Marinum*), BCG::RD1$_{M.\ tuberculosis}$ (also named BCG::RD1-2F9) and *M. tuberculosis* H37Rv.

The infectious doses at day 1 and 6 weeks after the aerosol infection are shown in Table below and in FIG. 23A (day 1) and FIG. 23B (6 weeks).

| | CFU/lung at day 1 after infection | CFU/lung at 6 weeks post infection | CFU/spleen at 6 weeks post infection |
|---|---|---|---|
| BCG::RD1-Marinum | 208 | below detection level | below detection level |
| BCG::RD1-2F9 | 212 | 1.25E+05 | 6.89E+04 |
| H37Rv | 293 | 2.63E+06 | 7.59E+05 |

From previous experiments it is known that the above described aerosol procedure results in about 100-500 CFU per lung at day 1.

Figure 23:
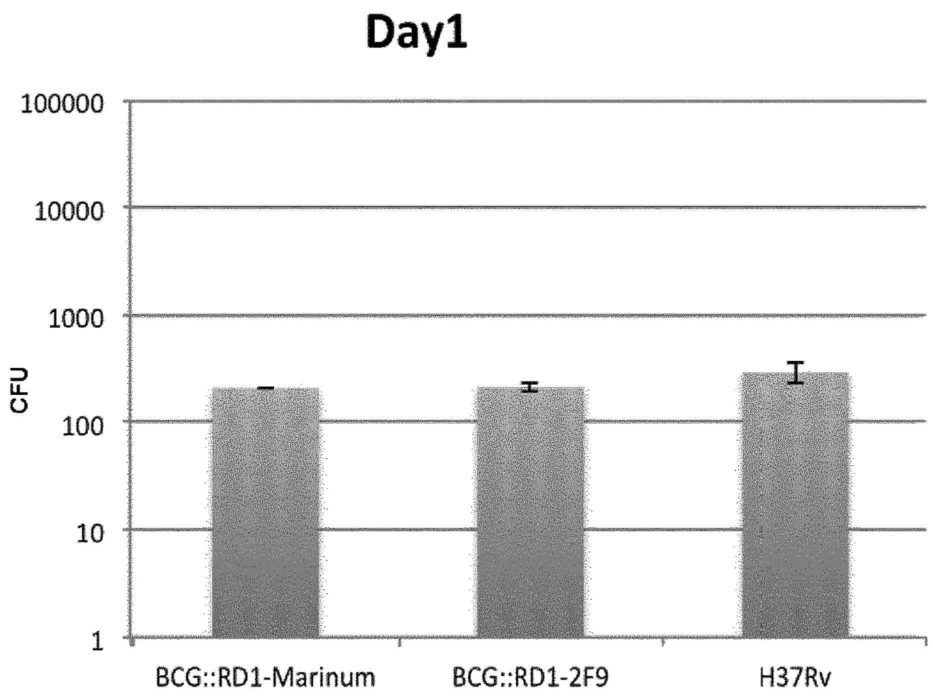
FIG. 23. Virulence test of the BCG::ESX$1_{M.\ marinum}$ in guinea pigs. The recombinant BCG strains BCG::RD$1_{M.\ marinum}$ (=BCG::RD1-*marinum*), BCG::RD$1_{M.\ tuberculosis}$ (=BCG::RD1-2F9) and the virulent *M. tuberculosis* H37Rv strain are administered by aerosol to groups of 6 guinea pigs each. A. One day after aerosol infection of guinea pigs, the dose, measured in CFU, of each of tested *mycobacterium* strains is evaluated in lungs of two guinea pigs. B. Six weeks after aerosol infection of guinea pigs by the different *mycobacterium* strains, the dose of each *mycobacterium* strain, measured in CFU, is evaluated in lungs and spleen of the four guinea pigs of each group. Dark grey bars show CFU in lungs, light grey bars show CFU in spleens.
Figure 23:
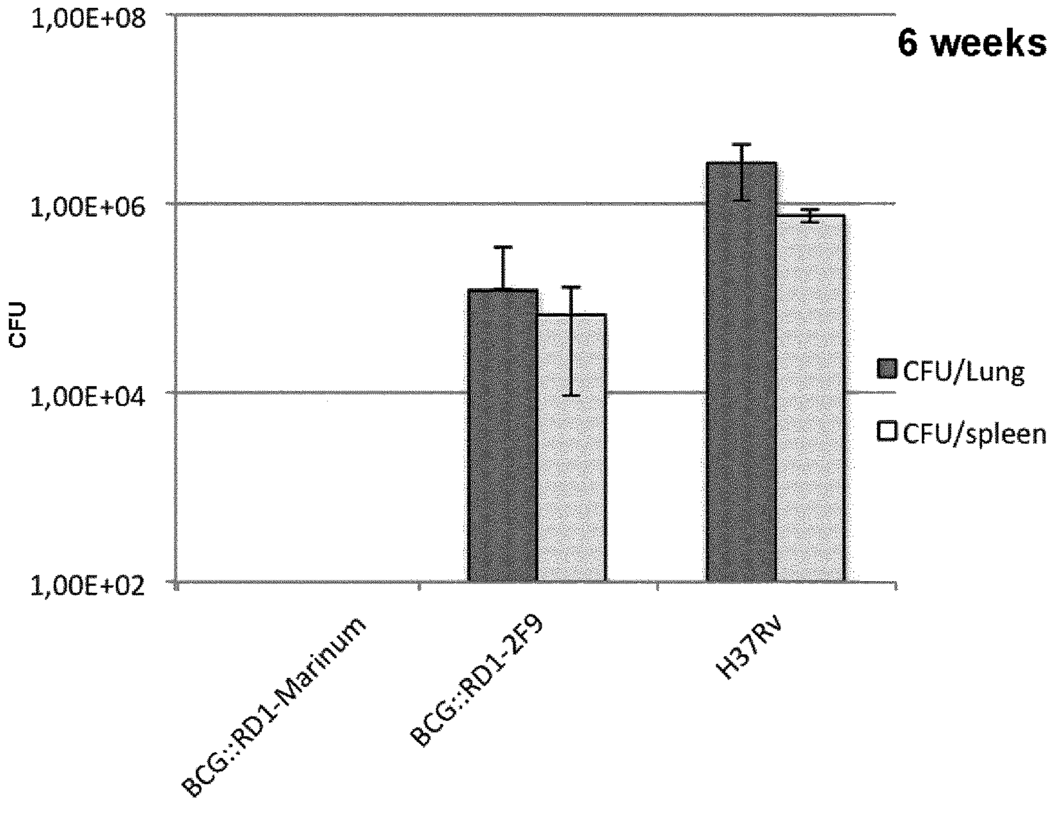

As shown in FIG. 23B and Table above BCG::RD1$_{M.\ marinum}$ was found below detection level at 6 weeks, suggesting that this recombinant strain is strongly attenuated in this sensitive animal model.

From a general aspect of the organs of guinea pigs infected with BCG::ESX-*marinum*, we conclude that they are not affected by pathology.

Example 11: Induction of CD4$^+$ T-Cell Responses Specific to ESX-1 or ESX-5 Substrates in C57BL/6 (H-2$^b$) and in C3H (H-2k) Mice Immunized with BCG::RD1$_{M.\ marinum}$ Mice (n=3/group) were immunized subcutaneously by 1×10$^6$ CFU of mycobacterial strains of vaccine interest. Three weeks post immunization, splenocytes were stimulated in vitro with different antigens to measure the CD4+ T-cell responses.

These data showed that BCG::Esx-1$_{M.\ marinum}$ induced strong T cell responses against ESAT-6 and CFP-10 (Rv3875 and Rv3874), similar to *M. tuberculosis* and BCG::ESX-1-mtb, and the same was true for the ESX-1 associated antigen EspC (Rv3615c), which was also strongly induced in the BCG::ESX-1 complemented BCG strains. Results are presented in FIGS. 20 and 21.

Figure 20:
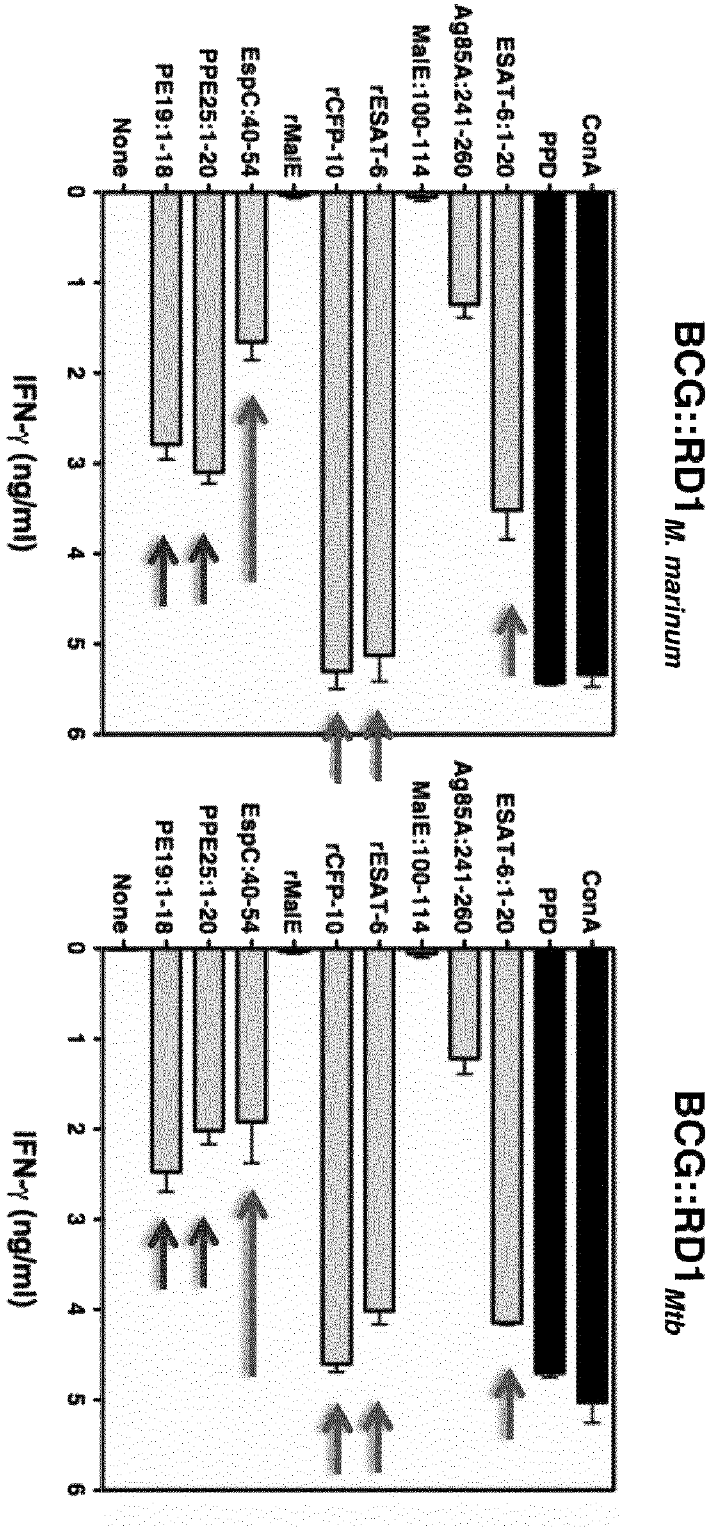
FIG. 20: Induction of CD4+ T-cell responses (as determined by IFN-gamma release by splenocytes) specific to ESX-1 or ESX-5 substrates in C57BL/6 (H-2b) mice, immunized with BCG::pyub (vector control), BCG::RD1-*marinum* (=BCG::ESX-$1_{M.\ marinum}$), BCG::RD1-Mtb strains and *M. tuberculosis* H37Rv as control strain. The light gray arrows point to the responses against ESX-1 antigens, the dark-gray arrows point to responses against epitopes from ESX-5 antigens.
Figure 20:
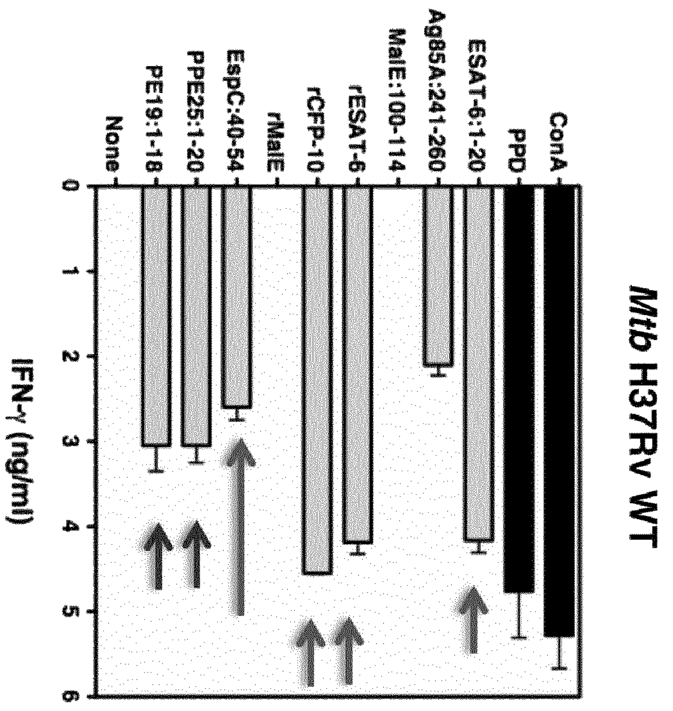
Figure 20:
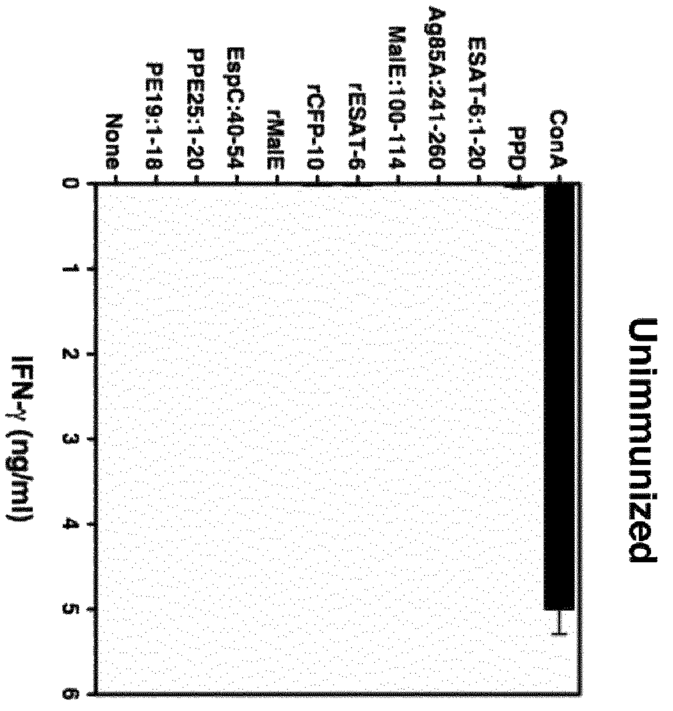
Figure 20:
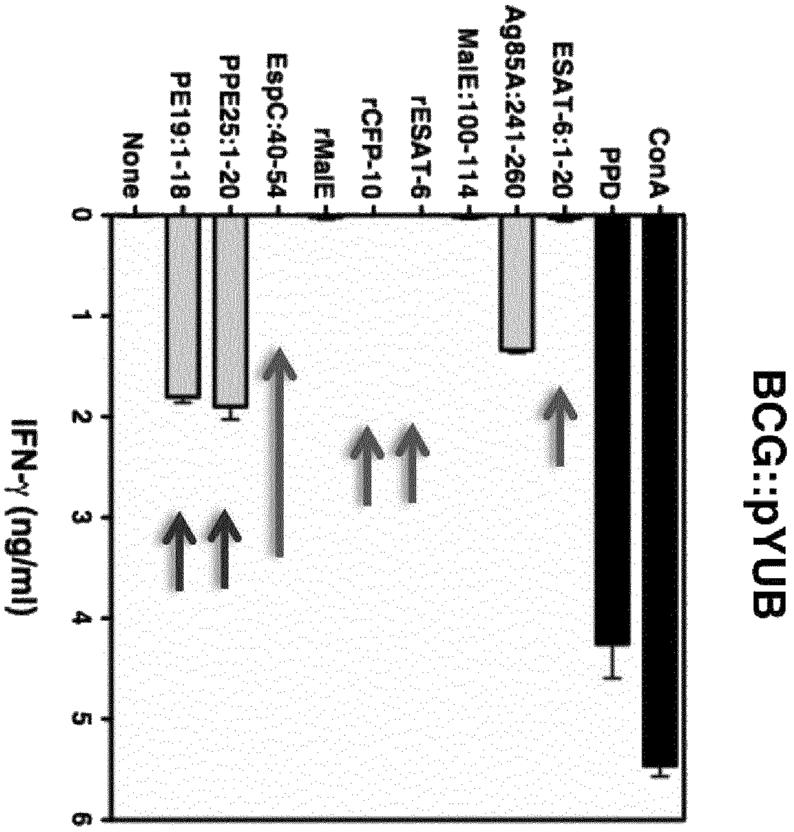

In contrast, no response was obtained for EspA (Rv3616c), which already in *M. tuberculosis* produced a weaker response than the gene product of its neigboring—gene EspC (results on FIGS. 20 and 21).

Example 12: New Vaccination Experiment in which C57BL/6 Mice were Vaccinated with Different Vaccine Candidates and BCG Pasteur-Vector as the Comparator Strain Mice (n=5/group) were immunized subcutaneously by 1×10$^6$ CFU of mycobacterial strains of vaccine interest. Four weeks post immunization, mice were challenged by aerosol with *M. tuberculosis* H37Rv virulent strain in order to deliver approximately 150 CFU/mouse.

Figure 22:
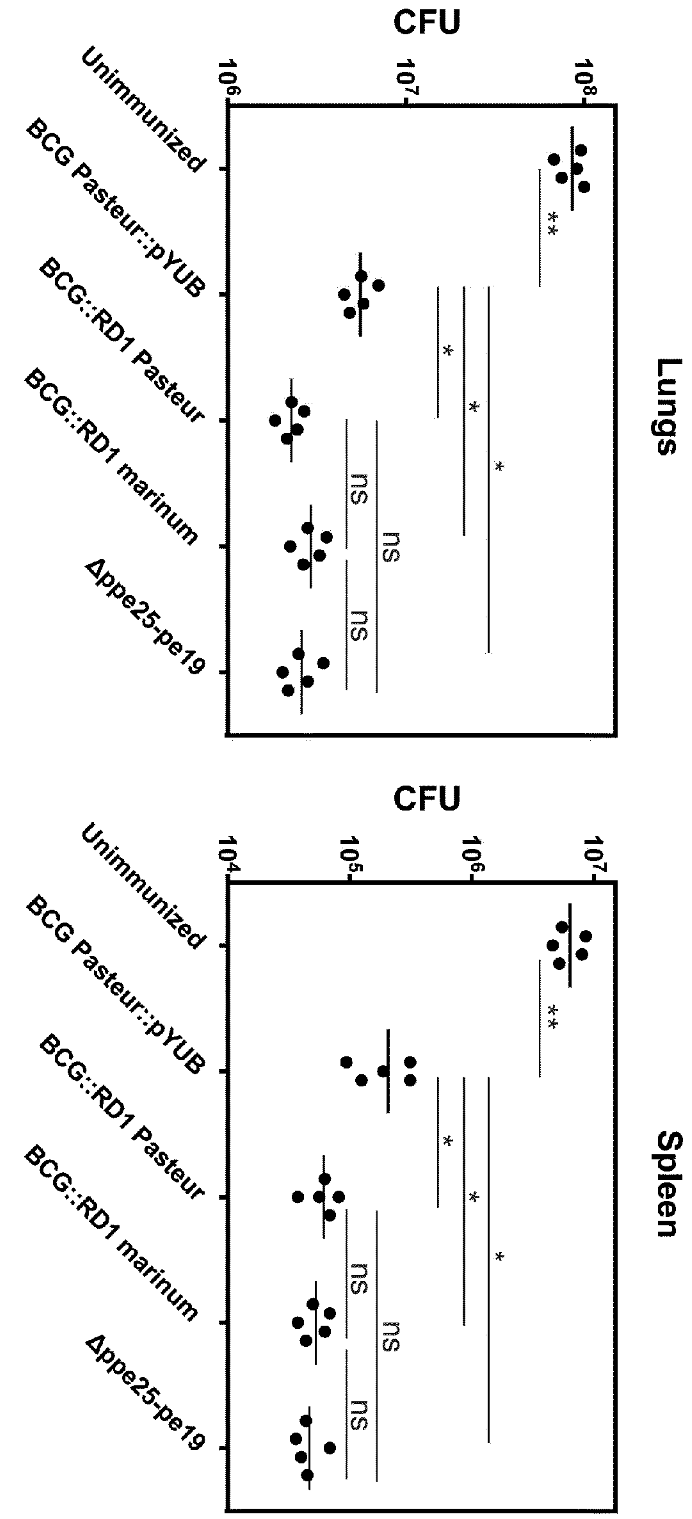
FIG. 22: Readout of the vaccination experiment using BCG::pYUb (vector control), BCG::RD1-Mtb, BCG::RD1-*marinum* and the Δppe25-pe19 attenuated Mtb vaccine (the latter described in Sayes et al., Cell Host Microbe 2012) in C57BL/6 mice. Mice (n=5/group) were immunized subcutaneously by $1\times10^6$ CFU of mycobacterial strains of interest. Four weeks post immunization, mice were challenged by aerosol with *M. tuberculosis* H37Rv virulent strain in order to deliver approximately 150 CFU/mouse. Mycobacterial loads in the spleen and lungs were determined at four weeks post challenge.

Mycobacterial loads in the spleen and lungs were determined at four weeks post challenge. As seen from these experiments, BCG::ESX-1$_{M.\ marinum}$ similarly to BCG::ESX-1-mtb and an attenuated *M. tuberculosis* ESX-5-ko vaccine (named MtbΔppe25-pe19) induced significantly better protection in lungs and spleens against an aerosol challenge with virulent *M. tuberculosis* H37Rv. Results are shown in FIG. 22.

Taken together, these data show that the BCG::ESX-1$_{M.\ marinum}$ strain has a very good vaccine profile.

C. Discussion

In this study a TB vaccine candidate was created based on a recombinant BCG encoding the ESX-1 secretion system of *M. marinum* (BCG::ESX-1MM, also named BCG::ESX1$_{M.\ marinum}$, or BCG::RD1-*Marinum*). In vitro and in vivo screens suggest that the BCG::ESX-1MM A strain is immunogenic due to export of the potent T-cell antigens ESAT-6 and CFP-10.

The BCG Pasteur strain was first complemented with the ESX-1 region of *M. marinum*. While the RD1 deletion in BCG includes only some of the core ESX-1 proteins, the genetic addition spanned the entire ESX-1 locus of *M. marinum*.

While the genomes of BCG and *Mycobacterium tuberculosis* (Mtb) are highly conserved (>99.9%) as reflected in the good tolerance of the Mtb ESX-1 genetic addition into BCG we here introduced a genomic region from a more distantly related *mycobacterium, M. marinum*, that encodes many more non-synonymous Single Nucleotide Polymorphisms and hence amino acid differences than its Mtb homologues. We could ascertain the establishment and functioning of the genetic addition in the BCG genome using different immunoblotting and antigen presenting assays. Both Western blot and T-cell hybridoma assays detected secretion of ESX-1 encoded proteins. Notably, these results indicate that the *M. marinum* genes share enough similarities with their Mtb counterparts to be tolerated in the BCG genome and recognized by the BCG promoters for transcription, despite sequence differences of up to 50% (Rv3876 and its homologue MMAR_5451). This creates a range of possibilities to complement more virulence factors, such as the ESX-5 system of *M. marinum* [36] to achieve the optimal level of immunogenicity while maintaining low levels of virulence for the needed vaccine properties.

To get a detailed picture of the induced immune response and immunogenicity properties of the BCG::ESX-1MM A clone a major step would be the identification of further T7SS substrates and their function. Little is known about most of the substrates but the role of the ESAT-6/CFP-10 pair has recently been reviewed [17]. They are associated with suppression of a pro-inflammatory response, necrosis, apoptosis, membrano-lysis and cytolysis. It remains questionable whether ESAT-6 and CFP-10 actually are the effectors causing these effects or rather building blocks in the process of secretion to facilitate the way for other effectors [84]. This is an intense area of research as it is unclear if other substrates apart from the ESAT-6/CFP-10 family exist. The PE/PPE proteins are heavily secreted by the T7SS, mainly ESX-5, while having many paralogues in the genome (up to 10% of Mtb genome encodes proteins of the PE/PPE family), suggesting that there are many more substrates than initially thought [85]. The ESX-1 region, for instance, is required to arrest phagosome maturation in macrophages yet the known ESX-1 substrates are not involved in this process proposing other secreted proteins via this pathway [86]. Likewise, the fact that T7SS are found in other gram-positive bacteria, among which some non-pathogenic and non-virulent, implies that the ESX-1 system fulfils other functions apart from virulence. As such the T7SS in *Listeria monocytogenes* is not required for growth [87], suggesting that also in Mtb, there could be other T7SS substrates not yet identified that are responsible for virulence. In support of this the C-terminal sequence of CFP-10 was shown to be portable when attached to yeast ubiquitin underpinning the notion that other substrates can be transported via the ESX-1 secretion machinery [53]. Also, the ESX-1 substrate EspA lacks this specific C-terminal sequence proposing that it could bind to another protein, such as EspC, and be transported together. Based on this the range of potential substrates widens even further.

In this study we made use of a newly developed assay using FRET to investigate the potential of BCG::ESX-1MM A to induce phagosomal rupture [80]. Our vaccine candidate clone demonstrated its ability of phagosomal escape compared to its control partner, the Western blot negative clone B. Arising evidence that mycobacteria are able to leave the phagosome has challenged the long standing paradigm that mycobacteria reside inside the phagosome postulating that they are able to induce vacuolar rupture to access the cytosol [79]. Presence of mycobacterial antigens in the cytosol would offer an explanation for the strong CD-8+ T-cell response that Mtb antigens are able to elicit, as antigens could get access to the cytosolic MHC-I presentation machinery only upon translocation [88]. It is well established that the membrane bound phagosome of the macrophage is the in vivo niche of Mtb [20] where they avoid phagolysosome fusion to circumvent the host immune response [9]. How exactly the bacilli interacts with the macrophage remains to be elucidated [20] however it was shown to be a very dynamic relationship [89]. While electron microscopy studies showed that the translocation into the cytosol is ESX-1 dependent [79] this explains that the negative control in our study, BCG::pYUB did not cause a shift in the FRET signal. A potential explanation is the described role of ESAT-6 in pore forming [65,90] so it could be a crucial player in offering other proteins access into the cytosol. More is known about the host-pathogen interactions for *M. marinum*. Stamm and colleagues [91] showed that *M. marinum* recruits host actin upon phagosomal rupture to be able to translocate within the cytosol. Yet Mtb, in contrast to *M. marinum*, does not recruit actin [92] suggesting that Mtb might have lost its ability to move around in favour of its persistence under harsh host conditions [20].

An interesting aspect we observed was the tolerance of the *M. marinum* genetic addition in BCG. While the ESX-1 region of Mtb is well tolerated and functional in BCG [64] our data imply that the distance of the *M. marinum* genes may cause cellular lysis of BCG. To verify secretion of the ESX-1 encoded proteins we employed T-cell hybridomas, which are sophisticated immunological tools that sense even minute levels of secreted bacterial proteins presented by Bone Marrow-Dendritic Cells. This confirmed that the ESX-1 substrates ESAT-6, CFP-10 and EspC are indeed secreted, even though at a much lower level than H37Rv WT. To control that the presence of ESX-1 proteins in the culture supernatant is actually due to secretion and not to lysis of the cells we employed anti-GroEl2-antibody, binding to an intracellular chaperone that is not found in culture supernatants. For the BCG::ESX-1MM clones we continued to detect this chaperone in the supernatant from mid-log phase grown cultures starting at day 3. The suggested lysis after 3-4 days may therefore represent the intolerance of BCG towards the *M. marinum* proteins, and function as self-limiting process.

This phenomenon has multiple repercussions on pathogenicity and virulence of this recombinant BCG strain. In a recent study, Simeone and colleagues (manuscript in preparation) showed that induction of early phase phagosomal rupture, a pathogenicity determinant, is independent of replication. Our data are in accordance with these observations as the BCG::ESX-1MM A strain produces a blue shift in our FRET assay indicating cytosolic presence of mycobacteria. This underpins the pathogenic potential of this strain in the light of the observed lysis. Indeed, this feature could exemplify a new vaccine strategy with initial antigen presentation by secretion of virulence factors followed by lysis and hence self-limiting infection, reducing the risk for BCG disease [93] in immunocompromised patients.

Taken together, the immunogenicity and virulence data obtained for the BCG::ESX-1MM A strain make it a promising candidate. Eliciting strong T-cell immunity while being safe are essential features of a vaccine. In a next step the protective efficacy of this strain have been evaluated in a murine model demonstrating that it can protect mice from developing TB upon aerosol challenge with Mtb.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

1. Raviglione M, Marais B, Floyd K, Lönnroth K, Getahun H, Migliori G B, et al. Scaling up interventions to achieve global *tuberculosis* control: progress and new developments. Lancet. 2012 May 19; 379(9829):1902-13.
2. WHO. Global *Tuberculosis* Report 2013. World Health Organization. Geneva.
3. Taylor G M, Young D B, Mays S A. Genotypic analysis of the earliest known prehistoric case of *tuberculosis* in Britain. Journal of Clinical Microbiology. 2005 May; 43(5):2236-40.
4. Jakubowiak W M, Bogorodskaya E M, Borisov S E, Borisov E S, Danilova I D, Danilova D I, et al. Risk factors associated with default among new pulmonary TB patients and social support in six Russian regions. Int J Tuberc Lung Dis. 2007 January; 11(1):46-53.
5. Faustini A. Risk factors for multidrug resistant *tuberculosis* in Europe: a systematic review. Thorax. 2006 Jan. 16; 61(2):158-63.
6. van der Werf M J, Langendam M W, Huitric E, Manissero D. Multidrug resistance after inappropriate *tuberculosis* treatment: a meta-analysis. Eur Respir J. 2012 June; 39(6): 1511-9.
7. Migliori G B, Centis R, D'Ambrosio L, Spanevello A, Borroni E, Cirillo D M, et al. Totally Drug-Resistant and Extremely Drug-Resistant *Tuberculosis*: The Same Disease? Clin Infect Dis. 2012 Apr. 9; 54(9):1379-80.
8. Raghavan S, Alagarasu K, Selvaraj P Immunogenetics of HIV and HIV associated *tuberculosis*. *Tuberculosis* (Edinb). Elsevier Ltd; 2012 Jan. 1; 92(1):18-30.
9. Prabowo S A, Gröschel M I, Schmidt E D L, Skrahina A, Mihaescu T, Hastürk S, et al. Targeting multidrug-resistant *tuberculosis* (MDR-TB) by therapeutic vaccines. Med Microbiol Immunol. 2012 Nov. 10; 202(2):95-104.
10. Hett E C, Rubin E J. Bacterial growth and cell division: a mycobacterial perspective. Microbiol Mol Biol Rev. 2008 March; 72(1):126-56.
11. Whitman W B, Parte A, Goodfellow M, Kämpfer P, Busse H-J, Trujillo M E, et al. Bergey's Manual of Systematic Bacteriology. New York: Springer; 2012. 9 p.
12. Bayan N, Houssin C, Chami M, Leblon G. Mycomembrane and S-layer: two important structures of *Corynebacterium glutamicum* cell envelope with promising biotechnology applications. J Biotechnol. 2003 Sep. 4; 104 (1-3):55-67.
13. Faller M, Niederweis M, Schulz G E. The structure of a mycobacterial outer-membrane channel. Science. 2004 Feb. 20; 303(5661):1189-92.
14. Houben E N G, Korotkov K V, Bitter W. Take five—Type VII secretion systems of Mycobacteria. Biochim Biophys Acta. 2013 Nov. 18.
15. Sørensen A L, Nagai S, Houen G, Andersen P, Andersen A B. Purification and characterization of a low-molecular-mass T-cell antigen secreted by *Mycobacterium tuberculosis*. Infect Immun. 1995 May; 63(5):1710-7.
16. Feltcher M E, Sullivan J T, Braunstein M. Protein export systems of *Mycobacterium tuberculosis*: novel targets for drug development? Future Microbiol. 2010 October; 5(10):1581-97.

17. Simeone R, Bottai D, Brosch R. ESX/type VII secretion systems and their role in host-pathogen interaction. Curr Opin Microbiol. 2009 February; 12(1):4-10.

18. Cole S T, Brosch R, Parkhill J, Garnier T, Churcher C, Harris D, et al. Deciphering the biology of *Mycobacterium tuberculosis* from the complete genome sequence. Nat Med. 1998 Jun. 11; 393(6685):537-44.

19. Stoop E J M, Bitter W, van der Sar A M. Tubercle bacilli rely on a type VII army for pathogenicity. Trends Microbiol. 2012 October; 20(10):477-84.

20. Stanley S A, Cox J S. Host-Pathogen Interactions During *Mycobacterium tuberculosis* infections. Curr Top Microbiol Immunol. 2013; 374:211-41.

21. van Broekhoven A, Shapiro F, Anné J. Novel Frontiers in the Production of Compounds for Biomedical Use. Springer; 2001. 1 p.

22. Johnson T L, Abendroth J, Hol W G J, Sandkvist M. Type II secretion: from structure to function. FEMS Microbiol Lett. 2006 February; 255(2):175-86.

23. Palmer T, Berks B C. The twin-arginine translocation (Tat) protein export pathway. Nat Rev Microbiol. 2012 July; 10(7):483-96.

24. Bingle L E, Bailey C M, Pallen M J. Type VI secretion: a beginner's guide. Curr Opin Microbiol. 2008 February; 11(1):3-8.

25. Abdallah A M, Gey van Pittius N C, Champion PAD, Cox J, Luirink J, Vandenbroucke-Grauls CMJE, et al. Type VII secretion—mycobacteria show the way. Nat Rev Microbiol. 2007 November; 5(11):883-91.

26. Brodin P, Rosenkrands I, Andersen P, Cole S T, Brosch R. ESAT-6 proteins: protective antigens and virulence factors? Trends Microbiol. 2004 November; 12(11):500-8.

27. Gey van Pittius N C, Gamieldien J, Hide W, Brown G D, Siezen R J, Beyers A D. The ESAT-6 gene cluster of *Mycobacterium tuberculosis* and other high G+C Gram-positive bacteria. Genome Biol. 2001; 2(10): RESEARCH0044.

28. Brown G D, Dave J A, Gey van Pittius N C, Stevens L, Ehlers M R, Beyers A D. The mycosins of *Mycobacterium tuberculosis* H37Rv: a family of subtilisin-like serine proteases. Gene. 2000 Aug. 22; 254(1-2):147-55.

29. Bitter W, Houben E N G, Bottai D, Brodin P, Brown E J, Cox J S, et al. Systematic genetic nomenclature for type VII secretion systems. PLoS Pathog. 2009 October; 5(10): e1000507.

30. Tekaia F, Gordon S V, Garnier T, Brosch R, Barrell B G, Cole S T. Analysis of the proteome of *Mycobacterium tuberculosis* in silico. Tuber Lung Dis. 1999; 79(6):329-42.

31. Målen H, Berven F S, Fladmark K E, Wiker H G. Comprehensive analysis of exported proteins from *Mycobacterium tuberculosis* H37Rv. Proteomics. 2007 May; 7(10):1702-18.

32. Sassetti C M, Boyd D H, Rubin E J. Genes required for mycobacterial growth defined by high density mutagenesis. Mol Microbiol. 2003 April; 48(1):77-84.

33. Lightbody K L, Ilghari D, Waters L C, Carey G, Bailey M A, Williamson R A, et al. Molecular features governing the stability and specificity of functional complex formation by *Mycobacterium tuberculosis* CFP-10/ESAT-6 family proteins. J Biol Chem. 2008 Jun. 20; 283(25): 17681-90.

34. Sayes F, Sun L, Di Luca M, Simeone R, Degaiffier N, Fiette L, et al. Strong immunogenicity and cross-reactivity of *Mycobacterium tuberculosis* ESX-5 type VII secretion: encoded PE-PPE proteins predicts vaccine potential. Cell Host & Microbe. 2012 Apr. 19; 11(4):352-63.

35. Weerdenburg E M, Abdallah A M, Mitra S, de Punder K, van der Wel N N, Bird S, et al. ESX-5-deficient *Mycobacterium marinum* is hypervirulent in adult zebrafish. Cell Microbiol. 2012 May; 14(5):728-39.

36. Abdallah A M, Bestebroer J, Savage N D L, de Punder K, van Zon M, Wilson L, et al. Mycobacterial secretion systems ESX-1 and ESX-5 play distinct roles in host cell death and inflammasome activation. J Immunol. 2011 Nov. 1; 187(9):4744-53.

37. Daleke M H, Cascioferro A, de Punder K, Ummels R, Abdallah A M, van der Wel N, et al. Conserved Pro-Glu (PE) and Pro-Pro-Glu (PPE) protein domains target LipY lipases of pathogenic mycobacteria to the cell surface via the ESX-5 pathway. J Biol Chem. 2011 May 27; 286(21): 19024-34.

38. Abdallah A M, Savage N D L, van Zon M, Wilson L, Vandenbroucke-Grauls C M J E, van der Wel N N, et al. The ESX-5 secretion system of *Mycobacterium marinum* modulates the macrophage response. J Immunol. 2008 Nov. 15; 181(10):7166-75.

39. Gey van Pittius N C, Sampson S L, Lee H, Kim Y, van Heiden P D, Warren R M. Evolution and expansion of the *Mycobacterium tuberculosis* PE and PPE multigene families and their association with the duplication of the ESAT-6 (esx) gene cluster regions. BMC Evol Biol. 2006; 6:95.

40. Bottai D, Di Luca M, Majlessi L, Frigui W, Simeone R, Sayes F, et al. Disruption of the ESX-5 system of *Mycobacterium tuberculosis* causes loss of PPE protein secretion, reduction of cell wall integrity and strong attenuation. Mol Microbiol. 2012 March; 83(6): 1195-209.

41. Di Luca M, Bottai D, Batoni G, Orgeur M, Aulicino A, Counoupas C, et al. The ESX-5 associated eccB-EccC locus is essential for *Mycobacterium tuberculosis* viability. PLoS ONE. 2012; 7(12):e52059.

42. Burts M L, Williams W A, DeBord K, Missiakas D M. EsxA and EsxB are secreted by an ESAT-6-like system that is required for the pathogenesis of *Staphylococcus aureus* infections. Proc Natl Acad Sci USA. 2005 Jan. 25; 102(4):1169-74.

43. São-José C, Baptista C, Santos M A. *Bacillus subtilis* operon encoding a membrane receptor for bacteriophage SPP1. Journal of Bacteriology. 2004 December; 186(24): 8337-46.

44. Geluk A, van Meijgaarden K E, Franken K L M C, Subronto Y W, Wieles B, Arend S M, et al. Identification and characterization of the ESAT-6 homologue of *Mycobacterium leprae* and T-cell cross-reactivity with *Mycobacterium tuberculosis*. Infect Immun. 2002 May; 70(5): 2544-8.

45. Cole S T, Eiglmeier K, Parkhill J, James K D, Thomson N R, Wheeler P R, et al. Massive gene decay in the leprosy *bacillus*. Nat Med. 2001 Feb. 22; 409(6823): 1007-11.

46. Pallen M J. The ESAT-6/WXG100 superfamily—and a new Gram-positive secretion system? Trends Microbiol. 2002 May; 10(5):209-12.

47. Pym A S, Brodin P, Brosch R, Huerre M, Cole S T. Loss of RD1 contributed to the attenuation of the live *tuberculosis* vaccines *Mycobacterium bovis* BCG and *Mycobacterium microti*. Mol Microbiol. 2002 November; 46(3):709-17.

48. Teutschbein J, Schumann G, Möllmann U, Grabley S, Cole S T, Munder T. A protein linkage map of the ESAT-6 secretion system 1 (ESX-1) of *Mycobacterium tuberculosis*. Microbiol Res. 2009; 164(3):253-9.

49. Renshaw P S, Panagiotidou P, Whelan A, Gordon S V, Hewinson R G, Williamson R A, et al. Conclusive evidence that the major T-cell antigens of the *Mycobacterium tuberculosis* complex ESAT-6 and CFP-10 form a tight, 1:1 complex and characterization of the structural properties of ESAT-6, CFP-10, and the ESAT-6*CFP-10 complex. Implications for pathogenesis and virulence. J Biol Chem. 2002 Jun. 14; 277(24):21598-603.
50. Stanley S A, Raghavan S, Hwang W W, Cox J S. Acute infection and macrophage subversion by *Mycobacterium tuberculosis* require a specialized secretion system. Proc Natl Acad Sci USA. 2003 Oct. 28; 100(22):13001-6.
51. Renshaw P S, Lightbody K L, Veverka V, Muskett F W, Kelly G, Frenkiel T A, et al. Structure and function of the complex formed by the *tuberculosis* virulence factors CFP-10 and ESAT-6. EMBO J. 2005 Jul. 20; 24(14): 2491-8.
52. Brodin P, de Jonge M I, Majlessi L, Leclerc C, Nilges M, Cole S T, et al. Functional analysis of early secreted antigenic target-6, the dominant T-cell antigen of *Mycobacterium tuberculosis*, reveals key residues involved in secretion, complex formation, virulence, and immunogenicity. J Biol Chem. 2005 Oct. 7; 280(40):33953-9.
53. Champion P A D, Stanley S A, Champion M M, Brown E J, Cox J S. C-terminal signal sequence promotes virulence factor secretion in *Mycobacterium tuberculosis*. Science. 2006 Sep. 15; 313(5793):1632-6.
54. Daleke M H, Ummels R, Bawono P, Heringa J, Vandenbroucke-Grauls C M J E, Luirink J, et al. General secretion signal for the mycobacterial type VII secretion pathway. Proc Natl Acad Sci USA. 2012 Jul. 10; 109(28): 11342-7.
55. Christie P J, Atmakuri K, Krishnamoorthy V, Jakubowski S, Cascales E. Biogenesis, architecture, and function of bacterial type IV secretion systems. Annu Rev Microbiol. 2005; 59:451-85.
56. Houben E N G, Bestebroer J, Ummels R, Wilson L, Piersma S R, Jiménez C R, et al. Composition of the type VII secretion system membrane complex. Mol Microbiol. 2012 October; 86(2):472-84.
57. Mahairas G G, Sabo P J, Hickey M J, Singh D C, Stover C K. Molecular analysis of genetic differences between *Mycobacterium bovis* BCG and virulent *M. bovis*. Journal of Bacteriology. 1996 March; 178(5):1274-82.
58. Weltman A C, Rose D N. The safety of Bacille Calmette-Guérin vaccination in HIV infection and AIDS. AIDS. 1993 February; 7(2):149-57.
59. McShane H. *Tuberculosis* vaccines: beyond bacille Calmette-Guerin. Philos Trans R Soc Lond B Biol Sci. 2011 Oct. 12; 366(1579):2782-9.
60. Kaufmann S H, Hussey G, Lambert P-H. New vaccines for *tuberculosis*. The Lancet. Elsevier Ltd; 2010 Jun. 12; 375(9731):2110-9.
61. Lewis K N, Liao R, Guinn K M, Hickey M J, Smith S, Behr M A, et al. Deletion of RD1 from *Mycobacterium tuberculosis* mimics bacille Calmette-Guérin attenuation. J Infect Dis. 2003 Jan. 1; 187(1):117-23.
62. Brosch R, Gordon S V, Garnier T, Eiglmeier K, Frigui W, Valenti P, et al. Genome plasticity of BCG and impact on vaccine efficacy. Proc Natl Acad Sci USA. 2007 Mar. 27; 104(13):5596-601.
63. Calmette A, Guerin C, Boquet A, Negre L. La vaccination preventive contre la tuberculose par le "BCG." Paris: Masson et cie; 1927. 1 p.
64. Pym A S, Brodin P, Majlessi L, Brosch R, Demangel C, Williams A, et al. Recombinant BCG exporting ESAT-6 confers enhanced protection against *tuberculosis*. Nat Med. 2003 May; 9(5):533-9.
65. Hsu T, Hingley-Wilson S M, Chen B, Chen M, Dai A Z, Morin P M, et al. The primary mechanism of attenuation of *bacillus* Calmette-Guerin is a loss of secreted lytic function required for invasion of lung interstitial tissue. Proc Natl Acad Sci USA. 2003 Oct. 14; 100(21):12420-5.
66. Brosch R, Pym A S, Gordon S V, Cole S T. The evolution of mycobacterial pathogenicity: clues from comparative genomics. Trends Microbiol. 2001 September; 9(9):452-8.
67. Brosch R, Gordon S V, Marmiesse M, Brodin P, Buchrieser C, Eiglmeier K, et al. A new evolutionary scenario for the *Mycobacterium tuberculosis* complex. Proc Natl Acad Sci USA. 2002 Mar. 19; 99(6):3684-9.
68. Travis W D, Travis L B, Roberts G D, Su D W, Weiland L W. The histopathologic spectrum in *Mycobacterium marinum* infection. Arch Pathol Lab Med. 1985 December; 109(12):1109-13.
69. Gao L-Y, Guo S, McLaughlin B, Morisaki H, Engel J N, Brown E J. A mycobacterial virulence gene cluster extending RD1 is required for cytolysis, bacterial spreading and ESAT-6 secretion. Mol Microbiol. 2004 September; 53(6):1677-93.
70. Zumla A, Atun R, Maeurer M, Kim P S, Jean-Philippe P, Hafner R, et al. Eliminating *Tuberculosis* and *Tuberculosis*-HIV Co-Disease in the 21st Century: Key Perspectives, Controversies, Unresolved Issues, and Needs. J Infect Dis. 2012 Apr. 23; 205(suppl 2):S141-6.
71. Beresford B, Sadoff J C. Update on Research and Development Pipeline: *Tuberculosis* Vaccines. Clin Infect Dis [Internet]. 2010 May 15; 50(s3):5178-83. Available from: http://cid.oxfordjournals.org/content/50/Supplement_3/S178.short
72. Tameris M D, Hatherill M, Landry B S, Scriba T J, Snowden M A, Lockhart S, et al. Safety and efficacy of MVA85A, a new *tuberculosis* vaccine, in infants previously vaccinated with BCG: a randomised, placebo-controlled phase 2b trial. Lancet. 2013 Mar. 23; 381(9871): 1021-8.
73. Hoft D F, Blazevic A, Abate G, Hanekom W A, Kaplan G, Soler J H, et al. A new recombinant bacille Calmette-Guérin vaccine safely induces significantly enhanced *tuberculosis*-specific immunity in human volunteers. J Infect Dis. 2008 Nov. 15; 198(10):1491-501.
74. Ottenhoff T H M, Kaufmann S H E. Vaccines against *Tuberculosis*: Where Are We and Where Do We Need to Go? Chitnis C E, editor. PLoS Pathog. 2012 May 10; 8(5):e1002607-12.
75. Kamath A B, Woodworth J, Xiong X, Taylor C, Weng Y, Behar S M. Cytolytic CD8+ T cells recognizing CFP10 are recruited to the lung after *Mycobacterium tuberculosis* infection. J Exp Med. 2004 Dec. 6; 200(11):1479-89.
76. Bange F C, Collins F M, Jacobs W R. Survival of mice infected with *Mycobacterium smegmatis* containing large DNA fragments from *Mycobacterium tuberculosis*. Tuber Lung Dis. 1999; 79(3):171-80.
77. Gradmann C. Robert Koch and the pressures of scientific research: *tuberculosis* and tuberculin. Medical history. 2001. 32 p.
78. Grange J M, Brunet L R, Rieder H L. Immune protection against *tuberculosis*—When is immunotherapy preferable to vaccination? *Tuberculosis* (Edinb). Elsevier Ltd; 2011 Mar. 1; 91(2):179-85.

79. van der Wel N, Hava D, Houben D, Fluitsma D, van Zon M, Pierson J, et al. *M. tuberculosis* and *M. leprae* translocate from the phagolysosome to the cytosol in myeloid cells. Cell. 2007 Jun. 29; 129(7):1287-98.
80. Houben D, Demangel C, van Ingen J, Perez J, Baldeón L, Abdallah A M, et al. ESX-1-mediated translocation to the cytosol controls virulence of mycobacteria. Cell Microbiol. 2012 August; 14(8):1287-98.
81. Simeone R, Bobard A, Lippmann J, Bitter W, Majlessi L, Brosch R, et al. Phagosomal rupture by *Mycobacterium tuberculosis* results in toxicity and host cell death. PLoS Pathog. 2012 February; 8(2):e1002507.82. Nothelfer K, Dias Rodrigues C, Bobard A, Phalipon A, Enninga J. Monitoring *Shigella flexneri* vacuolar escape by flow cytometry. Virulence. 2011 January; 2(1):54-7.
83. Voladri R K, Lakey D L, Hennigan S H, Menzies B E, Edwards K M, Kernodle D S. Recombinant expression and characterization of the major beta-lactamase of *Mycobacterium tuberculosis*. Antimicrob Agents Chemother. 1998 June; 42(6):1375-81.
84. Fortune S M, Jaeger A, Sarracino D A, Chase M R, Sassetti C M, Sherman D R, et al. Mutually dependent secretion of proteins required for mycobacterial virulence. Proc Natl Acad Sci USA. 2005 Jul. 26; 102(30):10676-81.
85. Abdallah A M, Verboom T, Weerdenburg E M, Gey van Pittius N C, Mahasha P W, Jiménez C, et al. PPE and PE_PGRS proteins of *Mycobacterium marinum* are transported via the type VII secretion system ESX-5. Mol Microbiol. 2009 August; 73(3):329-40.
86. MacGurn J A, Cox J S. A genetic screen for *Mycobacterium tuberculosis* mutants defective for phagosome maturation arrest identifies components of the ESX-1 secretion system. Infect Immun. 2007 June; 75(6):2668-78.
87. Way S S, Wilson C B. The *Mycobacterium tuberculosis* ESAT-6 homologue in *Listeria monocytogenes* is dispensable for growth in vitro and in vivo. Infect Immun. 2005 September; 73(9):6151-3.
88. Majlessi L, Brodin P, Brosch R, Rojas M-J, Khun H, Huerre M, et al. Influence of ESAT-6 secretion system 1 (RD1) of *Mycobacterium tuberculosis* on the interaction between mycobacteria and the host immune system. J Immunol. 2005 Mar. 15; 174(6):3570-9.
89. Rohde K H, Veiga D F T, Caldwell S, Balázsi G, Russell D G. Linking the transcriptional profiles and the physiological states of *Mycobacterium tuberculosis* during an extended intracellular infection. PLoS Pathog. 2012; 8(6): e1002769.
90. de Jonge M I, Pehau-Arnaudet G, Fretz M M, Romain F, Bottai D, Brodin P, et al. ESAT-6 from *Mycobacterium tuberculosis* dissociates from its putative chaperone CFP-10 under acidic conditions and exhibits membrane-lysing activity. Journal of Bacteriology. 2007 August; 189(16): 6028-34.
91. Stamm L M, Morisaki J H, Gao L-Y, Jeng R L, McDonald K L, Roth R, et al. *Mycobacterium marinum* escapes from phagosomes and is propelled by actin-based motility. J Exp Med. 2003 Nov. 3; 198(9):1361-8.
92. Smith J, Manoranjan J, Pan M, Bohsali A, Xu J, Liu J, et al. Evidence for pore formation in host cell membranes by ESX-1-secreted ESAT-6 and its role in *Mycobacterium marinum* escape from the vacuole. Infect Immun. 2008 December; 76(12):5478-87.
93. Hesseling A C, Marais B J, Gie R P, Schaaf H S, Fine P E M, Godfrey-Faussett P, et al. The risk of disseminated Bacille Calmette-Guerin (BCG) disease in HIV-infected children. Vaccine. 2007 January; 25(1):14-8.
94. Wells, A. Q. 1937. *Tuberculosis* in wild voles. Lancet i:1221
95. Van Soolingen, D., A. G. M. van der Zanden, P. E. W. De Haas, G. T. Noordhoek, A. Kiers, N. A. Foudraine, F. Portaels, A. H. J. Kolk, K. Kremer, and J. D. A. van Embden. 1998. Diagnosis of *Mycobacterium microti* infections among humans by using novel genetic markers. J. Clin. Microbiol. 36:1840-1845
96. Brodin P, Eiglmeier K, Marmiesse M, Billault A, Garnier T, Niemann S, Cole S T, Brosch R. 2002. Bacterial artificial chromosome-based comparative genomic analysis identifies *Mycobacterium microti* as a natural ESAT-6 deletion mutant. Infect Immun. 70(10):5568-78

The invention claimed is:

1. A recombinant strain of *Mycobacterium bovis* bacille Calmette-Guérin (*M. bovis* BCG) comprising a heterologous nucleic acid sequence comprising a plurality of open reading frames, wherein the plurality of open reading frames comprise open reading frames that encode proteins each at least 95% homologous to the *Mycobacterium marinum* (*M. marinum*) proteins MMAR5445 having the sequence of SEQ ID NO: 18, MMAR5446 having the sequence of SEQ ID NO: 19, MMAR5447 having the sequence of SEQ ID NO: 20, MMAR5448 having the sequence of SEQ ID NO: 21, MMAR5449 having the sequence of SEQ ID NO: 22, MMAR5450 having the sequence of SEQ ID NO: 23, MMAR5451 having the sequence of SEQ ID NO: 24, MMAR5452 of SEQ ID NO: 25, MMAR5453 having the sequence of SEQ ID NO: 26, and MMAR5455 having the sequence of SEQ ID NO: 28.

2. The recombinant strain of *M. bovis* BCG according to claim 1, wherein the plurality of open reading frames further comprise an open reading frame that encodes a protein at least 95% homologous to the *M. marinum* proteins MMAR5443 having the sequence of SEQ ID NO: 16, MMAR5444 having the sequence of SEQ ID NO: 17, and MMAR5457 having the sequence of SEQ ID NO: 30.

3. The recombinant strain of *M. bovis* BCG according to claim 2, wherein the plurality of open reading frames further comprise open reading frames that encode proteins at least 95% homologous to the *M. marinum* proteins MMAR5429 having the sequence of SEQ ID NO: 68, MMAR5430 having the sequence of SEQ ID NO: 3, MMAR5431 having the sequence of SEQ ID NO: 4, MMAR5432 having the sequence of SEQ ID NO: 5, MMAR5433 having the sequence of SEQ ID NO: 6, MMAR5434 having the sequence of SEQ ID NO: 7, MMAR5435 having the sequence of SEQ ID NO: 8, MMAR5436 having the sequence of SEQ ID NO: 9, MMAR5437 having the sequence of SEQ ID NO: 10, MMAR5438 having the sequence of SEQ ID NO: 11, MMAR5439 having the sequence of SEQ ID NO: 12, MMAR5440 having the sequence of SEQ ID NO: 13, MMAR5441 having the sequence of SEQ ID NO: 14, MMAR5442 having the sequence of SEQ ID NO: 15, MMAR5454 having the sequence of SEQ ID NO: 27, MMAR5456 having the sequence of SEQ ID NO: 29, MMAR5458 having the sequence of SEQ ID NO: 31, MMAR5459 having the sequence of SEQ ID NO: 32, MMAR5460 having the sequence of SEQ ID NO: 33, and MMAR5461 having the sequence of SEQ ID NO: 34.

4. The recombinant strain of *M. bovis* BCG according to claim 1, wherein the open reading frames that encode the listed proteins have the sequence of the corresponding open reading frames listed in SEQ ID NO:51-59 and 61.

5. A recombinant strain of *M. bovis* BCG according to claim 1, wherein the heterologous nucleic acid sequence comprises the nucleic acid sequence of SEQ ID NO:1.

6. The recombinant strain of *M. bovis* BCG according to claim 1, wherein the heterologous nucleic acid sequence is present on a plasmid.

7. The recombinant strain of *M. bovis* BCG according to claim 1, wherein the heterologous nucleic acid sequence is integrated into the *M. bovis* BCG chromosome.

8. The recombinant strain of *M. bovis* BCG according to claim 1, wherein the recombinant strain secretes the CFP-10 and ESAT-6 proteins of *M. marinum.*

9. The recombinant strain of *M. bovis* BCG according to claim 1, wherein the recombinant strain induces a protective immune response greater than the parent *M. bovis* BCG when introduced into a subject, and wherein the virulence of the recombinant strain is equal to or lower than the virulence of the parent *M. bovis* BCG.

10. A pharmaceutical composition comprising a recombinant strain of *M. bovis* BCG according to claim 1 and a carrier.

11. A kit comprising a recombinant strain of *M. bovis* BCG according to claim 1 in a container.

12. The kit of claim 11, further comprising at least one protein or peptide antigen of a *mycobacterium.*

13. A method for inducing a protective immune response against *M. tuberculosis* in a subject, comprising administering an effective dose of a pharmaceutical composition according to claim 10 to a subject and inducing an immune response in the subject that is protective against *M. tuberculosis.*

14. The method of claim 13, further comprising administering at least one isolated recombinant protein or peptide antigen of a *mycobacterium* to the subject.

15. The method of claim 14, wherein the at least one isolated recombinant protein or peptide antigen is selected from CFP-10 protein, ESAT-6 protein, and peptides thereof.

16. The recombinant strain of *M. bovis* BCG according to claim 5, wherein the heterologous nucleic acid sequence comprises the *M. marinum* nucleic acid sequence inserted in the recombinant pYUB412 vector carried by the bacteria deposited at the CNCM under the reference number I-4858 on Jun. 3, 2014.

* * * * *